(12) United States Patent
Bhatia et al.

(10) Patent No.: US 10,081,609 B2
(45) Date of Patent: Sep. 25, 2018

(54) COMPOUNDS FOR INDUCING PROLIFERATION AND DIFFERENTIATION OF CELLS, AND METHODS OF USE THEREOF

(71) Applicants: The Broad Institute, Inc., Cambridge, MA (US); Massachusetts Institute of Technology, Cambridge, MA (US)

(72) Inventors: Sangeeta Bhatia, Lexington, MA (US); Jing Shan, Cambridge, MA (US); Michelle Palmer, Harvard, MA (US); Nathan Ross, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/772,284

(22) PCT Filed: Mar. 14, 2014

(86) PCT No.: PCT/US2014/028408
§ 371 (c)(1),
(2) Date: Sep. 2, 2015

(87) PCT Pub. No.: WO2014/144125
PCT Pub. Date: Sep. 18, 2014

(65) Prior Publication Data
US 2016/0031837 A1     Feb. 4, 2016

Related U.S. Application Data

(60) Provisional application No. 61/798,902, filed on Mar. 15, 2013.

(51) Int. Cl.
| C12N 5/00 | (2006.01) |
| C07D 263/24 | (2006.01) |
| C12N 5/071 | (2010.01) |
| A01K 67/027 | (2006.01) |
| A61K 31/137 | (2006.01) |
| A61K 31/403 | (2006.01) |
| A61K 31/4035 | (2006.01) |
| A61K 31/4174 | (2006.01) |
| A61K 31/4409 | (2006.01) |
| A61K 35/407 | (2015.01) |
| C07C 211/32 | (2006.01) |
| C07D 209/48 | (2006.01) |
| C07D 209/88 | (2006.01) |
| C07D 213/75 | (2006.01) |

(52) U.S. Cl.
CPC ........ *C07D 263/24* (2013.01); *A01K 67/0278* (2013.01); *A61K 31/137* (2013.01); *A61K 31/403* (2013.01); *A61K 31/4035* (2013.01); *A61K 31/4174* (2013.01); *A61K 31/4409* (2013.01); *A61K 35/407* (2013.01); *C07C 211/32* (2013.01); *C07D 209/48* (2013.01); *C07D 209/88* (2013.01); *C07D 213/75* (2013.01); *C12N 5/067* (2013.01); *A01K 2227/105* (2013.01); *A01K 2267/0331* (2013.01); *C12N 2501/02* (2013.01); *C12N 2501/115* (2013.01); *C12N 2501/12* (2013.01); *C12N 2501/155* (2013.01); *C12N 2501/16* (2013.01); *C12N 2501/237* (2013.01); *C12N 2501/999* (2013.01); *C12N 2503/02* (2013.01); *C12N 2506/45* (2013.01); *C12N 2533/90* (2013.01); *Y02A 50/387* (2018.01); *Y02A 50/463* (2018.01)

(58) Field of Classification Search
CPC ............................. C12N 5/067; C07D 263/24
See application file for complete search history.

(56) References Cited

U.S. PATENT DOCUMENTS

| 5,849,774 A | 12/1998 | Jackson et al. |
| 2010/0009442 A1 | 1/2010 | Sasai et al. |
| 2011/0027236 A1 | 2/2011 | Bastianelli |
| 2011/0151561 A1 | 6/2011 | Davis et al. |
| 2012/0058561 A1 | 3/2012 | Sato |
| 2012/0129260 A1 | 5/2012 | Egli et al. |

FOREIGN PATENT DOCUMENTS

| EP | 1810692 | 7/2007 |
| WO | 2005/054436 | 6/2005 |

OTHER PUBLICATIONS

Supplemental European Search Report issued in European Application No. 14763499.2 dated Aug. 31, 2016.
Notification of Transmittal of the International Search Report and the Written Opinion of the International Searching Authority, for corresponding PCT/US2014/028408, dated Jul. 10, 2014 (12 pages).
J. Shan, et al., "Identification of small molecules for human hepatocyte expansion and iPS differentiation," Nature Chemical Biology, published online Jun. 2, 2013 (36 pages).

(Continued)

*Primary Examiner* — Marcia Stephens Noble
(74) *Attorney, Agent, or Firm* — Melissa Hunter-Ensor; Leslie Serunian; Greenberg Traurig, LLP

(57) ABSTRACT

The present invention provides methods of inducing proliferation of and/or differentiating cells comprising contacting cells with compounds within the methods of the invention. The present invention further provides cells obtainable by the methods of the invention. Liver disease affects more than 500 million people worldwide. Organ transplantation is the gold standard for treatment of liver failure, but organ shortages are acute.

8 Claims, 56 Drawing Sheets

(56) References Cited

OTHER PUBLICATIONS

PubChem Open Chemistry Database (IYOZTVGMEWJPKR-VOMCLLRMSA-N), Compound CID 448042, Y 27632, IUPAC Name: 4-[(1R)-1-aminoethyl]-N-pyridin-4-ylcyclohexane-1-carboxamide). Retrieved from the Internet (Apr. 27, 2018) at URL: https://pubchem.ncbi.nlm.nih.gov/compound/448042 (25 pages).

PubChem Open Chemistry Database (IDDDVXIUIXWAGJ-DDSAHXNVSA-N), Compound CID 9901617, Y 27632 dihydrochloride, IUPAC Name: 4-[(1R)-1-aminoethyl]-N-pyridin-4-ylcyclohexane-1-carboxamide, dihydrochloride). Retrieved from this Internet (Apr. 27, 2018) at URL: https://pubchem.ncbi.nlm.nih.gov/compound/Y-27532_dihydrochloride (20 pages).

European Patent Office Communication pursuant to Article 94(3) as issued in corresponding European Patent Application No. 14763499.2, dated Jun. 4, 2018 (4 pages).

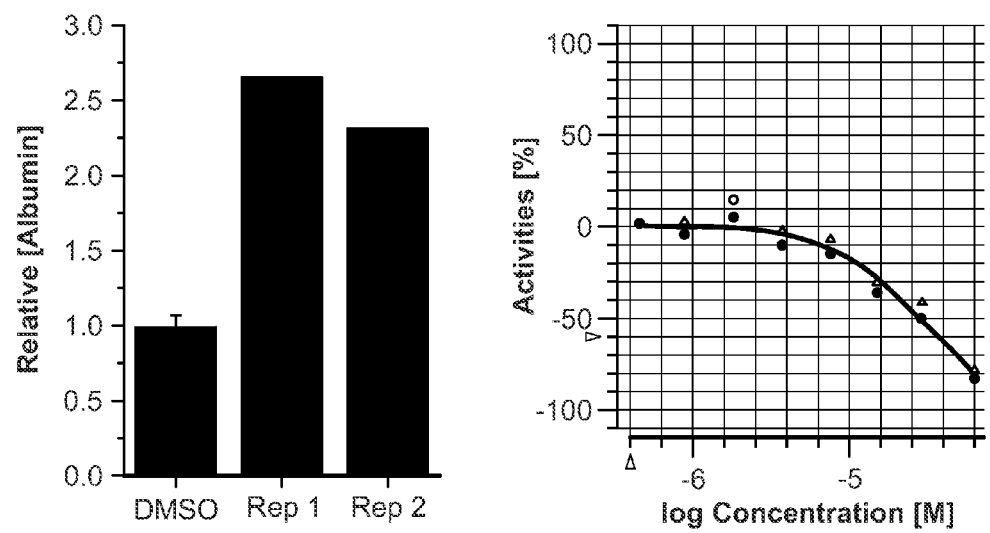
FIG. 4A
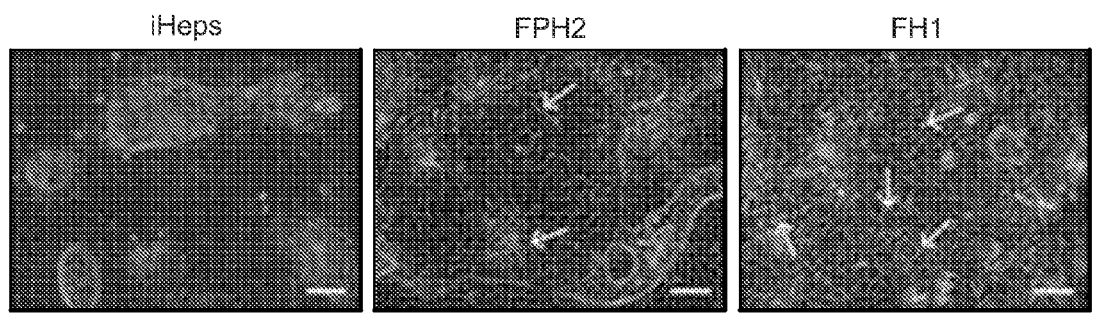
FIG. 4B
| FIG. 4C-1 | FIG. 4C-3 |
| --- | --- |
| FIG. 4C-2 | FIG. 4C-4 |
FIG. 4C

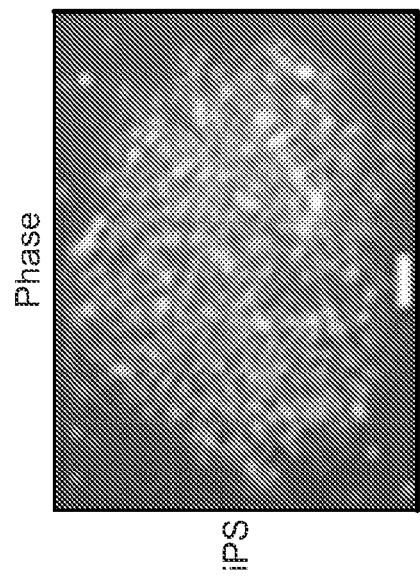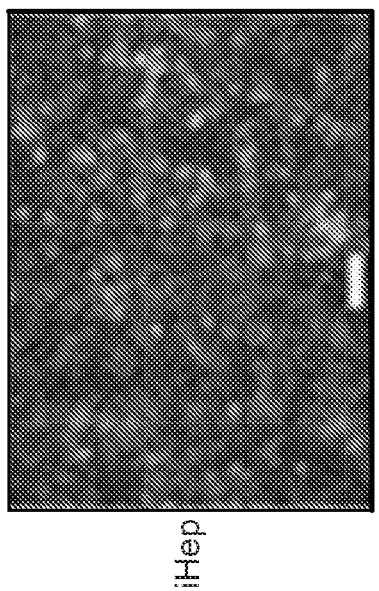

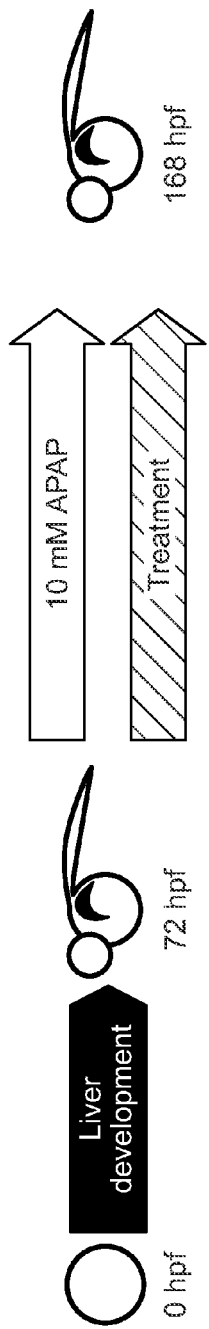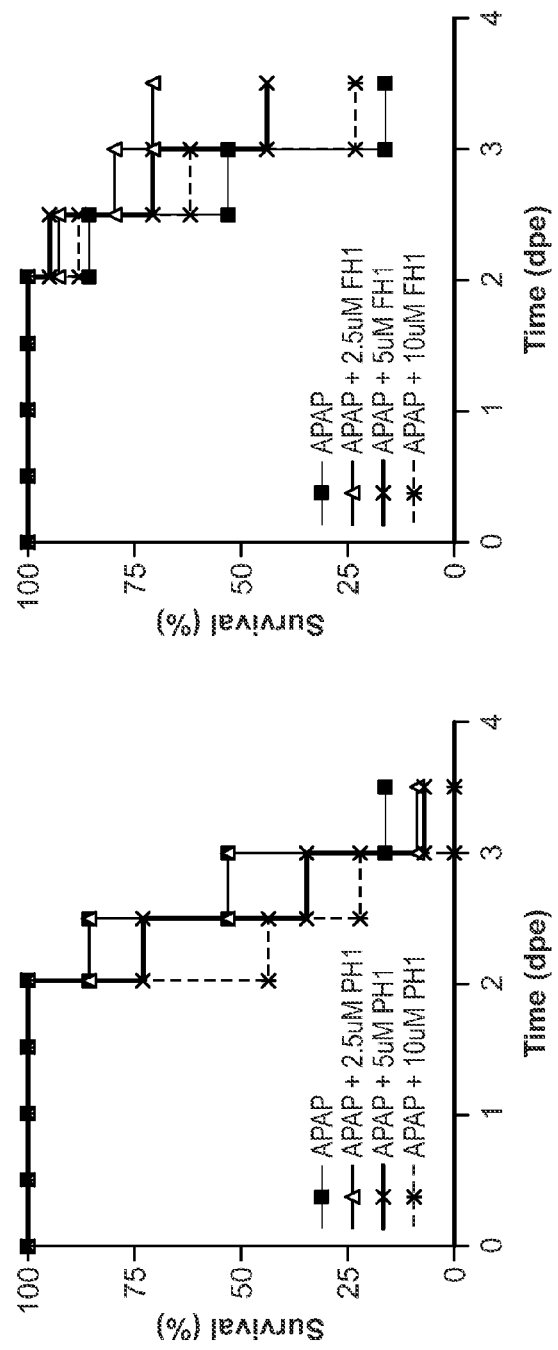
FIG. 9A
FIG. 9B

| Compound | Relative Cell Count | Compound | Relative Cell Count |
|---|---|---|---|
| Null | 1.00 | 235 | 1.45 |
| 201 | 1.13 | 236 | 1.53 |
| 202 | 1.14 | 237 | 1.49 |
| 203 | 1.16 | 238 | 1.72 |
| 204 | 0.66 | 239 | 1.74 |
| 205 | 1.25 | 240 | 1.59 |
| 206 | 1.27 | 241 | 1.22 |
| 207 | 1.17 | 242 | 1.21 |
| 208 | 1.05 | 243 | 1.34 |
| 209 | 1.01 | 244 | 1.59 |
| 210 | 1.09 | 245 | 1.46 |
| 211 | 1.25 | 246 | 1.39 |
| 212 | 1.04 | 247 | 1.02 |
| 215 | 1.24 | 248 | 2.00 |
| 217 | 0.79 | 249 | 1.37 |
| 224 | 1.02 | 250 | 1.41 |
| 225 | 0.87 | 251 | 1.13 |
| 226 | 0.91 | 252 | 1.55 |
| 227 | 0.89 | 253 | 1.17 |
| 228 | 0.82 | 107 | 1.10 |
| 229 | 0.92 | 254 | 1.19 |
| 230 | 0.88 | 255 | 1.36 |
| 231 | 0.92 | 108 | 1.01 |
| 232 | 0.95 | 106 | 1.24 |
| 233 | 0.78 | 256 | 1.15 |
| 234 | 0.88 | 257 | 1.54 |

FIG. 11F

| Compound | Relative Differentiation Potential | Compound | Relative Differentiation Potential |
|---|---|---|---|
| Null | 1 | 236 | 7.68 |
| 201 | 7.14 | 237 | 7.94 |
| 202 | 6.54 | 238 | 9.53 |
| 203 | 7.25 | 239 | 9.57 |
| 204 | 6.48 | 240 | 8.83 |
| 205 | 7.84 | 241 | 7.95 |
| 206 | 7.60 | 242 | 8.17 |
| 207 | 7.88 | 243 | 8.83 |
| 208 | 7.52 | 244 | 8.06 |
| 209 | 7.67 | 245 | 9.58 |
| 210 | 7.09 | 246 | 9.33 |
| 211 | 7.08 | 247 | 9.82 |
| 212 | 7.70 | 248 | 10.27 |
| 217 | 5.05 | 249 | 9.92 |
| 224 | 7.69 | 250 | 10.20 |
| 225 | 7.50 | 251 | 9.85 |
| 226 | 8.27 | 252 | 9.69 |
| 227 | 8.93 | 253 | 9.66 |
| 228 | 8.28 | 107 | 9.67 |
| 229 | 7.48 | 254 | 8.27 |
| 230 | 7.24 | 255 | 10.31 |
| 231 | 8.37 | 108 | 10.28 |
| 232 | 8.72 | 106 | 10.69 |
| 233 | 8.96 | 256 | 9.59 |
| 234 | 8.80 | 257 | 9.44 |
| 235 | 9.07 | | |

FIG. 12C

COMPOUNDS FOR INDUCING PROLIFERATION AND DIFFERENTIATION OF CELLS, AND METHODS OF USE THEREOF

CROSS-REFERENCE TO RELATED APPLICATIONS

The present application is the U.S. national phase application, pursuant to 35 U.S.C. § 371, of PCT international application Ser. No. PCT/US2014/028408, filed Mar. 14, 2014, designating the United States and published in English, which claims priority under 35 U.S.C. § 119(e) to U.S. Provisional Application No. 61/798,902, filed Mar. 15, 2013, which applications are hereby incorporated by reference in their its entirety herein.

STATEMENT OF RIGHTS TO INVENTIONS MADE UNDER FEDERALLY SPONSORED RESEARCH

This invention was made with government support under grant numbers HG005032, DK065152, and DK56966 awarded by the National Institutes of Health. The government has certain rights in the invention.

BACKGROUND OF THE INVENTION

Liver disease affects more than 500 million people worldwide. Organ transplantation is the gold standard for treatment of liver failure, but organ shortages are acute. Cell-based therapies, such as cell transplantation, engineered hepatocellular tissue constructs and bioartificial liver devices, have long held promise as alternatives to whole organ transplantation. Such therapies require the use of human hepatocytes due to substantial species-specific differences between animal and human hepatocellular functions.

Human hepatocytes, within the stromal context of the liver in vivo, are capable of extensive proliferation, enough to fully regenerate the liver following up to 66% partial hepatectomy. However, this ability is lost in vitro, despite extensive gene-by-gene and protein-by-protein approaches towards harnessing this tremendous replication potential of human hepatocytes. Investigations have yielded many different culture conditions that can support moderate expansion of mouse and rat hepatocytes, including a multi-factor media formulation that expands rat hepatocytes through a dedifferentiated bi-potential intermediate. However, translation of these findings to human cultures has not been reported. Human cells are critical for cell-based therapies due to substantial differences between animal and human hepatocellular functions, including apolipoprotein expression, metabolic regulation of cholesterol, and phase I detoxification enzymes. To overcome the growth limitations of primary human cells, various human hepatocyte cell lines have been developed. Although these cell lines are growth-competent, they introduce safety concerns and underperform primary cells in terms of liver function.

In addition to their use in the transplantation therapies to treat liver diseases, human hepatocytes are in high demand for drug toxicity screening and development, because of their critical function in the detoxification of drugs or other xenobiotics, as well as endogenous substrates. However, human primary hepatocytes quickly lose their functions when cultured in vitro. Moreover, the drug metabolic ability of human primary hepatocytes exhibits significant variance among individuals. The availability of an unlimited supply of patient-specific functional hepatocytes would greatly facilitate both the drug development and the eventual clinical application of hepatocyte transplantation.

Alternative sources for hepatic cells are being investigated, such as various stem cell populations. Stem cells hold great promise as a biologics source due to their ability to self-renew without limit and to differentiate along many lineages. Induced pluripotent stem cells (iPS cells) additionally create the possibility of establishing patient-specific cell types, thus empowering personalized medicine. Human iPS cells are generated from somatic cells via forced expression of reprogramming factors, and can be differentiated towards hepatocyte-like cells (iHeps) in a step-wise manner, using defined factors. Mouse iHeps can also be generated directly from fibroblasts via cellular reprogramming. Although diverse stem and progenitor cell types exhibit vast potential for integration into hepatic treatments, many challenges remain, including the ability to completely dictate differentiation into fully mature hepatocytes. While human iHeps closely resemble mature hepatocytes, key differences in their phenotypes tlimit their use as a renewable source of functional hepatocytes. Notably, iHeps persistently express fetal markers like alpha fetoprotein (AFP) and lack key mature hepatocyte functions, as reflected by drastically reduced activity (0.1%) of many CYP450s (e.g. CYP2A6 and CYP3A4). Consequently, for decades, human hepatocyte sourcing has been a bottleneck for many fields of research and clinical therapies.

There is a need for identifying compounds that induce proliferation and/or differentiation of cells, such as somatic cells. Such compounds may be used, for example, to produce hepatic lineage cells for therapeutic and research use, such as human hepatocytes. The present invention addresses and satisfies this unmet need.

BRIEF SUMMARY OF THE INVENTION

As described herein, the present invention provides compounds that induce proliferation of cells, such as hepatocytes, in vitro or in vivo, and/or induces differentiation of pluripotent stem cells so as to provide functional cells, such as functional hepatocytes. The present invention further provides methods of inducing proliferation of hepatocytes in vitro or in vivo, and/or inducing differentiation of pluripotent stem cells, and cells prepared according to the methods of the invention.

The invention provides a method of inducing proliferation of one or more primary cells, the method comprising contacting the one or more primary cells with a compound of the invention.

The invention further provides a method of inducing differentiation of one or more induced pluripotent stem cells (iPS cell), the method comprising contacting the one or more iPS cells with at least one compound of the invention, whereby contacting the one or more iPS cells with the at least one compound induces differentiation of the one or more iPS cells.

The invention further provides a cell produced by a method of the invention.

The invention further provides a method of treating, alleviating or preventing a disease or condition in a subject in need thereof, the method comprising administering to a subject a therapeutically effective amount of at least one agent selected from the group consisting of: (i) at least one compound of the invention; (ii) one or more cells obtained by a method of the invention; (iii) one or more cells of the invention; and, any combinations thereof.

The invention further provides a method of performing tissue or organ transplant in a subject in need thereof, the method comprising administering to the subject a therapeutically effective amount of at least one agent selected from the group consisting of: (i) at least one compound of the invention; (ii) one or more cells obtained by a method of the invention; (iii) one or more cells of the invention; and, any combinations thereof.

The invention further provides a method of repairing damaged, diseased or aged tissue in a subject in need thereof, the method comprising administering to the subject a therapeutically effective amount of at least one agent selected from the group consisting of: (i) at least one compound of the invention; (ii) one or more cells obtained by a method of the invention; (iii) one or more cells of the invention; and, any combinations thereof.

The invention further provides a method of providing cell replacement therapy to a subject in need thereof, the method comprising: (i) contacting one or more cells with at least one compound of the invention, thereby generating one or more differentiated cells; and (ii) administering the one or more differentiated cells to the subject.

The invention further provides a method of developing a humanized mouse model, the method comprising administering to a mouse at least one cell selected from the group consisting of (i) one or more cells obtained by a method of the invention; (ii) one or more cells of the invention; and any combinations thereof.

In various embodiments of any of the above aspects or any other aspect of the invention delineated herein, the compound is selected from the group consisting of:
Compound 109 (PH1, or 4-(3-butoxy-4-methoxybenzyl) imidazolidin-2-one);
Compound 110 ((1R,4R)-4-((R)-1-aminoethyl)-N-(pyridin-4-yl)cyclohexane-1-carboxamide);
Compound 111 ((1R,4R)-4-((R)-1-aminoethyl)-N-(pyridin-4-yl)cyclohexane carboxamide);
Compound 112 (1-((9H-carbazol-4-yl)oxy)-3-((2-(2-methoxyphenoxy)ethyl)amino) propan-2-ol);
Compound 113 (3-(5H-dibenzo[a,d][7]annulen-5-ylidene)-N,N-dimethylpropan-1-amine);
Compound 114 (2-(2-(1,3-dioxoisoindolin-2-yl)acetamido) acetic acid);
a compound of Formula (I):

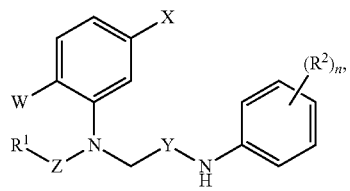

wherein in (I):
W is H, F, Cl, Br, I, OH, lower alkyl or lower alkoxy; X is F, Cl, Br or I; Y and Z are independently C(=O) or S(=O)$_2$; R$^1$ is lower alkyl; each occurrence of R$^2$ is independently selected from the group consisting of H, OH, F, Cl, Br, I, alkyl, perfluoroalkyl, alkoxy, perfluoroalkoxy, NH$_2$, acylamino, amido, carboxyl, alkoxycarbonyl, acyloxy, formyl, acyl, thioester, carbamate, urea, sulfonate, sulfamoyl, sulfone, sulfonamide, CN, NO$_2$, and alkylthio; and, n is 0, 1, 2, 3, 4 or 5;

a compound of Formula (II):

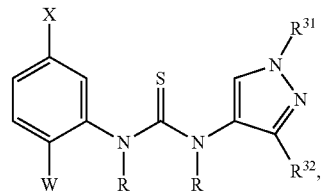

wherein in (II):
W is H, F, Cl, Br, I, OH, lower alkyl or lower alkoxy; X is F, Cl, Br or I; each occurrence of R is independently H or lower alkyl; R$^{31}$ is H or lower alkyl; and, R$^{32}$ is amido, carboxyl, alkoxycarbonyl or sulfonamide;

a compound of Formula (III):

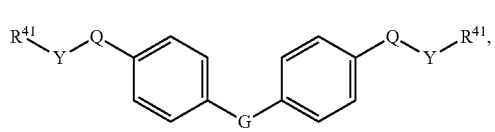

wherein in (III):
G is C(R)$_2$, O or N(R); each occurrence of Q is independently O or N(R); each occurrence of R is independently H or lower alkyl; each occurrence of Y is independently C(=O) or S(O)$_2$; and, R$^{41}$ is lower alkyl or lower alkoxy;

a compound of Formula (IV):

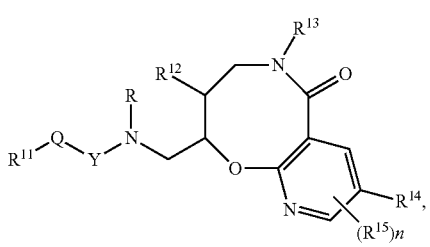

wherein in (IV):
each occurrence of R is independently H or lower alkyl; Q is a bond, O or N(R); Y is C(=O) or S(O)$_2$; R$^{11}$ is substituted or unsubstituted alkyl, cycloalkyl, aryl, heteroaryl or aralkyl; R$^{12}$ is H or lower alkyl; R$^{13}$ is H or substituted or unsubstituted lower alkyl; R$^{14}$ is H, F, Cl, Br, I, substituted or unsubstituted aryl or heteroaryl, or —C≡C—R$^{16}$, where R$^{16}$ is substituted or unsubstituted aminoalkyl, alkoxyalkyl, aryl or heteroaryl; each occurrence of R$^{15}$ is independently OH, F, Cl. Br, I, NH$_2$, CN, NO$_2$, lower alkyl, or lower alkoxy; and, n is 0, 1 or 2;

a compound of Formula (V):

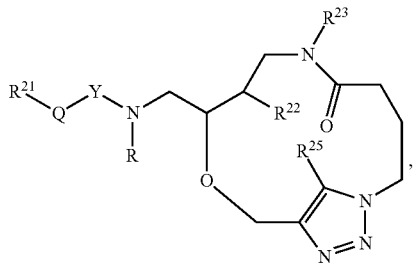

wherein in (V):
each occurrence of R is independently H or lower alkyl; Q is a bond, O or NR; Y is C=O or S(O)$_2$, preferably C=O; R$^{21}$ is substituted or unsubstituted alkyl, aralkyl, cycloalkyl, aryl or heteroaryl; R$^{22}$ is H or lower alkyl; R$^{23}$ is H or substituted or unsubstituted lower alkyl; and, R$^{25}$ is H, OH, F, Cl, Br, I, lower alkyl, lower alkoxy, NH$_2$, CN, or NO$_2$;
enantiomers or diastereoisomers thereof, prodrugs thereof, pharmaceutically acceptable salts thereof, and any combinations thereof.

In certain embodiments, the at least one compound is selected from the group consisting of Compounds 109-114, a compound of Formula (I)-(V), enantiomers or diastereoisomers thereof, prodrugs thereof, pharmaceutically acceptable salts thereof and any combinations thereof.

In certain embodiments, the at least one compound is selected from the group consisting of:

| compound | nomenclature |
|---|---|
| 101 (FPH2) | 2-(N-(5-chloro-2-methylphenyl)methylsulfonamido)-N-(2,6-difluorophenyl)acetamide |
| 102 | 2-(N-(5-chloro-2-methylphenyl)methylsulfonamido)-N-(2-(methylthio)phenyl)acetamide |
| 103 | N-(4-bromo-3-methylphenyl)-2-(N-(5-chloro-2-methylphenyl)methylsulfonamido)acetamide |
| 104 (FPH1) | 4-(3-(5-chloro-2-methoxyphenyl)thioureido)-1-ethyl-1H-pyrazole-3-carboxamide |
| 105 (FH1) | N,N'-(methylenebis(4,1-phenylene))diacetamide |
| 106 | 1-(((2R,3S)-8-(benzofuran-2-yl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 107 | 3-(4-fluorophenyl)-1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 108 | N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 109 (PH1) | 4-(3-butoxy-4-methoxybenzyl)imidazolidin-2-one |
| 110 | (1R,4R)-4-((R)-1-aminoethyl)-N-(pyridin-4-yl)cyclohexane-1-carboxamide |
| 111 | (1R,4R)-4-((R)-1-aminoethyl)-N-(pyridin-4-yl)cyclohexanecarboxamide |
| 112 | 1-((9H-carbazol-4-yl)oxy)-3-((2-(2-methoxyphenoxy)ethyl)amino)propan-2-ol |
| 113 | 3-(5H-dibenzo[a,d][7]annulen-5-ylidene)-N,N-dimethylpropan-1-amine |
| 114 | 2-(2-(1,3-dioxoisoindolin-2-yl)acetamido)acetic acid |
| 201 | 1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-3-isopropyl-1-methylurea |
| 202 | 1-(((2R,3S)-8-((3,4-dimethoxyphenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 203 | 2-fluoro-N-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-N-methylbenzamide |
| 204 | 1-(((2R,3S)-8-(3-cyclopentylprop-1-yn-1-yl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 205 | 3-(4-fluorophenyl)-1-(((2R,3R)-8-((4-fluorophenyl)ethynyl)-5-((S)-1-hydroxypropan-2-yl)-3-methyl-6-oxo-3,4,5,6-tetrahydro-2H-pyrido[2,3-b][1,5]oxazocin-2-yl)methyl)-1-methylurea |
| 206 | N-(((4R,5R,Z)-7-((S)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 207 | 3-(4-fluorophenyl)-1-(((2R,3S)-5-((R)-1-hydroxypropan-2-yl)-3-methyl-6-oxo-8-phenyl-3,4,5,6-tetrahydro-2H-pyrido[2,3-b][1,5]oxazocin-2-yl)methyl)-1-methylurea |
| 208 | isobutyl(((4R,5S,Z)-7-((S)-1-hydroxypropan-2-yl)-5-methyl-8-oxo-11H-3-oxa-7-aza-1(4,1)-triazolacycloundecaphane-4-yl)methyl)(methyl)carbamate |
| 209 | 1-(((2R,3S)-8-(4-cyanophenyl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 210 | N-(((4S,5R,Z)-7-((S)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 211 | N-(((4R,5S,Z)-7-((R)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 212 | N-(((4S,5R,Z)-7-((R)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |

-continued

| compound | nomenclature |
| --- | --- |
| 215 | N-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-2-methoxy-N-methylacetamide |
| 217 | isopropyl(((4R,5S,Z)-7-((S)-1-hydroxypropan-2-yl)-5-methyl-8-oxo-11H-3-oxa-7-aza-1(4,1)-triazolacycloundecaphane-4-yl)methyl)(methyl)carbamate |
| 224 | 3-(4-fluorophenyl)-1-(((2R,3S)-8-((3-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 225 | 4-(dimethylamino)-N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylbutanamide |
| 226 | N-(((4S,5S,Z)-7-((S)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 227 | N-(((4S,5S,Z)-7-((R)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 228 | N-(((4R,5R,Z)-7-((R)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 229 | 1-(((2R,3S)-8-(cyclopropylethynyl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 230 | 3-(4-fluorophenyl)-1-(((2R,3S)-8-((R)-3-hydroxybut-1-yn-1-yl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 231 | 1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methyl-3-phenylurea |
| 232 | 3-(4-fluorophenyl)-1-(((2S,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 233 | 3-(4-fluorophenyl)-1-(((2R,3R)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 234 | 3-(4-fluorophenyl)-1-(((2S,3R)-8-((4-fluorophenyl)ethynyl)-5-((S)-1-hydroxypropan-2-yl)-3-methyl-6-oxo-3,4,5,6-tetrahydro-2H-pyrido[2,3-b][1,5]oxazocin-2-yl)methyl)-1-methylurea |
| 235 | 3-(4-fluorophenyl)-1-(((2R,3S)-8-((4-fluorophenyl)ethynyl)-5-((S)-1-hydroxypropan-2-yl)-3-methyl-6-oxo-3,4,5,6-tetrahydro-2H-pyrido[2,3-b][1,5]oxazocin-2-yl)methyl)-1-methylurea |
| 236 | 3-(4-fluorophenyl)-1-(((2R,3S)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 237 | 1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-methoxyphenyl)-1-methylurea |
| 238 | 3-(4-fluorophenyl)-1-(((2S,3S)-8-((4-fluorophenyl)ethynyl)-5-((S)-1-hydroxypropan-2-yl)-3-methyl-6-oxo-3,4,5,6-tetrahydro-2H-pyrido[2,3-b][1,5]oxazocin-2-yl)methyl)-1-methylurea |
| 239 | 3-(4-fluorophenyl)-1-(((2S,3R)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 240 | N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylcyclohexanecarboxamide |
| 241 | N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methyl-2-phenylacetamide |
| 242 | N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylbenzamide |
| 243 | 1-(((2R,3S)-8-(3-(dimethylamino)prop-1-yn-1-yl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 244 | 1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methyl-3-(naphthalen-1-yl)urea |
| 245 | N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N,1-dimethyl-1H-indole-6-carboxamide |
| 246 | N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methyl-5-phenylisoxazole-3-carboxamide |
| 247 | N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylisonicotinamide |
| 248 | 3-(3,5-dimethylisoxazol-4-yl)-1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 249 | 3-(4-fluorophenyl)-1-(((2R,3S)-8-(3-hydroxyhex-1-yn-1-yl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 250 | benzyl(((4R,5S,Z)-7-((S)-1-hydroxypropan-2-yl)-5-methyl-8-oxo-11H-3-oxa-7-aza-1(4,1)-triazolacycloundecaphane-4-yl)methyl)(methyl)carbamate |
| 251 | ethyl(((4R,5S,Z)-7-((S)-1-hydroxypropan-2-yl)-5-methyl-8-oxo-11H-3-oxa-7-aza-1(4,1)-triazolacycloundecaphane-4-yl)methyl)(methyl)carbamate |

-continued

| compound | nomenclature |
|---|---|
| 252 | 3-(4-fluorophenyl)-1-(((2R,3S)-5-((R)-1-hydroxypropan-2-yl)-3-methyl-6-oxo-8-(phenylethynyl)-3,4,5,6-tetrahydro-2H-pyrido[2,3-b][1,5]oxazocin-2-yl)methyl)-1-methylurea |
| 253 | 1-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-3-isopropyl-1-methylurea |
| 254 | 3-(4-fluorophenyl)-1-(((2R,3S)-5-((R)-1-hydroxypropan-2-yl)-3-methyl-6-oxo-8-((4-(trifluoromethyl)phenyl)ethynyl)-3,4,5,6-tetrahydro-2H-pyrido[2,3-b][1,5]oxazocin-2-yl)methyl)-1-methylurea |
| 255 | 1-(((2R,3S)-8-bromo-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 256 | 4,4,4-trifluoro-N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylbutanamide |
| 257 | 3-(4-fluorophenyl)-1-(((2R,3S)-5-((R)-1-hydroxypropan-2-yl)-3-methyl-6-oxo-8-(3-(trifluoromethyl)phenyl)-3,4,5,6-tetrahydro-2H-pyrido[2,3-b][1,5]oxazocin-2-yl)methyl)-1-methylurea | enantiomers or diastereoisomers thereof, prodrugs thereof, pharmaceutically acceptable salts thereof, and any combinations thereof.

In certain embodiments, the at least one compound is selected from the group consisting of Compounds 101-114, 201-212, 215, 217, 224-257, enantiomers or diastereoisomers thereof, prodrugs thereof, pharmaceutically acceptable salts thereof and any combinations thereof.

In certain embodiments, the one or more primary cells comprise one or more somatic cells. In other embodiments, the one or more primary cells are obtained from a subject or are part of a subject's body. In yet other embodiments, the one or more primary cells comprise one or more adult cells. In yet other embodiments, the one or more primary cells comprise one or more epithelial cells or endothelial cells. In yet other embodiments, the one or more primary cells comprise one or more hepatocytes.

In certain embodiments, the one or more primary cells comprise one or more stem cells. In other embodiments, the one or more stem cells comprise a pluripotent or non-pluripotent cell. In yet other embodiments, the one or more stem cells are selected from the group consisting of a multipotent stem cell, oligopotent stem cell, unipotent stem cell, and any combinations thereof. In yet other embodiments, the pluripotent stem cell is selected from the group consisting of induced pluripotent stem cell; embryonic stem cell; pluripotent stem cell derived by nuclear transfer, cell fusion, or forced expression of reprogramming factors; and any combinations thereof. In yet other embodiments, the one or more stem cells comprise a fetal stem cell or adult stem cell. In yet other embodiments, the one or more stem cells comprise an epithelial stem cell or endothelial stem cell.

In certain embodiments, the one or more iPS cells are differentiated into one or more hepatocyte-like cells (iHep cells). In other embodiments, the one or more iHep cells are contacted on day 21 to day 35 after the differentiation with at least one compound of the invention. In yet other embodiments, the one or more iHep cells are contacted with at least one compound of the invention after the differentiation for a period of at least 5 days.

In various embodiments of any of the above aspects or any other aspect of the invention delineated herein, the compounds of the invention induce functional proliferation of endogenous cells. In other embodiments, the compounds of the invention promote differentiation of endogenous cells. In yet other embodiments, the disease or condition comprises liver disease. In yet other embodiments, the liver disease is selected from acetaminophen toxicity, alcoholic liver disease, primary liver cancer, liver cirrhosis, liver cysts, fatty liver disease, liver fibrosis, hepatitis, primary sclerosing cholangitis, jaundice, and any combinations thereof. In yet other embodiments, the organ comprises liver. In yet other embodiments, the tissue comprises liver tissue. In yet other embodiments, one or more cells are obtained from the subject.

In various embodiments of any of the above aspects or any other aspect of the invention delineated herein, a bio-artificial liver device comprising one or more cells of the invention is implanted in the subject. In other embodiments, the subject is further administered an effective amount of at least one compound of the invention.

In certain embodiments, the hepatitis is caused by a virus selected from the group consisting of hepatitis A-E virus, herpes simplex, cytomegalovirus, Epstein-Barr virus, yellow fever, and any combinations thereof. In other embodiments, the at least one compound is administered by a route selected from the group consisting of oral, parenteral, intramuscular, intranasal, sublingual, intratracheal, inhalation, ocular, vaginal, rectal, and intracerebroventricular, and any combinations thereof. In yet other embodiments, the subject is a human.

Other aspects, embodiments, advantages, and features of the present invention will become apparent from the following specification.

BRIEF DESCRIPTION OF THE FIGURES

The following detailed description of preferred embodiments of the invention will be better understood when read in conjunction with the appended drawings. For the purpose of illustrating the invention, specific embodiments are illustrated in the drawings. It should be understood, however, that the invention is not limited to the precise arrangements and instrumentalities of the embodiments shown in the drawings.

FIG. 1A top comprises an image illustrating the design of the screening platform, which includes a sparse population of hepatocytes co-cultivated on top of a confluent layer of J2-3T3 fibroblasts within 384-well plates. FIG. 1A bottom comprises a series of graphs and high content images illustrating the finding that compounds of the invention stabilized hepatocyte phenotypic function in vitro (Example 2). FIG. 1B top comprises an illustration of the workflow of the primary screening of small molecules. FIG. 1B bottom comprises a set of bar graphs illustrating the type of compounds that constituted the initial set of 93 compounds that met all hit selection criteria qualifying as functional proliferation hits (FPHs) and also scatterplots of primary screening data (Example 3).

FIG. 2A comprises a bar graph (top) and images (bottom) illustrating that FPH2 induced a 1.5 fold increase in hepatocyte nuclei numbers during the primary screening (Example 4). FIG. 2B comprises a bar graph (left) and images (right) illustrating that treatment of hepatocyte with FPH2 elevated the number of hepatocyte nuclei in culture and the number of nuclei undergoing mitosis (Example 4). FIG. 2C comprises a dose-response graph illustrating that the effects of FPH2 on hepatocytes were dose-responsive (Example 4). FIG. 2D comprises a series of phase contrast images illustrating that hepatocyte morphology remained normal throughout the treatment period (Example 4). FIG. 2E comprises a series of images illustrating the effects of FPH1 and FPH2 on human primary hepatocytes cultured for seven days and treated with compound on days 1 and 5 at a concentration of 20 µM (Example 4). FIG. 2F comprises a set of bar graphs showing an increase in the area of albumin-positive colonies in FPH1- and FPH2-treated cultures (Example 4). FIG. 2G comprises a set of bar graphs and FIG. 2H comprises a set of FACS plots illustrating that there was up to 10 fold increase in the number of hepatocytes when treated with FPH compounds (Example 4).

FIG. 3, comprising FIG. 3A comprises a series of bar graphs illustrating that albumin secretion, urea synthesis and CYP450 activity were all normal throughout FPH treatment (Example 4). FIG. 3B comprises a set of images illustrating active transport of fluorometric substrate into the bile cannaliculi between hepatocytes (Example 4). FIG. 3C comprises graphs and summaries of gene expression profiles illustrating that the profiles of treated hepatocytes more closely resembled mature hepatocytes than untreated controls (Example 4).

FIG. 4, comprising FIGS. 4A-4F, illustrates characterization of hepatocytes treated with compounds of the invention. FIG. 4A (left) comprises a bar graph illustrating that FH1 doubled albumin secreted during primary screening and FIG. 4A (right) comprises a graph illustrating that the effects were dose responsive (Example 5). FIG. 4B is a set of images illustrating that colonies of hepatocyte-like cells increased in size and improved in morphology with treatment of compounds of the invention (Example 5). FIG. 4C comprises a series of graphs and gene expression profiles illustrating that the profiles of treated iHeps more closely resembled mature hepatocytes than untreated (Example 5). FIG. 4D comprises a series of images (top) and bar graphs (bottom) illustrating dramatic increases of albumin and CYP3A staining upon FH1 and FPH2 treatment. There was also marked decrease of AFP staining (Example 5). FIG. 4E comprises a set of graphs illustrating that AFP secretion decreased while albumin secretion, CYP3A4 and CYP2A6 activity increased upon treatment with a compound of the invention (Example 5). FIG. 4F comprises a a set of graphs relating to hepatocyte induction kinetics with black arrows indicating addition of the inducer and white arrows indicating removal of the inducer (Example 5).

FIG. 5, comprising FIG. 5A comprises a series of images illustrating that treated iHeps maintained mature phenotypes for 9 days after removal of FPH2 and FH1 (Example 5). FIG. 5B comprises a set of bar graphs illustrating that treated iHeps maintained elevated expression of the mature phenotypic marker albumin and minimal expression of the fetal markers AFP for 9 days after removal of FPH2 and FH1 (Example 5). FIG. 5C comprises a set of bar graphs illustrating that treated iHeps maintained elevated levels of CYP34A and CYP2A6 activity for 9 days after removal of FPH2 and FH1 (Example 5).

FIG. 6, comprising FIG. 6A comprises a series of images illustrating the effects of FPH1 and FPH2 on multiple different donors of primary human hepatocytes (Example 6). FIG. 6B comprises a set of bar graphs illustrating the quantification of hepatocytes in FPH treated and control cultures (Example 6).

FIG. 7, comprising FIG. 7A comprises a set of phase contrast images of iPS and iHep cells in culture (Example 7). FIG. 7B comprises a series of images illustrating the expression of hepatic lineage markers in iPS and iHep cells in culture (Example 7). FIG. 7C comprises a series of FACS plots illustrating the expression profile of hepatic and immature lineage markers in iPS and iHep cells in culture (Example 7).

FIG. 8, comprising FIG. 8A comprises an image illustrating the experimental protocol of compound treatment in zebrafish (Example 8). FIGS. 8B-8C comprise images illustrating that treated zebrafish had larger livers compared to controls (Example 8). FIG. 8D comprises a bar graph showing the increase in liver size of treated zebrafish compared to controls (Example 8).

FIG. 9, comprising FIGS. 9A-9D, illustrates experiments in which zebrafish were treated with toxic amounts of acetyl-para-aminophenol (APAP). FIG. 9A comprises an image illustrating the experimental protocol for APAP induced toxicity-induced in zebrafish embryos (Example 9). FIG. 9B comprises a set of graphs illustrating the percentage of zebrafish embryos that survived a fatal dose of APAP (Example 9). FIG. 9C comprises an image illustrating the experimental protocol for APAP induced toxicity-induced in adult zebrafish (Example 9). FIG. 9D comprises a graph illustrating the percentage of adult zebrafish that survived a fatal dose of APAP (Example 9).

FIG. 10, comprising FIG. 10A comprises an image illustrating the experimental protocol for APAP induced toxicity-induced in adult zebrafish and assessment of therapeutic window (Example 9). FIG. 10B comprises a series of images illustrating that FH1 and PH1 enhance embryonic liver size following a non-fatal dose of APAP (Example 9).

FIG. 11, comprising FIGS. 11A-11F, illustrates the activity of compounds of the invention on hepatocytes. FIG. 11A comprises a bar graph illustrating that compounds 106, 107 and 108 induced proliferation of hepatocytes (Example 10). FIG. 11B comprises a series of images of cannaliculi staining of compounds 106-, 107- and 108-treated hepatocytes indicated that cells exhibit functional liver phenotypes (Example 10). FIG. 11C comprises a bar graph showing treated hepatocytes have increased CYP450 activity (Example 10). FIG. 11D comprises a set of graphs and summary of gene expression profiles illustrating that the profiles of treated hepatocytes more closely resembled mature hepatocytes than untreated controls (Example 10). FIG. 11E comprises a series of images illustrating that compound 107 treatment increased Ki67 staining, which not only co-localized with Hoechst stains for cell nuclei but also with human albumin stains for hepatocytes. FIG. 11F comprises a set of tables illustrating the effects of compounds on hepatocyte proliferation (Example 10).

FIG. 12, comprising FIGS. 12A-12C, illustrates the effects of compounds of the invention on iHeps. FIG. 12A comprises a set of graphs, FIG. 12B comprises a set of images, and FIG. 12C comprises a set of tables illustrating that treated iHeps develop more mature hepatocyte phenotypes (Example 11).

FIG. 19, comprising FIG. 19A relates to a mature marker (albumin) and FIG. 19B relates to an immature marker (AFP). Compounds tested were DOS 1 (BRD-K17976466; 108), and DOS 3 (BRD-K37628956; 107).

FIG. 20, comprising

DETAILED DESCRIPTION OF THE INVENTION

Figure 1A:
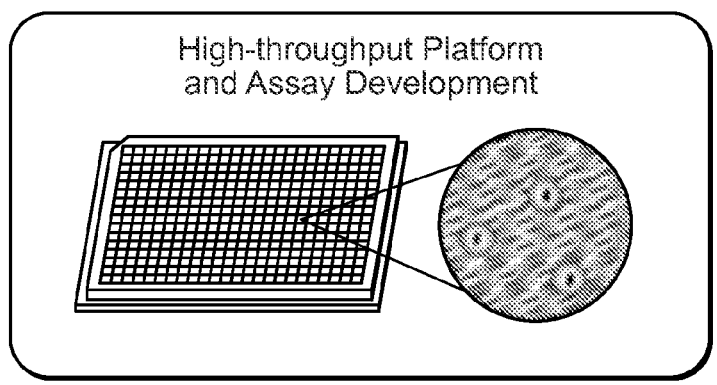
FIGS. 1A-1B, is a set of images and graphs illustrating a representative screening of the invention.
Figure 1A:
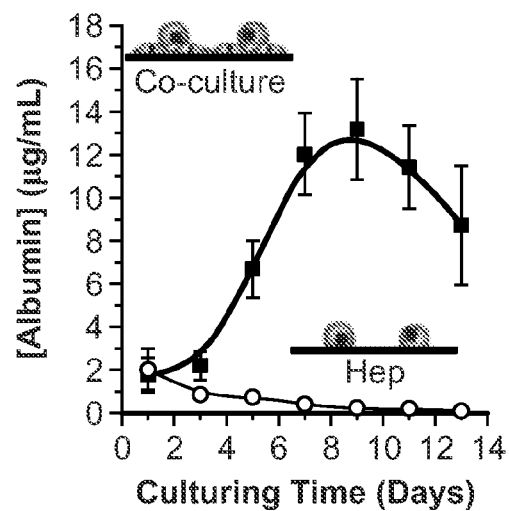
Figure 1A:
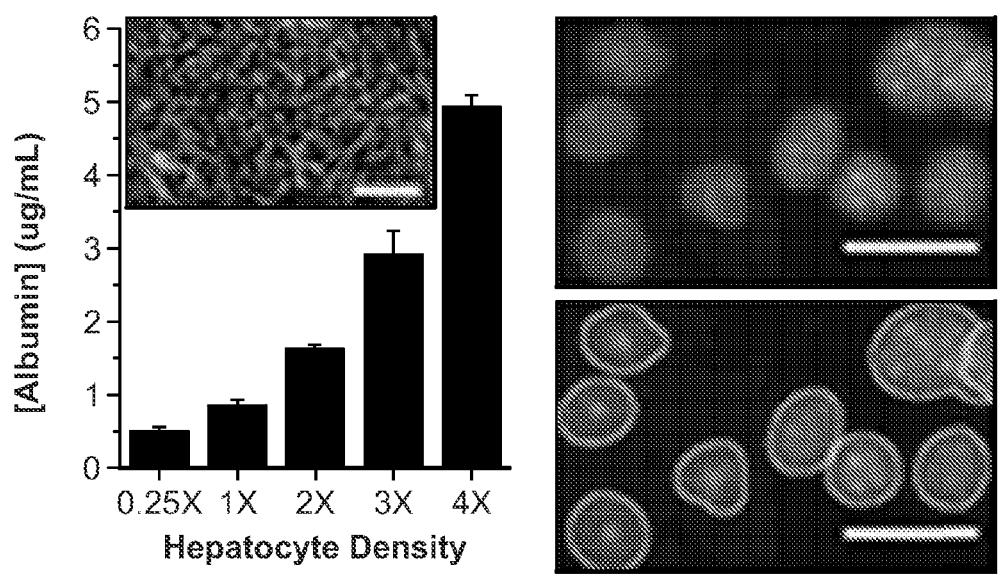

Cell-based therapies hold the potential to alleviate the growing burden of liver diseases. Such therapies require human hepatocytes, whose sourcing has limited medical and scientific research for decades. The present invention overcomes several problems with current technologies by providing methods and compounds for the growth and differentiation of cells.

The present invention provides methods and compounds for the growth and differentiation of cells, such as hepatocytes. In certain aspects, the present invention relates to compounds that can be used to generate functional human hepatocytes. In other aspects, compounds of the invention induce functional proliferation of hepatocytes in vitro or in vivo, and can thus be used to expand mature human primary hepatocytes. In yet other aspects, compounds of the invention enhance the functions of cultured hepatocytes, and thus can be used to differentiate iPS-derived hepatocytes toward a more differentiated/mature phenotype. In yet other aspects, compounds of the invention and the cells produced using these compounds are useful for the treatment and prevention of disease.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the terms "a," "an" and "the" are understood to be singular or plural. Thus, for example, reference to "an amino acid substitution" includes reference to more than one amino acid substitution.

Unless specifically stated or obvious from context, as used herein, the term "about" is understood as within a range of normal tolerance in the art, for example within two standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The term "acyl" refers to a group represented by the general formula hydrocarbyl-C(=O)—, preferably alkyl-C(=O)—.

The term "acylamino" refers to an amino group substituted with an acyl group and may be represented, for example, by the formula hydrocarbyl-C(O)NH—.

The term "acyloxy" refers to a group represented by the general formula hydrocarbyl-C(=O)O—, preferably alkyl-C(=O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl-.

The term "alkenyl" as used herein refers to an aliphatic group containing at least one double bond and is intended to include both "unsubstituted alkenyls" and "substituted alkenyls," the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed elsewhere herein, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon that is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. Such substituents, if not otherwise specified, can include, for example, a halogen, hydroxyl, carbonyl (such as a carboxyl, an alkoxycarbonyl, a formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described elsewhere herein. Cycloalkyls can be further substituted with alkyls, alkenyls, alkoxys, alkylthios, aminoalkyls, carbonyl-substituted alkyls, —$CF_3$, —CN, and the like.

The term "alkylamino" as used herein refers to an amino group substituted with at least one alkyl group.

The term "alkylthio" as used herein refers to a thiol group substituted with an alkyl group and may be represented by the general formula alkyl-S—.

The term "alkynyl" as used herein refers to an aliphatic group containing at least one triple bond and is intended to include both "unsubstituted alkynyls" and "substituted alkynyls," the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed elsewhere herein, except where stability is prohibitive. For example, substitution of alkynyl groups by one or more alkyl, carbocyclyl, aryl, heterocyclyl, or heteroaryl groups is contemplated.

The term "amide" as used herein refers to a group —C(=O)N($R^{10}$)($R^{10}$) wherein each $R^{10}$ is independently H or hydrocarbyl group, or two $R^{10}$ are taken together with the N atom to which they are attached to form a heterocycle having 4-8 atoms in the ring structure.

The terms "amine" and "amino" refer to both unsubstituted and substituted amines and salts thereof, e.g., a moiety that can be represented by —N($R^{10}$)($R^{10}$) or —$N^+$($R^{10}$)($R^{10}$)($R^{10}$), wherein each $R^{10}$ is independently H or a hydrocarbyl group, or two $R^{10}$ are taken together with the N atom to which they are attached to form a heterocycle having 4-8 atoms in the ring structure.

The term "aminoalkyl" as used herein refers to an alkyl group substituted with an amino group.

The term "APAP" refers to acetyl para-aminophenol.

The term "aralkyl" as used herein refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "$C_{x-y}$," when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, and the like. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "carbamate" refers to a group —OC(=O)N$R^9R^{10}$ or —N($R^9$)C(=O)O$R^{10}$, wherein $R^9$ and $R^{10}$ are represent H or a hydrocarbyl group, such as an alkyl group, or $R^9$ and $R^{10}$ are taken together with the intervening atom(s) to form a 4 heterocycle having 4-8 atoms in the ring structure.

The terms "carbocycle" and "carbocyclic" as used herein refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl" as used herein refers to an alkyl group substituted with a carbocycle group.

The term "carbonate" refers to a group —OC(=O)O$R^{10}$, wherein $R^{10}$ is hydrocarbyl.

The term "carboxy" as used herein refers to a group represented by the formula —$CO_2H$.

The term "cell" is used herein in its broadest sense in the art and refers to a living body that is a structural unit of tissue of a multicellular organism, surrounded by a membrane structure which separates the contents of the cell from the surrounding environment, has the capability of self replicating, and has genetic information and a mechanism for expressing it. Cells used herein may be naturally-occurring cells or artificially modified cells (e.g., fusion cells, genetically modified cells, etc.).

"A cell of the invention" or "cells of the invention" as used herein mean a cell, cells, and/or a population of cells as described herein and/or obtainable by methods described herein.

As used herein, "cellular differentiation" or "differentiation" is the process by which a less specialized cell becomes a more specialized cell type.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3-8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "detect" refers to identifying the presence, absence, level, or concentration of an analyte.

As used herein, the term "DOS 0" refers to BRD-K05085281; or 106.

As used herein, the term "DOS 1" refers to BRD-K17976466; or 108.

As used herein, the term "DOS 3" refers to BRD-K37628956; or 107.

"Embryonic stem (ES) cells" are pluripotent stem cells derived from early embryos. ES cells have been applied to production of knockout mice, and human ES cells have been established and made available for regenerative medicine.

The term "ester," as used herein, refers to a group —C(=O)OR$^{10}$ wherein R$^{10}$ is hydrocarbyl.

The term "ether" as used herein refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "hepatocyte" as used herein includes hepatocyte-like cells that exhibit some but not all characteristics of mature hepatocytes, as well as mature and fully functional hepatocytes.

The terms "hetaralkyl" and "heteroaralkyl" as used herein refers to an alkyl group substituted with a heteroaryl group.

The term "heteroalkyl" as used herein refers to a saturated or unsaturated chain of carbon atoms and at least one heteroatom, wherein no two heteroatoms are adjacent, with the exception of N—O and N—N.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more atoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl," "heterocycle" and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more atoms are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl" as used herein refers to an alkyl group substituted with a heterocycle group.

The term "hydrocarbyl" as used herein refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl" as used herein refers to an alkyl group substituted with a hydroxy group.

The term "iHep" relating to cells refers to hepatocyte-like cells.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by inserting certain genes, referred to as reprogramming factors.

As used herein, "isolated" refers to a molecule that is substantially free of other elements present in its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl," for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

In contrast, many progenitor cells are "multipotent stem cells," i.e., they are capable of differentiating into a limited number of cell fates. Multipotent progenitor cells can give rise to several other cell types, but those types are limited in number. An example of a multipotent stem cell is a hematopoietic cell—a blood stem cell that can develop into several types of blood cells, but cannot develop into brain cells or other types of cells. At the end of the long series of cell divisions that form the embryo are cells that are terminally differentiated, or that are considered to be permanently committed to a specific function.

Unless specifically stated or obvious from context, as used herein, the term "or" is understood to be inclusive.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

"Pluripotency" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent stem cells or induced pluripotent stem cells.

The terms "polycyclyl," "polycycle" and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "prodrug" is intended to encompass compounds which, under physiologic conditions, are converted into the therapeutically active agents of the present invention (e.g., a compound of Formula (I)-(V) or of Table 1). A common method for making a prodrug is to include one or more selected moieties which are hydrolyzed and/or metabolized under physiologic conditions to reveal the desired molecule. In other embodiments, the prodrug is converted by an enzymatic activity of the host animal. For example, esters or carbonates (e.g., esters or carbonates of alcohols or carboxylic acids) are prodrugs of the present invention. In certain embodiments, some or all of the compounds of the invention can be replaced with a suitable corresponding prodrug, e.g., wherein a hydroxyl in the parent compound is presented as an ester or a carbonate or carboxylic acid present in the parent compound is presented as an ester.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention. Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, hydroxybutyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

The term "silyl" refers to a silicon moiety with three hydrocarbyl moieties attached thereto.

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

As used herein, the term "stem cell" refers to a cell capable of giving rise to at least one type of a more specialized cell. A stem cell has the ability to self-renew, i.e., to go through numerous cycles of cell division while maintaining the undifferentiated state, and has potency, i.e., the capacity to differentiate into specialized cell types. Typically, stem cells can regenerate an injured tissue. Stem cells herein may be, but are not limited to, embryonic stem (ES) cells, induced pluripotent stem cells, or tissue stem cells (also called tissue-specific stem cells or somatic stem cells). Any artificially produced cell which can have the above-described abilities (e.g., fusion cells, reprogrammed cells, or the like used herein) may be a stem cell.

Cells are "substantially free" of certain undesired cell types, as used herein, when they have less that 10% of the undesired cell types, and are "essentially free" of certain cell types when they have less than 1% of the undesired cell types. However, even more desirable are cell populations wherein less than 0.5% or less than 0.1% of the total cell population comprises the undesired cell types. Thus, cell populations wherein less than 0.1% to 1% (including all intermediate percentages) of the cells of the population comprise undesirable cell types are essentially free of these cell types. A medium may be "essentially free" of certain reagents, as used herein, when there is no external addition of such agents. More preferably, these agents are absent or present at an undetectable amount.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, and the like. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" refers to the group —$OSO_3H$, or a pharmaceutically acceptable salt thereof.

The term "sulfonamide" refers to the group represented by the general formulae —$S(=O)_2NR^9N^{10}$ or —$N(R^9)S(=O)_2R^{10}$, wherein $R^9$ and $R^{10}$ are independently H or hydrocarbyl, such as alkyl, or $R^9$ and $R^{10}$ taken together with the intervening atom(s) complete a heterocycle having from 4 to 8 atoms in the ring structure.

The term "sulfoxide" refers to the group —$S(O)$—$R^{10}$, wherein $R^{10}$ is hydrocarbyl.

The term "sulfonate refers to the group $SO_3H$, or a pharmaceutically acceptable salt thereof.

The term "sulfone" refers to the group —$S(O)_2$—$R^{10}$, wherein $R^{10}$ is hydrocarbyl.

The term "thioalkyl" as used herein refers to an alkyl group substituted with a thiol group.

The term "thioester" as used herein refers to a group —$C(=O)SR^{10}$ or —$SC(=O)R^{10}$ wherein $R^{10}$ is hydrocarbyl.

The term "thioether" as used herein is equivalent to an ether, wherein the oxygen is replaced with a sulfur.

Unlike ES cells, "tissue stem cells: have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

As used herein, "totipotent stem cells" refers to cells has the ability to differentiate into all cells constituting an organism, such as cells that are produced from the fusion of an egg and sperm cell. Cells produced by the first few divisions of the fertilized egg are also totipotent. These cells can differentiate into embryonic and extraembryonic cell types. Pluripotent stem cells can give rise to any fetal or adult cell type. However, alone they cannot develop into a fetal or adult animal because they lack the potential to contribute to extraembryonic tissue, such as the placenta.

The term "treating" comprises administration to the host of one or more of the subject compositions, e.g., to diminish, ameliorate, or stabilize the existing unwanted condition or side effects thereof.

The term "urea" is art-recognized and may be represented by the general formula —$N(R^9)C(=O)NR^9R^{10}$, wherein $R^9$ and $R^{10}$ are independently H or hydrocarbyl, such as alkyl, or either occurrence of $R^9$ taken together with $R^{10}$ and the intervening atom(s) complete a heterocycle having 4-8 atoms in the ring structure.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Compounds

The invention provides compounds or pharmaceutically acceptable salts thereof, pharmaceutical compositions comprising the same, and methods for using the same.

In certain embodiments, the compound is a compound of Formula (I) or a pharmaceutically acceptable salt thereof:

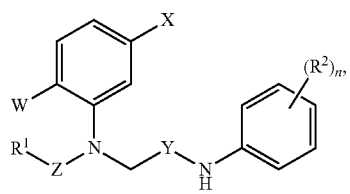

(I)

wherein in (I):
W is H, F, Cl, Br, I, OH, lower alkyl, or lower alkoxy; X is F, Cl, Br or I; Y and Z are independently C(=O) or S(=O)$_2$; $R^1$ is lower alkyl; each occurrence of $R^2$ is independently selected from the group consisting of H, OH, F, Cl, Br, I, alkyl, perfluoroalkyl (e.g., trifluoromethyl)), alkoxy, perfluoroalkoxy (e.g., trifluoromethoxy), NH$_2$, acylamino, amido, carboxyl, alkoxycarbonyl, acyloxy, formyl, acyl (including perfluoroacyl, e.g., C(=O)CF$_3$)), thioester (e.g., thioacetate or thioformate), carbamate, urea, sulfonate, sulfamoyl, sulfone, sulfonamide, CN, NO$_2$, and alkylthio; and, n is 0, 1, 2, 3, 4 or 5.

In certain embodiments, n is 0, 1, 2, 3, 4 or 5, and (i) $R_2$ substituent occupies the para position relative to NH group and is selected from the group comprising H, Cl, F, NH$_2$, and OH; preferably, $R_2$ substituent is H, or (ii) at least one non-hydrogen substituent is disposed ortho to the NH, preferably selected (independently, if non-hydrogen substituents are present at both ortho positions) from halogen (preferably fluorine), hydroxy, cyano, nitro, lower alkyl, lower alkoxy, and lower alkylthio, or (iii) both.

In certain embodiments, n is 0, 1, 2, 3, 4 or 5, and $R_2$ occupies the para position relative to NH group and is selected from the group comprising H, Cl, F, NH$_2$, and OH; preferably, $R_2$ is H. In certain embodiments, n is 0, 1, 2, 3, 4 or 5, and at least one $R_2$ is not H and occupies the ortho position relative to the NH group; preferably, at least one $R_2$ is selected from the group consisting of halogen (preferably fluorine), hydroxy, cyano, nitro, lower alkyl, lower alkoxy, and lower alkylthio, and occupies the ortho position relative to the NH group.

In certain embodiments, n is 0, 1, 2, 3, 4 or 5, and (i) $R_2$ occupies the para position relative to NH group and is selected from the group comprising H, Cl, F, NH$_2$, and OH; preferably, $R_2$ is H; and (ii) at least one $R_2$ is not H and occupies the ortho position relative to the NH group; preferably, at least one $R_2$ is selected from the group consisting of halogen (preferably fluorine), hydroxy, cyano, nitro, lower alkyl, lower alkoxy, and lower alkylthio, and occupies the ortho position relative to the NH group.

In certain embodiments, Y is C(=O) and Z is S(=O)$_2$. In certain embodiments, X is chlorine and W is methyl. Non-limiting presentative compounds of Formula (I) include FPH2 and compounds 102 and 103.

In certain embodiments, the compound is a compound of Formula (II) or a pharmaceutically acceptable salt thereof:

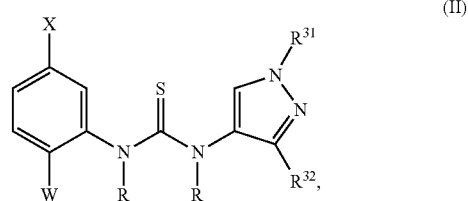

(II)

wherein in (II):
W is H, F, Cl, Br, I, OH, lower alkyl, or lower alkoxy; X is F, Cl, Br or I; each occurrence of R is independently H or lower alkyl; $R^{31}$ is H or lower alkyl; and $R^{32}$ is amido, carboxyl, alkoxycarbonyl, or sulfonamide.

In certain embodiments, X is Cl and W is methyl. Non-limiting representative compounds of Formula (II) include FPH1.

In certain embodiments, the compound is a compound of Formula (III) or a pharmaceutically acceptable salt thereof:

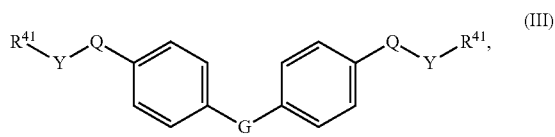

(III)

wherein in (III):
G is C(R)$_2$, O or N(R); each occurrence of Q is independently O or N(R); each occurrence of R is independently H or lower alkyl; each occurrence of Y is independently C(=O) or S(O)$_2$; and $R^{41}$ is lower alkyl or lower alkoxy.

In certain embodiments, the compound is symmetrical (i.e., both occurrences of Q, Y, and $R^{41}$ are identical). In certain embodiments, both occurrences of Q are NH. In other embodiments, both occurrences of Y are C(=O). In yet other embodiments, both occurrences of $R^{41}$ are methyl. In yet other embodiments, both occurrences of Q are NH; both occurrences of Y are C(=O); and both occurrences of $R^{41}$ are methyl. In certain embodiments, each occurrence of Y is C(=O). Non-limiting representative compounds of Formula (III) include FH1.

In certain embodiments, the compound is a compound of Formula (IV) or a pharmaceutically acceptable salt thereof:

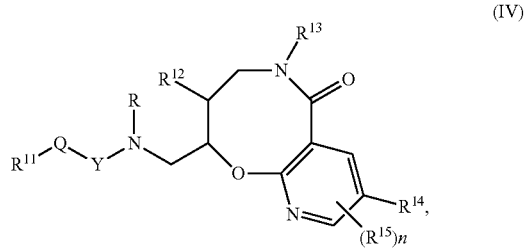

(IV)

wherein in (IV):
each occurrence of R is independently H or lower alkyl; Q is a bond, O or N(R); Y is C(=O) or S(O)$_2$; R$^{11}$ is substituted or unsubstituted alkyl (including alkoxyalkyl and aminoalkyl), cycloalkyl, aryl, heteroaryl or aralkyl; R$^{12}$ is H or lower alkyl; R$^{13}$ is H or substituted or unsubstituted lower alkyl (e.g., hydroxyalkyl); le is H, F, Cl, Br, I, substituted or unsubstituted aryl or heteroaryl, or —C≡C—R$^{16}$, where R$^{16}$ is substituted or unsubstituted aminoalkyl, alkoxyalkyl, aryl or heteroaryl; each occurrence of R$^{15}$ is independently OH, F, Cl. Br, I, NH$_2$, CN, NO$_2$, lower alkyl (such as perfluoroalkyl, e.g., trifluoromethyl), or lower alkoxy; and, n is 0, 1 or 2.

In certain embodiments, Q is N(R). In other embodiments, Y is C(=O). In yet other embodiments, R$^{11}$ is substituted or unsubstituted aryl, alkyl, alkoxyalkyl or heteroaryl. In yet other embodiments, R$^{13}$ is hydroxyalkyl. Non-limiting representative compounds of Formula (IV) include 106-107, 201-205, 207, 209, 215, 223-224, 229-239, 243-244, 248-249, 252, 254-255 and 257. In certain embodiments, Q is O, and R$^{11}$ is substituted or unsubstituted aralkyl, alkyl, or alkoxyalkyl; and most preferably substituted or unsubstituted alkyl or alkoxyalkyl.

In certain embodiments, the substituents on the central eight-membered ring of a compound of Formula (IV) have the relative and/or absolute stereochemical orientation as shown for any one of the representative compounds 106-107, 201-205, 207, 209, 215, 223-224, 229-239, 243-244, 248-249, 252, 254-255 and 257.

In certain embodiments, the compound is a compound of Formula (V) or a pharmaceutically acceptable salt thereof:

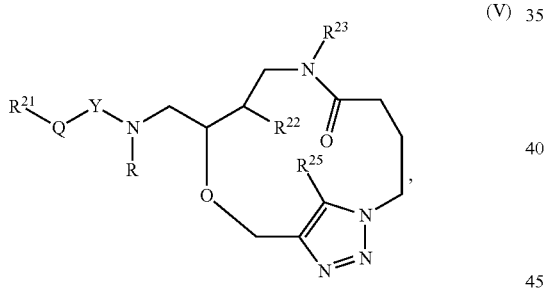

(V)

wherein in (V):
each occurrence of R is independently H or lower alkyl; Q is a bond, O or NR; Y is C=O or S(O)$_2$, preferably C=O; R$^{21}$ is substituted or unsubstituted alkyl (including alkoxyalkyl and aminoalkyl), aralkyl, cycloalkyl, aryl or heteroaryl; R$^{22}$ is H or lower alkyl; R$^{23}$ is H or substituted or unsubstituted lower alkyl (e.g., hydroxyalkyl); and R$^{25}$ is H, OH, F, Cl, Br, I, lower alkyl (such as perfluoroalkyl, e.g., trifluoromethyl), lower alkoxy, NH$_2$, CN, or NO$_2$.

In certain embodiments, Y is C=O. In other embodiments, R$^{21}$ is substituted or unsubstituted cycloalkyl, aralkyl, C$_2$-C$_6$ alkyl, aminoalkyl, aryl or heteroaryl. Non-limiting representative compounds of Formula (V) include 108, 206, 208, 210-212, 217, 225-228, 240-242, 245-247, 250-251, 253 and 256. In certain embodiments, Q is O, and R$^{21}$ is substituted or unsubstituted aralkyl, alkyl, or alkoxyalkyl; most preferably substituted or unsubstituted alkyl or alkoxyalkyl.

In certain embodiments, the substituents on the macrocycle of a compound of Formula (V) have the absolute and/or relative stereochemical orientation as shown for any one of the representative compounds 108, 206, 208, 210-212, 217, 225-228, 240-242, 245-247, 250-251, 253 and 256.

Those of skill in the art will recognize that, with respect to Formulas (IV) and (V), there is significant structural homology among the substituents around the central ring and around the heterocyclic rings. Accordingly, activity relationships observed with respect to Q, Y, R, R$^{11}$, R$^{12}$, and R$^{13}$ in the compounds of Formula (IV) herein may indicate suitable substituents for Q, Y, R, R$^{21}$, R$^{22}$, and R$^{23}$ in compounds of Formula (V), and vice versa.

In certain embodiments, the invention provides a compound of Table 1, or a pharmaceutically acceptable salt or prodrug thereof.

TABLE 1

| compound no. | structure |
| --- | --- |
| 101 (FPH2) | 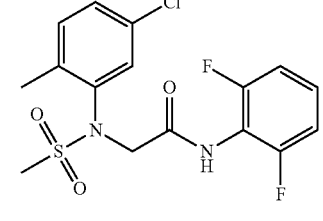<br>2-(N-(5-chloro-2-methylphenyl)methylsulfonamido)-N-(2,6-difluorophenyl)acetamide |
| 102 | 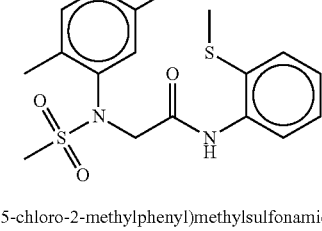<br>2-(N-(5-chloro-2-methylphenyl)methylsulfonamido)-N-(2-(methylthio)phenyl)acetamide |
| 103 | 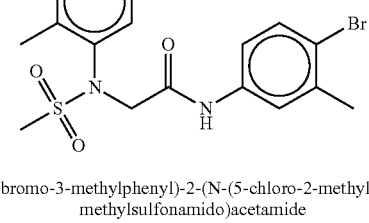<br>N-(4-bromo-3-methylphenyl)-2-(N-(5-chloro-2-methylphenyl)methylsulfonamido)acetamide |
| 104 (FPH1) | 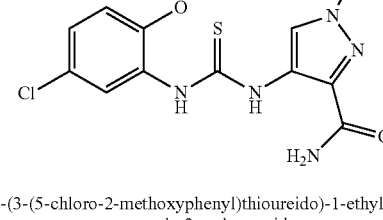<br>4-(3-(5-chloro-2-methoxyphenyl)thioureido)-1-ethyl-1H-pyrazole-3-carboxamide |

TABLE 1-continued

| compound no. | structure |
|---|---|
| 105 (FH1) | N,N'-(methylenebis(4,1-phenylene))diacetamide |
| 106 | 1-(((2R,3S)-8-(benzofuran-2-yl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 107 | 3-(4-fluorophenyl)-1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 108 | N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 109 (PH1) | 4-(3-butoxy-4-methoxybenzyl)imidazolidin-2-one |
| 110 | (1R,4R)-4-((R)-1-aminoethyl)-N-(pyridin-4-yl)cyclohexane-1-carboxamide |
| 111 | (1R,4R)-4-((R)-1-aminoethyl)-N-(pyridin-4-yl) cyclohexanecarboxamide |
| 112 | 1-((9H-carbazol-4-yl)oxy)-3-((2-(2-methoxyphenoxy)ethyl)amino) propan-2-ol |

TABLE 1-continued

| compound no. | structure |
|---|---|
| 113 | 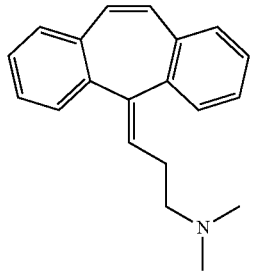 [SMILES: CN(C)CCC=C1c2ccccc2C=Cc2ccccc21] 3-(5H-dibenzo[a,d][7]annulen-5-ylidene)-N,N-dimethylpropan-1-amine |
| 114 | 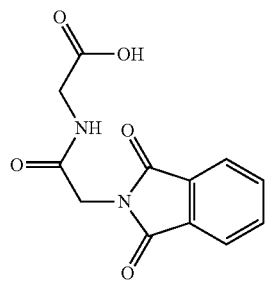 [SMILES: O=C(O)CNC(=O)CN1C(=O)c2ccccc2C1=O] 2-(2-(1,3-dioxoisoindolin-2-yl)acetamido)acetic acid |
| 201 | 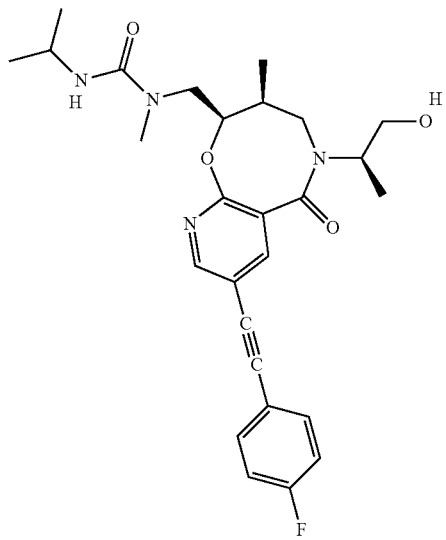 1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-3-isopropyl-1-methylurea |
| 202 | 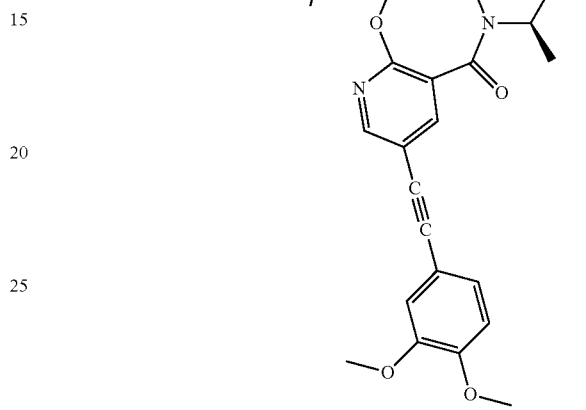 1-(((2R,3S)-8-((3,4-dimethoxyphenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 203 | 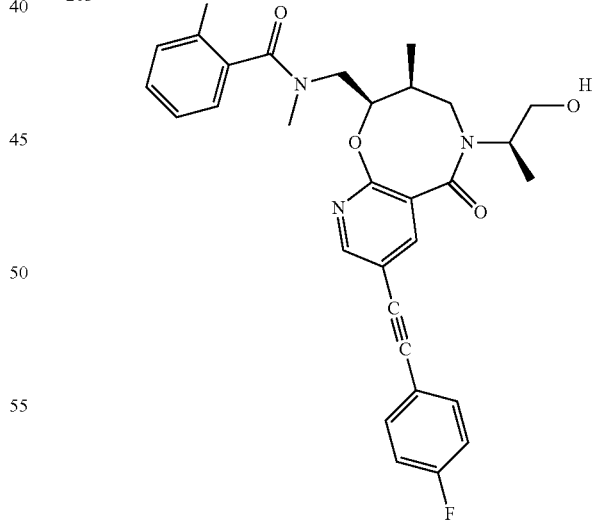 2-fluoro-N-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-N-methylbenzamide |

TABLE 1-continued

| compound no. | structure |
|---|---|
| 204 | 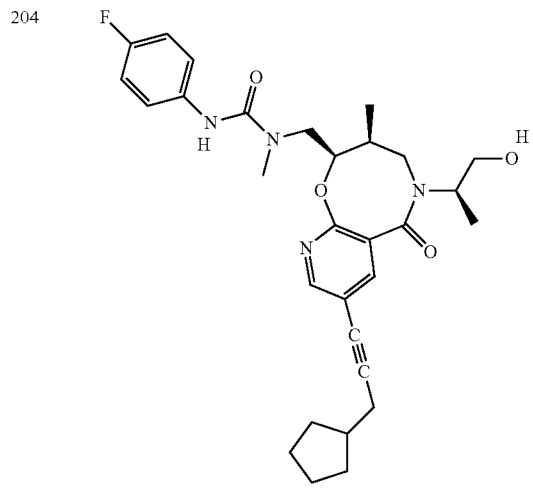 1-(((2R,3S)-8-(3-cyclopentylprop-1-yn-1-yl)-5-((R)-1-hydroxy-propan-2-yl)-3-methyl-6-oxo-3,4,5,6-tetrahydro-2H-pyrido[2,3-b][1,5] oxazocin-2-yl)methyl)-3-(4-fluorophenyl)-1-methylurea |
| 205 | 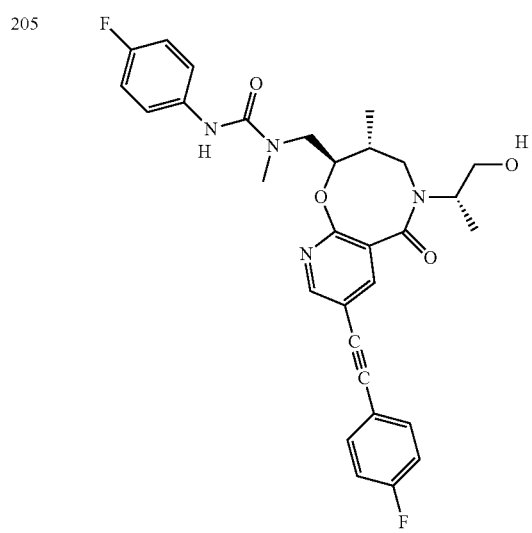 3-(4-fluorophenyl)-1-(((2R,3R)-8-((4-fluorophenyl)ethynyl)-5-((S)-1-hydroxypropan-2-yl)-3-methyl-6-oxo-3,4,5,6-tetrahydro-2H-pyrido[2,3-b][1,5]oxazocin-2-yl)methyl)-1-methylurea |

TABLE 1-continued

| compound no. | structure |
|---|---|
| 206 | 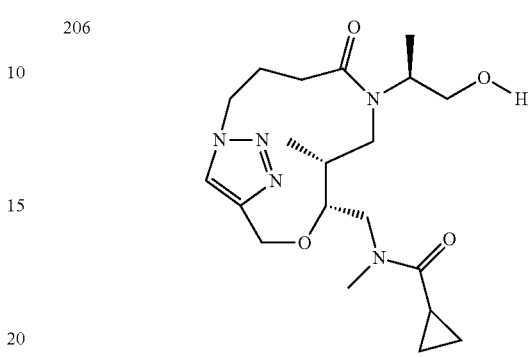 N-(((4R,5R,Z)-7-((S)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 207 | 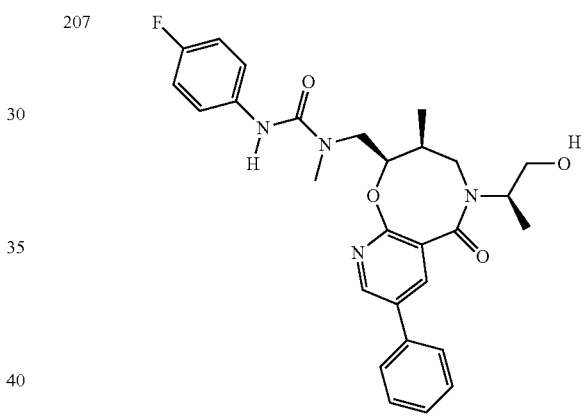 3-(4-fluorophenyl)-1-(((2R,3S)-5-((R)-1-hydroxypropan-2-yl)-3-methyl-6-oxo-8-phenyl-3,4,5,6-tetrahydro-2H-pyrido[2,3-b][1,5] oxazocin-2-yl)methyl)-1-methylurea |
| 208 | 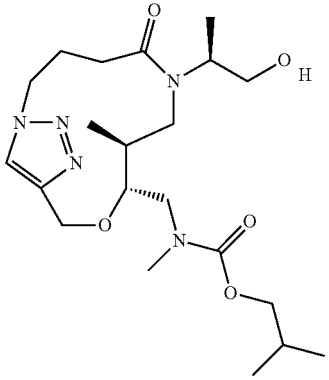 isobutyl (((4R,5S,Z)-7-((S)-1-hydroxypropan-2-yl)-5-methyl-8-oxo-11H-3-oxa-7-aza-1(4,1)-triazolacycloundecaphane-4-yl)methyl)(methyl)carbamate |

TABLE 1-continued

| compound no. | structure |
|---|---|
| 209 | 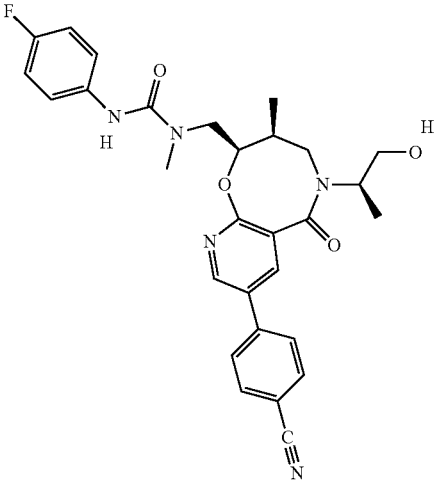<br>1-(((2R,3S)-8-(4-cyanophenyl)-5-(R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 210 | 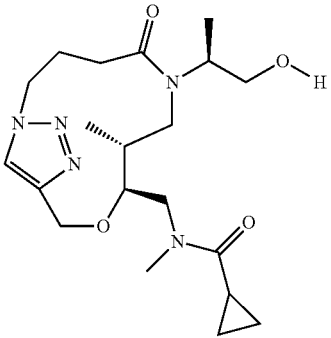 [SMILES: C[C@@H]1CN([C@@H](C)CO)C(=O)CCCn2cc(nn2)CO[C@@H]1CN(C)C(=O)C1CC1]<br>N-(((4S,5R,Z)-7-((S)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 211 | 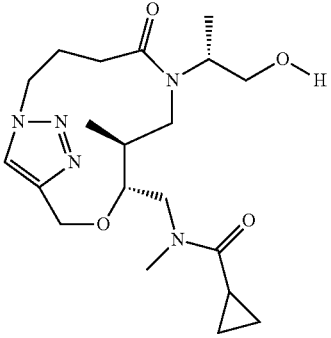 [SMILES: C[C@H](CO)N1C[C@H](C)[C@H](CN(C)C(=O)C2CC2)OCc2cn(nn2)CCCC1=O]<br>N-(((4R,5S,Z)-7-((R)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |

TABLE 1-continued

| compound no. | structure |
|---|---|
| 212 | 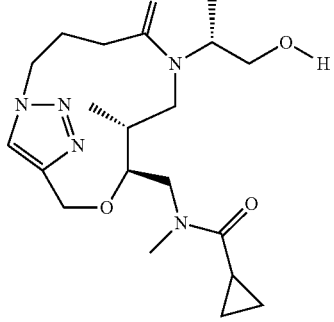<br>N-(((4S,5R,Z)-7-((R)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 215 | 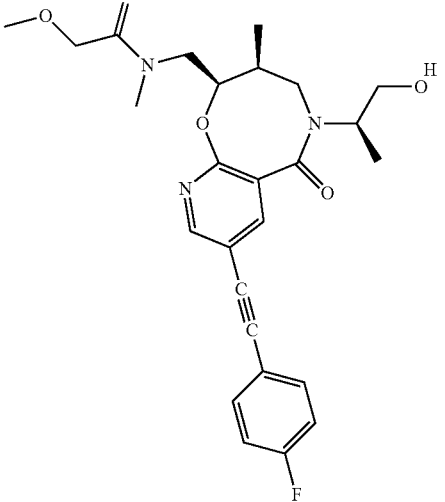<br>N-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-2-methoxy-N-methylacetamide |
| 217 | 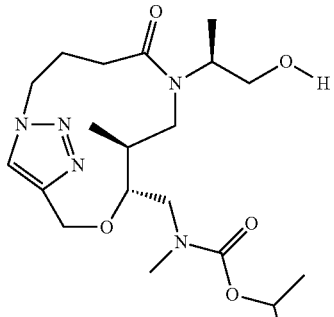<br>isopropyl (((4R,5S,Z)-7-((S)-1-hydroxypropan-2-yl)-5-methyl-8-oxo-11H-3-oxa-7-aza-1(4,1)-triazolacycloundecaphane-4-yl)methyl)(methyl)carbamate |

TABLE 1-continued

| compound no. | structure |
|---|---|
| 224 | 3-(4-fluorophenyl)-1-(((2R,3S)-8-((3-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 225 | 4-(dimethylamino)-N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylbutanamide |
| 226 | N-(((4S,5S,Z)-7-((S)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 227 | N-(((4S,5S,Z)-7-((R)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 228 | N-(((4R,5R,Z)-7-((R)-1-hydroxypropan-2-yl)-5-methyl-8-oxo-11H-3-oxa-7-aza-1(4,1)-triazolacycloundecaphane-4-yl)methyl)-N-methylcyclopropanecarboxamide |
| 229 | 1-(((2R,3S)-8-(cyclopropylethynyl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |

TABLE 1-continued

| compound no. | structure |
|---|---|
| 230 | 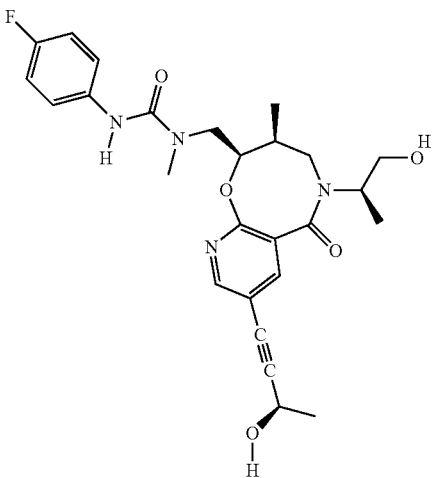<br>3-(4-fluorophenyl)-1-(((2R,3S)-8-((R)-3-hydroxybut-1-yn-1-yl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 231 | 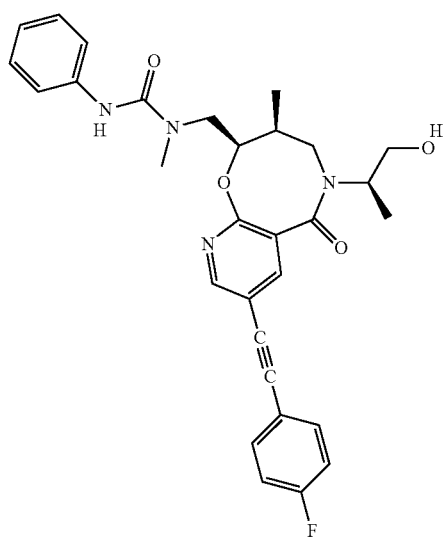<br>1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methyl-3-phenylurea |
| 232 | 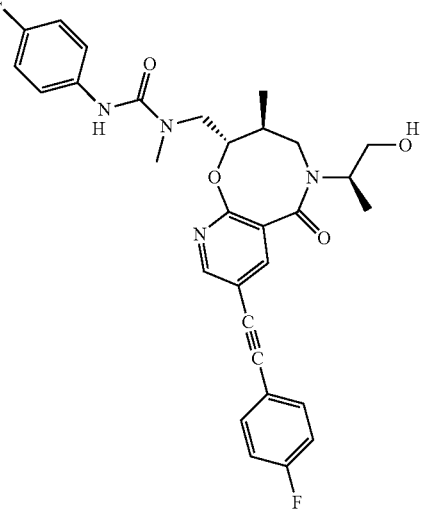<br>3-(4-fluorophenyl)-1-(((2S,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 233 | 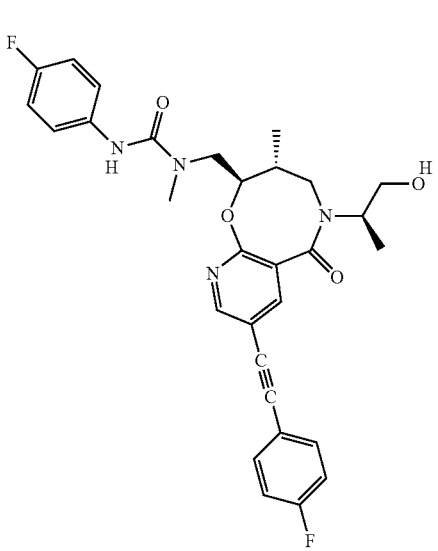<br>3-(4-fluorophenyl)-1-(((2R,3R)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |

TABLE 1-continued

| compound no. | structure |
|---|---|
| 234 | 3-(4-fluorophenyl)-1-(((2S,3R)-8-((4-fluorophenyl)ethynyl)-5-((S)-1-hydroxypropan-2-yl)-3-methyl-6-oxo-3,4,5,6-tetrahydro-2H-pyrido[2,3-b][1,5]oxazocin-2-yl)methyl)-1-methylurea |
| 235 | 3-(4-fluorophenyl)-1-(((2R,3S)-8-((4-fluorophenyl)ethynyl)-5-((S)-1-hydroxypropan-2-yl)-3-methyl-6-oxo-3,4,5,6-tetrahydro-2H-pyrido[2,3-b][1,5]oxazocin-2-yl)methyl)-1-methylurea |
| 236 | 3-(4-fluorophenyl)-1-(((2R,3S)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 237 | 1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-methoxyphenyl)-1-methylurea |

TABLE 1-continued

| compound no. | structure |
|---|---|
| 238 | 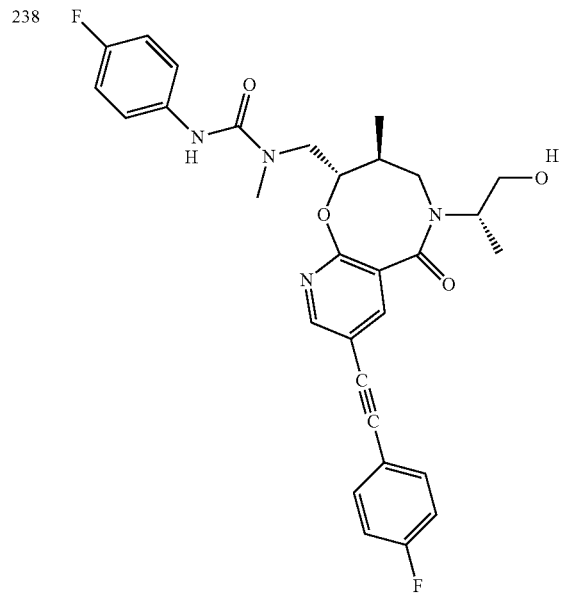 3-(4-fluorophenyl)-1-(((2S,3S)-8-((4-fluorophenyl)ethynyl)-5-((S)-1-hydroxypropan-2-yl)-3-methyl-6-oxo-3,4,5,6-tetrahydro-2H-pyrido[2,3-b][1,5]oxazocin-2-yl)methyl)-1-methylurea |
| 239 | 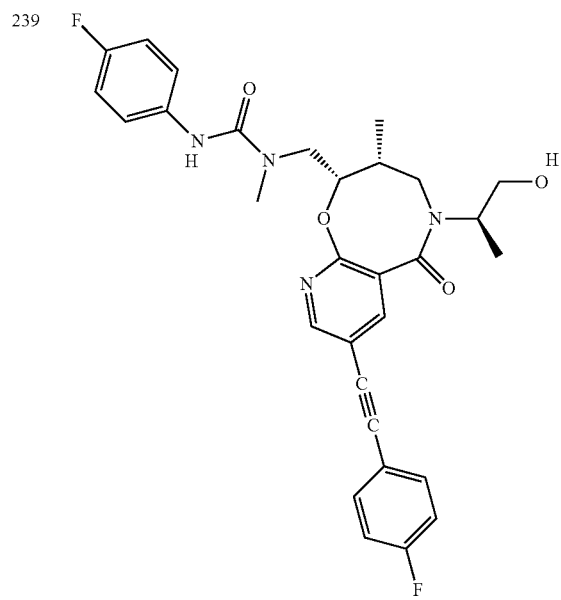 3-(4-fluorophenyl)-1-(((2S,3R)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 240 | 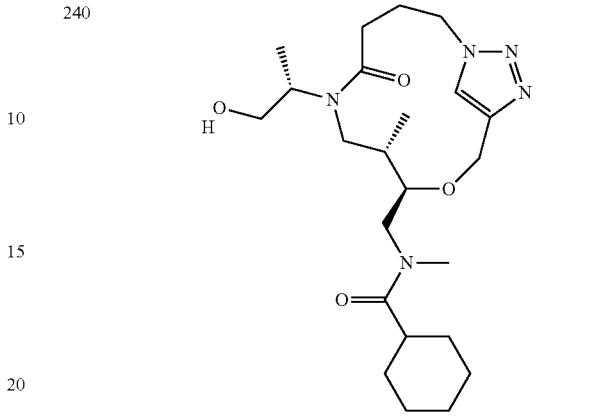 N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylcyclohexanecarboxamide |
| 241 | 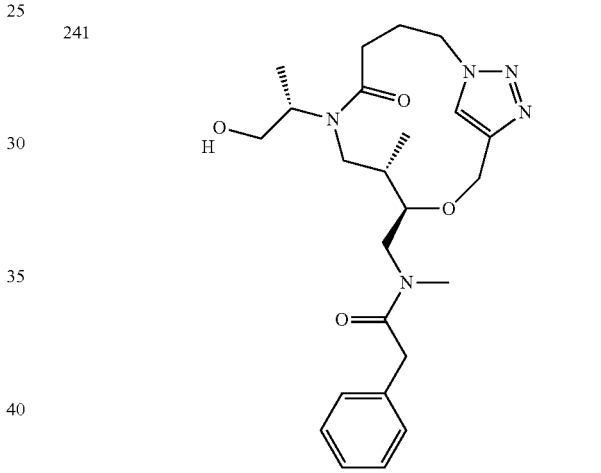 N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methyl-2-phenylacetamide |
| 242 | 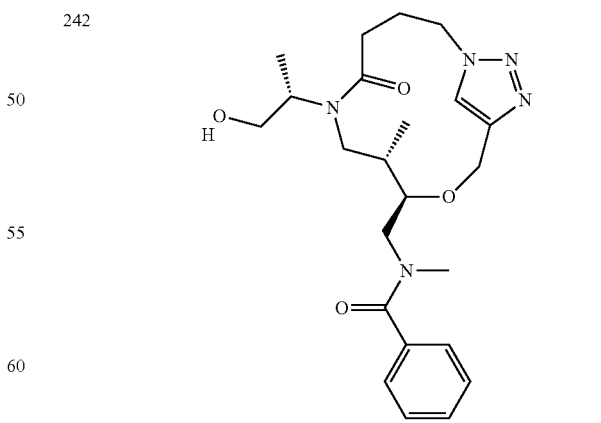 N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylbenzamide |

TABLE 1-continued

| compound no. | structure |
|---|---|
| 243 | 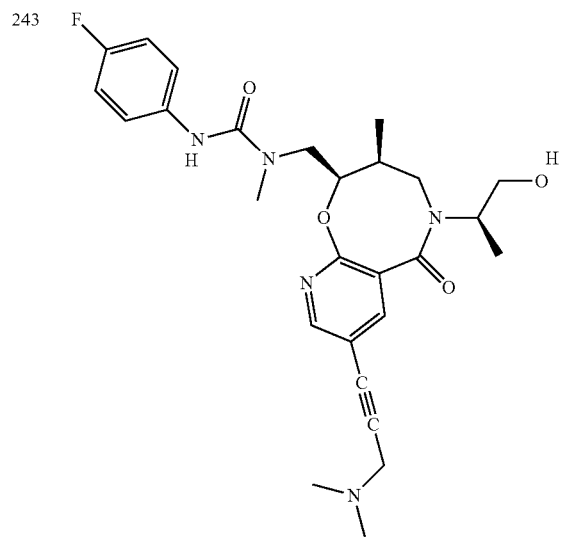<br>1-(((2R,3S)-8-(3-(dimethylamino)prop-1-yn-1-yl)-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 244 | 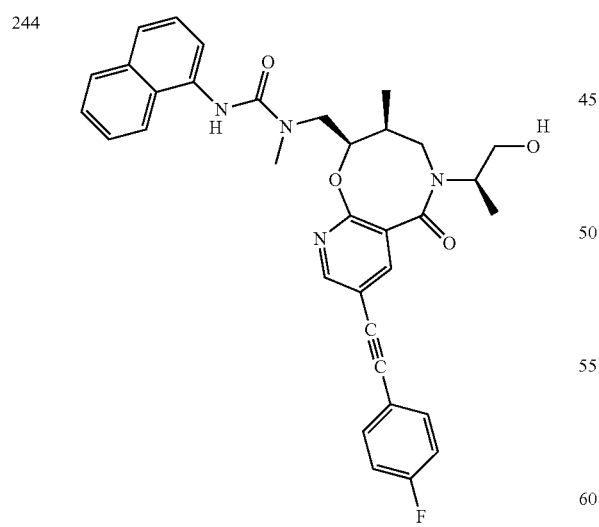<br>1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methyl-3-(naphthalen-1-yl)urea |

TABLE 1-continued

| compound no. | structure |
|---|---|
| 245 | 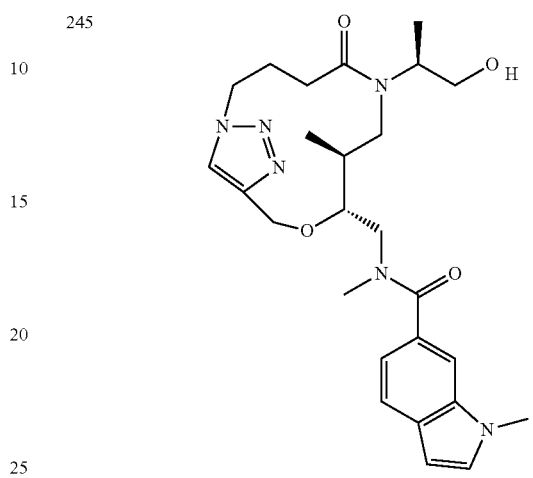<br>N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N,1-dimethyl-1H-indole-6-carboxamide |
| 246 | 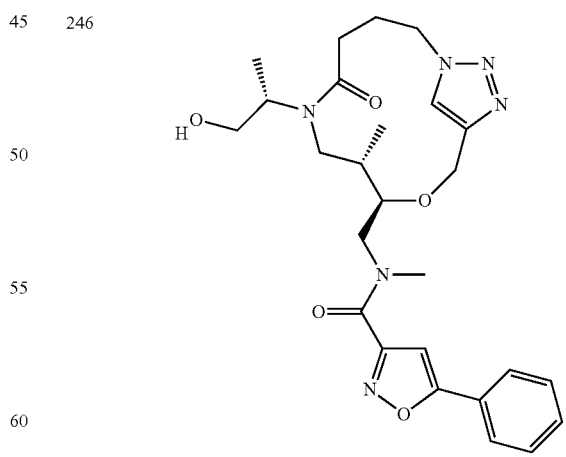<br>N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methyl-5-phenylisoxazole-3-carboxamide |

TABLE 1-continued

| compound no. | structure |
|---|---|
| 247 | 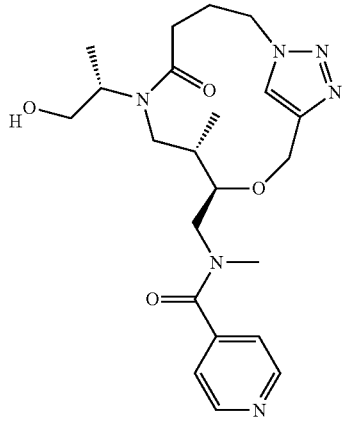 N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylisonicotinamide |
| 248 | 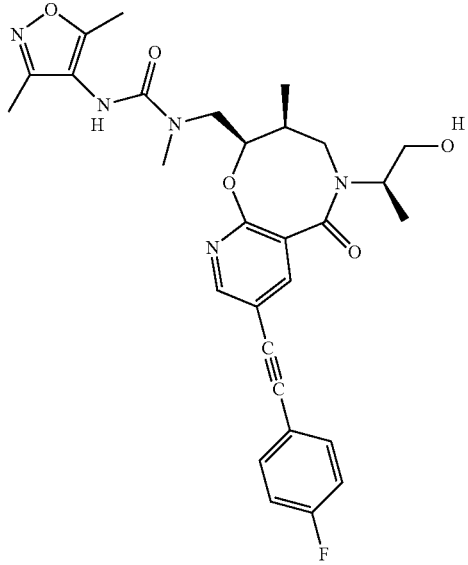 3-(3,5-dimethylisoxazol-4-yl)-1-(((2R,3S)-8-((4-fluorophenyl)ethynyl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 249 | 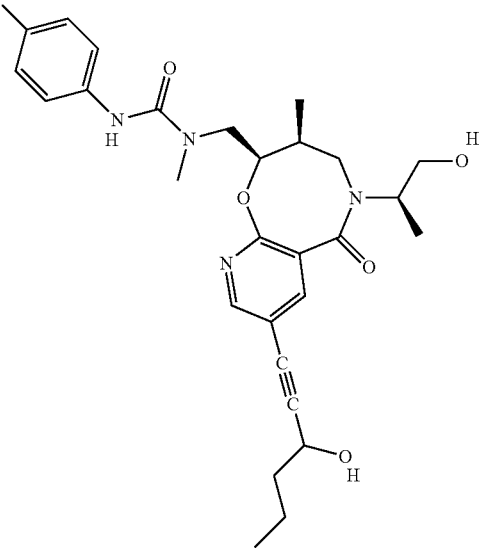 3-(4-fluorophenyl)-1-(((2R,3S)-8-(3-hydroxyhex-1-yn-1-yl)-5-((R)-1-hydroxypropan-2-yl)-3-methyl-6-oxo-3,4,5,6-tetrahydro-2H-pyrido[2,3-b][1,5]oxazocin-2-yl)methyl)-1-methylurea |
| 250 | 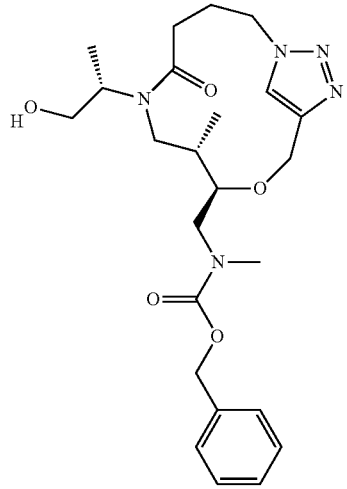 benzyl (((4R,5S,Z)-7-((S)-1-hydroxypropan-2-yl)-5-methyl-8-oxo-11H-3-oxa-7-aza-1(4,1)-triazolacycloundecaphane-4-yl)methyl)(methyl)carbamate |

TABLE 1-continued

| compound no. | structure |
|---|---|
| 251 | 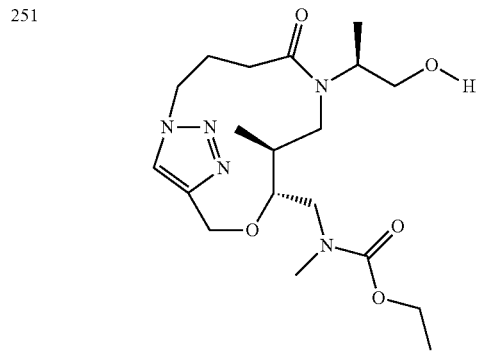 ethyl (((4R,5S,Z)-7-((S)-1-hydroxypropan-2-yl)-5-methyl-8-oxo-11H-3-oxa-7-aza-1(4,1)-triazolacycloundecaphane-4-yl)methyl)(methyl)carbamate |
| 252 | 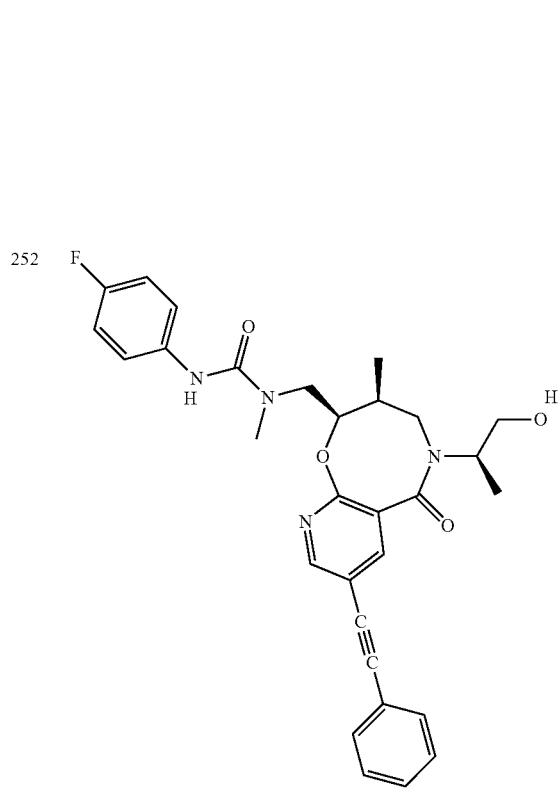 3-(4-fluorophenyl)-1-(((2R,3S)-5-((R)-1-hydroxypropan-2-yl)-3-methyl-6-oxo-8-(phenylethynyl)-3,4,5,6-tetrahydro-2H-pyrido[2,3-b][1,5]oxazocin-2-yl)methyl)-1-methylurea |
| 253 | 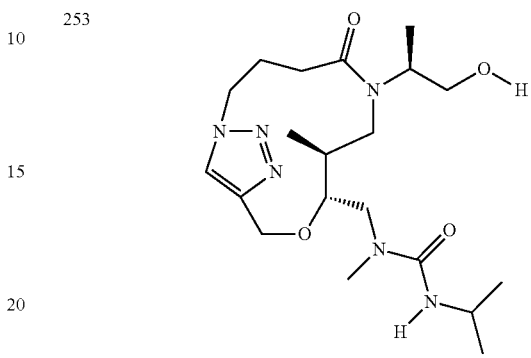 1-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-3-isopropyl-1-methylurea |
| 254 | 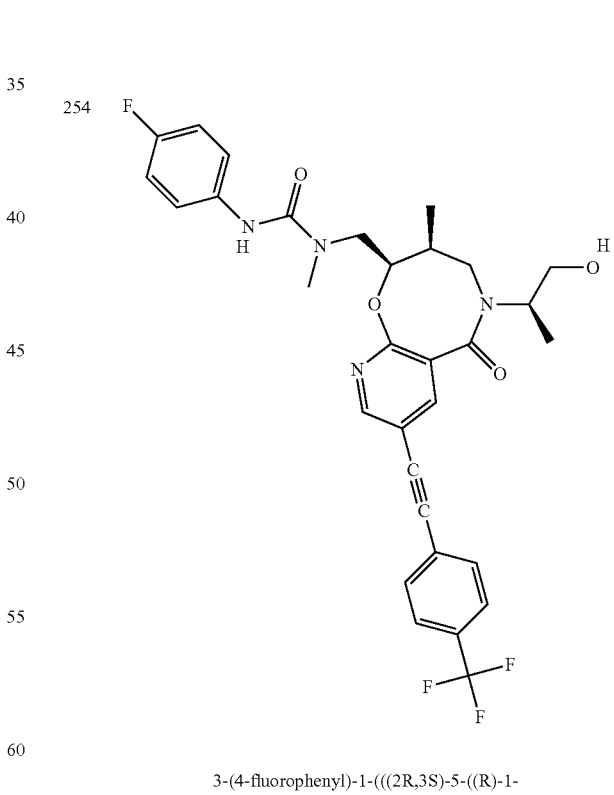 3-(4-fluorophenyl)-1-(((2R,3S)-5-((R)-1-hydroxypropan-2-yl)-3-methyl-6-oxo-8-((4-(trifluoromethyl)phenyl)ethynyl)-3,4,5,6-tetrahydro-2H-pyrido[2,3-b][1,5]oxazocin-2-yl)methyl)-1-methylurea |

TABLE 1-continued

| compound no. | structure |
|---|---|
| 255 | 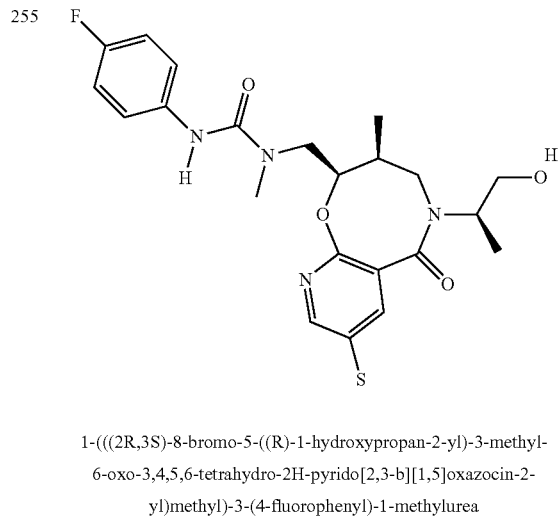<br>1-(((2R,3S)-8-bromo-5-((R)-1-hydroxypropan-2-yl)-3-methyl-6-oxo-3,4,5,6-tetrahydro-2H-pyrido[2,3-b][1,5]oxazocin-2-yl)methyl)-3-(4-fluorophenyl)-1-methylurea |
| 256 | 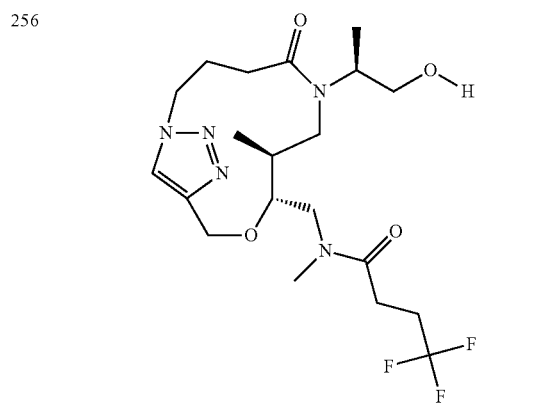<br>4,4,4-trifluoro-N-(((4R,5S,Z)-7-((S)-1-hydroxypropan-2-yl)-5-methyl-8-oxo-11H-3-oxa-7-aza-1(4,1)-triazolacycloundecaphane-4-yl)methyl)-N-methylbutanamide |
| 257 | 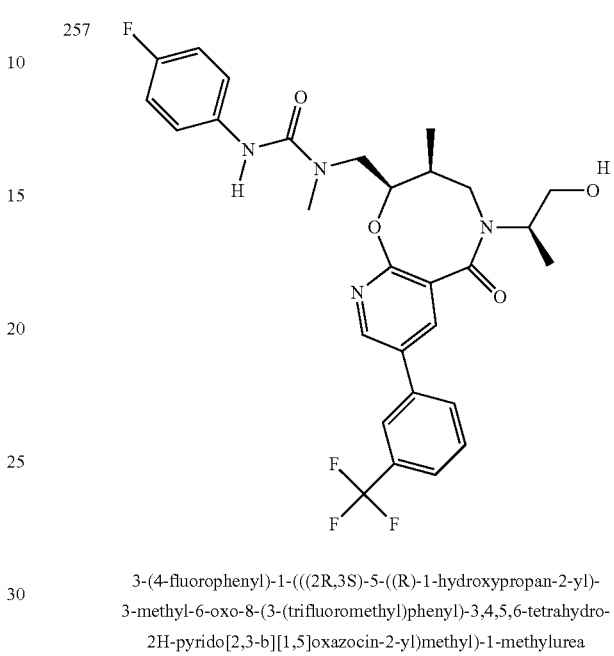<br>3-(4-fluorophenyl)-1-(((2R,3S)-5-((R)-1-hydroxypropan-2-yl)-3-methyl-6-oxo-8-(3-(trifluoromethyl)phenyl)-3,4,5,6-tetrahydro-2H-pyrido[2,3-b][1,5]oxazocin-2-yl)methyl)-1-methylurea |

In certain embodiments, compounds for inducing differentiation of cells, such as endodermal or mesodermal derived cells, comprise PH1, FH1, FPH1, FPH2, and compounds 106-108, 112-114, 201-212, 217 and 223-257. In certain embodiments, compounds for inducing differentiation of cells comprise FH1, FPH1, FPH2, and compounds 106, 108, 201-212, 217 and 223-257. In certain embodiments, compounds for inducing proliferation of cells, such as endodermal or mesodermal derived cells, include PH1, FPH1, FPH2, and compounds 102-103, 106-108, 110-112, 205, 211, 215, 235-246, 248-250, 252, 255 and 257. In certain embodiments, compounds for inducing proliferation of cells, comprise PH1, FPH1, FPH2, and compounds, 102, 106-108, 236, 238-240, 244, 248, 252 and 257.

In certain embodiments, the invention provides a pharmaceutical composition comprising an effective amount of a compound of the invention or a pharmaceutically acceptable salt or prodrug thereof, and a pharmaceutical carrier, diluent, or excipient.

In certain embodiments, the present invention provides a pharmaceutical composition suitable for use in a human patient, comprising at least one of the compounds illustrated herein (e.g., a compound of the invention, such as a compound of Table 1 or of Formulas (I)-(V)) and one or more pharmaceutically acceptable excipients. In other embodiments, the pharmaceutical preparations may be used in treating or preventing a condition or disease as described herein. In yet other embodiments, the pharmaceutical preparations have a low enough pyrogen activity to be suitable for administration into a human patient by, for example, injection.

Scheme 1
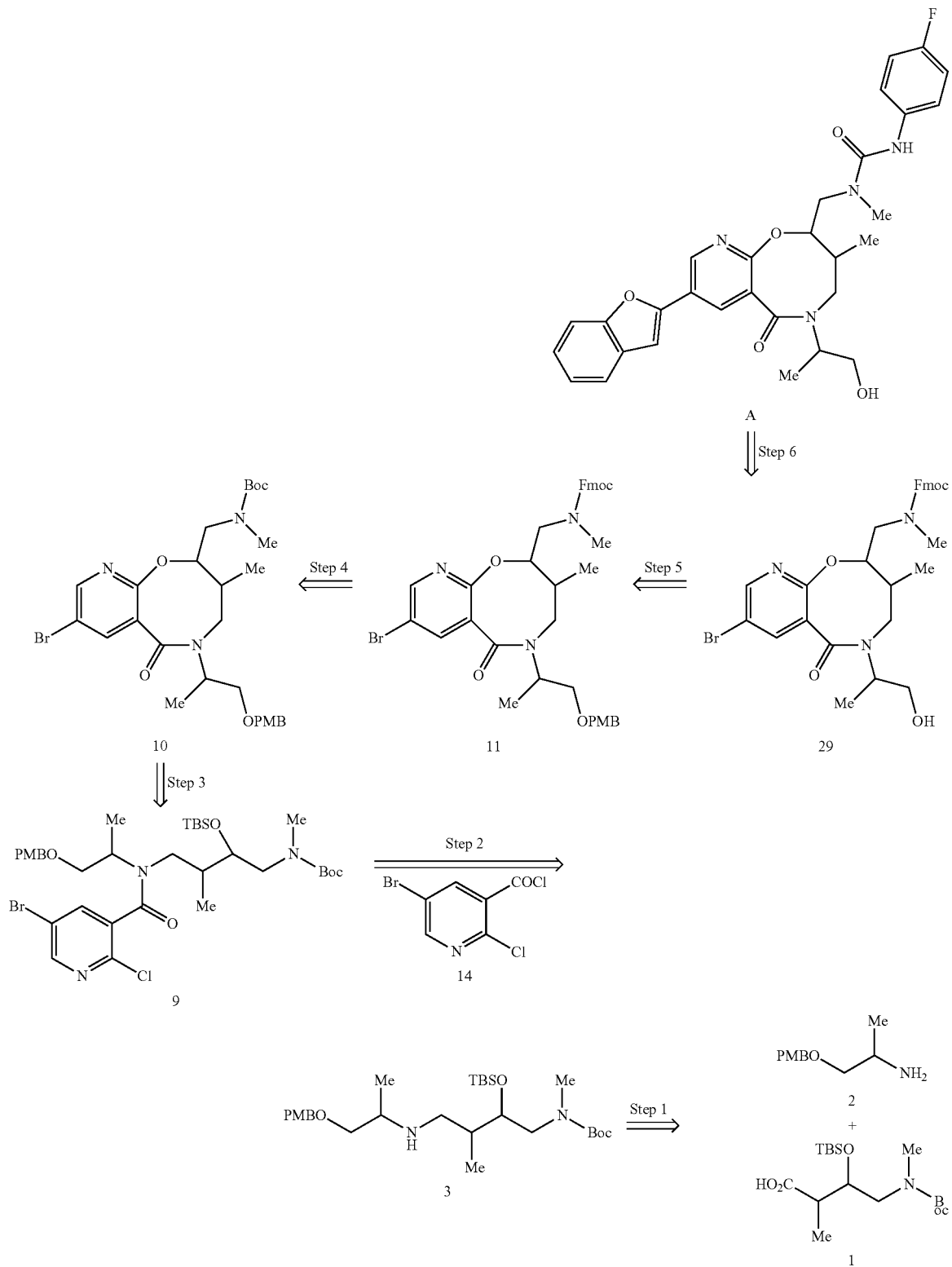
Compounds of the invention can be prepared according to methods known in the art. More specifically, compounds of formula (IV) can be prepared using the retrosynthesis outlined in Scheme 1 for compound 106. Step 1 comprises the coupling of compounds 1 and 2 to form compound 3. For example, compound 1 is reacted with compound 2 in the presence of PyBOP to generate the intermediate amide, which is then reduced to the amine using BH₃-DMS, followed by quenching with Rochelle's salt in MeOH to form compound 3. Compounds 1 and 2 can be generated using reported literature procedures: Marcaurelle, L. A. et al., 2010, J. Am. Chem. Soc. 132:16962-16976. Step 2 comprises the acylation of compound 3 with compound 14 to afford tertiary amide 9 in the presence of Et₃N. Step 3 comprises the cyclization of compound 9 to form compound 10 in the presence of CsF/NaH or TBAF. Step 4 comprises a manipulation of the amine protective group. Step 5 comprises the removal of the PMB group using DDQ to afford compound 29. Step 6 comprises the functionalization of the compound 29. In one embodiment, compound 29 is loaded onto a solid support. For example, the solid support can be silicon-functionalized Lanterns. Compound 29 is deprotected and capped with the appropriate 4-fluorophenyl isocyanate to form the desired urea. Subsequent Suzuki cross-coupling with 2-benzofuranylboronic acid forms compound 106. In one aspect, the cleavage from the Lantern can be achieved by treatment with acid, such as 15% HF/pyridine in THF.

Compound 107 can be synthesized similar to the procedures employed for the synthesis of compound 106. For example, in Step 6, compound 29 is functionalized with the desired functional groups to form compound 107. After the formation of the urea, identical to the synthesis of compound 106, Sonogashira cross coupling with 4-fluorophenylacetylene gives compound 107. In one embodiment, the cleavage from the Lantern can be achieved by treatment with 15% HF/pyridine in THF.

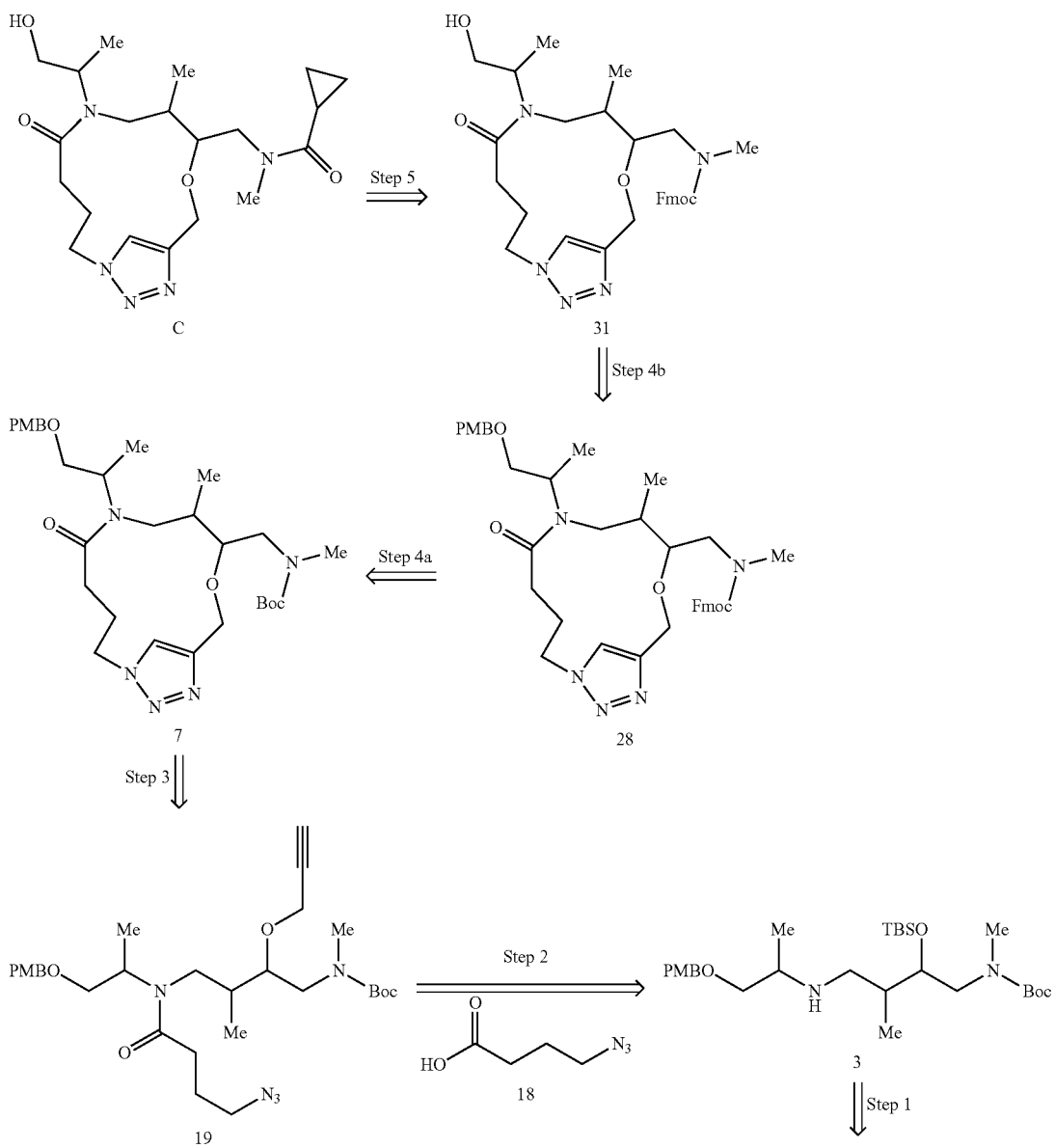

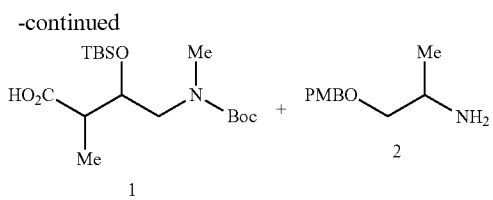

Compound 108 can be prepared following the retrosynthesis of Scheme 2. Step 1 comprises the coupling of compounds 1 and 2 to form compound 3. Compound 1 is reacted with compound 2 in the presence of PyBOP to generate the intermediate amide, which was then reduced to the amine using BH$_3$-DMS, followed by quenching with Rochelle's salt in MeOH to form compound 3. Compounds 1 and 2 can be generated using reported literature procedures: Marcaurelle, L. A. et al., 2010, J. Am. Chem. Soc. 132:16962-16976. Step 2 comprises the formation of compound 19. Compound 3 is acylated with azido acid 18, and then deprotection of the TBS group produced the alcoholic intermediate. Propargylation of the alcoholic intermediate using NaHMDS in THF and DMF leads to compound 19. Step 3 comprises the cyclization of compound 19 using polystyrene-bound copper catalyst, PS—CuPF$_6$, to form compound 7. Steps 4a and 4b comprise protection manipulations. Step 4a comprises the removal of the Boc group using TBSOTf followed by HF-pyridine to afford the desired amine, which is then protected as the Fmoc carbamate 28. Step 4b comprises the removal of the PMB group using DDQ to afford compound 31. Step 5 comprises the functionalization of the compound 31. In one embodiment, compound 31 is loaded onto a solid support. For example, the solid support can be silicon-functionalized Lanterns. The Fmoc group of compound 31 can be removed using 20% piperidine in DMF. The intermediate is then treated with cyclopropanecarboxylic acid to form compound 108. In one embodiment, the cleavage from the Lantern can be achieved by treatment with 15% HF/pyridine in THF.

In certain embodiments, compounds of the invention may be prodrugs of the compounds of Table 1 and Formulas (I)-(V). A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound. For example, a hydroxyl in the parent compound is presented as an ester or a carbonate in the pro-drug, or a carboxylic acid present in the parent compound is presented as an ester in the pro-drug. In certain such embodiments, the prodrug is metabolized to the active parent compound in vivo (e.g., the ester is hydrolyzed to the corresponding hydroxyl, or carboxylic acid).

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically-labeled compounds are useful in drug and/or substrate tissue distribution studies. In certain embodiments, substitution with heavier isotopes such as deuterium affords greater metabolic stability (for example, increased in vivo half-life or reduced dosage requirements). In certain embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, the present invention relates to methods of treatment with a compound of the invention, or a pharmaceutically acceptable salt thereof. In certain embodiments, the therapeutic preparation may be enriched to provide predominantly one enantiomer of a compound (e.g., of Formula (IV) or (V)). An enantiomerically enriched mixture may comprise, for example, at least 60 mole % of one enantiomer, or more preferably at least 75, 90, 95, or even 99 mole %. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of Formula (IV) or (V)). A diastereomerically enriched mixture may comprise, for example, at least 60 mole % of one diastereomer, or more preferably at least 75, 90, 95, or even 99 mole %.

Cells and Cell Populations

The invention provides cells and populations of cells that may be obtained by methods described herein.

Methods of Expansion of Primary Cells

The invention provides a method for inducing proliferation of primary cells, comprising contacting the primary cells with a compound of the invention, thereby inducing proliferation of the primary cells. In certain embodiments, the resulting primary cells are differentiated. The method may be conducted in vitro or in vivo.

The invention provides a cell (or a population of cells) produced by a method for inducing proliferation as described herein. The invention further includes a cell (or a population of cells) produced by a method for inducing proliferation as described herein and characterized by one or more of the assays described herein.

In certain embodiments, the primary cells comprise stem cells or a progeny thereof. In certain embodiments, the stem cells are pluripotent or non-pluripotent. Exemplary pluripotent stem cells comprise induced pluripotent stem cells, embryonic stem cells, and pluripotent stem cells derived by nuclear transfer, cell fusion, or forced expression of reprogramming factors. In certain embodiments, the stem cells are selected from multipotent stem cells, oligopotent stem cells, and unipotent stem cells. In certain embodiments, the stem cells comprise fetal stem cells or adult stem cells. In certain embodiments, the stem cells comprise epithelial stem cells; in other embodiments, the stem cells comprise endothelial stem cells. In certain embodiments, the primary cells comprise somatic cells. In certain embodiments, the primary cells are derived from endoderm or mesoderm. In certain embodiments, the primary cells comprise primary hepatocytes.

In certain embodiments, the differentiated cells produced by the methods described herein are characterized by one or more different assays, e.g., high content imaging and competitive ELISA. In certain embodiments, the differentiated cells produced by the methods described herein are characterized by proliferation of normally quiescent cells (e.g., Ki67 staining). In certain embodiments, proliferation is detectable by Ki67 via immunofluorescent staining (e.g., using antibodies Ab15580 from Abcam, and AB9260 from Millipore). In certain embodiments, proliferation is 105%-infinite (if starting material had zero Ki67-positive cells), such as 1,250%-1,900%.

In certain embodiments, the following functions are present in primary cells (prior to compound contact) and remain present in the differentiated cells produced by the methods described herein (after compound contact): albumin secretion, urea secretion, general cytochrome P450 activity, expression of mature liver genes, and bile transport (directional MRP-2 transport of CFDA as indicated by linear fluorescent regimes at the intercellular interface).

In certain embodiments, albumin secretion in the differentiated cells is detectable via ELISA as compared to the primary hepatocytes. In other embodiments, albumin secretion in the differentiated cells is 65%-130% changed as compared to the primary hepatocytes, e.g., 85%-110% changed as compared to primary hepatocytes.

In certain embodiments, urea secretion in the differentiated cells is detectable via an assay kit (Stanbio Lab) as compared to the primary hepatocytes. In other embodiments, urea secretion in the differentiated cells is 80%-125% changed as compared to the primary hepatocytes, e.g., 95%-100% changed as compared to primary hepatocytes.

In certain embodiments, general cytochrome P450 activity in the differentiated cells is 105%-1,000% as compared to the primary hepatocytes. In other embodiments, general cytochrome P450 activity in the differentiated cells is 115%-730% changed as compared to the primary hepatocytes, e.g., 125%-730% changed as compared to primary hepatocytes.

In certain embodiments, expression of mature liver genes in the differentiated cells is detectable via Luminex (Broad) as compared to the primary hepatocytes. In other embodiments, expression of mature liver genes in the differentiated cells is 20%-820% changed as compared to the primary hepatocytes, e.g., 20%-755% changed as compared to primary hepatocytes.

In certain embodiments, bile transport (directional MRP-2 transport of CFDA as indicated by linear fluorescent regimes at the intercellular interface) in the differentiated cells is detectable by fluorescent imaging as compared to the primary hepatocytes. In other embodiments, bile transport in the differentiated cells is 80%-1,000% changed as compared to the primary hepatocytes, e.g., 80%-120% changed as compared to primary hepatocytes.

In certain embodiments, the increase in number of cell nuclei after contact with a compound of the invention is determined. In other embodiments, the number of cell nuclei is increased in the population of differentiated cells in comparison to the number of cell nuclei in the original population of primary cells, e.g., by at least about 5-, 3-, 1.5- or 0.5-fold.

In certain embodiments, the number of cell nuclei undergoing mitosis after contact with a compound of the invention is determined. In other embodiments, the number of cell nuclei undergoing mitosis is elevated in the population of differentiated cells in comparison to the number of cell nuclei undergoing mitosis in the original population of primary cells.

In certain embodiments, the extent of the proliferation is measured by one or more image-based readouts. In other embodiments, the image readouts are obtained by a process comprising quantifying the number of nuclei in interphase, quantifying the number of nuclei in metaphase, and/or quantifying the number of nuclei in anaphase.

In certain embodiments, the level of secreted albumin as a marker for protein synthesis after contact with a compound of the invention is determined. In other embodiments, the albumin secretion of the differentiated cells is increased at least about 2-fold in comparison to the albumin secretion of the original population of primary cells.

In certain embodiments, the size of the colony of cells after contact with a compound of the invention is determined. In other embodiments, the colony of differentiated cells is increased in size in comparison to the colony size of the original population of primary cells. In yet other embodiments, the increase in colony size is at least about 4-fold, e.g., at least about 5-fold.

In certain embodiments, the phenotype of the cells is assessed after contact with a compound of the invention. In other embodiments, the differentiated cells produced comprise normal morphology. The phenotype of the differentiated cells can be assessed using imaging, biochemical analyses, and gene expression profiling.

In certain embodiments, the phenotype of functional hepatocytes produced by methods described herein is assessed using imaging, biochemical analyses and gene expression profiling. In other embodiments, normal morphology for functional hepatocytes produced by methods described herein comprises a stable secretion of albumin at about 25 ug/$10^6$ heps/day. In yet other embodiments, normal morphology for functional hepatocytes produced by methods described herein comprises a stable synthesis of urea at about 150 ug/$10^6$ heps/day. In yet other embodiments, normal morphology for hepatocytes produced by methods described herein comprises cytochrome P450 activity at 0.3 uM/$10^6$ heps/hr. In yet other embodiments, normal morphology for hepatocytes comprises liver-specific gene expression.

Differentiation of iPS Cells

The invention provides a method for inducing the differentiation of a population of induced pluripotent stem cells (iPS cells). In certain embodiments, the method comprises contacting the population of iPS cells with a compound of the invention, thereby inducing differentiation of the population of iPS cells into a population of differentiated cells. The method can be conducted in vitro or in vivo. Induced pluripotent stem cells (iPS cells) create the possibility of establishing patient-specific cell types, thus empowering personal medicine. The invention provides a cell or a population of cells produced by a method for inducing the differentiation of induced pluripotent stem cells (iPS cells) as described elsewhere herein. The invention further provides a cell or a population of cells produced by the method for inducing the differentiation of induced pluripotent stem cells (iPS cells) as described herein and characterized by one or more of the assays described herein.

In certain embodiments, the population of iPS cells prior to said differentiation is a population of hepatocyte-like cells (iHep cells). In certain embodiments, the iHep cells express one or more fetal markers. In certain embodiments, the fetal marker comprises alpha fetoprotein (AFP). In certain embodiments, the alpha fetoprotein is expressed at a level detectable via immunofluorescent staining (e.g., using antibody from Fitzgerald, 10-A05A).

In certain embodiments, the iHep cells prior to differentiation lack mature hepatocyte function. In certain embodiments, the mature hepatocyte function comprises CYP450 activity. In certain embodiments, the CYP450 activity is one or more selected from the group consisting of CYP2A6 and CYP3A4 activity. In certain embodiments, the CYP2A6 activity is less than 0.1% of that found in mature hepatocytes. In certain embodiments, the CYP3A4 activity is less than 0.1% of that found in mature hepatocyte.

The iHep cells prior to differentiation may be produced by any suitable method. In certain embodiments, the iHep cells prior to said differentiation are produced by (i) culturing undifferentiated iPS cells on Matrigel®; (ii) transferring confluent iPS cells to differentiation media; and (iii) adding growth factors (Activin A, BMP-4, bFGF, HGF, and OSM).

In certain embodiments, the methods comprise treating a population of iHep cells with a compound of the invention. In certain embodiments, the population of iHep cells is treated with a compound of the invention on at least one of day 21-35 post differentiation. The population of iHep cells may be treated with a compound of the invention on day 21, 22, 23, 24, 25, 26, 27, 28, 29, 30, 31, 32, 33, 34, or 35 after said differentiation. In certain embodiments, the population of iHep cells is cultured with a compound of the invention for a period of at least 1, 2, 3, 4, 5, 6, 7, 8, 9, or 10 days, e.g., at least 5 days.

In certain embodiments, the population of differentiated cells produced by the methods described herein is characterized by one or more different assays. In certain embodiments, the population of differentiated functional cells produced by the methods described herein is characterized by an up regulation of CYP3A4 activity and a down regulation of AFP as compared to iPS-derived hepatocyte like cells (as defined by Si-Tayeb K. et al., 2010, Hepatology 51:297-305, doi:10.1002/hep.23354 ("Si-Tayeb et al.")). In certain embodiments, the population of differentiated cells is characterized by an increase in one or more of the following functions: albumin secretion, intracellular albumin stain, general CYP450 activity, expression of mature liver genes, CYP 2A6 activity, CYP 3A4 activity, CYP 3A stain, albumin and CYP3A double positive staining.

In certain embodiments, the population of differentiated cells is characterized by an increase in albumin secretion as compared to iPS-derived hepatocyte like cells (as defined by Si-Tayeb et al.). In certain such embodiments, the increase is 100%-2,000%, e.g., the increase is 100%-1650%, or even 170%-1,185%.

In certain embodiments, the population of differentiated cells is characterized by an increase in intracellular albumin stain as compared to iPS-derived hepatocyte like cells (as defined by Si-Tayeb et al.). In certain such embodiments, the increase is detectable via immunofluorescent staining (e.g., using antibody from Bethyl Laboratories, A80-229A). In certain such embodiments, the increase is 100%-10,000%, or even 200%-6,975%.

In certain embodiments, the population of differentiated cells is characterized by an increase in general CYP450 activity as compared to iPS-derived hepatocyte like cells (as defined by Si-Tayeb et al.). In certain such embodiments, the increase is 100%-150%, e.g., 105%-150%, or even 130%-145%.

In certain embodiments, the population of differentiated cells is characterized by an increase in expression of mature liver genes as compared to iPS-derived hepatocyte like cells (as defined by Si-Tayeb et al.). In certain such embodiments, the increase is 100%-33,335%, e.g., 100%-780%, or even 100%-675%.

In certain embodiments, the population of differentiated cells is characterized by an increase in CYP 2A6 activity as compared to iPS-derived hepatocyte like cells (as defined by Si-Tayeb et al.). In certain embodiments, the increase is 105%-100,000%, such as 900%-7,270%, e.g., 2,330%-3,335%.

In certain embodiments, the population of differentiated cells is characterized by an increase in CYP 3A4 activity as compared to iPS-derived hepatocyte like cells (as defined by Si-Tayeb et al.). In certain embodiments, the increase is 105%-100,000%, e.g., 300%-5,250%, such as 1,600%-4,590%.

In certain embodiments, the population of differentiated cells is characterized by an increase in albumin and CYP3A double positive staining as compared to iPS-derived hepatocyte like cells (as defined by Si-Tayeb et al.). In certain embodiments, the increase is detectable via immunofluorescent staining (e.g., using CYP3A antibody from Santa Cruz sc271033, and albumin antibody from Bethyl Laboratories A80-229A. In certain embodiments, the increase is 105%-100,000%, such as 3640%-3,750%.

In certain embodiments, the population of differentiated cells is characterized by a decrease in alpha-fetoprotein secretion as compared to iPS-derived hepatocyte like cells (as defined by Si-Tayeb et al.). In certain embodiments, the decrease is 0.0%-95%, such as 8.0%-30%, e.g., 8.5%-20%.

In certain embodiments, the population of differentiated cells is characterized by a decrease in AFP stain as compared to iPS-derived hepatocyte like cells (as defined by Si-Tayeb et al). In certain embodiments, the decrease is 0.0%-95% (e.g., using antibody from Fitzgerald, 10-A05A), such as 0.0%-50%, or even 0.0%-2.0%.

In certain embodiments, the population of differentiated cells produced by the method for inducing the differentiation described herein comprises cells that are increased in size as compared to iPS-derived hepatocyte like cells (as defined by Si-Tayeb et al.). In certain embodiments, the population of differentiated cells comprises cells with more pronounced hepatocyte morphologies and with more noticeable bile cannaliculi transport between hepatocytes. In certain embodiments, the population of differentiated cells comprises cells having CYP3A4 activity at >0.1% of that found in mature hepatocytes. In certain embodiments, the population of differentiated cells comprises cells having GSTP1 expression at <60% of that found in undifferentiated iPS cells. In certain embodiments, the population of differentiated cells comprises cells having an AFP protein level at <40% of AFP levels found in hepatocyte-like cells, as defined by Si-Tayeb et al. In certain embodiments, the population of differentiated cells comprises cells having albumin protein level at >1.5 fold of albumin levels found in hepatocyte-like cells, as defined by Si-Tayeb et al. In certain embodiments, the population of differentiated cells comprises cells having a CYP3A4 protein level at >5 fold of CYP3A4 levels found in hepatocyte-like cells, as defined by Si-Tayeb et al.

Methods of Use

Compounds of the invention can be used to grow and differentiate cells, thereby producing differentiated cells for use in a variety of in vitro and in vivo applications. A compound of the invention may be useful in any methods and applications that utilize such cells. Furthermore, a cell of the invention (or a population of cells of the invention, i.e., differentiated cells obtainable by the methods disclosed herein) may also be useful in any methods and applications that employ such cells. In certain embodiments, the cells for use in the methods for inducing proliferation of primary cells and the methods for inducing differentiation of a population of cells described herein may be stem cells or a progeny cell thereof. The stem cells may be pluripotent stem cells or any non-pluripotent stem cells. The pluripotent stem cells may be induced pluripotent stem cells, embryonic stem cells, or pluripotent stem cells derived by nuclear transfer or cell fusion. The stem cells may also be multipotent stem cells, oligopotent stem cells, or unipotent stem cells. The stem cells may be fetal stem cells or adult stem cells, for example, epithelial stem cells or endothelial stem cells. In certain embodiments, the cells may be somatic cells, either immortalized or not. In certain embodiments, the cells are derived from endoderm or mesoderm. The cells may also be hepatocytes, more particularly, mature hepatocytes or immature hepatocytes (e.g., hepatocyte-like cells).

Compounds of the invention can be used to grow and differentiate hepatocytes. A compound of the invention and/or cells obtainable by the methods described herein may be useful in methods and applications that utilize hepatocytes. For example, hepatocytes are used in methods of assessing a pharmaceutical compound, comprising assaying a pharmacological or toxicological property of the pharmaceutical compound on hepatocytes or a tissue engineered liver. Additional uses of hepatocytes include, but are not limited to, transplantation or implantation of the hepatocytes in vivo; screening cytotoxic compounds, carcinogens, mutagens, growth/regulatory factors, pharmaceutical compounds, and the like, in vitro; elucidating the mechanism of liver diseases and infections; studying the mechanism by which drugs and/or growth factors operate; diagnosing and monitoring cancer in a patient; gene therapy; and the production of biologically active products, to name but a few.

Additional uses for compounds of the invention and/or cells of the invention may be for distribution for commercial, therapeutic, and research purposes. For purposes of manufacture, distribution, and use, the cells of the invention may be supplied in the form of a cell culture or suspension in an isotonic excipient or culture medium, optionally frozen to facilitate transportation or storage. Compounds of the invention may be useful for producing cells that may be used in methods of screening e.g., drug testing, toxicity assays, factors that promote maturation, proliferation, and/or maintenance of cells in culture. Compounds of the invention and/or cells of the invention may also be used in numerous therapies and medical treatments. Compounds of the invention and/or cells of the invention may be used in research, e.g., to elucidate cellular growth mechanisms leading to the identification of novel targets for cancer therapies, to elucidate mechanisms involved in cell fate determination leading to new strategies for cellular reprogramming, and to generate genotype-specific cells for disease modeling, including the generation of new therapies customized to different genotypes. Such customization can reduce adverse drug effects and help identify therapies appropriate to the patient's genotype.

Test Compound Screening

Compounds of the invention can be used to produce cells that can be used to screen for factors (such as solvents, small molecule drugs, peptides, and polynucleotides) or environmental conditions (such as culture conditions or manipulation) that affect the characteristics of cells.

In one aspect, the invention provides a method of assessing a compound for a pharmacological or toxicological effect on a population of differentiated cells, comprising: (a) contacting a population of primary cells or a population of induced pluripotent stem cells with a first compound of the invention to produce a population of differentiated cells; (b) contacting the population of differentiated cells with a test agent, and (c) assaying for a pharmacological or toxicological effect of the test compound on said population. In certain embodiments, the cells comprise hepatocytes.

In certain embodiments, a compound of the invention can be used to produce hepatocytes that can be used to screen for factors (such as solvents, small molecule drugs, peptides, and polynucleotides) or environmental conditions (such as culture conditions or manipulation) that affect the characteristics of hepatocytes. Over the past decade, in vitro models have been established, such as precision-cut liver slices, primary hepatocytes, and liver cell lines and a few studies examining the relevance of drug testing with hepatocyte cell lines, found that cell lines poorly reproduce and predict drug metabolism and hepatotoxicity as opposed to primary hepatocytes or liver slices. Thus, primary human hepatocytes are the "gold standard" for in vitro drug testing. However, the limited supply of human hepatocytes and the fact that such hepatocytes may not adequately represent the genetic variation of the patient population limit the ability to detect all potential drug toxicities. Consequently, utilization of cells derived from a diverse group of donors, e.g., by obtaining stem cells from a diverse group of donors (for instance by generating iPS cells) and differentiating them to hepatocytes (e.g., with differing cytochrome P450 profiles) would allow drug testing to more closely examine and predict potential problems for particular groups or individuals.

In some aspects, compounds of the invention are used to produce (un)differentiated stem cells that are used to screen factors that promote maturation of cells along the hepatocyte lineage, or promote proliferation and maintenance of such cells in long-term culture. For example, candidate hepatocyte maturation factors or growth factors are tested by adding them to stem cells in different wells, and then determining any phenotypic change that results, according to desirable criteria for further culture and use of the cells.

Particular screening applications of this invention relate to the testing of pharmaceutical compounds in drug research (see In vitro Methods in Pharmaceutical Research, Academic Press, 1997, and U.S. Pat. No. 5,030,015). In certain aspects of this invention, compounds of the invention are used to grow and differentiate hepatocytes to serve as test cells for standard drug screening and toxicity assays, as have been previously performed on hepatocyte cell lines or primary hepatocytes in short-term culture. Assessment of the activity of candidate pharmaceutical compounds generally involves contacting the hepatocytes produced by one or more compounds of the invention with the candidate compound, determining any change in the morphology, marker phenotype, or metabolic activity of the cells that is attributable to the candidate compound (e.g., by comparing the effects with control cells, such as untreated cells or cells treated with an inert compound or vehicle), and then correlating the effect of the candidate compound with the observed change. The screening may be done either because the candidate compound is being tested to see if it has a pharmacological effect on liver cells (e.g., a therapeutic effect), or because a candidate compound designed to have effects elsewhere may have unintended hepatic side effects. Two or more drugs can be tested in combination (by combining with the cells either simultaneously or sequentially) to detect possible drug-drug interaction effects.

In some applications, hepatocytes produced by one or more compounds of the invention are used to screen pharmaceutical compounds for potential hepatotoxicity (Castell et al., In: *In vitro Methods in Pharmaceutical Research*, Academic Press, 375-410, 1997. *Cell Encapsulation Technology and Therapeutics*, Kuhtreiber et al. eds., Birkhauser, Boston, Mass., 1999). Cytotoxicity can be determined in the first instance by the effect on cell viability, morphology, and leakage of enzymes into the culture medium. More detailed analysis is conducted to determine whether the pharmaceutical compounds affect cell function (such as gluconeogenesis, ureogenesis, and plasma protein synthesis) without causing toxicity. Lactate dehydrogenase (LDH) is a good marker because the hepatic isoenzyme (type V) is stable in culture conditions, allowing reproducible measurements in culture supernatants after 12-24 h incubation. Leakage of enzymes such as mitochondrial glutamate oxaloacetate transaminase and glutamate pyruvate transaminase can also be used. Gomez-Lechon et al., *Anal. Biochem.*, 236:296, 1996 describes a microassay for measuring glycogen, which can be used to measure the effect of pharmaceutical compounds on hepatocyte gluconeogenesis.

Other markers/functions useful to evaluate hepatotoxicity include determination of the synthesis and secretion of albumin, cholesterol, and lipoproteins; transport of conjugated bile acids and bilirubin; ureagenesis; cytochrome p450 levels and activities; glutathione levels; release of alpha-glutathione s-transferase; ATP, ADP, and AMP metabolism; intracellular $K^+$ and $Ca^{2+}$ concentrations; the release of nuclear matrix proteins or oligonucleosomes; and induction of apoptosis (indicated by cell rounding, condensation of chromatin, and nuclear fragmentation). DNA synthesis can be measured as [$^3$H]-thymidine or BrdU incorporation. Effects of a drug on DNA synthesis or structure can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. See Vickers in *In vitro Methods in Pharmaceutical Research*, Academic Press, 375-410, 1997 for further elaboration.

Research Tools

In certain embodiments, the invention provides a method of developing a humanized mouse model comprising administering to the mouse (i) human cells obtained by any of the methods described herein; (ii) one or more cells as described herein; or (iii) a combination thereof.

In certain embodiments, the invention further provides administering to the mouse an effective amount of one or more compounds of invention, or a pharmaceutically acceptable salt or prodrug thereof. For example, a mouse receiving human liver cells or tissue may also be treated with a compound of the invention to induce proliferation and/or differentiation of cells in the implanted material. Similarly, human liver cells or tissue may be grown ex vivo from human liver cells using the methods described herein or using cells as described herein, optionally through the use of one or more compounds of the invention to proliferate and/or differentiate the cells. In certain such embodiments, the tissue is grown, at least in part, from cells obtained from the subject (i.e., autologous cells). The mouse model may be used for the development of a new therapy, e.g., for liver disease.

Methods of Treatment

Compounds of the invention and/or cells of the invention are useful in methods of treating, alleviating, and/or preventing a disease or condition, such as a liver disease or condition, in a subject in need thereof. In certain embodiments, compounds of the invention and/or cells of the invention are useful in methods for treating a subject having or at risk of a liver dysfunction. In certain embodiments, cells of the invention can enable personalized medicine. For example, patient-specific cells can be obtained by using one or more compounds of the invention to expand patient biopsies and/or to differentiate patient iPS cells.

In certain embodiments, the invention provides a method of treating, alleviating, and/or preventing a disease or condition in a subject, such as a human, comprising administering to a subject in need thereof (i) an effective amount of one or more compounds of the invention; (ii) one or more cells obtained by any of the methods described herein; or (iii) one or more cells described herein; or (iv) a combination thereof.

In certain embodiments, the invention provides a method wherein a compound of the invention induces proliferation of endogenous cells. In certain embodiments, the invention provides a method, wherein a compound of the invention promotes differentiation of endogenous cells, e.g., toward a more mature phenotype.

In certain embodiments, the endogenous cells are stem cells or a progeny cell thereof. In certain embodiments, the stem cells are pluripotent or non-pluripotent. Representative pluripotent stem cells include induced pluripotent stem cells, embryonic stem cells, and pluripotent stem cells derived by nuclear transfer, cell fusion, or forced expression of reprogramming factors. In certain embodiments, the stem cells are selected from multipotent stem cells, oligopotent stem cells, and unipotent stem cells. In certain embodiments, the stem cells are fetal stem cells or adult stem cells. In certain embodiments, the stem cells are epithelial stem cells; in others, endothelial stem cells. In certain embodiments, the cells are somatic cells. In certain embodiments, the cells are derived from endoderm or mesoderm. In certain embodiments, the cells are hepatocytes.

In certain embodiments, the invention provides a method of treating a disease or condition in a subject. In certain embodiments, the invention provides a method of alleviating a disease or condition in a subject. In certain embodiments, the invention provides a method of preventing a disease or condition in a subject.

In certain embodiments, the disease or condition is a liver disease or condition, e.g., acetaminophen toxicity, alcoholic liver disease, primary liver cancer, liver cirrhosis, liver cysts, fatty liver disease, liver fibrosis, hepatitis, primary sclerosing cholangitis, and jaundice. In certain embodiments, the method further comprises implanting into the subject a bio-artificial liver device. In certain embodiments, the disease is hepatitis, e.g., caused by a virus selected from hepatitis A virus, hepatitis B virus, hepatitis C virus, hepatitis D virus, or hepatitis E virus, herpes simplex, cytomegalovirus, Epstein-Barr virus, and yellow fever.

In certain embodiments, the compound is administered by a route selected from the group consisting of oral, parenteral, intramuscular, intranasal, sublingual, intratracheal, inhalation, ocular, vaginal, rectal, and intracerebroventricular. In certain embodiments, the administration comprises oral.

In certain embodiments, the invention contemplates that the compound or cells being administered are encapsulated, such as in a nanoparticle or hydrogel.

The invention also includes a method for transplanting an organ or tissue into a subject in need thereof, comprising administering to the subject (i) an effective amount of one or more compounds of the invention; (ii) one or more cells obtained by any of the methods described herein; (iii) one or more cells described herein; or (iv) a combination thereof.

In certain embodiments, the invention provides a method for transplanting an organ, such as a liver transplant. For example, a patient receiving an organ transplant may also be treated with a compound of the invention to induce proliferation and/or differentiation of cells in the transplanted organ. Similarly, the transplanted organ may be an organ grown ex vivo from cells obtained by the methods described herein or using cells as described herein, optionally through the use of one or more compounds of the invention to proliferate and/or differentiate the cells. In other embodiments, the organ is grown, at least in part, from cells obtained from the subject (i.e., autologous cells).

In certain embodiments, the invention provides a method for transplanting tissue. In certain embodiments, the tissue comprises liver tissue. For example, a patient receiving a tissue transplant may also be treated with a compound of the invention to induce proliferation and/or differentiation of cells in the transplanted tissue. Similarly, the transplanted tissue may be tissue grown ex vivo from cells obtained by the methods described herein or using cells as described herein, optionally through the use of one or more compounds of the invention to proliferate and/or differentiate the cells. In other embodiments, the tissue is grown, at least in part, from cells obtained from the subject (i.e., autologous cells).

In certain embodiments, the invention provides a method for the repair of damaged, diseased, or aged tissue, such as liver tissue, in a subject comprising administering to a subject in need thereof (i) an effective amount of one or more compounds of the invention; (ii) one or more cells obtained by any of the methods described herein; (iii) one or more cells described herein; or (iv) a combination thereof.

In certain embodiments, the compound is administered systemically or locally. In certain embodiments, the compound or cells are administered prior to an organ or tissue transplant. In certain embodiments, the compound or cells are administered during an organ or tissue transplant. In certain embodiments, the compound or cells are administered after an organ or tissue transplant.

In certain embodiments, the invention provides a method of treating a subject in need cell replacement therapy, comprising: providing a population of cells; inducing differentiation of said population of cells by exposing said cells to a compound of the invention to produce a population of differentiated cells (e.g., hepatic cells); and administering the population of differentiated cells to said subject in need thereof. In certain embodiments, the population of cells is derived from the subject in need of cell replacement therapy. In certain embodiments, the compound induces proliferation of the cells. In certain embodiments, the compound promotes differentiation of the cells.

Liver Therapy and Transplantation

The invention also provides methods of using compounds of the invention and/or cells of the invention to restore a degree of liver function to a subject needing such therapy, e.g., due to an acute, chronic, or inherited impairment of liver function.

One of the unique features of the liver is its enormous natural regeneration ability. This regeneration is due in large part to the re-entry of terminally differentiated hepatocytes in the cell cycle, resulting in multiple cell divisions to regenerate the liver. When the hepatocytes are damaged, liver stem/progenitor cells, termed oval cells in rodents, located in the peri-portal zone, are activated and differentiate to mature hepatocytes. Hence, most liver diseases ending in liver failure are caused by a combination of decreased proliferation of hepatocytes and exhaustion of the stem/progenitor cell pool. Liver failure is caused by a number of disorders, including cirrhosis due to infections, excessive alcohol consumption, genetic and idiopatic reasons. In addition, acute liver failure is caused by ingestion of certain drugs or foods. Liver transplantation is the only successful treatment for end stage liver disease, and is in many instances also the only curative therapy for certain forms of genetic disorders of the liver. Many liver disorders treated by whole liver transplantation result from hepatocyte dysfunction. Hepatocyte transplantation is of great interest. There is significant evidence that grafted hepatocytes can assume the full range of liver functions in vivo. Hepatocyte transplantation has several advantages over whole liver transplant: lower morbidity, a single donor organ can be used for several recipients, cells can be cryopreserved, and cells grafts are less immunogenic than whole organ grafts. However, lack of donor cells curtails further exploration of this therapy. As a consequence, there is also great interest in therapies to promote the growth and differentiation of hepatocytes for the treatment of acute and chronic liver failure, as well as inherited metabolic disorders. Compounds of the invention and/or cells of the invention may be useful in the therapies described above.

Accordingly the invention is also directed to methods of treating liver deficiencies by administering a compound of the invention and/or cells of the invention to a subject with the liver deficiency. Such deficiencies include, but are not limited to, toxic liver disease, metabolic liver disease, acute liver necrosis, effects of acetaminophen, hemochromatosis, Wilson's Disease, Crigler Najar, hereditary tyrosinemia, familial intrahepatic cholestatis type 3, ornithine transcarbamylase (OTC) deficiency, and urea cycle disorder.

Further diseases include, but are not limited to viral hepatitis, chronic viral hepatitis A, B, C, acute hepatitis A, B, C, D, E, cytomegalovirus and herpes simplex virus; liver dysfunction in other infectious diseases such as, without limitation, toxoplasmosis, hepatosplenic schistosomiasis, liver disease in syphilis, leptospirosis and amoebiasis; metabolic diseases such as, without limitation, haemochromatosis, Gilbert's syndrome, Dubin-Johnson syndrome and Rotor's syndrome; alcoholic liver disease such as, without limitation, fatty liver, fibrosis, sclerosis and cirrhosis; and toxic liver disease.

Compounds of the invention and/or cells of the invention may be assessed for their ability to restore liver function in an animal lacking full liver function. Compounds of the invention and/or cells of the invention may be assessed for their ability to restore liver function in an animal with a humanized liver. For models of liver disease or failure, see: Braun et al., 2000, Nature Med., 6:320; Rhim et al., 1995, Proc. Natl. Acad. Sci. USA 92:4942; Lieber et al., 1995, Proc. Natl. Acad. Sci. USA 92:6210; Mignon et al., 1998, Nature Med., 4:1185; Overturf et al., 1009, Human Gene Ther., 9:295. Acute liver disease can be modeled by 90% hepatectomy or by treating animals with a hepatotoxin such as galactosamine, $CCl_4$, or thioacetamide.

Chronic liver diseases such as cirrhosis can be modeled by treating animals with a sub-lethal dose of a hepatotoxin long enough to induce fibrosis (Rudolph et al., 2000, Science 287:1253). Assessing the ability of compounds of the invention and/or the cells of the invention to reconstitute liver function involves administering the compounds and/or cells to such animals, and then determining survival over a 1 to 8 week period or more, while monitoring the animals for progress of the condition. Effects on hepatic function can be determined by evaluating markers expressed in liver tissue, cytochrome P450 activity, and blood indicators, such as alkaline phosphatase activity, bilirubin conjugation, and prothrombin time), and survival of the host. Any improvement in survival, disease progression, or maintenance of hepatic function according to any of these criteria relates to effectiveness of the therapy.

Compounds of the invention may be administered orally. For purposes of hemostasis, the compounds of the invention can be administered at any site that has adequate access to the circulation, typically within the abdominal cavity. For some metabolic and detoxification functions, it is advantageous for the compounds of the invention to have access to the biliary tract. Accordingly, in certain embodiments, a compound of the invention is administered locally, e.g., near the liver (e.g., in the treatment of chronic liver disease) or the spleen (e.g., in the treatment of fulminant hepatic failure). In certain embodiments, a compound of the invention is administered into the hepatic circulation either through the hepatic artery, or through the portal vein, by infusion through an in-dwelling catheter. A catheter in the portal vein can be manipulated so that the cells flow principally into the spleen, or the liver, or a combination of both. In certain embodiments, a compound of the invention is administered by placing a bolus in a cavity near the target organ, typically in an excipient or matrix that will keep the bolus in place. In certain embodiments, a compound of the invention is injected directly into a lobe of the liver or the spleen.

A compound of the invention or cells of the invention can be used for therapy of any subject in need of having hepatic function restored or supplemented. Human conditions that may be appropriate for such therapy include fulminant hepatic failure due to any cause, viral hepatitis, drug-induced liver injury, cirrhosis, inherited hepatic insufficiency (such as Wilson's disease, Gilbert's syndrome, or $alpha_1$-antitrypsin deficiency), hepatobiliary carcinoma, autoimmune liver disease (such as autoimmune chronic hepatitis or primary biliary cirrhosis), and any other condition that results in impaired hepatic function.

Use in a Liver Assist Device

Certain aspects of this invention include a compound of the invention that is encapsulated or part of a bioartificial liver device. Certain aspects of this invention include cells of the invention that are encapsulated or part of a bioartificial liver device. In another aspect, a compound of the invention is administered to a subject with a bioartificial liver (BAL) device. In another aspect, a compound of the invention is used to produce hepatocytes that can be encapsulated according to such methods for use either in vitro or in vivo.

Bioartificial organs for clinical use are designed to support an individual with impaired liver function, either as a part of long-term therapy, or to bridge the time between a fulminant hepatic failure and hepatic reconstitution or liver transplant. See Macdonald et al., pp. 252-286 of *Cell Encapsulation Technology and Therapeutics*, Kuhtreiber et al. eds., Birkhauser, Boston, Mass., 1999, and exemplified in U.S. Pat. Nos. 5,290,684, 5,624,840, 5,837,234, 5,853,717, and 5,935,849.

BAL devices are designed to support the detoxification functions performed by the liver, hence decreasing the risk and severity of CNS complications associated with acute liver failure. It is also noted that compounds of the invention and/or cells of the invention may be used in conjunction with a BAL device to replace other liver functions. BAL devices could benefit three groups of patients: with fulminant hepatic failure, waiting for an imminent transplant, and with early failure of a liver transplant. Although some positive results have been seen in patients with liver failure, further exploration of the usefulness of BAL devices has been hampered by lack of suitable cells. Currently, tumor-derived cell lines or animal cells, which might be associated with possible tumor cell seeding, immune responses, and xenozoonoses, are used. The availability of cells with fully mature hepatic function of human origin, would enable investigators to further test and optimize BAL devices to bridge patients till the liver spontaneously regenerates or a donor-liver is available. Accordingly, a compound of the invention can be used to grow and differentiate hepatocytes for use with bioartificial liver devices.

Suspension-type bioartificial livers may comprise a compound of the invention suspended with hepatocytes in plate dialysers, microencapsulated in a suitable substrate, or attached to microcarrier beads coated with extracellular matrix. Alternatively, a compound of the invention and hepatocytes can be placed on a solid support in a packed bed, in a multiplate flat bed, on a microchannel screen, or surrounding hollow fiber capillaries. The device has an inlet and outlet through which the subject's blood is passed, and sometimes a separate set of ports for supplying nutrients to the cells.

Suspension-type bioartificial livers may comprise cells of the invention suspended in plate dialysers, microencapsulated in a suitable substrate, or attached to microcarrier beads coated with extracellular matrix. Alternatively, cells of the invention can be placed on a solid support in a packed bed, in a multiplate flat bed, on a microchannel screen, or surrounding hollow fiber capillaries. The device has an inlet and outlet through which the subject's blood is passed, and sometimes a separate set of ports for supplying nutrients to the cells.

A compound of the invention and/or cells of the invention can be plated into the device on a suitable substrate, such as a matrix of Matrigel® or collagen. The efficacy of the device can be assessed by comparing the composition of blood in the afferent channel with that in the efferent channel—in terms of metabolites removed from the afferent flow, and newly synthesized proteins in the efferent flow.

In certain embodiments, a compound of the invention may be used for the treatment of viral hepatitis. In certain embodiments, a compound of the invention and/or cells of the invention may be used to empower hepatitis research by providing for the development of novel disease models. Viral hepatitis is liver inflammation due to a viral infection. It may present in acute (recent infection, relatively rapid onset) or chronic forms. The most common causes of viral hepatitis are the five unrelated hepatotropic viruses Hepatitis A, Hepatitis B, Hepatitis C, Hepatitis D, and Hepatitis E. In addition to the hepatitis viruses, other viruses that can also cause hepatitis include Herpes simplex, Cytomegalovirus, Epstein-Barr virus, or Yellow fever.

Organ and Tissue Transplant

A compound of the invention and/or cells of the invention may be used in methods of organ or tissue transplantation. Organ transplantation is the moving of an organ from one body to another or from a donor site on the patient's own body, for the purpose of replacing the recipient's damaged or absent organ. Organs may be re-grown from the patient's own cells (stem cells, or cells extracted from the failing organs). Organs and/or tissues that are transplanted within the same person's body are called autografts. Transplants that are performed between two subjects of the same species are called allografts. Allografts can either be from a living or cadaveric source. Organs that can be transplanted include liver.

The compounds of the invention and cells of the invention further enable the development of implantable systems and/or tissue engineered constructs.

Cell Replacement Therapy

A compound of the invention and/or cells of the invention may be used in a method of cell replacement therapy. Cell replacement therapy introduces new cells into damaged tissue in order to treat disease or injury. The ability of cells to self-renew and give rise to subsequent generations with variable degrees of differentiation capacities allows for generating tissues that can replace diseased and damaged areas in the body, with minimal risk of rejection and side effects.

Formulations & Administration

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any suitable methods. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention are administered at dosage levels greater than about 0.001 mg/kg, such as greater than about 0.01 mg/kg or greater than about 0.1 mg/kg. For example, the dosage level may be from about 0.001 mg/kg to about 50 mg/kg such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can also be administered to a subject.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The compounds described herein may form salts with acids, and such salts are included in the present invention. In one embodiment, the salts are pharmaceutically acceptable salts.

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage of the compounds of the invention for use in humans. The dosage of such agents lies preferably within a range of circulating concentrations that include the ED50 with little or no toxicity. The dosage may vary within this range depending upon the dosage form employed and the route of administration utilized. For any compound used in the method of the invention, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Multiple doses of the compounds of the invention are also contemplated.

Cell Administration

Any of the cells produced by the methods described herein can be used in the clinic to treat a subject. They can, therefore, be formulated into a pharmaceutical composition. Therefore, in certain embodiments, the isolated or purified cell populations are present within a composition adapted for and suitable for delivery, i.e., physiologically compatible. Accordingly, compositions of the cell populations will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. In certain embodiments, the isolated or purified cell populations are present within a composition adapted for or suitable for freezing or storage.

Suitable means of delivery for administering the cells produced by the methods described herein include but are not limited to intravenous delivery, direct delivery into the liver, delivery to other extrahepatic sites.

In certain embodiments, the purity of the cells for administration to a subject is about 100%. In certain embodiments, it is 95% to 100%. In certain embodiments, it is 85% to 95%. Particularly in the case of admixtures with other cells, the percentage can be about 10%-15%, 15%-20%, 20%-25%, 25%-30%, 30%-35%, 35%-40%, 40%-45%, 45%-50%, 60%-70%, 70%-80%, 80%-90%, or 90%-95%. Or isolation/purity can be expressed in terms of cell doublings where the cells have undergone, for example, 10-20, 20-30, 30-40, 40-50 or more cell doublings.

The numbers of cells in a given volume can be determined by well known and routine procedures and instrumentation. The % of the cells in a given volume of a mixture of cells can be determined by much the same procedures. Cells can be readily counted manually or by using an automatic cell counter. Specific cells can be determined in a given volume using specific staining and visual examination and by automated methods using specific binding reagent, typically antibodies, fluorescent tags, and a fluorescence activated cell sorter.

The choice of formulation for administering the cells for a given application depends on a variety of factors. Prominent among these are the species of subject, the nature of the disease or condition being treated and its state and distribution in the subject, the nature of other therapies and agents that are being administered, the optimum route for administration, survivability via the route, the dosing regimen, and other factors that will be apparent to those skilled in the art. In particular, for instance, the choice of suitable carriers and other additives will depend on the exact route of administration and the nature of the particular dosage form.

For example, cell survival can be an important determinant of the efficacy of cell-based therapies. This is true for both primary and adjunctive therapies. Another concern arises when target sites are inhospitable to cell seeding and cell growth. This may impede access to the site and/or engraftment there of therapeutic cells. Various embodiments of the invention comprise measures to increase cell survival and/or to overcome problems posed by barriers to seeding and/or growth.

In certain embodiments, final formulations of the aqueous suspension of cells/medium will typically involve adjusting the ionic strength of the suspension to isotonicity (i.e., about 0.1 to 0.2) and to physiological pH (i.e., about pH 6.8 to 7.5). In certain embodiments, the final formulation will also typically contain a fluid lubricant, such as maltose, which must be tolerated by the body. Exemplary lubricant components include glycerol, glycogen, maltose and the like.

Organic polymer base materials, such as polyethylene glycol and hyaluronic acid as well as non-fibrillar collagen, preferably succinylated collagen, can also act as lubricants. Such lubricants are generally used to improve the injectability, intrudability and dispersion of the injected biomaterial at the site of injection and to decrease the amount of spiking by modifying the viscosity of the compositions. This final formulation is by definition the cells in a pharmaceutically acceptable carrier.

The cells are subsequently placed in a syringe or other injection apparatus for precise placement at the site of the tissue defect. The term "injectable" means the formulation can be dispensed from syringes having a gauge as low as 25 under normal conditions under normal pressure without substantial spiking. Spiking can cause the composition to ooze from the syringe rather than be injected into the tissue. For this precise placement, needles as fine as 27 gauge (200 µI.D.) or even 30 gauge (150 µI.D.) are desirable. The maximum particle size that can be extruded through such needles will be a complex function of at least the following: particle maximum dimension, particle aspect ratio (length:width), particle rigidity, surface roughness of particles and related factors affecting particle:particle adhesion, the viscoelastic properties of the suspending fluid, and the rate of flow through the needle. Rigid spherical beads suspended in a Newtonian fluid represent the simplest case, while fibrous or branched particles in a visco elastic fluid are likely to be more complex.

The desired isotonicity of the cell compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected, and allows for the selected viscosity. Viscous compositions are normally prepared from solutions by the addition of such thickening agents.

A pharmaceutically acceptable preservative or stabilizer can be employed to increase the life of cell/medium compositions. If such preservatives are included, it is well within the purview of the skilled artisan to select compositions that will not affect the viability or efficacy of the cells.

Those skilled in the art will recognize that the components of the cell compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells/medium utilized in practicing the present invention in the required amount of the appropriate solvent with various amounts of the other ingredients, as desired.

In some embodiments, the cells or medium are formulated in a unit dosage injectable form, such as a solution, suspension, or emulsion. Pharmaceutical formulations suitable for injection of cells/medium typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

In some embodiments, cells are encapsulated for administration, particularly where encapsulation enhances the effectiveness of the therapy, or provides advantages in handling and/or shelf life. Encapsulation in some embodiments where it increases the efficacy of cell mediated immunosuppression may, as a result, also reduce the need for immunosuppressive drug therapy.

Also, encapsulation in some embodiments provides a barrier to a subject's immune system that may further reduce a subject's immune response to the cells (which generally are not immunogenic or are only weakly immunogenic in allogeneic transplants), thereby reducing any graft rejection or inflammation that might occur upon administration of the cells. Cells may be encapsulated by membranes, as well as capsules, prior to implantation. Any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval.

A wide variety of materials may be used in various embodiments for microencapsulation of cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation of cells that may be used for administration of cells are known to those of skill in the art and are described, for example, in European Patent Publication No. 301,777 and U.S. Pat. Nos. 5,639,275, 4,353,888; 4,744,933; 4,749,620; 4,814,274; 5,084,350; 5,089,272; 5,578,442; 5,639,275; and 5,676,943. All of the foregoing is incorporated herein by reference in parts pertinent to encapsulation of cells.

Certain embodiments incorporate cells into a polymer, such as a biopolymer or synthetic polymer. Examples of biopolymers include, but are not limited to, fibronectin, fibin, fibrinogen, thrombin, collagen, and proteoglycans. Other factors, such as the cytokines discussed above, can also be incorporated into the polymer. In other embodiments of the invention, cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

In the case of treating liver deficiency, in particular, the cells may be enclosed in a device that can be implanted in a subject. Cells can be implanted in or near the liver or elsewhere to replace or supplement liver function. Cells can also be implanted without being in a device, e.g., in existing liver tissue.

Cell compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of cells/medium appropriate to be used in accordance with various embodiments of the invention will depend on numerous factors. It may vary considerably for different circumstances. The parameters that will determine optimal doses to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the cells are syngeneic, autologous, allogeneic, or xenogeneic; their potency (specific activity); the site and/or distribution that must be targeted for the cells/medium to be effective; and such characteristics of the site such as accessibility to cells/medium and/or engraftment of cells. Additional parameters include co-administration with other factors (such as growth factors and cytokines). The optimal dose in a given situation also will take into consideration the way in which the cells/medium are formulated, the way they are administered, and the degree to which the cells/medium will be localized at the target sites following administration. Finally, the determination of optimal dosing necessarily will provide an effective dose that is neither below the threshold of maximal beneficial effect nor above the threshold where the deleterious effects associated with the dose outweighs the advantages of the increased dose.

In certain embodiments, for human therapy, the dose is generally between about $10^9$ and $10^{12}$ cells, making adjustments for body weight of the subject, nature and severity of the affliction, and the replicative capacity of the administered cells. In certain embodiments, the optimal dose of cells for some embodiments will be in the range of doses used for autologous, mononuclear bone marrow transplantation. For fairly pure preparations of cells, optimal doses in various embodiments will range from $10^4$ to $10^8$ cells/kg of recipient mass per administration. In some embodiments the optimal dose per administration will be between $10^5$ to $10^7$ cells/kg. In many embodiments the optimal dose per administration will be $5\times10^5$ to $5\times10^6$ cells/kg. By way of reference, higher doses in the foregoing are analogous to the doses of nucleated cells used in autologous mononuclear bone marrow transplantation. Some of the lower doses are analogous to the number of CD34+ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, cells/medium may be administered in an initial dose, and thereafter maintained by further administration. Cells/medium may be administered by one method initially and thereafter administered by the same method or one or more different methods. The levels can be maintained by the ongoing administration of the cells/ medium. Various embodiments administer the cells/medium either initially or to maintain their level in the subject or both by intravenous injection. In a variety of embodiments, other forms of administration are used, dependent upon the patient's condition and other factors, discussed elsewhere herein.

It is noted that human subjects are generally treated longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regimens can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer the cells/medium.

In some embodiments, cells/medium are administered to a subject in one dose. In others cells/medium are administered to a subject in a series of two or more doses in succession. In some other embodiments wherein cells/medium are administered in a single dose, in two doses, and/or more than two doses, the doses may be the same or different, and they are administered with equal or with unequal intervals between them.

Cells/medium may be administered in many frequencies over a wide range of times. In some embodiments, they are administered over a period of less than one day. In other embodiment they are administered over two, three, four, five, or six days. In some embodiments they are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

Kits

In various embodiments, the invention provides kits comprising a compound, a cell of the invention and/or a cell obtainable using the compounds or methods of the invention. Such kits are useful in in vitro and in vivo methods recited herein. In some embodiments, the kit provides a sterile container comprising a composition of the invention; such containers can be boxes, ampoules, bottles, vials, tubes, bags, pouches, blister-packs, or other suitable container forms known in the art. Such containers can be made of plastic, glass, laminated paper, metal foil, or other materials suitable for holding reagents. If desired a composition of the invention is provided together with instructions for implementating a method of the invention. The instructions may be printed directly on the container (when present), or as a label applied to the container, or as a separate sheet, pamphlet, card, or folder supplied in or with the container.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples are put forth so as to provide those of ordinary skill in the art with a complete disclosure and description of how to make and use the compositions of the invention, and are not intended to limit the scope of what the inventors regard as their invention.

EXAMPLES

Methods & Materials

The compounds of the invention can be synthesized according to methods known in the art, and/or as outlined in Schemes 1 and 2 provided elsewhere herein.

Starting materials 1 and 2 may be prepared according to Marcaurelle, et al., 2010, J. Am. Chem. Soc. 132:16962-16976.

Figure 14A:
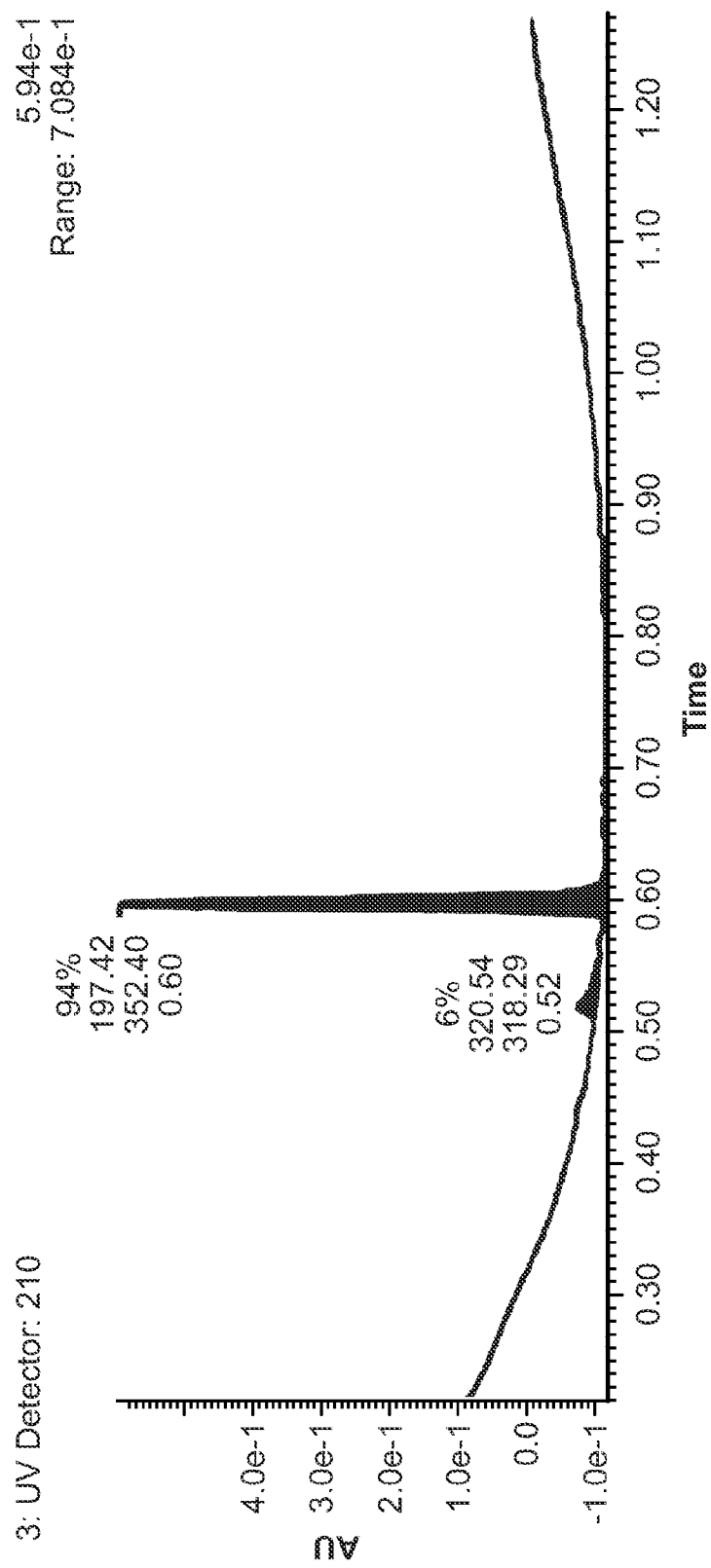
FIG. 14, comprising FIGS. 14A-14C, comprises a set of plots illustrating analytical data for FPH1: liquid chromatography (FIG. 14A) and NMR (FIGS. 14B-14C).
Figure 14B:
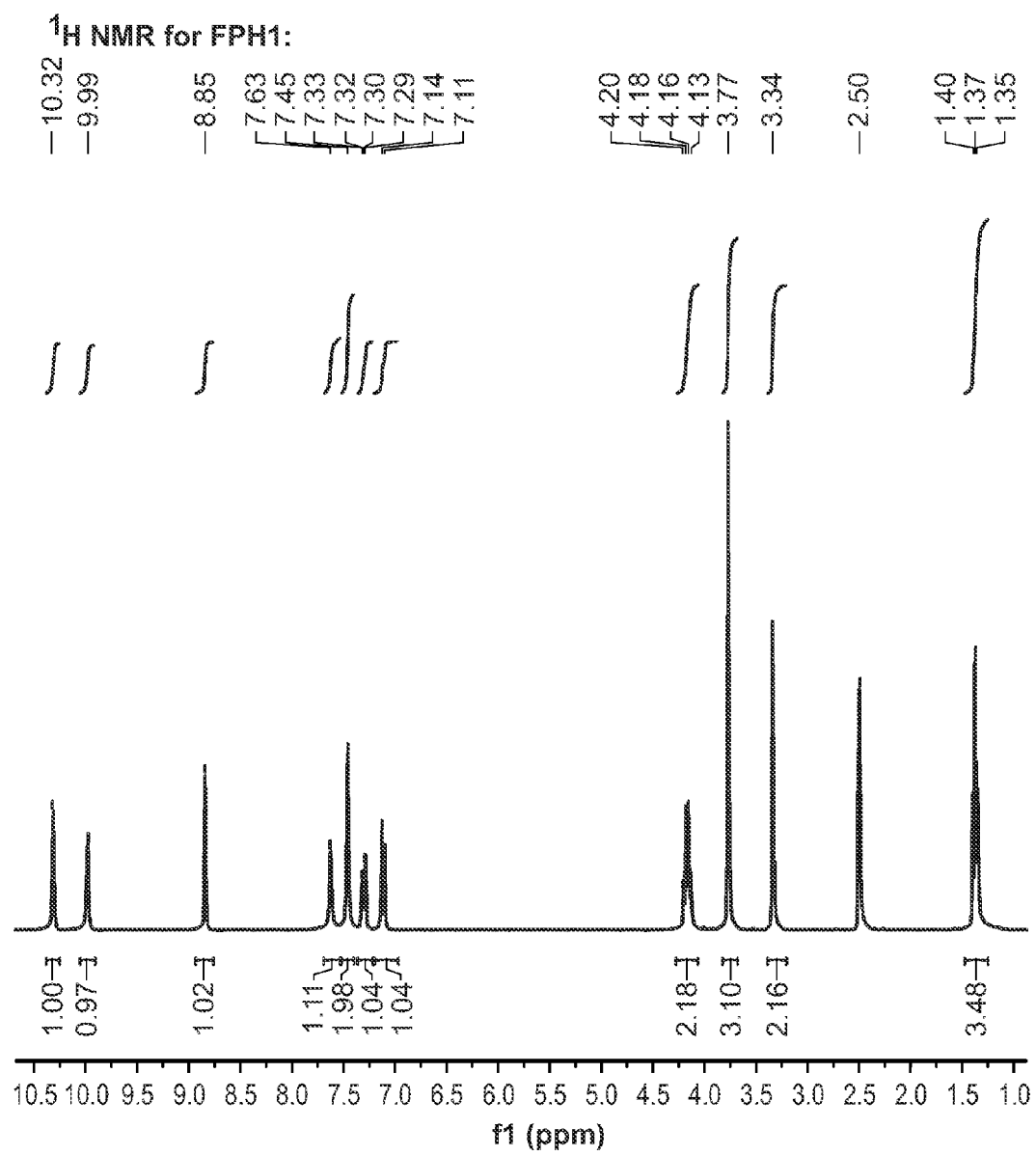
Figure 14C:
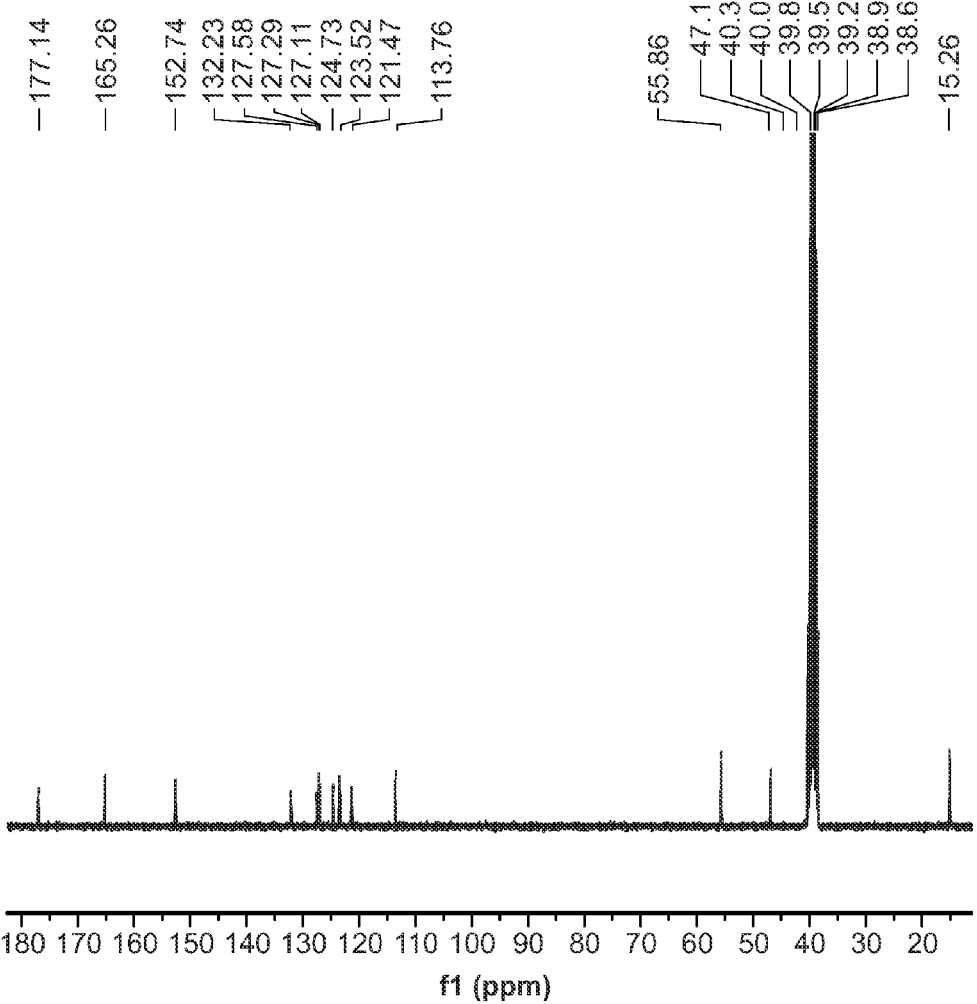
Figure 15A:
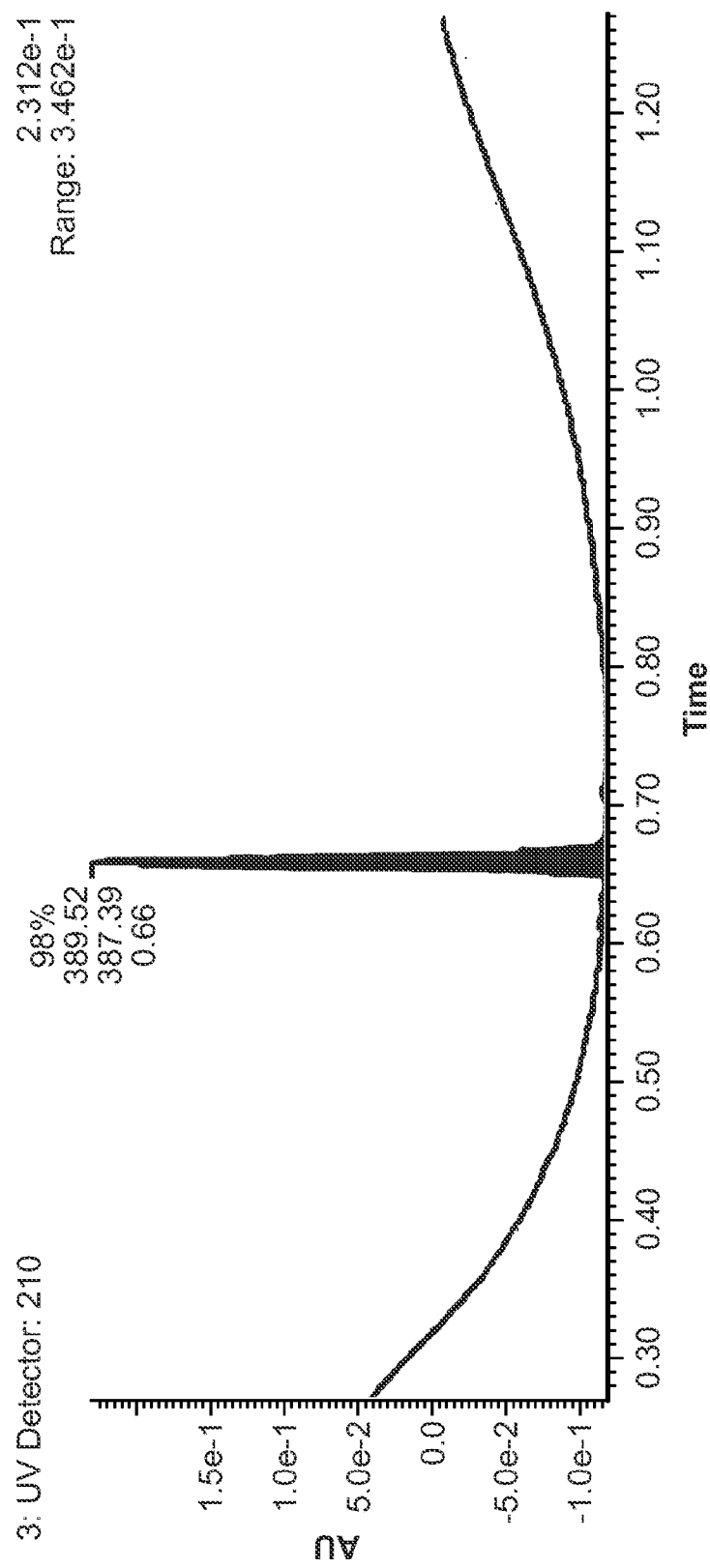
FIG. 15, comprising FIGS. 15A-15C, comprises a set of plots illustrating analytical data for FPH2: liquid chromatography (FIG. 15A) and NMR (FIGS. 15B-15C).
Figure 15B:
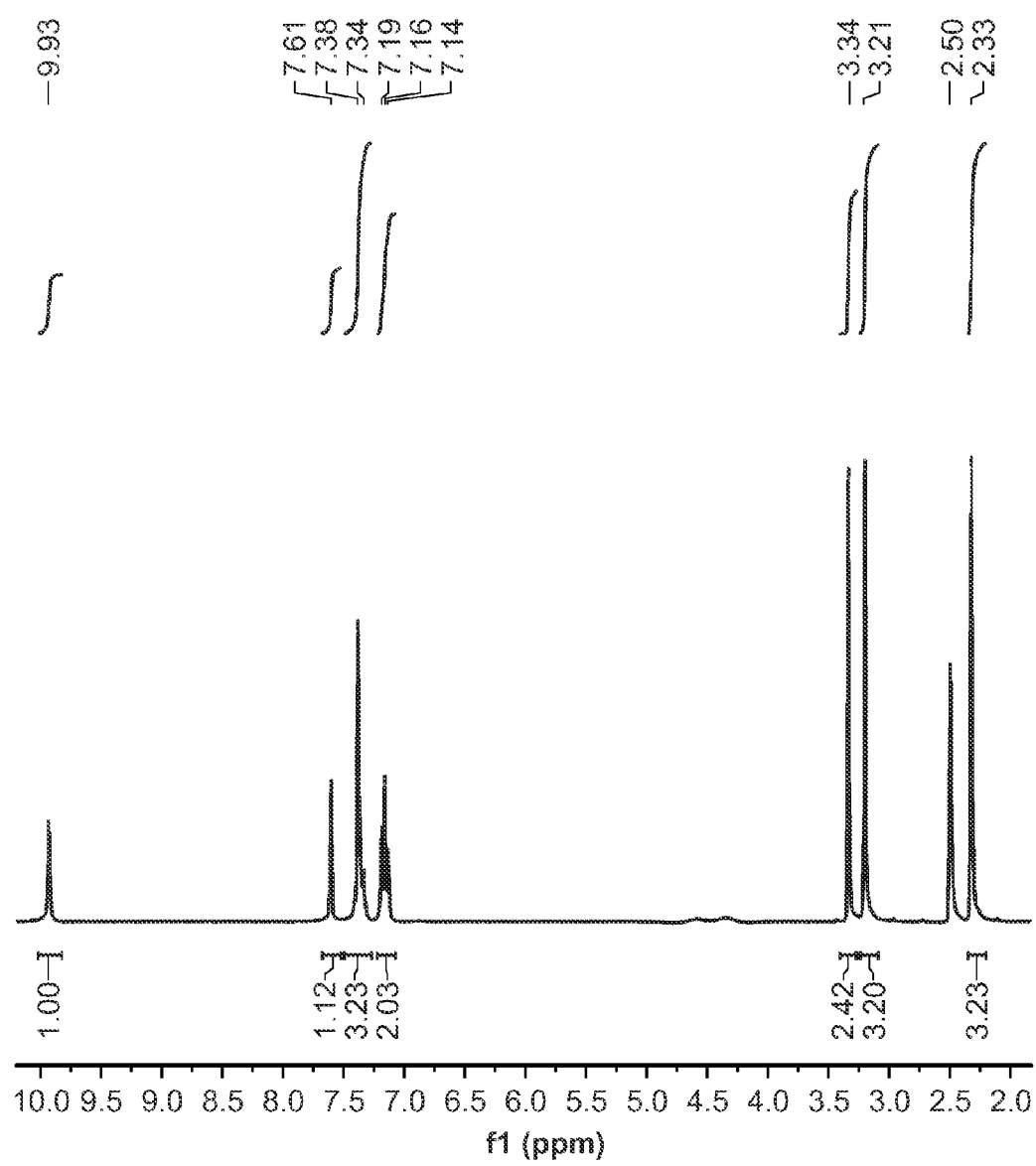
Figure 15C:
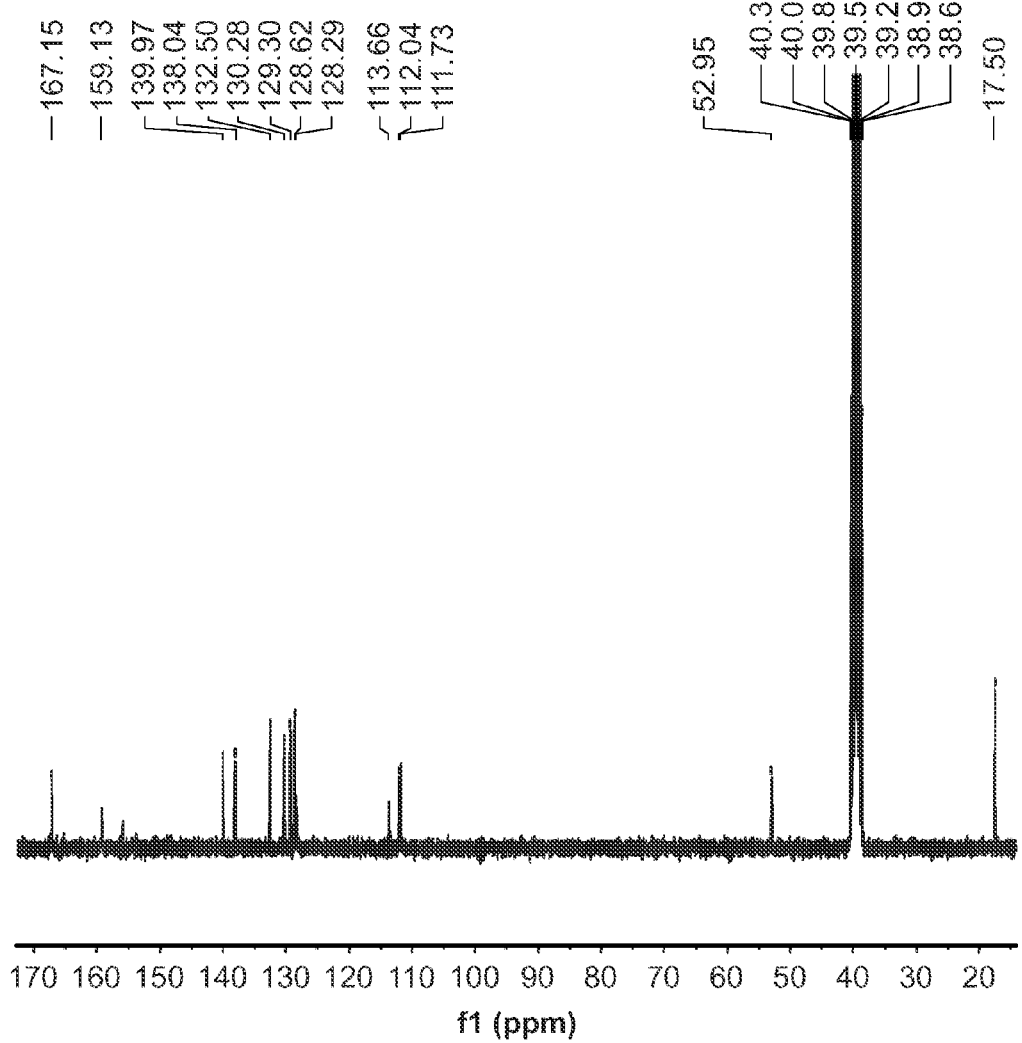
Figure 16:
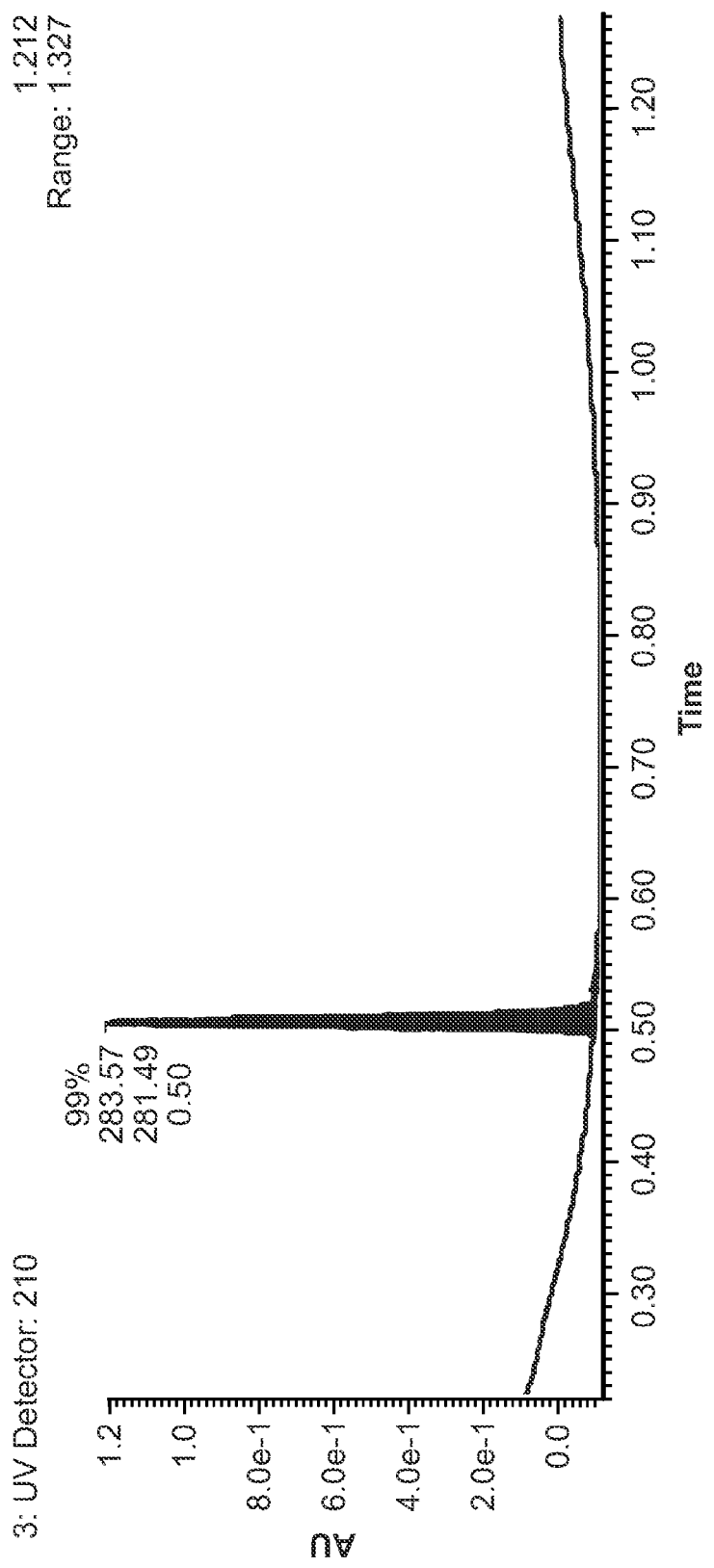
FIG. 16 comprises a plot illustrating liquid chromatography data for FH1.

Compounds were purchased from commercial suppliers and analyzed by liquid chromatography (FIGS. 14A, 15A and 16), $^1$H-NMR mass spectrometry (FIGS. 14B and 15B) and $^{13}$C-NMR mass spectrometry (FIGS. 14C and 15C). FPH1 and FH1 were purchased as a dry powder from Molport. FPH2 was purchased as a dry powder from ChemBridge Corporation.

FPH1:

LCMS: Expected [M+H]+ 354.0786, Determined [M+H]+ 354.0793; HPLC: 94% (@ 210 nm) (Rt; 0.60). $^1$H NMR (300 MHz, DMSO-$_{d6}$) δ 10.32 (s, 1H), 9.99 (s, 1H), 8.85 (s, 1H), 7.63 (s, 1H), 7.46 (s, 2H), 7.31 (dd, J=8.8, 2.4 Hz, 1H), 7.12 (d, J=8.9 Hz, 1H), 4.17 (q, J=7.2 Hz, 2H), 3.77 (s, 3H), 3.34 (s, 2H), 1.37 (t, J=7.2 Hz, 3H). $^{13}$C NMR (75 MHz, DMSO-d$_6$) δ 177.14, 165.26, 152.74, 132.23, 127.58, 127.29, 127.11, 124.73, 123.52, 121.47, 113.76, 55.86, 47.10, 15.26.

FPH2:

LCMS: Expected [M+H]+ 389.0533, Determined [M+H]+ 389.0534; HPLC: 98% (@ 210 nm) (Rt; 0.66). $^1$H NMR (300 MHz, DMSO-d$_6$) δ 9.93 (s, 1H), 7.61 (s, 1H), 7.36 (m, 3H), 7.16 (t, J=8.2 Hz, 2H), 3.34 (s, 2H), 3.21 (s, 3H), 2.33 (s, 3H). $^{13}$C NMR (75 MHz, DMSO-d$_6$) δ 167.15, 159.13, 139.97, 138.04, 132.50, 130.28, 129.30, 128.62, 128.29, 113.66, 112.04, 111.73, 52.95, 17.50.

Luminex Analysis

Cells were lysed using RLT buffer (Qiagen) or Trizol (Invitrogen) and purified using the Mini-RNeasy kit (Qiagen). Gene expression was determined using Luminex analysis, as previously described. Briefly, total RNA was immobilized on a Qiagen turbo capture 384-well plate, and reverse-transcribed using oligodT priming A biotinylated FlexMap tag sequence unique to each gene of interest and a phosphorylated downstream probe were then added to resulting cDNAs to generate biotinylated FlexMap-tagged amplicons. Universal PCR was then performed for 35 cycles using a biotinylated T7 forward primer and T3 reverse primer in buffer with dNTPs and Taq polymerase. FlexMap microsphere beads conjugated with antitag oligonucleotides were then added and allowed to hybridize. Amplicons were captured by streptavidin-phyoerythrin, and 100 events per bead were analyzed for internal bead color and phyoerythrin reporter fluorescence on a Luminex FlexMap 3D analyzer. Data for replicate loadings, expressed in mean fluorescent intensity of at least 100 beads per sample, were scaled to the human transferrin gene and row-normalized for heat map representation using GeneE open software (Broad Institute).

Biochemical Assays

Culture media were collected and frozen at −20° C. until analysis. Albumin content was measured through sandwich ELISA assays (MP Biomedicals, Fitzgerald, Bethyl Laboratories) using horseradish peroxidase detection and 3,3',5,5'-tetramethylbenzidine (TMB, Fitzgerald Industries) as a substrate. Urea concentration was determined colorimetrically using diacetylmonoxime with acid and heat (Stanbio Labs). To quantify CYP450 activity, at 48 hours after small molecule exposure, cultures were incubated with substrates (coumarin from Sigma for CYP2A6, luciferin-IPA from Promega for CYP3A4) for 4 hours at 37° C. Incubation medium was collected and metabolite concentration quantified via luminescence, or fluorescence after hydrolization of potential metabolite conjugates by β-glucuronidase/arylsulfatase (Roche, Ind.).

Example 1: Preparation of Compounds 2 and 4 (Scheme 1)

General Protocol for Coupling of TBS-Protected Acid with PMB-Protected Alaninol

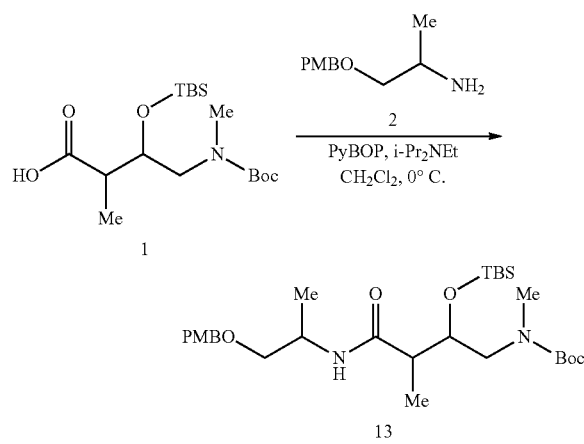

tert-Butyl 2-(tert-butyldimethylsilyloxy)-4-(1-(4-methoxybenzyloxy)propan-2-ylamino)-3-methyl-4-oxobutyl(methyl)carbamate (13)

An oven-dried, 3-L, 3-neck round bottom flask was equipped with an overhead stirrer, addition funnel and a temperature probe. Under a positive flow of $N_2$, the vessel was charged with 4-(tert-butoxycarbonyl(methyl)amino)-3-(tert-butyldimethylsilyloxy)-2-methylbutanoic acid 1 (1.0 equiv) dissolved in $CH_2Cl_2$ (80% of total solvent, final concentration of 1 was 0.2 M), followed by PyBOP (1.0 equiv), and diisopropyl ethylamine (DIPEA) (3.0 equiv). The resulting mixture was cooled in an ice bath before 1-(4-methoxybenzyloxy)propan-2-amine 2 (1.1-1.2 equiv) was added as a solution in $CH_2Cl_2$ (remaining 20% of total solvent) by addition funnel. The rate of addition was controlled so as to maintain an internal temperature between 3-5° C. When addition was complete, the mixture was warmed to ambient temperature and allowed to stir for 15 h. The reaction was quenched with water, and extracted with $CH_2Cl_2$. The combined organic extracts were dried over $MgSO_4$, filtered and concentrated. The yellow oil was taken up in ethyl ether, and the phosphoramide byproducts were removed via filtration. The solvent was removed in vacuo and the crude product was isolated. Flash chromatography on silica gel (4:1 Hexanes/EtOAc to 7:3 Hexanes/EtOAc) gave the product 13 as a colorless oil.

Linear Amide (13a)

Following the general reaction protocol (−)-1a (124 g, 343 mmol, 1.0 equiv) was reacted with PyBOP (179 g, 343 mmol, 1.0 equiv), DIPEA (180 mL, 1030 mmol, 3.0 equiv) and (R)-alaninol (−)-2 (73.7 g, 378 mmol, 1.1 equiv) in $CH_2Cl_2$ (1450 mL), which provided pure product (2R,5R,6R)-13 (176 g, 95%) as a clear oil.

(2R,5R,6R)-13a: $[\alpha]_D^{20}$ −22.0 (c 1.0, $CHCl_3$). IR ($cm^{-1}$) 3337, 2930, 1695, 1673, 1513, 1460, 1390, 1364, 1247, 1156. $^1$H NMR (500 MHz, $CDCl_3$, 55° C.) δ 7.20 (d, J=8.5 Hz, 2H), 6.84 (d, J=8.5 Hz, 2H), 6.57 (br s, 1H, NH), 4.46 (d, J=11.6, 1H), 4.40 (d, J=11.6, 1H), 4.24-4.17 (m, 1H), 4.12-4.05 (m, 1H), 3.77 (s, 3H), 3.46 (dd, J=3.7, 14.4 Hz, 1H), 3.43 (dd, J=4.4, 9.6 Hz, 1H), 3.38 (dd, J=4.8, 9.6 Hz, 1H), 3.03-2.87 (m, 1H), 2.79 (s, 3H), 2.38 (dq, J=3.7, 7.2 Hz, 1H), 1.44 (s, 9H), 1.15 (d, J=6.7 Hz, 3H), 1.12 (d, J=7.2, 3H), 0.90 (s, 9H), 0.07 (s, 3H), 0.05 (s, 3H). $^{13}$C NMR (125 MHz, $CDCl_3$, 55° C.) δ 172.4 (br), 159.4, 155.7 (br), 130.4, 129.1 (2C), 113.8 (2C), 79.4 (br), 73.9 (br), 72.9, 72.8, 55.2, 51.5, 44.7, 44.5, 36.7 (br), 28.5 (3C), 25.8 (3C), 17.8, 17.7, 12.4, −4.8, −4.9. HRMS (ESI) calcd for $C_{28}H_{50}N_2NaO_9Si$ $[M+Na]^+$: 561.3330. Found: 561.3351.

(2S,5S,6S)-13a: $[\alpha]_D^{20}$ +26.2 (c 1.0, $CHCl_3$).

Linear Amide (13b)

Following the general reaction protocol, (−)-1a (131 g, 362 mmol, 1.0 equiv) was reacted with PyBOP (189 g, 362 mmol, 1.0 equiv), DIPEA (190 mL, 1087 mmol, 3.0 equiv) and (S)-alaninol (+)-2 (78 g, 399 mmol, 1.1 equiv) in $CH_2Cl_2$ (1812 mL), which provided pure product (2S,5R,6R)-13b (156 g, 80%) as a clear oil.

(2S,5R,6R)-13b: $[\alpha]_D^{20}$ −39.9 (c 1.0, $CHCl_3$). IR ($cm^{-1}$) 3338, 2930, 1697, 1675, 1513, 1460, 1390, 1365, 1248, 1157. $^1$H NMR (500 MHz, $CDCl_3$, 55° C.) δ 7.21 (d, J=8.5 Hz, 2H), 6.85 (d, J=8.5 Hz, 2H), 6.41 (br s, 1H, NH), 4.45 (d, J=11.7, 1H), 4.41 (d, J=11.7, 1H), 4.20-4.14 (m, 1H), 4.13-4.04 (m, 1H), 3.78 (s, 3H), 3.47 (dd, J=3.6, 14.3 Hz, 1H), 3.39 (d, J=4.3 Hz, 2H), 3.00-2.85 (m, 1H), 2.86 (s, 3H), 2.38 (dq, J=3.8, 7.2 Hz, 1H), 1.45 (s, 9H), 1.19 (d, J=6.7 Hz, 3H), 1.12 (d, J=7.2, 3H), 0.89 (s, 9H), 0.07 (s, 3H), 0.05 (s, 3H). $^{13}$C NMR (125 MHz, $CDCl_3$, 55° C.) δ 172.3 (br), 159.4, 155.8 (br), 130.5, 129.2 (2C), 113.9 (2C), 79.5 (br), 73.5 (br), 72.93, 72.85, 55.2, 51.8, 44.87, 44.85, 36.7 (br), 28.5 (3C), 25.9 (3C), 17.89, 17.88, 12.6, −4.7, −4.8. HRMS (ESI) calcd for $C_{28}H_{50}N_2NaO_6Si$ [M+Na]$^+$: 561.3330. Found: 561.3313.

(2R,5S,6S)-13b: $[\alpha]_D^{20}$ +42.1 (c 1.0, CHCl$_3$).

Linear Amide (13c)

Following the general reaction protocol, (−)-1b (38.1 g, 105 mmol, 1.0 equiv) was reacted with PyBOP (60.4 g, 116 mmol, 1.1 equiv), DIPEA (55.3 mL, 316 mmol, 3.0 equiv) and (R)-alaninol (−)-2 (24.7 g, 127 mmol, 1.2 equiv) in CH$_2$Cl$_2$ (820 mL), which provided pure product (2R,5R,6S)-13c (51.9 g, 91%) as a clear oil.

(2R,5R,6S)-13c: $[\alpha]_D^{20}$ +17.6 (c 1.0, CHCl$_3$). IR (cm$^{-1}$) 3365, 2930, 1696, 1670, 1513, 1460, 1390, 1365, 1248, 1156. $^1$H NMR (500 MHz, CDCl$_3$, 55° C.) δ 7.22 (d, J=8.5 Hz, 2H), 6.86 (d, J=8.5 Hz, 2H), 6.75 (br s, 1H, NH), 4.46 (d, J=11.7, 1H), 4.41 (d, J=11.7, 1H), 4.22-4.15 (m, 1H), 4.05-3.98 (m, 1H), 3.80 (s, 3H), 3.39 (d, J=4.6 Hz, 2H), 3.34 (dd, J=6.4, 14.0 Hz, 1H), 3.18 (dd, J=6.3, 14.0 Hz, 1H), 2.88 (s, 3H), 2.41 (dq, J=2.9, 7.3 Hz, 1H), 1.46 (s, 9H), 1.22 (d, J=7.2 Hz, 3H), 1.18 (d, J=6.7 Hz, 3H), 0.91 (s, 9H), 0.12 (s, 3H), 0.11 (s, 3H). $^{13}$C NMR (125 MHz, CDCl$_3$, 55° C.) δ 173.4, 159.4, 156.0 (br), 130.6, 129.1 (2C), 113.9 (2C), 79.7 (br), 72.9, 72.8, 72.6 (br), 55.3, 53.5, 44.8, 44.5, 36.6 (br), 28.5 (3C), 25.9 (3C), 18.0, 17.9, 15.6, −4.5, −4.9. HRMS (ESI) calcd for $C_{28}H_{50}N_2NaO_6Si$ [M+Na]$^+$: 561.3330. Found: 561.3498.

(2S,5S,6R)-13c: $[\alpha]_D^{20}$ −16.5 (c 1.0, CHCl$_3$).

Linear Amide (13d)

Following the general reaction protocol, (−)-1b (92 g, 254 mmol, 1.0 equiv) was reacted with PyBOP (132 g, 254 mmol, 1.0 equiv), DIPEA (133 mL, 763 mmol, 3.0 equiv) and (S)-alaninol (+)-2 (59.6 g, 305 mmol, 1.2 equiv) in CH$_2$Cl$_2$ (1957 mL), which provided pure product (S,R,S)-13d (145 g, 70%) as a clear oil.

(2S,5R,6S)-13d: $[\alpha]_D^{20}$ −0.6 (c 1.0, CHCl$_3$). IR (cm$^{-1}$) 3356, 2930, 1695, 1669, 1514, 1466, 1390, 1365, 1248, 1156. $^1$H NMR (500 MHz, CDCl$_3$, 55° C.) δ 7.20 (d, J=8.5 Hz, 2H), 6.87 (br s, 1H, NH), 6.85 (d, J=8.5 Hz, 2H), 4.46 (d, J=11.6, 1H), 4.42 (d, J=11.6, 1H), 4.26-4.17 (m, 1H), 4.02-3.96 (m, 1H), 3.78 (s, 3H), 3.44 (dd, J=4.4, 9.5 Hz, 1H), 3.40-3.30 (m, 1H), 3.36 (dd, J=5.0, 9.5 Hz, 1H), 3.18-3.11 (m, 1H), 2.80 (s, 3H), 2.39 (dq, J=2.8, 7.2 Hz, 1H), 1.44 (s, 9H), 1.22 (d, J=7.3 Hz, 3H), 1.14 (d, J=6.7 Hz, 3H), 0.92 (s, 9H), 0.11 (s, 6H). $^{13}$C NMR (125 MHz, CDCl$_3$, 55° C.) δ 173.6, 159.4, 155.9 (br), 130.5, 129.2 (2C), 113.9 (2C), 79.6 (br), 73.7 (br), 73.0, 72.8, 55.3, 53.5, 44.6, 44.4, 36.8, 28.5 (3C), 25.9 (3C), 18.0, 17.7, 16.0, −4.3, −4.8. HRMS (ESI) calcd for $C_{28}H_{50}N_2NaO_6Si$ [M+Na]$^+$: 561.3330. Found: 561.3331.

(2R,5S,6R)-13d: $[\alpha]_D^{20}$ +1.4 (c 1.0, CHCl$_3$).

General Protocol for the Reduction of Amide

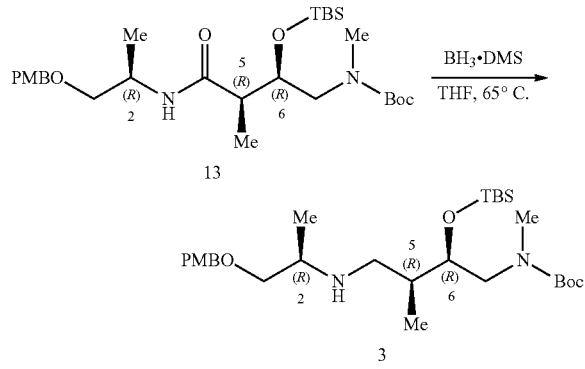

tert-Butyl 2-(tert-butyldimethylsilyloxy)-4-(1-(4-methoxybenzyloxy)propan-2-ylamino)-3-methylbutyl(methyl)carbamate (3)

An oven-dried, 2-L, 1-necked round bottom flask was equipped with a magnetic stirrer. Under a positive flow of N$_2$, the flask was charged with tert-butyl 2-(tert-butyldimethylsilyloxy)-4-(1-(4-methoxybenzyloxy)propan-2-ylamino)-3-methyl-4-oxobutyl(methyl)carbamate 13 (1.0 equiv) and anhydrous THF (final concentration 0.1 M). Borane dimethylsulfide complex (BH$_3$DMS) (5.0 equiv) was added dropwise via syringe. Afterwards the reaction mixture was heated at 65° C. for 5 h. After cooling to ambient temperature, excess hydride was quenched by the careful addition of MeOH. The mixture was concentrated under reduced pressure to afford a colorless oil, which was then co-evaporated with MeOH three times to remove excess B(OMe)$_3$. The oil was then re-dissolved in MeOH and 10% aqueous potassium sodium tartrate (2:3 ratio, final concentration 0.067 M). The resulting slurry was heated at reflux for 12 h. The volatiles were removed under reduced pressure and aqueous layer was extracted three times with ethyl acetate. The combined organic layers were washed once with brine, dried over magnesium sulfate, filtered and concentrated to provide the desired amine 3 as a colorless oil.

Linear Amine (3a)

Following the general reaction protocol (2R,5R,6R)-13a (100 g, 186 mmol, 1.0 equiv) was reacted with BH$_3$DMS (88.0 mL, 930 mmol, 5.0 equiv) in THF (1860 mL), and worked up with 10% aqueous potassium sodium tartrate (2 L) in MeOH (1.70 L), which provided pure product (2R,5S,6R)-(−)-3a (92.7 g, 95%) as a clear oil.

(2R,5S,6R)-(−)-3a: $[\alpha]_D^{20}$ −16.15 (c 1.38, MeOH). IR (cm$^{-1}$) 3010, 2929, 1687, 1513, 1462, 1389, 1247, 1153. $^1$H NMR (500 MHz, CDCl$_3$, 60° C.) δ 7.20 (d, J=8.5 Hz, 2H), 6.83 (d, J=8.5 Hz, 2H), 4.41 (s, 2H), 3.95 (ddd, J=11, 6, 5 Hz, 1H), 3.76 (s, 3H), 3.36 (dd, J=14, 6 Hz, 1H), 3.31 (m, 2H), 2.97 (dd, J=14, 7 Hz, 1H), 2.83 (m, 4H), 2.60 (dd, J=11, 6 Hz, 1H), 2.45 (dd, J=11, 6 Hz, 1H), 1.65 (ddd, J=12, 6, 5 Hz, 1H), 1.43 (s, 9H), 0.98 (d, J=6 Hz, 3H), 0.90 (d, J=6 Hz, 3H), 0.87 (s, 9H), 0.03 (s, 6H). $^{13}$C NMR (125 MHz, CDCl$_3$, 60° C.) δ 159.4, 155.7, 130.8, 129.1, 113.9, 79.3, 74.7, 72.9, 72.3, 55.2, 52.9, 52.3, 50.1, 37.3, 36.2, 28.6, 26.0, 18.1, 17.5, 12.8, −4.7. HRMS (ESI) calcd for $C_{28}H_{53}N_2O_5Si$ [M+H]$^+$: 525.3718. Found: 525.3709.

(2S,5R,6S)-(+)-3a: $[\alpha]_D^{20}$ +19.09 (c 2.98, CHCl$_3$).

Linear Amine (3b)

Following the general reaction protocol, (2S,5R,6R)-13b (33.15 g, 61.5 mmol, 1.0 equiv) was reacted with BH$_3$DMS (29.2 mL, 308 mmol, 5.0 equiv) in THF (615 mL), and worked up with 10% aqueous potassium sodium tartrate (650 mL) in MeOH (450 mL), which provided pure product (2S,5S,6R)-(−)-3b (30.96 g, 96%) as a clear oil.

(2S,5S,6R)-(−)-3b: $[\alpha]_D^{20}$ −13.82 (c 1.23, MeOH). IR (cm$^{-1}$) 3010, 2929, 1692, 1513, 1461, 1389, 1247, 1152. $^1$H NMR (500 MHz, CDCl$_3$, 60° C.) δ 7.14 (d, J=8.5 Hz, 2H), 6.76 (d, J=8.5 Hz, 2H), 4.36 (d, J=12 Hz, 1H), 4.33 (d, J=12 Hz, 1H), 3.94 (ddd, J=11, 6, 5 Hz, 1H), 3.68 (s, 3H), 3.32-3.26 (m, 2H), 3.22 (dd, J=14, 7 Hz, 1H), 2.91 (dd, J=13, 6.5 Hz, 1H), 2.76 (m, 4H), 2.61 (m, 1H), 2.31 (dd, J=11, 7.5 Hz, 1H), 1.60 (m, 1H), 1.38 (s, 9H), 0.93 (d, J=6 Hz, 3H), 0.83 (d, J=6 Hz, 3H), 0.82 (s, 9H), −0.02 (s, 3H), −0.028 (s, 3H). $^{13}$C NMR (125 MHz, CDCl$_3$, 60° C.) δ 159.3, 155.7, 130.7, 129.1, 113.9, 79.2, 74.6, 72.9, 71.7, 55.1, 52.9, 52.3, 50.1, 36.9, 36.0, 28.5, 26.0, 18.0, 17.6, 12.6, −4.6. HRMS (ESI) calcd for $C_{28}H_{53}N_2O_5Si$ [M+H]$^+$: 525.3718. Found: 525.3702.

(2R,5R,6S)-(+)-3b: $[\alpha]_D^{20}$ +15.89 (c 7.30, CHCl$_3$).

Linear Amine (3c)

Following the general reaction protocol, (2R,5R,6S)-13c (36.0 g, 66.8 mmol, 1.0 equiv) was reacted with BH$_3$DMS (31.7 mL, 334 mmol, 5.0 equiv) in THF (668 mL), and worked up with 10% aqueous potassium sodium tartrate (900 mL) in MeOH (600 mL), which provided pure product (2R,5S,6S)-(+)-3c (31.5 g, 90%) as a clear oil.

(2R,5S,6S)-(+)-3c: $[\alpha]_D^{20}$ +7.77 (c 0.99, MeOH). IR (cm$^{-1}$) 3010, 2929, 1693 1513 1461, 1389, 1247, 1152. $^1$H NMR (500 MHz, CDCl$_3$, 60° C.) δ 7.19 (d, J=8.5 Hz, 2H), 6.82 (d, J=8.5 Hz, 2H), 4.40 (s, 2H), 3.89 (m, 1H), 3.74 (s, 3H), 3.29 (m, 4H), 2.98 (dd, J=13.5, 7.5 Hz, 1H), 2.85 (m, 4H), 2.63 (m, 1H), 2.41 (dd, J=11, 9 Hz, 1H), 1.72 (m, 1H), 1.41 (s, 9H), 0.98 (d, J=6.5 Hz, 1H), 0.92 (d, J=6.5 Hz, 1H), 0.86 (s, 9H), 0.02 (s, 3H), 0.00 (s, 3H). $^{13}$C NMR (125 MHz, CDCl$_3$, 60° C.) δ 159.3, 155.7, 130.8, 129.1, 113.9, 79.1, 74.6, 73.3, 72.8, 55.2, 52.5, 52.0, 49.4, 38.7, 36.4, 28.6, 26.0, 18.0, 17.6, 13.7, −4.5. HRMS (ESI) calcd for $C_{28}H_{53}N_2O_5Si$ [M+H]$^+$: 525.3718. Found: 525.3698.

(2S,5R,6R)-(−)-3c: $[\alpha]_D^{20}$ −10.65 (c 2.46, CHCl$_3$).

Linear Amine (3d)

Following the general reaction protocol, (2S,5R,6S)-13d (55.0 g, 102 mmol, 1.0 equiv) was reacted with BH$_3$DMS (48.4 mL, 510 mmol, 5.0 equiv) in THF (1030 mL), and worked up with 10% aqueous potassium sodium tartrate (900 mL) in MeOH (600 mL), which provided pure product (2S,5S,6S)-(−)-3d (52.76 g, 98%) as a clear oil.

(2S,5S,6S)-(+)-3d: $[\alpha]_D^{20}$ +13.7 (c 2.62, CHCl$_3$). IR (cm$^{-1}$) 3010, 2929, 1692, 1512, 1461, 1389, 1247, 1152. $^1$H NMR (500 MHz, CDCl$_3$, 60° C.) δ 7.19 (d, J=8.5 Hz, 2H), 6.81 (d, J=8.5 Hz, 2H), 4.41 (d, J=12 Hz, 1H), 4.39 (d, J=12 Hz, 1H), 3.92-3.90 (m, 1H), 3.74 (s, 3H), 3.35-3.28 (m, 3H), 2.98 (dd, J=14, 7.5 Hz, 1H), 2.84-2.80 (m, 4H), 2.70 (m, 1H), 2.32 (dd, J=11, 7.5 Hz, 1H), 1.75 (ddd, J=14, 7 Hz, 1H), 1.42 (s, 9H), 0.98 (d, J=6.5 Hz, 3H), 0.91 (d, J=6.5 Hz, 3H), 0.86 (s, 9H), 0.02 (s, 3H), 0.00 (s, 3H). $^{13}$C NMR (125 MHz, CDCl$_3$, 60° C.) δ 159.4, 155.9, 130.8, 129.2, 114.0, 79.3, 74.6, 73.3, 73.0, 55.3, 53.3, 52.0, 49.8, 38.7, 36.5, 28.7, 26.1, 18.1, 17.6, 13.7, −4.2. HRMS (ESI) calcd for $C_{28}H_{53}N_2O_5Si$ [M+H]$^+$: 525.3718. Found: 525.3718.

(2R,5R,6R)-(−)-3d: $[\alpha]_D^{20}$ −15.07 (c 6.40, CHCl$_3$).

General Protocol for Preparation of S$_N$Ar Precursors (S$_N$Ar-Pyr)

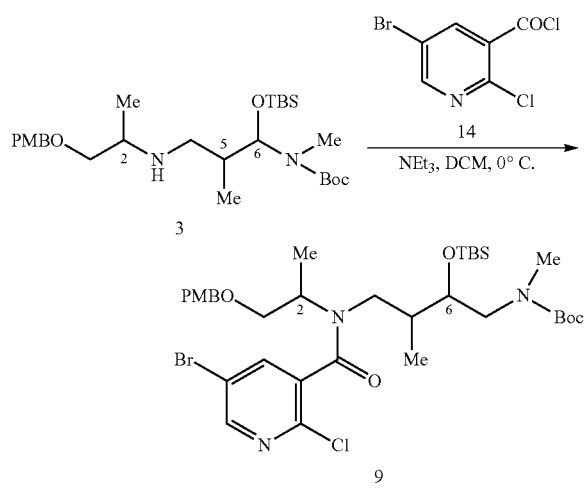

Triethylamine (4.0 equiv) was added to a solution of amine 3 (1.0 equiv) and 5-bromo-2-chloronicotinoyl chloride (Cho, et al., 2010, J. Bioorg. Med. Chem. Lett. 20:4223-4227) 14 (2.0 equiv) in CH$_2$Cl$_2$ (0.2 M) at 0° C. under dry nitrogen atmosphere. The reaction was warmed to RT and stirred until complete consumption of starting amine was observed (1-2 h). The reaction was quenched with a saturated NH$_4$Cl solution and the resulting mixture was extracted with CH$_2$Cl$_2$. The combined organic extracts were dried over MgSO$_4$, filtered and concentrated. Flash chromatography on silica gel (gradient: 10% to 30% EtOAc in hexanes) provided the product 9 as a white foaming solid.

S$_N$Ar Precursor (9a)

Following the general reaction protocol (2R,5S,6R)-3a (26.4 g, 50.3 mmol, 1.0 equiv) was reacted with 5-bromo-2-chloronicotinoyl chloride 14 (25.6 g, 101 mmol, 2.0 equiv) and triethylamine (27.9 mL, 201 mmol, 4.0 equiv) in CH$_2$Cl$_2$ (250 mL), which provided pure product (2R,5S,6R)-9a (35.6 g, 95%).

(2R,5S,6R)-9a: $[\alpha]_D^{20}$ +9.1 (c 1.0, CHCl$_3$). IR (cm$^{-1}$) 2954, 2930, 2857, 1696, 1645, 1249, 1155, 836. $^1$H NMR (500 MHz, CDCl$_3$, 2.3:1 mixture of rotamers) δ 8.47-8.42 (m, 1H, ×0.3), 8.39-8.35 (m, 1H×0.7), 7.73-7.69 (m, 1H×0.3), 7.57-7.53 (m, 1H×0.7), 7.24 (d, J=8.5 Hz, 2H×0.3), 7.19 (d, J=8.5 Hz, 2H×0.7), 6.90-6.83 (m, 2H), 4.50-4.41 (m, 2H×0.3), 4.39-4.31 (m, 2H×0.7), 4.01-3.85 (m, 1H), 3.80 (s, 3H×0.7), 3.78 (s, 3H×0.3), 3.85-3.56 (m, 2H), 3.51-3.32 (m, 1H), 3.27-3.09 (m, 1H), 3.20 (d, J=10.0 Hz, 1H), 2.90 (d, J=13.6 Hz, 2H), 2.75 (d, J=10.5 Hz, 1H), 2.12 (br s, 1H×0.7), 1.93 (br s, 1H×0.3), 1.45 (s, 9H), 1.40 (d, J=6.9 Hz, 3H×0.7), 1.17 (d, J=6.9 Hz, 3H×0.3), 1.10 (s, 9H×0.3), 0.92 (s, 9H×0.7), 0.73 (s, 3H×0.3), 0.68 (s, 3H×0.7), 0.07 (s, 3H×0.7), 0.03 (s, 3H×0.3), 0.06 (s, 3H×0.7), −0.14 (s, 3H×0.3). $^{13}$C NMR (125 MHz, CDCl$_3$, reported as a mixture of rotamers) δ 167.5, 165.9, 159.7, 159.4, 156.1, 155.8, 150.7, 150.4, 145.6, 145.3, 141.9, 140.2, 138.9, 138.5, 135.0, 134.9, 129.9, 129.8, 129.7, 129.6, 119.5, 119.3, 114.3, 114.1, 114.0, 113.9, 79.9, 79.6, 74.1, 73.3, 73.2, 73.1, 70.3, 70.2, 55.5, 54.4, 55.1, 55.0, 52.0, 51.9, 43.1, 42.7, 38.5, 38.0, 36.8, 36.7, 28.8, 28.7, 26.3, 26.2, 18.2, 17.9, 16.5, 16.4, 13.3, 13.0, −4.2. HRMS (ESI) calcd for $C_{34}H_{55}BrClN_3O_6Si$ [M+H]$^+$: 742.2576. Found: 742.2642.

S$_N$Ar Precursor (9b)

Following the general reaction protocol (2S,5S,6R)-3b (26.2 g, 49.9 mmol, 1.0 equiv) was reacted with 5-bromo-2-chloronicotinoyl chloride 14 (25.5 g, 100 mmol, 2.0 equiv) and triethylamine (27.7 mL, 200 mmol, 4.0 equiv) in CH$_2$Cl$_2$ (250 mL), which provided pure product (2S,5S,6R)-9b (34.8 g, 94%).

(2S,5S,6R)-9b: $[\alpha]_D^{20}$ −36.2 (c 1.8, CHCl$_3$). IR (cm$^{-1}$) 2954, 2930, 2857, 1687, 1637, 1513, 1462, 1401, 1249, 1155, 1098, 1034. $^1$H NMR (500 MHz, CDCl$_3$, 3:1 mixture of rotamers) δ 8.38 (s, 1H×0.25), 8.33 (s, 1H×0.75), 7.69 (s, 1H×0.25), 7.59 (s, 1H×0.75), 7.24-7.16 (2H, m), 6.90-6.81 (m, 2H×0.75), 6.89-6.80 (m, 2H×0.25), 4.50-4.40 (m, 2H × 0.25), 4.34-4.26 (m, 2H×0.75), 4.01-3.96 (m, 1H×0.25), 3.89-3.83 (m, 1H×0.75), 3.77 (s, 3H×0.75), 3.75 (s, 3H×0.25), 3.72-3.65 (m, 1H), 3.60-3.55 (m, 1H), 3.35-3.24 (m, 3H), 3.00 (s, 3H), 2.86-2.81 (m, 1H), 2.47-2.42 (m, 1H), 1.47 (s, 9H), 1.19 (s, 3H×0.75) 1.05 (s, 3H×0.25), 0.92 (s, 9H), 0.90-0.70 (m, 3H), 0.11-0.09 (m, 6H). $^{13}$C NMR (125 MHz, CDCl$_3$, reported as a mixture of rotamers) δ 167.5, 167.4, 159.7, 155.9, 150.5, 150.4, 145.1, 134.8, 134.7, 129.8, 129.6, 119.4, 114.3, 113.9, 79.7, 74.0, 73.3, 73.2, 73.0, 71.0, 55.5, 54.9, 54.8, 52.4, 51.9, 43.4, 43.0, 36.8, 36.6, 35.7, 35.6, 35.0, 28.9, 28.8, 28.6, 26.2, 25.9, 18.2, 18.0, 16.0, 15.9, 14.4, −4.3. HRMS (ESI) calcd for $C_{34}H_{55}BrClN_3O_6Si$ [M+H]$^+$: 742.2576. Found: 742.2662.

S$_N$Ar Precursor (9c)

Following the general reaction protocol, (2R,5S,6S)-3c (36.0 g, 68.6 mmol, 1.0 equiv) was reacted with 5-bromo-2-chloronicotinoyl chloride 14 (35.0 g, 137 mmol, 2.0 equiv) and triethylamine (38.0 mL, 274 mmol, 4.0 equiv) in CH$_2$Cl$_2$ (500 mL), which provided pure product (2R,5S,6S)-9c (42.8 g, 84%).

(2R,5S,6S)-9c: [α]$_D^{20}$ +19.9 (c 1.0, CHCl$_3$). IR (cm$^{-1}$) 2956, 2933, 2857, 1693, 1643, 1249, 1157, 837. $^1$H NMR (500 MHz, CDCl$_3$, 2:1 mixture of rotamers) δ 8.46 (br s, 1H×0.33), 8.37 (br s, 1H×0.66), 7.69 (br s, 1H×0.33), 7.61 (br s, 1H×0.66), 7.24 (d, J=7.5 Hz, 2H×0.33), 7.18 (d, J=7.5 Hz, 2H×0.66), 6.91-6.85 (m, 2H), 4.50-4.22 (m, 2H), 4.16-4.10 (m, 1H×0.33), 3.97-3.91 (m, 1H×0.66), 3.81 (s, 3H×0.66), 3.79 (s, 3H×0.33), 3.69-3.62 (m, 1H), 3.57-3.51 (m, 1H), 3.47-3.29 (m, 1H), 3.29-3.16 (m, 1H), 3.13-2.98 (m, 1H), 2.96-2.89 (m, 2H), 2.84-2.76 (m, 1H), 2.13 (br s, 1H×0.66), 1.92 (br s, 1H×0.33), 1.46 (s, 9H×0.66), 1.44 (s, 9H×0.33), 1.43 (s, 3H×0.33), 1.18 (s, 3H×0.66), 1.10 (s, 9H×0.33), 0.92 (s, 9H×0.66), 0.75 (s, 3H×0.33), 0.66 (s, 3H×0.66), 0.08 (s, 3H×0.66), −0.05 (s, 3H×0.33), −0.06 (s, 3H×0.66), −0.13 (s, 3H×0.33). $^{13}$C NMR (125 MHz, CDCl$_3$, reported as a mixture of rotamers) δ 167.2, 165.9, 159.6, 159.2, 156.1, 155.9, 150.4, 150.2, 141.9, 141.7, 140.0, 138.5, 135.1, 134.8, 129.7, 129.5, 129.4, 129.3, 119.3, 119.2, 114.2, 114.0, 79.8, 79.5, 74.4, 73.3, 73.1, 72.9, 71.8, 70.4, 55.5, 55.4, 55.1, 54.9, 52.6, 52.0, 51.8, 50.3, 42.8, 42.2, 38.4, 38.1, 37.3, 36.8, 28.7, 28.5, 26.1, 25.8, 18.1, 17.9, 16.3, 15.9, −4.3, −4.4. HRMS (ESI) calcd for $C_{34}H_{55}BrClN_3O_6Si$ [M+H]$^+$: 742.2576. Found: 742.2648.

S$_N$Ar Precursor (9d)

Following the general reaction protocol (2S,5S,6S)-3d (36.0 g, 68.6 mmol, 1.0 equiv) was reacted with 5-bromo-2-chloronicotinoyl chloride 14 (35.0 g, 137 mmol, 2.0 equiv) and triethylamine (38.0 mL, 274 mmol, 4.0 equiv) in CH$_2$Cl$_2$ (500 mL), which provided pure product (2S,5S,6S)-9d (48.5 g, 95%).

(2S,5S,6S)-9d: [α]$_D^{20}$ −28.4 (c 2.4, CHCl$_3$). IR (cm$^{-1}$) 2954, 2930, 2856, 1694, 1643, 1513, 1401, 1249, 1155, 1098, 1034. $^1$H NMR (500 MHz, CDCl$_3$, 2:1 mixture of rotamers) δ 8.37 (s, 1H×0.33), 8.32 (s, 1H×0.66), 7.70 (d, J=2.5 Hz, 2H×0.33), 7.57 (d, J=2.5 Hz, 2H×0.66), 7.25 (d, J=8.5 Hz, 2H, x 0.33), 7.16 (d, J=8.5 Hz, 2H×0.66), 6.87 (d, J=8.5 Hz, 2H×0.66), 6.80 (d, J=8.5 Hz, 2H×0.33), 4.55-4.43 (m, 2H×0.33), 4.35-4.25 (m, 2H×0.66), 4.02-3.96 (m, 1H), 3.76 (3H, s) 3.71-3.54 (2H, m), 3.48 (dd, J=8.5, 5.0 Hz, 1H), 3.25-3.16 (m, 2H), 3.04-2.92 (m, 2H), 2.88-2.85 (m, 3H), 2.80-2.73 (m, 1H), 1.44 (s, 9H), 1.13-0.98 (m, 3H), 0.90 (s, 9H), 0.08 (s, 6H). $^{13}$C NMR (125 MHz, CDCl$_3$, reported as a mixture of rotamers) δ 167.4, 165.8, 159.5, 159.3, 150.5, 150.2, 145.5, 145.0, 142.0, 134.8, 130.3, 129.7, 129.5, 129.3, 119.3, 119.2, 114.1, 113.9, 113.8, 79.7, 79.3, 73.1, 72.8, 72.2, 71.0, 70.8, 55.3, 55.3, 52.5, 51.9, 44.9, 44.8, 36.0, 34.9, 34.7, 28.6, 28.5, 26.0, 25.6, 18.1, 17.7, 15.7, 14.3, 12.2, −4.3. HRMS (ESI) calcd for $C_{34}H_{55}BrClN_3O_6Si$ [M+H]$^+$: 742.2576. Found: 742.2646.

General Protocol for the S$_N$Ar Cycloetherification (S$_N$Ar-Pyr)

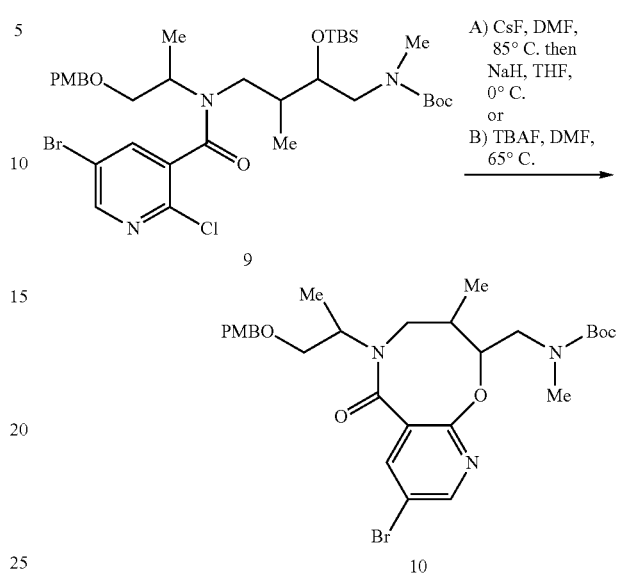

Protocol A:

Cesium fluoride (5 equiv) was added to a solution of amide 9 (1.0 equiv) in DMF (0.1 M) at RT under N$_2$. The reaction was heated to 85° C. and stirred until complete consumption of starting material was observed (8-12 h). The reaction was cooled and quenched with a saturated NH$_4$Cl solution. The resulting mixture was extracted with EtOAc. The combined organic extracts were dried over MgSO$_4$, filtered and concentrated. The resulting crude product was dissolved in THF before NaH (1.0 equiv) was added. The mixture was stirred at 60° C. until the reaction was complete by LC/MS (~1 h). The mixture was cooled and quenched with a saturated NH$_4$Cl solution. The resulting mixture was extracted with EtOAc. The combined organic extracts were dried over MgSO$_4$, filtered and concentrated to provide desired 10 in >95% purity. The material was used without further purification.

Protocol B:

Tetrabutylammonium fluoride (5 equiv) was added to a solution of amide 9 (1.0 equiv) in DMF (0.1 M) at 65° C. under N$_2$. The reaction was monitored by LC/MS (7-8 h) and upon completion, cooled and concentrated. The resulting crude product was taken up in a saturated NH$_4$Cl solution and extracted with EtOAc. The combined organic extracts were dried over MgSO$_4$, filtered and concentrated. Flash chromatography on silica gel (gradient: 0% to 30% EtOAc in hexanes) provided cyclic product 10.

Eight-Atom Membered Lactam (10a)

Following protocol A, (2R,5S,6R)-9a (20.9 g, 28.1 mmol, 1.0 equiv) was reacted with cesium fluoride (21.4 g, 141 mmol, 5.0 equiv) in DMF (280 mL), followed by reaction with NaH (60% dispersion in oil, 1.2 g, 28.1 mmol, 1.0 equiv) in THF (280 mL) which provided product (2R,5S,6R)-10a (16.4 g, 98%).

(2R,5S,6R)-10a: [α]$_D^{20}$ +37.7 (c 1.0, CHCl$_3$). IR (cm$^{-1}$) 2974, 1690, 1627, 1424, 1246, 1153. $^1$H NMR (500 MHz, DMSO-d$_6$, 110° C.) δ 8.23 (d, J=2.5 Hz, 1H), 7.97 (d, J=2.5 Hz, 1H), 7.25 (d, J=8.5 Hz, 2H), 6.90 (d, J=8.5 Hz, 2H), 4.68 (t, J=5.5 Hz, 1H), 4.49 (m, 1H), 4.45 (s, 3H), 3.76 (s, 3H), 3.73 (dd, J=10, 7 Hz, 1H), 3.51 (dd, J=10, 5.5 Hz, 1H), 3.44 (dd, J=15.5, 7 Hz, 1H), 3.39 (dd, J=15.5, 5.5 Hz, 1H), 3.01 (dd, J=12.5, 12 Hz, 1H), 2.79 (s, 3H), 2.06 (m, 1H), 1.36 (s, 9H), 1.24 (d, J=6.5 Hz, 3H), 0.93 (d, J=6.5 Hz, 3H). $^{13}$C

NMR (125 MHz, DMSO-$d_6$, 110° C.) δ 165.6, 158.5, 158.4, 154.3, 149.8, 144.0, 129.8, 128.5, 128.4, 113.4, 110.6, 78.5, 74.6, 71.4, 70.5, 54.7, 51.8, 50.0, 48.4, 34.6, 32.2, 27.5, 14.0, 9.7. HRMS (ESI) calcd for $C_{28}H_{39}BrN_3O_6$ [M+H]$^+$: 592.2017. Found: 592.2040.

Eight-Atom Membered Lactam (10b)

Following protocol A, (2S,5S,6R)-9b (29.2 g, 39.3 mmol, 1.0 equiv) was reacted with cesium fluoride (29.8 g, 196 mmol, 5.0 equiv) in DMF (400 mL), followed by reaction with NaH (60% dispersion in oil, 1.6 g, 39.3 mmol, 1.0 equiv) in THF (400 mL) which provided product (2S,5S,6R)-10b (22.4 g, 96%).

(2S,5S,6R)-10b: $[α]_D^{20}$ +33.7 (c 1.0, CHCl$_3$). IR (cm$^{-1}$) 2930, 1682, 1628, 1426, 1247, 1153. $^1$H NMR (500 MHz, DMSO-$d_6$, 110° C.) δ 8.32 (d, J=2.5 Hz, 1H), 7.88 (d, J=2.5 Hz, 1H), 7.21 (d, J=8.5 Hz, 2H), 6.88 (d, J=8.5 Hz, 2H), 4.69 (m, 1H), 4.44 (d, J=12 Hz, 1H), 4.41 (d, J=12 Hz, 1H), 3.76 (s, 3H), 3.66 (dd, J=10.5, 8 Hz, 1H), 3.51 (m, 2H), 3.40 (m, 2H), 2.96 (m, 2H), 2.85 (s, 3H), 2.03 (m, 1H), 1.36 (s, 9H), 1.22 (d, J=6.5 Hz, 1H), 0.94 (d, J=6.5 Hz, 1H). $^{13}$C NMR (125 MHz, DMSO-$d_6$, 110° C.) δ 165.9, 158.5, 158.2, 154.2, 149.7, 143.8, 129.9, 128.3, 128.3, 113.3, 110.6, 78.5, 74.5, 71.3, 70.1, 54.7, 50.2, 50.1, 47.3, 34.9, 34.0, 27.4, 14.0, 9.7. HRMS (ESI) calcd for $C_{28}H_{39}BrN_3O_6$ [M+H]$^+$: 592.2017. Found: 592.1998.

Eight-Atom Membered Lactam (10c)

Following protocol B, (2R,5S,6S)-9c (34.0 g, 45.7 mmol, 1.0 equiv) was reacted with tetrabutylammonium fluoride (1.0 M solution in THF, 229 mL, 229 mmol, 5.0 equiv) in DMF (460 mL) which provided product (2R,5S,6S)-10c (21.4 g, 84%).

(2R,5S,6S)-10c: $[α]_D^{20}$ +32.3 (c 1.0, CHCl$_3$). IR (cm$^{-1}$) 2974, 1676, 1632, 1434, 1246, 1151. $^1$H NMR (500 MHz, DMSO-$d_6$, 110° C.) δ 8.46 (d, J=2.5 Hz, 1H), 7.96 (d, J=2.5 Hz, 1H), 7.26 (d, J=8.5 Hz, 2H), 6.91 (d, J=8.5 Hz, 2H), 4.49 (d, J=12 Hz, 1H), 4.45 (d, J=12 Hz, 1H), 4.42 (m, 1H), 4.04 (ddd, J=10.5, 8, 2.5 Hz, 1H), 3.77 (s, 3H), 3.76 (dd, J=7.5, 7 Hz, 1H), 3.64 (dd, J=14.5, 2 Hz, 1H), 3.60 (dd, J=10.5, 5.5 Hz, 1H), 3.25 (m, 1H), 3.19 (m, 1H), 3.06 (dd, J=16, 2 Hz, 1H), 2.98 (s, 3H), 2.02 (m, 1H), 1.43 (s, 9H), 1.26 (d, J=6.5 Hz, 3H), 0.81 (d, J=6.5 Hz, 1H). $^{13}$C NMR (125 MHz, DMSO-$d_6$, 110° C.) δ 164.7, 158.5, 154.5, 150.5, 140.2, 129.9, 128.4, 125.6, 114.7, 113.4, 87.1, 78.1, 71.5, 70.9, 54.6, 51.6, 50.5, 35.3, 35.2, 34.8, 27.6, 14.7, 13.9. HRMS (ESI) calcd for $C_{28}H_{39}BrN_3O_6$ [M+H]$^+$: 592.2017. Found: 592.1989.

Eight-Atom Membered Lactam (10d)

Following protocol B (2S,5S,6S)-9d (36.0 g, 48.4 mmol, 1.0 equiv) was reacted with tetrabutylammonium fluoride (1.0 M solution in THF, 242 mL, 242 mmol, 5.0 equiv) in DMF (480 mL) which provided product (2S,5S,6S)-10d (21.5 g, 80%).

(2S,5S,6S)-10d: $[α]_D^{20}$ +43.9 (c 1.0, CHCl$_3$). IR (cm$^{-1}$) 2974, 1688, 1632, 1434, 1246, 1151. $^1$H NMR (500 MHz, DMSO-$d_6$, 110° C.) δ 8.47 (d, J=2.5 Hz, 1H), 7.91 (d, J=2.5 Hz, 1H), 7.25 (d, J=8.5 Hz, 2H), 6.90 (d, J=9 Hz, 2H), 4.46 (q, J=11.5, 20 Hz, 2H), 4.43 (m, 1H), 4.04 (m, 1H), 3.73 (dd, J=7, 10 Hz, 1H), 3.66 (dd, J=2.5, 15 Hz, 1H), 3.60 (dd, J=5.5, 10 Hz, 1H), 3.29 (dd, J=8, 15 Hz, 1H), 3.20 (dd, J=10.0, 16.5 Hz, 1H), 3.10 (dd, J=1.5, 16.5 Hz, 1H), 2.03 (m, 1H), 1.33 (d, J=7 Hz, 3H), 0.83 (d, J=7.0 Hz, 3H). $^{13}$C NMR (125 MHz, DMSO-$d_6$, 110° C.) δ 164.7, 159.9, 158.5, 154.5, 150.4, 140.2, 130.0, 128.4, 128.3, 125.7, 114.7, 113.3, 87.0, 78.5, 71.4, 70.1, 54.7, 51.6, 51.4, 50.5, 35.6, 27.7, 14.8, 14.7. HRMS (ESI) calcd for $C_{28}H_{39}BrN_3O_6$ [M+H]$^+$: 592.2017. Found: 592.1989.

Elaboration of $S_N$Ar Compounds to Final Core ($S_N$Ar-Pyr)

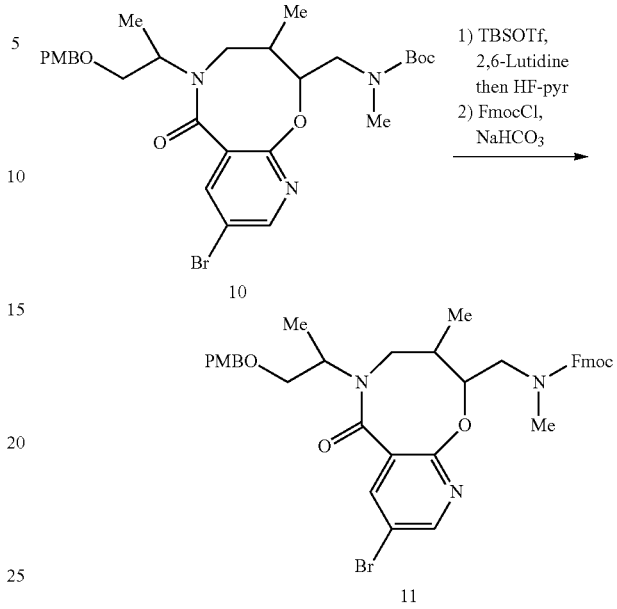

2,6-Lutidine (4.0 equiv) and TBSOTf (3.0 equiv) were added to a solution of lactam 10 (1.0 equiv) in CH$_2$Cl$_2$ (0.1 M) at RT. The mixture was stirred until complete consumption of starting material was observed by LCMS (<2 h). The reaction was quenched with saturated NH$_4$Cl solution and extracted with EtOAc. The combined organic extracts were dried over MgSO$_4$, filtered and concentrated to give the crude silyl carbamate. The resulting oil was dissolved in THF (0.2 M) before HF.pyridine (70%, 1.0 equiv) was added. The mixture was stirred for 40 min, quenched with saturated NaHCO$_3$ solution and extracted with EtOAc. The combined organic extracts were dried over MgSO$_4$, filtered and concentrated to provide the secondary amine, which was used without any further purification.

The secondary amine (1.0 equiv) was taken up in 1,4-dioxane (0.15 M) and an excess of a 10% NaHCO$_3$ solution was added. The reaction was cooled to 0° C. before a solution of FmocCl (1.2 equiv) in minimal 1,4-dioxane was added. The reaction was stirred at RT until no more starting material was observed (~1 h) and reaction was quenched with a saturated NH$_4$Cl solution. The resulting mixture was extracted with EtOAc. The combined organic extracts were dried over MgSO$_4$, filtered and concentrated. Flash chromatography on silica gel (gradient: 30% to 50% EtOAc in hexanes) provided the desired product 11.

Fmoc Protected Lactam (11a)

Following the general reaction protocol, (2R,5S,6R)-10a (16.7 g, 28.1 mmol, 1.0 equiv) was reacted with TBSOTf (19.4 mL, 84.0 mmol, 3.0 equiv) and 2,6-Lutidne (13.1 mL, 112 mmol, 4.0 equiv) in CH$_2$Cl$_2$ (300 mL) followed by HF.pyr (3.5 mL, 28.1 mmol, 1.0 equiv) in THF (150 mL). Fmoc protection was carried out using FmocCl (8.7 g, 33.7 mmol, 1.2 equiv) and a 10% NaHCO$_3$ solution (50 mL) in 1,4-dioxane (200 mL) which provided pure product (2R,5S,6R)-11a (17.5 g, 87% over 2 steps).

(2R,5S,6R)-11a: $[α]_D^{20}$ +33.5 (c 1.0, CHCl$_3$). IR (cm$^{-1}$) 2936, 1698, 1627, 1424, 1246, 1165. $^1$H NMR (500 MHz, DMSO-$d_6$, 110° C.) δ 8.31 (d, J=2.5 Hz, 1H), 7.97 (d, J=2.5 Hz, 1H), 7.82 (dd, J=12.5, 6.5 Hz, 2H), 7.56 (dd, J=12.5, 6.5 Hz, 2H), 7.38 (td, J=7.5 Hz, 2H), 7.27 (td, J=7.5 Hz, 2H), 7.21 (d, J=8.5 Hz, 2H), 6.88 (d, J=8.5 Hz, 2H), 4.68 (dd,

J=10.5, 5 Hz, 1 Hz), 4.50 (m, 1H), 4.44 (d, J=12 Hz, 2H). 4.42 (d, J=12 Hz, 2H), 4.30 (dd, J=10.5, 6.5 Hz, 1H), 4.24 (dd, J=12.5, 6.5 Hz, 1H), 3.75 (s, 3H), 3.70 (dd, J=10.5, 7 Hz, 1H), 3.49 (m, 1H), 3.36 (dd, J=15.5, 5.5 Hz, 1H), 3.00 (dd, J=15.5, 15 Hz, 1H), 2.94 (s, 3H), 2.00 (m, 1H), 1.20 (d, J=6.5 Hz, 3H), 0.90 (d, J=6.5 Hz, 3H). $^{13}$C NMR (125 MHz, DMSO-$d_6$, 110° C., reported as a mixture of rotamers) δ 165.9, 165.6, 158.5, 158.3, 155.0, 149.8, 149.6, 143.9, 143.8, 143.3, 142.3, 140.3, 140.2, 139.0, 137.0, 129.9, 128.4, 128.2, 126.8, 126.6, 126.3, 124.2, 120.6, 119.3, 119.2, 118.6, 113.4, 110.2, 108.2, 75.7, 71.4, 70.5, 66.2, 54.7, 52.5, 50.1, 50.0, 47.8, 47.7, 46.5, 35.3, 34.3, 33.4, 33.2, 13.9, 9.8, 9.6. HRMS (ESI) calcd for $C_{38}H_{41}BrN_3O_6$ [M+H]$^+$: 714.2179. Found: 714.2187.

Fmoc Protected Lactam (11b)

Following the general reaction protocol (2S,5S,6R)-10b (23.3 g, 39.3 mmol, 1.0 equiv) was reacted with TBSOTf (27.1 mL, 118 mmol, 3.0 equiv) and 2,6-Lutidne (18.3 mL, 157 mmol, 4.0 equiv) in $CH_2Cl_2$ (400 mL) followed by HF.pyr (4.9 mL, 39.3 mmol, 1.0 equiv) in THF (200 mL). Fmoc protection was carried out using FmocCl (12.2 g, 47.2 mmol, 1.2 equiv) and a 10% $NaHCO_3$ solution (50 mL) in 1,4-dioxane (250 mL) which provided pure product (2S,5S, 6R)-11b (24.7 g, 88% over 2 steps).

(2S,5S,6R)-11b: [α]$^{20}$ +28.0 (c 1.0, CHCl$_3$). IR (cm$^{-1}$): 2935, 1701, 1630, 1427, 1292, 1248, 759, 719. $^1$H NMR (500 MHz, DMSO-$d_6$, 110° C.) δ 8.32 (d, J=2.5 Hz, 1H), 7.90 (d, J=2.5 Hz, 1H), 7.83 (dd, J=7.5, 5.0 Hz, 2H), 7.57 (t, J=8.4 Hz, 2H), 7.41-7.37 (m, 2H), 7.31-7.24 (m, 2H), 7.21 (d, J=8.5 Hz, 2H), 6.88 (d, J=8.5 Hz, 2H), 4.70-4.64 (m, 1H), 4.60-4.51 (m, 1H), 4.46-4.40 (m, 1H), 4.42 (d, J=4.4 Hz, 2H), 4.34-4.31 (m, 1H), 4.25 (t, J=6.4 Hz, 1H), 3.76 (s, 3H), 3.68 (dd, J=10.0, 8.0 Hz, 1H), 3.53 (q, J=5.0 Hz, 2H), 3.51-3.47 (m, 1H), 3.46-3.35 (m, 2H), 2.97 (dd, J=15.0, 7.5 Hz, 1H), 2.83 (s, 3H), 2.03-1.96 (m, 1H), 1.19 (d, J=6.9 Hz, 3H), 0.90 (d, J=6.6 Hz, 3H). $^{13}$C NMR (125 MHz, DMSO-$d_6$, 110° C., reported as a mixture of rotamers) δ 167.1, 159.8, 159.5, 156.3, 151.04, 151.00, 145.1, 144.66, 144.63, 141.58, 141.55, 131.2, 129.6, 129.5, 128.2, 127.6, 125.4, 120.6, 114.6, 112.0, 95.0, 75.7, 72.6, 71.3, 67.5, 56.0, 55.9, 52.3, 51.5, 49.1, 47.8, 35.84, 35.78, 35.2, 15.4, 10.9. HRMS (ESI) calcd for $C_{38}H_{41}BrN_3O_6$[M+H]$^+$: 714.2179. Found: 714.2178.

Fmoc Protected Lactam (11c)

Following the general reaction protocol (2R,5S,6S)-10c (19.0 g, 32.1 mmol, 1.0 equiv) was reacted with TBSOTf (22.1 mL, 96.0 mmol, 3.0 equiv) and 2,6-Lutidine (14.9 mL, 128 mmol, 4.0 equiv) in $CH_2Cl_2$ (320 mL) followed by HF.pyr (4.0 mL, 32.1 mmol, 1.0 equiv) in THF (160 mL). Fmoc protection was carried out using FmocCl (10.0 g, 38.5 mmol, 1.2 equiv) and a 10% $NaHCO_3$ solution (50 mL) in 1,4-dioxane (200 mL) which provided pure product (2R,5S, 6S)-11c (20.9 g, 91% over 2 steps).

(2R,5S,6S)-11c: [α]$_D^{20}$ +27.9 (c 1.0, CHCl$_3$). IR (cm$^{-1}$) 2936, 1699, 1633, 1435, 1427, 1171, 1086, 759, 741. $^1$H NMR (500 MHz, DMSO-$d_6$, 110° C.) α 8.44 (s, 1H), 7.96 (s, 1H), 7.83 (d, J=6.5 Hz, 2H), 7.64 (t, J=6.5 Hz, 2H), 7.39 (dd, J=16.5, 7.5 Hz, 2H), 7.30 (t, J=7.5 Hz, 2H), 7.25 (d, J=8.1 Hz, 2H), 6.89 (d, J=8.1 Hz, 2H), 4.48-4.41 (m, 5H), 4.30-4.25 (m, 1H), 3.98-3.88 (m, 1H), 3.76 (s, 3H), 3.74-3.70 (m, 1H), 3.62-3.51 (m, 2H), 3.34-3.24 (m, 1H), 3.18-3.10 (m, 2H), 3.05 (s, 1H), 3.02 (s, 3H), 2.04-1.93 (m, 1H), 1.24 (d, J=6.8 Hz, 3H), 0.68 (s, 3H). $^{13}$C NMR (125 MHz, DMSO-$d_6$, 110° C., reported as a mixture of rotamers) δ 164.71, 164.67, 160.1, 159.8, 158.5, 155.1, 150.5, 150.4, 143.4, 142.3, 140.4, 140.3, 139.0, 137.0, 129.92, 129.88, 128.4, 128.2, 126.83, 126.80, 126.5, 126.3, 125.6, 124.2, 120.5, 119.2, 119.1, 114.8, 114.6, 113.3, 108.1, 87.4, 86.7, 71.5, 70.9, 70.8, 65.9, 54.6, 54.1, 51.7, 51.6, 51.4, 50.7, 50.5, 46.6, 35.3, 35.0, 34.9, 34.7, 15.1, 14.7, 13.86, 13.85. HRMS (ESI) calcd for $C_{38}H_{41}BrN_3O_6$ [M+H]$^+$: 714.2179. Found: 714.2180.

Fmoc Protected Lactam (11d)

Following the general reaction protocol (2S,5S,6S)-10d (21.0 g, 35.4 mmol, 1.0 equiv) was reacted with TBSOTf (24.4 mL, 106 mmol, 3.0 equiv) and 2,6-Lutidne (16.5 mL, 142 mmol, 4.0 equiv) in $CH_2Cl_2$ (350 mL) followed by HF.pyr (4.4 mL, 35.4 mmol, 1.0 equiv) in THF (175 mL). Fmoc protection was carried out using FmocCl (11.0 g, 42.4 mmol, 1.2 equiv) and a 10% $NaHCO_3$ solution (50 mL) in 1,4-dioxane (250 mL) which provided pure product (2S,5S, 6S)-11d (25.2 g, 99% over 2 steps).

(2S,5S,6S)-11d: [α]$^{20}$+47.0 (c 1.0, CHCl$_3$). IR (cm$^{-1}$): 2936, 1699, 1634, 1436, 1248, 758, 742. $^1$H NMR (500 MHz, DMSO-$d_6$, 110° C., 8:1 mixture of rotamers, only the major rotamer reported) δ 8.45 (s, 1H), 7.94-7.91 (m, 1H), 7.85-7.83 (m, 2H), 7.65 (t, J=7.5 Hz, 2H), 7.41-7.39 (m, 2H), 7.33-7.27 (m, 2H), 7.24 (d, J=8.5 Hz, 2H), 6.90 (d, J=8.6 Hz, 2H), 4.51-4.37 (m, 5H), 4.27 (t, J=5.5 Hz, 1H), 3.98-3.88 (m, 1H), 3.77 (s, 3H), 3.75-3.68 (m, 1H), 3.60 (dd, J=10.5, 5.5 Hz, 1H), 3.59-3.52 (m, 1H), 3.37-3.26 (m, 1H), 3.17-3.05 (m, 2H), 3.02 (s, 3H), 2.03-1.91 (m, 1H), 1.31 (d, J=7.0 Hz, 3H), 0.77-0.63 (m, 3H). $^{13}$C NMR (125 MHz, DMSO-$d_6$, 110° C., reported as a mixture of rotamers) δ 166.0, 165.8, 161.1, 159.8, 156.5, 151.9, 151.8, 151.7, 151.6, 144.8, 141.6, 141.5, 132.0, 131.4, 129.7, 129.6, 128.2, 128.1, 127.7, 127.6, 127.0, 125.5, 125.4, 120.6, 116.1, 116.0, 114.7, 114.6, 88.0, 87.9, 72.7, 71.4, 71.3, 67.2, 65.1, 56.0, 55.9, 52.8, 52.7, 51.85, 47.9, 37.5, 37.1, 36.3, 29.6, 16.1, 16.0, 15.9. HRMS (ESI) calcd for $C_{38}H_{41}BrN_3O_6$ [M+H]$^+$: 714.2179. Found: 714.2177.

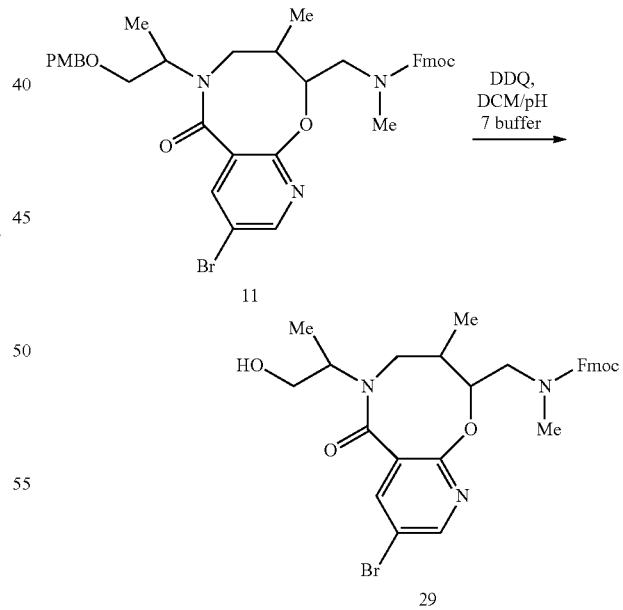

Lactam 11 (1.0 equiv) was dissolved in a 5:1 solution of $CH_2Cl_2$ and pH 7 buffer solution (0.15 M). The mixture was cooled to 0° C. and DDQ (1.2 equiv) was added. The mixture was stirred for 10 min at 0° C. and an additional 1 h at RT before being quenched with a saturated $NaHCO_3$ solution and filtered through a ceramic Buchner funnel equipped with filter paper. The organic and aqueous layers were separated and the aqueous layer extracted with CH$_2$Cl$_2$. The combined organic extracts were washed with saturated NaHCO$_3$ solution, dried over MgSO$_4$, filtered and concentrated. Flash chromatography on silica gel (50% to 100% EtOAc in hexanes) gave pure product 29 as a white foaming solid.

S$_N$Ar-Pyr Final Core (29a)

Following the general reaction protocol (2R,5S,6R)-11a (17.4 g, 24.4 mmol, 1.0 equiv) was reacted with DDQ (6.6 g, 29.2 mmol, 1.2 equiv) in CH$_2$Cl$_2$ (150 mL) and pH 7 buffer (30 mL) to give product (2R,5S,6R)-29a (14.0 g, 97%).

(2R,5S,6R)-29a: [α]$_D^{20}$ +29.0 (c 1.0, CHCl$_3$). IR (cm$^{-1}$) 3430, 3052, 2972, 1696, 1623, 1423, 1290, 1164. $^1$H NMR (500 MHz, DMSO-d$_6$, 110° C.) δ 8.31 (d, J=2.5 Hz, 1H), 7.98 (d, J=2.5 Hz, 1H), 7.84 (t, J=7.5 Hz, 2H), 7.59 (t, J=7.5 Hz, 2H), 7.38 (m, 2H), 7.28 (m, 2H), 4.76 (t, J=2 Hz, 1H), 4.50 (t, J=2 Hz, 1H), 4.37 (dd, J=6.5, 6 Hz, 1H), 4.30 (m, 3H), 3.64 (m, 1H), 3.51 (m, 3H), 3.36 (dd, J=15.5, 5.5 Hz, 1H), 3.00 (dd, J=14, 12.5 Hz, 1H), 2.95 (s, 3H), 2.84 (s, 3H), 2.10 (m, 1H), 1.18 (d, J=6.5 Hz, 3H), 0.91 (d, J=6.5 Hz, 3H). $^{13}$C NMR (125 MHz, DMSO-d$_6$, 110° C.) δ 165.7, 158.2, 155.0, 149.7, 144.0, 143.4, 140.2, 126.9, 126.8, 126.4, 124.3, 124.2, 119.3, 74.3, 66.2, 62.3, 54.1, 50.2, 48.5, 46.5, 34.4, 33.1, 13.5, 9.7. HRMS (ESI) calcd for C$_{30}$H$_{33}$BrN$_3$O$_5$ [M+H]: 594.1598. Found: 594.1570.

(2S,5R,6S)-ent-29a: [α]$_D^{20}$ −32.4 (c 1.0, CHCl$_3$).

S$_N$Ar-Pyr Final Core (29b)

Following the general reaction protocol (2S,5S,6R)-11b (24.7 g, 34.6 mmol, 1.0 equiv) was reacted with DDQ (9.4 g, 41.5 mmol, 1.2 equiv) in CH$_2$Cl$_2$ (200 mL) and pH 7 buffer (40 mL) to give product (2S,5S,6R)-29b (19.0 g, 92%).

(2S,5S,6R)-29b: [α]$_D^{20}$ +30.1 (c 1.0, CHCl$_3$). IR (cm$^{-1}$) 3435 (br), 2971, 1696, 1625, 1426, 1291, 757. $^1$H NMR (500 MHz, DMSO-d$_6$, 110° C.) δ 8.32 (d, J=2.5 Hz, 1H), 7.96 (d, J=2.5 Hz, 1H), 7.84 (dd, J=7.5, 4.6 Hz, 2H), 7.61-7.56 (m, 2H), 7.38 (dt, J=7.5, 5.0 Hz, 2H), 7.33-7.25 (m, 2H), 4.73 (br s, 1H), 4.46 (dd, J=10.6, 6.3 Hz, 1H), 4.41 (br s, 1H), 4.34 (dd, J=10.5, 6.3 Hz, 2H), 4.26 (t, J=6.3 Hz, 1H), 3.71-3.66 (m, 1H), 3.54 (dd, J=10.9, 5.0 Hz, 2H), 3.50-3.39 (m, 2H), 3.02 (dd, J=15.4, 12.4 Hz, 1H), 2.94 (s, 1H), 2.86 (s, 3H), 2.10-1.99 (m, 1H), 1.19 (d, J=6.9 Hz, 3H), 0.93 (d, J=6.6 Hz, 3H). $^{13}$C NMR (125 MHz, CDCl$_3$, 60° C., reported as a mixture of rotamers) δ 167.3, 159.3, 156.8, 151.1, 145.6, 144.2, 144.1, 141.6, 141.5, 127.9, 127.8, 127.2, 125.1, 125.0, 120.11, 120.08, 119.5, 112.4, 95.0, 76.9, 67.8, 63.3, 60.3, 53.0, 47.6, 36.6, 34.3, 14.9, 10.6. HRMS (ESI) calcd for C$_{30}$H$_{33}$BrN$_3$O$_5$ [M+H]$^+$: 594.1598. Found: 594.1599.

(2R,5R,6S)-ent-29b: [α]$_D^{20}$ −32.4 (c 1.0, CHCl$_3$).

S$_N$Ar-Pyr Final Core (29c)

Following the general reaction protocol (2R,5S,6S)-11c (20.9 g, 29.2 mmol, 1.0 equiv) was reacted with DDQ (8.0 g, 35.0 mmol, 1.2 equiv) in CH$_2$Cl$_2$ (175 mL) and pH 7 buffer (35 mL) to give product (2R,5S,6S)-29c (16.1 g, 93%).

(2R,5S,6S)-29c: [α]$_D^{20}$ + 28.3 (c 1.0, CHCl$_3$). IR (cm$^{-1}$) 3436 (br), 2936, 1694, 1626, 1435, 758. $^1$H NMR (500 MHz, DMSO-d$_6$, 110° C.) δ 8.45 (s, 1H), 7.99 (d, J=2.4 Hz, 1H), 7.84 (d, J=7.2 Hz, 2H), 7.66 (t, J=7.4 Hz, 2H), 7.39 (dd, J=16.0, 7.2 Hz, 2H), 7.33-7.25 (m, 2H), 4.50-4.40 (m, 2H), 4.46 (br s, 1H), 4.29 (t, J=6.0 Hz, 1H), 4.17 (q, J=6.5 Hz, 1H), 4.02-3.89 (m, 1H), 3.78-3.72 (m, 1H), 3.65-3.55 (m, 2H), 3.44-3.36 (m, 1H), 3.19-3.14 (m, 1H), 3.10-3.05 (m, 1H), 3.05 (s, 3H), 2.08 (s, 1H), 1.25 (d, J=6.7 Hz, 3H), 0.73 (s, 3H). $^{13}$C NMR (125 MHz, CDCl$_3$, 60° C., reported as a mixture of rotamers) δ 167.1, 161.2, 152.2, 144.3, 141.69, 141.65, 141.59, 127.8, 127.22, 127.18, 125.3, 120.1, 116.4, 88.3, 67.9, 65.3, 57.3, 54.1, 53.1, 47.7, 36.9, 35.3, 16.3, 15.8, 14.4, 14.3. HRMS (ESI) calcd for C$_{30}$H$_{33}$BrN$_3$O$_5$ [M+H]$^+$: 594.1598. Found: 594.1604.

(2S,5R,6R)-ent-29c: [α]$_D^{20}$ −26.6 (c 1.0, CHCl$_3$).

S$_N$Ar-Pyr Final Core (29d)

Following the general reaction protocol (2S,5S,6S)-11d (25.2 g, 35.3 mmol, 1.0 equiv) was reacted with DDQ (9.6 g, 42.3 mmol, 1.2 equiv) in CH$_2$Cl$_2$ (200 mL) and pH 7 buffer (40 mL) to give product (2S,5S,6S)-29d (20.0 g, 95%).

(2S,5S,6S)-29d: [α]$_D^{20}$ +38.0 (c 1.0, CHCl$_3$). IR (cm$^{-1}$): 3435 (br), 2937, 1693, 1624, 1435, 757. $^1$H NMR (500 MHz, DMSO-d$_6$, 110° C.) δ 8.45 (s, 1H), 7.97 (s, 1H), 7.84 (d, J=7.2 Hz, 2H), 7.66 (t, J=7.2 Hz, 2H), 7.43-7.35 (m, 2H), 7.35-7.25 (m, 2H), 4.51-4.42 (m, 2H), 4.38-4.33 (m, 1H), 4.31-4.21 (m, 2H), 3.99-3.88 (m, 1H), 3.69-3.55 (m, 3H), 3.44-3.35 (m, 1H), 3.14 (s, 2H), 3.04 (s, 3H), 2.00 (s, 1H), 1.29 (d, J=6.9 Hz, 3H), 0.73 (s, 3H). $^{13}$C NMR (125 MHz, CDCl$_3$, 60° C.) δ 167.3, 161.0, 157.0, 152.2, 144.3, 141.6, 141.6, 127.8, 127.2, 127.2, 125.3, 120.1, 116.5, 88.4, 67.9, 64.6, 57.3, 53.4, 53.2, 47.7, 36.9, 36.1, 16.1, 14.4. HRMS (ESI) calcd for C$_{30}$H$_{33}$BrN$_3$O$_5$ [M+H]$^+$: 594.1598. Found: 594.1603.

(2R,5R,6R)-ent-29d: [α]$_D^{20}$ −36.4 (c 1.0, CHCl$_3$).

Solid-Phase Library Synthesis

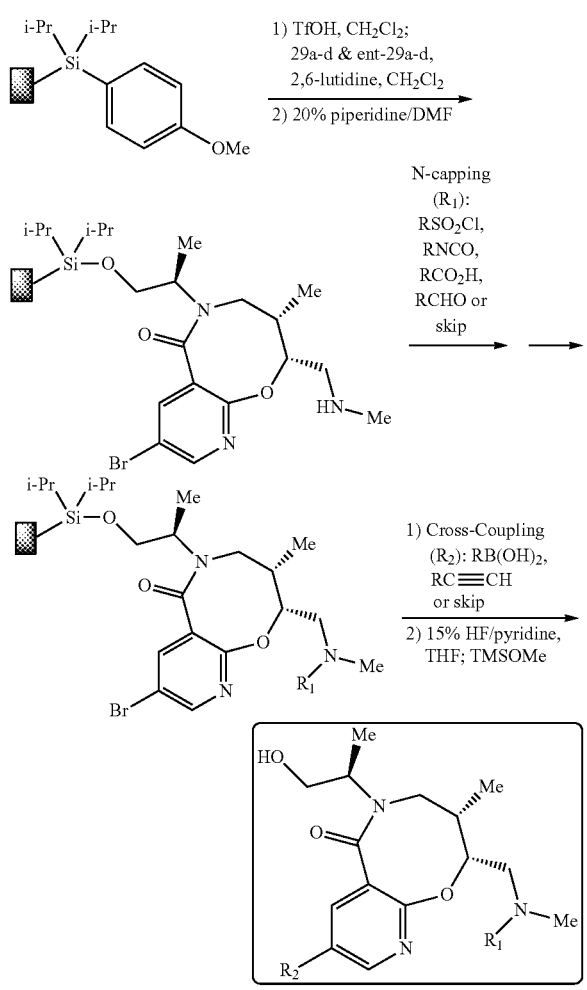

General Methods:

Solid-phase synthesis was conducted on silicon-functionalized polystyrene SynPhase™ Lanterns (L-series) equipped with radio frequency transponders (TranStems) for AccuTag directed sorting and compound tracking. Quality-control Lanterns were included at each synthesis step for reaction monitoring by UPLC (UV 210 nM) after HF-cleavage. All reactions were conducted in heavy wall pressure vessels from ChemGlass with agitation in New Brunswick Scientific incubator shakers.

Scaffold Loading:

To a flame-dried flask containing silicon-functionalized Lanterns was added a freshly prepared solution of TfOH in anhydrous DCM (9.0 equiv, 5 g of TfOH/100 mL of DCM) was added. Each flask was shaken at RT for 10 min at which time the Lanterns had turned bright orange. The deep red TfOH solution was removed via cannula and anhydrous 2,6-lutidine (12.0 equiv relative to Si) was added. Once the Lantern color had changed from orange to white, the scaffold (1.2 equiv. relative to Si) was added as a solution in anhydrous DCM (0.4 mL/Lantern) and the reaction mixture was shaken for 48 h overnight. The loading mixture was removed and set aside (to recover any unreacted alcohol) and the Lanterns were washed with the following solvents for 30 min intervals: DCM, THF, 3:1 THF/IPA, 3:1 THF/$H_2O$, DMF, 3:1 THF/$H_2O$, 3:1 THF/IPA, THF, DCM. The Lanterns were then dried on a lyophilizer overnight prior to sorting. All 8 stereoisomers of 29 were loaded via the same protocol.

Fmoc Removal:

To a flask containing Lanterns was added a solution of 20% piperidine in DMF (0.8 mL/Lantern). After shaking at RT for 30 min, the piperidine solution was removed and the Lanterns were washed with the following solvents for 30 min intervals: DMF, 3:1 THF/$H_2O$, 3:1 THF/IPA, THF, DCM. The Lanterns were then dried on a lyophilizer overnight prior to sorting.

N-Capping/Isocyanates:

To each flask containing Lanterns was added DCM (0.8 mL/Lantern) followed the desired isocyanate (15 equiv). The Lanterns were shaken at RT overnight and then washed with following solvents for 30 min intervals: DCM, DMF, 3:1 THF/$H_2O$, 3:1 THF/IPA, THF, DCM. The Lanterns were then dried on a lyophilizer overnight prior to sorting.

Cross-Coupling/Suzuki:

To each flask containing lanterns was added ethanol (0.800 mL/lantern) followed by the desired boronic acid (20 equiv), triethylamine (40 equiv) and Pd(PPh$_3$)$_2$Cl$_2$ (1 equiv). The resulting mixture was degassed with a stream of N$_2$ before shaking at 60° C. After 4 days, the reaction mixture was removed and the Lanterns were washed with following solvents for 30 min intervals: DCM, DMF, NaCN solution (0.1M) in 1:1 THF/$H_2O$, DMF, 3:1 THF/$H_2O$, 3:1 THF/IPA, THF, DCM. The lanterns were then dried on a lyophilizer overnight prior to sorting.

Cross-Coupling/Sonogashira:

To each flask containing lanterns was added DMF (0.800 mL/lantern) followed by the desired alkyne (20 equiv), CuI (3 equiv), diisopropylethylamine (30 equiv) and Pd(PPh$_3$)$_2$Cl$_2$ (1 equiv). The resulting mixture was degassed with a stream of N$_2$ before shaking at 60° C. overnight. After 24 h, the reaction mixture was removed and the Lanterns were washed with following solvents for 30 min intervals: DCM, DMF, NaCN solution (0.1 M) in 1:1 THF/$H_2O$ (30 min), DMF, 3:1 THF/$H_2O$, 3:1 THF/IPA, THF, DCM. The lanterns were then dried on a lyophilizer overnight prior to sorting.

Cleavage Protocol:

To a 96-well plate containing Lanterns was added a 15% solution of HF/pyridine in stabilized THF (350 µL/Lantern). After 2 h the cleavage solution was quenched with TMSOMe (700 µL/Lantern) and the contents of each well were transferred to a pre-weighed 2-mL vial. The Lanterns were washed with an additional 200 µL of stabilized THF (or THF/MeOH) and the solution was transferred to the 2-mL vial. The samples were concentrated on a Genevac® solvent evaporation system overnight without heating. Loading masses for each alcohol was determined on a FlexiWeigh® system.

Compound 106 was synthesized following the general methods for library synthesis. Compound 29 was loaded onto Lanterns followed by subsequent Fmoc removal. The secondary amine was capped with 4-fluorophenyl isocyanate. Suzuki cross coupling was carried out using 2-benzofuranylboronic acid. Compound 106 was then cleaved from the Lanterns and isolated following the standard cleavage protocol.

Compound 107 was synthesized following the general methods for library synthesis. Compound 29 was loaded onto Lanterns followed by subsequent Fmoc removal. The secondary amine was capped with 4-fluorophenyl isocyanate. Sonogashira cross coupling was carried out using 4-fluorophenyl acetylene. Compound 107 was then cleaved from the Lanterns and isolated following the standard cleavage protocol.

Preparation of Compound 8 in Table 1:

General Procedure for the Preparation of Azido Alkynes

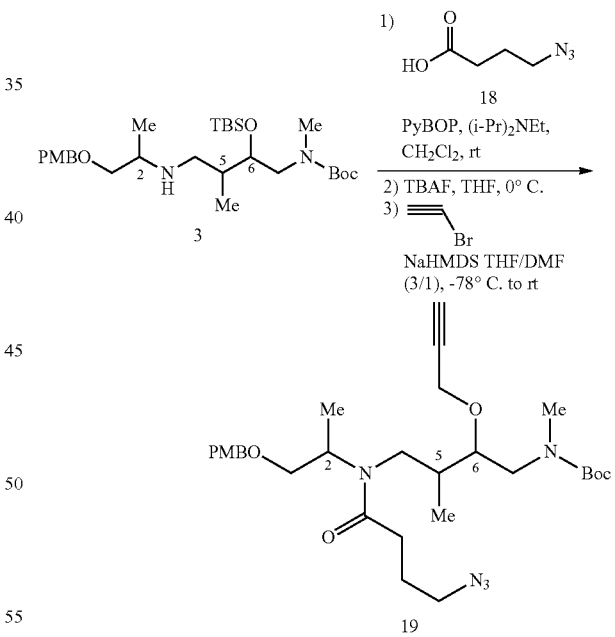

Step 1:

A solution of linear amine template 3 (1.0 equiv), carboxylic acid 18 (1.3 equiv) (Khoukhi, et al., 2000, Tetrahedron 43:1811-1822), and benzotriazol-1-yl-oxytripyrrolidinophosphonium hexafluorophosphate (PyBOP) (1.1-1.3 equiv) in dichloromethane (0.1-0.2 molar) was cooled to 0° C. in a water/ice bath. Then diisopropyl ethylamine (DIEA) (3.0 equiv) was added, and the reaction was stirred for 30 minutes before removing the ice bath, and allowing the reaction to stir overnight at RT. The reaction mixture was quenched with water, the layers were separated and the CH$_2$Cl$_2$ layer was washed twice with water, dried over sodium sulfate, and then filtered through a short plug of silica gel. The crude product was pure enough to be taken on to next step without further purification.

Step 2:

The crude product from step 1 (1.0 equiv) in THF (0.1 molar) was cooled to 0° C. using an ice bath. Tetrabutylammonium fluoride (TBAF) (1.0 M solution in THF, 2.0 equiv) was added drop wise and the reaction was stirred for 14 hours, slowly warming to RT. Analysis of the reaction by LC-MS indicated complete disappearance of the starting material. The reaction was quenched with saturated aqueous NH$_4$Cl and THF was removed using rotavap, the reaction was diluted with EtOAc and the organic layer was washed with water (acidified to pH=4, using AcOH). This step was repeated twice to remove excess TBAF. The combined organic layers were dried over sodium sulfate and concentrated to provide the crude product. Purification of crude product using silica gel provided the pure alcohol.

Step 3:

The product from previous step (1.0 equiv) was dissolved in THF/DMF (6:1) (0.2 molar). To this slightly yellow solution was added propargyl bromide (10 equiv) and the solution was cooled to −78° C. followed by dropwise addition of 1M NaHMDS (3 equiv). The ice bath was removed and the above mixture was warmed to RT gradually. The reaction was quenched with saturated ammonium chloride and the organic layer was evaporated. The aqueous layer was extracted with EtOAc, and the combined organic layers were washed with brine, dried over sodium sulfate and concentrated to yield the crude mixture. The crude mixture was purified using silica gel to yield 19.

Azido-Alkyne (19a)

Following general protocol for step 1, (2R,5S,6R)-(−)-3a (40.7 g, 78 mmol 1.0 equiv) was reacted with carboxylic acid 18 (11.09 g, 85 mmol 1.1 equiv), PyBOP (44.4 g, 85 mmol, 1.1 equiv) and DIEA (40.6 mL, 233 mmol, 3.0 equiv) in dichloromethane (400 mL, 0.18 molar) for 16 h. Workup as in general procedure yielded the crude product, which was used in the next step without further purification.

Following the general protocol for step 2, the crude product (49.6 g, 78 mmol 1.0 equiv) was dissolved in THF (500 mL) and reacted with TBAF (1.0 M in THF, 156 mL, 156 mmol, 2 equiv) for 14 h. Workup and purification provided the pure alcohol (37.8 g, 93% over 2 steps).

Following the general protocol for step 3, the purified alcohol (25.4 g, 48.7 mmol, 1.0 equiv) was dissolved in THF (209 ml) and DMF (34.8 ml) and cooled to −78° C., the solution was treated with propargyl bromide (36.7 mL, 487 mmol, 10 equiv) and NaHMDS (1.0 M in THF, 146 mL, 146 mmol, 30 equiv) and warmed to RT over 3 h. Flash chromatography using silica (10% to 50% EtOAc in hexanes) provided the pure product 19a (26.11 g, 96% yield).

(2R,5S,6R)-19a: $[\alpha]_D^{20}$ −7.7 (c 2.8, CHCl$_3$). IR (cm$^{-1}$) 3297, 2973, 1683, 1421, 1213, 1152. $^1$H NMR (300 MHz, CDCl$_3$, 1.1:1 mixture of rotamers, asterisk denotes minor rotamer peaks) δ 7.10 (d, J=8.0 Hz, 2H)*, 7.07 (d, J=7.7 Hz, 2H), 6.74 (d, J=8.0 Hz, 2H)*, 6.73 (d, J=7.7 Hz, 2H), 4.32-4.26 (m, 2H), 4.15-3.95 (m, 2H), 3.65 (s, 3H), 3.57-3.40 (m, 1H), 3.28-3.10 (m, 2H), 2.78 (s, 3H)*, 2.70 (s, 3H), 2.50-2.20 (m, 3H), 2.10-2.00 (m, 1H), 1.76 (p, J=6.6 Hz, 2H), 1.33 (s, 9H), 1.14 (d, J=6.6 Hz, 3H)*, 1.10 (d, J=6.6 Hz, 3H), 0.85 (d, J=6.6 Hz, 3H)*, 0.73 (d, J=6.6 Hz, 3H). $^{13}$C NMR (75 MHz, CDCl$_3$) δ 173.3, 172.3, 159.2, 159.1, 155.7, 155.4, 130.4, 129.8, 129.2, 113.7, 113.6, 80.5, 79.8, 79.7, 79.4, 79.2, 74.7, 74.1, 72.7, 72.6, 71.8, 71.3, 57.7, 57.4, 55.1, 54.3, 52.4, 50.9, 50.8, 50.5, 50.1, 49.7, 49.4, 43.4, 35.8, 35.2, 34.8, 34.0, 30.9, 30.5, 28.4, 24.6, 24.5, 16.3, 15.5, 12.4, 11.5 HRMS (ESI) calcd for C$_{29}$H$_{45}$N$_5$O$_6$ [M+H]$^+$: 560.3443. Found: 560.3445.

Azido-Alkyne (19b)

Following the general protocol for step 1, (2S,5S,6R)-(−)-3b (45.0 g, 86 mmol, 1.0 equiv) was reacted with carboxylic acid 18 (12.18 g, 94 mmol, 1.1 equiv), PyBOP (49.1 g, 94 mmol, 1.1 equiv) and DIEA (34.8 mL, 258 mmol, 3.0 equiv) in dichloromethane (400 mL, 0.2 molar) for 16 h. Workup as in general procedure yielded the crude product, which was used in the next step without further purification.

Following the general protocol for step 2, crude product (54.5 g, 1.0 equiv) was dissolved in THF (700 mL) and reacted with TBAF (1.0 M in THF, 171 mL, 171 mmol, 2 equiv) for 14 h. Workup and purification provided pure alcohol (41.89 g, 94% over 2 steps).

Following the general protocol for step 3, the purified alcohol (25.5 g, 48.7 mmol, 1.0 equiv) was dissolved in THF (210 ml) and DMF (35.0 ml) and cooled to −78° C., the solution was treated with propargyl bromide (36.8 mL, 489 mmol, 3.0 equiv) and NaHMDS (1.0 M in THF, 196 mL, 196 mmol, 4 equiv) and warmed to RT over 3 h. Flash chromatography using silica (10% to 50% EtOAc in hexanes) provided the pure product 19b (25.25 g, 92% yield). (2S,5S,6R)-19b: $[\alpha]_D^{20}$ −17.4 (c 2.1, CHCl$_3$).

Azido-Alkyne (19c)

Following general protocol for step 1, (2R,5S,6S)-(+)-3c (26.2 g, 49.9 mmol, 1.0 equiv) was reacted with carboxylic acid 18 (7.73 g, 59.9 mmol, 1.2 equiv), PyBOP (33.8 g, 64.9 mmol, 1.3 equiv) and DIEA (26.5 mL, 152 mmol, 3.0 equiv) in dichloromethane (500 mL, 0.1 molar) for 16 h. Workup as in general procedure yielded the crude product, which was used in the next step without further purification.

Following the general protocol for step 2, the crude product (31.7 g, 49.9 mmol, 1.0 equiv) was dissolved in THF (400 mL) and reacted with TBAF (1.0 M in THF, 100 mL, 100 mmol, 2 equiv) for 14 h. Workup and purification provided the pure alcohol (20.5 g, 79% over 2 steps).

Following the general protocol for step 3, the purified alcohol (19 g, 36.4 mmol, 1.0 equiv) was dissolved in THF (156 ml) and DMF (26 ml) and cooled to −78° C., the solution was treated with propargyl bromide (36.7 mL, 487 mmol, 10 equiv) and NaHMDS (1.0 M in THF, 109 mL, 109 mmol, 3.0 equiv) and warmed to RT over 3 h. Flash chromatography using silica (10% to 50% EtOAc in hexanes) provided pure product 19c (18.15 g, 91% yield).

(2R,5S,6S)-19c: $[\alpha]_D^{20}$ +9.9 (c 10.4, CHCl$_3$).

Azido-Alkyne (19d)

Following general protocol for step 1, (2S,5S,6S)-(+)-3d (35 g, 66.7 mmol, 1.0 equiv) was reacted with carboxylic acid 18 (9.47 g, 73.4 mmol, 1.1 equiv), PyBOP (38.2 g, 73.4 mmol, 1.1 equiv) and DIEA (34.9 mL, 200 mmol, 3.0 equiv) in dichloromethane (400 mL, 0.18 molar) for 16 h. Workup as in general procedure yielded the crude product, which was used in the next step without further purification.

Following the general protocol for step 2, the crude product (42.4 g, 66.7 mmol, 1.0 equiv) was dissolved in THF (400 mL) and reacted with TBAF (1.0 M in THF, 133 mL, 133 mmol, 2 equiv) for 14 h. Workup and purification provided the pure alcohol (37.8 g, 72% over 2 steps).

Following the general protocol for step 3, the purified alcohol (25.4 g, 48.7 mmol, 1.0 equiv) was dissolved in THF (209 ml) and DMF (34.8 ml) and cooled to −78° C., the solution was treated with propargyl bromide (36.7 mL, 487 mmol, 10 equiv) and NaHMDS (1.0 M in THF, 146 mL, 146 mmol, 3.0 equiv) and warmed to RT over 3 h. Flash chromatography using silica (10% to 50% EtOAc in hexanes) provided the pure product 19d (26.11 g, 96% yield).

(2S,5S,6S)-19d: $[\alpha]_D^{20}$ −9.8 (c 4.4, CHCl$_3$).

General Procedure for Cu Catalyzed [3+2] Cycloaddition

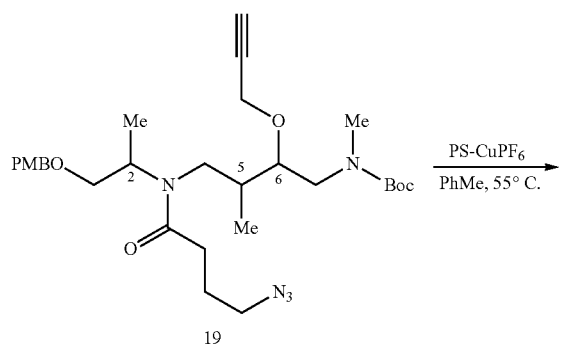

The Cu-catalyzed reactions were run in two batches and the crude products were combined and purified to yield the products. To a degassed solution of the azido alkyne 19 (1.0 equiv) in toluene (0.01 molar) at 55° C. was added Amberlyst-21 CuPF$_6$ (1.0 equiv) (Kelly, et al., 2009, Org. Lett. 11:2257-2260). The reaction was heated at 55° C. and monitored by LC. After 16 h the reaction was complete, beads were filtered and the solvent was removed under reduced pressure. The recovered beads were utilized to run a second batch of the reaction, the crude product from both batches were combined and purified to yield the product.

1,4-Macrocyclic Triazole (7a)

Following the general reaction protocol, 7.1 g and 6.7 g batches of (2R,5S,6R)-19a (1.0 equiv) was reacted with Amberlyst-21 CuPF$_6$ (70.0 g, 0.20 mmol/g, 1.0 equiv) in toluene (1200 mL) for 16 h. Flash chromatography using silica (80% to 100% EtOAc in hexanes) provided the pure product (2R,5S,6R)-7a (8.88 g, 57%). (2R,5S,6R)-7a: $[\alpha]_D^{20}$ +4.8 (c 0.5, CHCl$_3$). IR (cm$^{-1}$) 3014, 1674, 1449, 1141, 1058. $^1$H NMR (500 MHz, DMSO-d$_6$, 130° C.) δ 7.92 (s, 1H), 7.25 (d, J=7.6, 2H), 6.93 (d, J=8.4, 2H), 4.73 (s, 1H), 4.46-4.43 (m, 2H) 4.42 (s, 2H), 3.78 (s, 3H), 3.77-3.68 (m, 2H), 3.59-3.52 (m, 1H), 3.48-3.36 (m, 4H), 3.29-3.23 (m, 1H), 3.03-2.97 (m, 2H), 2.97 (s, 3H) 2.52 (s, 1H), 2.30-2.04 (m, 4H), 1.85-1.75 (m, 3H), 1.47 (s, 9H) 1.17 (d, J=6.4 Hz, 3H), 0.79 (d, J=6.7 Hz, 3H). $^{13}$C NMR (125 MHz, DMSO-d$_6$, 130° C.) δ 173.2, 160.1, 156.2, 145.2, 131.6, 129.8, 126.7, 115.0, 78.8, 73.3, 73.1, 62.6, 56.2, 52.9, 50.6, 50.0, 48.2, 36.3, 34.6, 31.0, 29.1, 26.2, 16.3, 12.3. HRMS (ESI) calcd for C$_{29}$H$_{45}$N$_5$O$_6$ [M+H]$^+$: 560.3443. Found: 560.3445.

1,4-Macrocyclic Triazole (7b)

Following the general reaction protocol, 6.4 g and 6.3 g batches of (2S,5S,6R)-19b (1.0 equiv) was reacted with Amberlyst-21 CuPF$_6$ (70.0 g, 0.18 mmol/g, 1.0 equiv) in toluene (1200 ml) for 16 h. Flash chromatography using silica (80% to 100% EtOAc in hexanes) provided the pure product (2S,5S,6R)-7b (7.33 g, 58%).

(2S,5S,6R)-7b: $[\alpha]_D^{20}$ +6.4 (c 5.7, CHCl$_3$).

1,4-Macrocyclic Triazole (7c)

Following the general reaction protocol, 5.0 g and 5.1 g batches of (2R,5S,6S)-19c (1.0 equiv) was reacted with Amberlyst-21 CuPF$_6$ (45.0 g, 0.22 mmol/g, 1.0 equiv) in toluene (1200 ml) for 16 h. Flash chromatography using silica (80% to 100% EtOAc in hexanes) provided the pure product (2R,5S,6S)-7c (7.70 g, 76%).

(2R,5S,6S)-7c: $[\alpha]_D^{20}$ +2.8 (c 4.8, CHCl$_3$).

1,4-Macrocyclic Triazole (7d)

Following the general reaction protocol, 5.0 g and 5.3 g batches of (2S,5S,6S)-19d (1.0 equiv) was reacted with Amberlyst-21 CuPF$_6$ (43.0 g, 0.22 mmol/g, 1.0 equiv) in toluene (890 ml) for 16 h. Flash chromatography using silica (80% to 100% EtOAc in hexanes) provided the pure product (2S,5S,6S)-7d (8.01 g, 78%).

(2S,5S,6S)-7d: $[\alpha]_D^{20}$ +31.0 (c 5.9, CHCl$_3$).

Elaboration of Compounds to Final Core

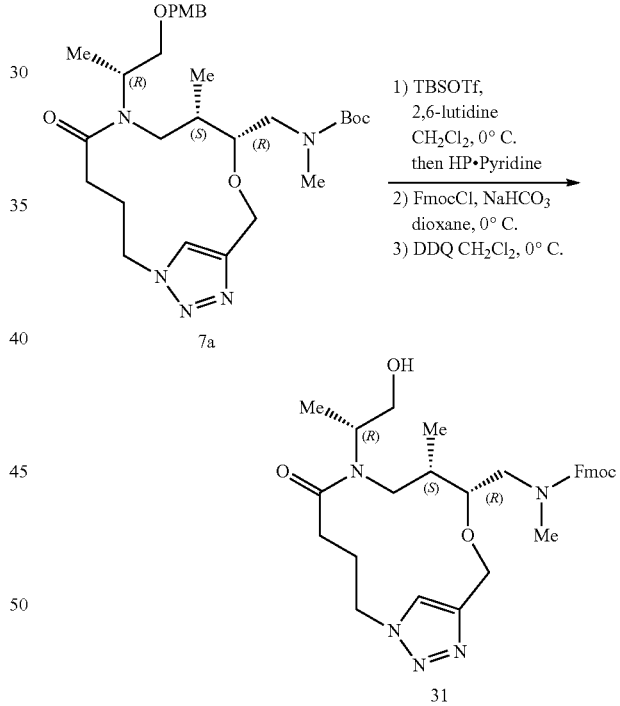

Step 1:

2,6-Lutidine (2.5 mL, 21.4 mmol, 2.0 equiv) and TBSOTf (7.39 mL, 32.2 mmol, 3.0 equiv) were added to a solution of 7a (16.0 g, 21.3 mmol, 1.0 equiv) in CH$_2$Cl$_2$ (536 mL, 0.02 M) at 0° C. The mixture was warmed to RT and stirred for 2 h before being quenched with saturated NH$_4$Cl solution and extracted with DCM. The combined organic extracts were dried over MgSO$_4$, filtered and concentrated to give 6.62 g of the crude silyl carbamate. The resulting oil was dissolved in DCM (107 mL) before HF.pyridine (70%, 2.23 mL, 10.7 mmol, 1.0 equiv) was added. The mixture was stirred for 45 min, quenched with saturated NH$_4$Cl solution and extracted with EtOAc. The combined organic extracts were dried over MgSO₄, filtered and concentrated and taken directly to next step.

Step 2:

The crude material was dissolved in THF (186 mL) before 10% NaHCO₃ solution (80 mL, excess) was added. The mixture was cooled to 0° C. and FmocCl (3.33 g, 12.86 mmol, 1.2 equiv was added, the mixture was stirred for 30 min at 0° C. and then for an additional 4 h at RT. The reaction was quenched with saturated aqueous NH₄Cl solution and the resulting mixture was extracted with EtOAc. The combined organic extracts were dried over MgSO₄, filtered and concentrated. Flash chromatography on silica gel (80% to 100% EtOAc in hexanes) gave the product 28a (5.56 g, 76% over 2 steps) as a white foamy solid.

Step 3:

(R,S,R)-28a (5.07 g, 7.44 mmol, 1.0 equiv) was dissolved in CH₂Cl₂ (119 mL) and pH 7 buffer solution (30 mL). The mixture was cooled to 0° C. and dichlorodicyanobenzoquinone (3.38 g, 24.9 mmol, 1.5 equiv) was added. The mixture was stirred for 10 min at 0° C. and an additional 1 h at RT before being quenched with saturated NH₄Cl and diluted with CH₂Cl₂. The mixture was then filtered through celite, and the filter cake was washed several times with hot CH₂Cl₂. The combined organic extracts were washed with saturated NaHCO₃ solution before activated carbon was added. The filtrate was concentrated and flash chromatography on silica gel (0% to 5% MeOH in CH₂Cl₂) gave pure product (2R,5S,6R)-31a (3.95 g, 97%).

(2R,5S,6R)-31: $[\alpha]_D^{20}$ +27.4 (c 8.6, CHCl₃). IR (cm⁻¹) 3382, 2929, 1636, 1449, 759. ¹H NMR (500 MHz, DMSO-d₆, 130° C.) δ 7.95 (s, 1H), 7.84 (d, J=7.1 Hz, 2H), 7.79 (d, J=7.0 Hz, 2H), 7.43-7.38 (m, 2H), 7.37-7.31 (m, 2H), 6.20 (s, 2H), 4.69 (d, J=15 Hz, 1H), 4.56 (d, J=15 Hz, 1H), 4.49-4.36 (m, 2H), 3.67-3.58 (m, 1H), 3.57-3.50 (s, 1H), 3.49-3.41 (s, 1H), 3.30-3.32 (m, 1H), 2.80-2.72 (m, 1H), 2.63-2.54 (m, 1H), 2.41 (s, 3H), 2.37-2.29 (m, 1H), 2.25-2.15 (s, 2H), 1.95-1.88 (m, 3H), 1.14 (d, J=6.3 Hz, 3H), 0.75 (d, J=6.4 Hz, 3H). ¹³C NMR (125 MHz, DMSO-d₆, 130° C.) δ 171.5, 142.3, 138.9, 136.9, 128.0, 126.4, 124.9, 120.3, 119.0, 107.8, 78.3, 63.3, 60.7, 53.6, 52.3, 45.9, 45.0, 48.5, 37.2, 35.6, 33.1, 29.6, 24.3, 13.9, 10.9. HRMS (ESI) calcd for C₃₁H₃₅N₅O₅ [M+H]⁺: 562.2951. Found: 562.3023.

Solid-Phase Library Synthesis:

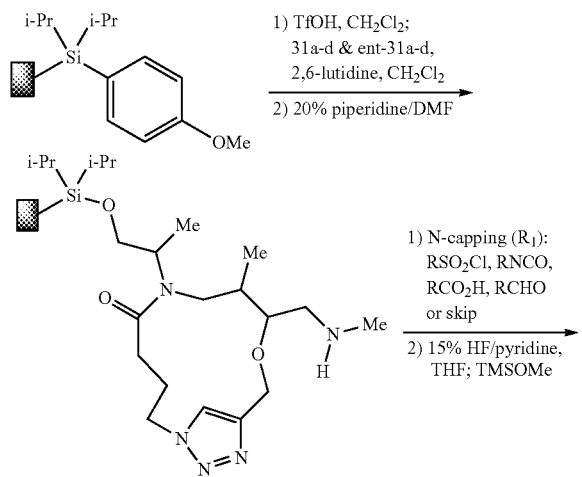

General Methods:

Solid-phase synthesis was conducted on silicon-functionalized polystyrene SynPhase™ Lanterns (L-series) equipped with radio frequency transponders (TranStems) for AccuTag directed sorting and compound tracking. Quality-control Lanterns were included at each synthesis step for reaction monitoring by UPLC (UV 210 nM) after HF-cleavage. All reactions were conducted in heavy wall pressure vessels from ChemGlass with agitation in New Brunswick Scientific incubator shakers.

Scaffold Loading:

To a flame-dried flask containing silicon-functionalized Lanterns was added a freshly prepared solution of TfOH in anhydrous DCM (9.0 equiv, 5 g of TfOH/100 mL of DCM) was added. Each flask was shaken at RT for 10 min at which time the Lanterns had turned bright orange. The deep red TfOH solution was removed via cannula and anhydrous 2,6-lutidine (12.0 equiv relative to Si) was added. Once the Lantern color had changed from orange to white, the scaffold (1.2 equiv. relative to Si) was added as a solution in anhydrous DCM (0.4 mL/Lantern) and the reaction mixture was shaken for 48 h overnight. The loading mixture was removed and set aside (to recover any unreacted alcohol) and the Lanterns were washed with the following solvents for 30 min intervals: DCM, THF, 3:1 THF/IPA, 3:1 THF/H₂O, DMF, 3:1 THF/H₂O, 3:1 THF/IPA, THF, DCM. The Lanterns were then dried on a lyophilizer overnight prior to sorting. All 8 stereoisomers of 29 were loaded via the same protocol.

Fmoc Removal:

To a flask containing Lanterns was added a solution of 20% piperidine in DMF (0.8 mL/Lantern). After shaking at RT for 30 min, the piperidine solution was removed and the Lanterns were washed with the following solvents for 30 min intervals: DMF, 3:1 THF/H₂O, 3:1 THF/IPA, THF, DCM. The Lanterns were then dried on a lyophilizer overnight prior to sorting.

N-Capping/Acids:

To each flask containing lanterns was added DCM (0.8 mL/Lantern) followed by triethylamine (30 equiv) and the desired acid (20 equiv). PyBOP (20 equiv) was added and the Lanterns were shaken at RT overnight and then washed with following solvents for 30 min intervals: DCM, DMF, 3:1 THF/H₂O, 3:1 THF/IPA, THF, DCM. The Lanterns were then dried on a lyophilizer overnight prior to sorting Cleavage Protocol:

To a 96-well plate containing Lanterns was added a 15% solution of HF/pyridine in stabilized THF (350 μL/Lantern). After 2 h the cleavage solution was quenched with TMSOMe (700 μL/Lantern) and the contents of each well were transferred to a pre-weighed 2-mL vial. The Lanterns were washed with an additional 200 μL of stabilized THF (or

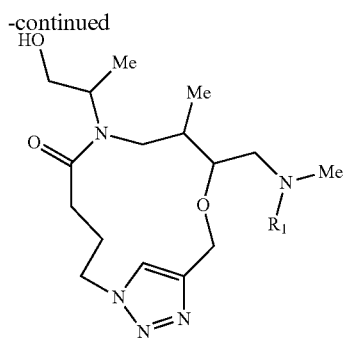
-continued

THF/MeOH) and the solution was transferred to the 2-mL vial. The samples were concentrated on a Genevac® solvent evaporation system overnight without heating. Loading masses for each alcohol was determined on a FlexiWeigh® system.

Compound 108 was synthesized following the general methods for library synthesis. Compound 31 was loaded onto Lanterns followed by subsequent Fmoc removal. The secondary amine was capped with cyclopropane carboxylic acid. Compound 108 was then cleaved from the Lanterns and isolated following the standard cleavage protocol.

Example 2: Design of a Primary Human Hepatocyte Platform for Chemical Screening

In order to generate renewable sources of functional human hepatocytes, a high-throughput liver platform was developed to enable unbiased chemical screening on primary human hepatocytes. The treatment of cells with small molecules may modulate a wide range of cellular processes, such as stem cell self-renewal and differentiation, and proliferation of normally quiescent mature cells. Compounds can act through various mechanisms to induce cell division, including activation of developmental signaling pathways such as Wnt or recruitment of GEFs to the plasma membrane for RAS/MAPK pathway activation.

In order to avoid species-specific differences and cell line mutations, the screen was conducted with human primary hepatocytes. Traditionally, chemical screening on such cells has been hindered by their availability in large quantities as well as their rapid loss of viability and phenotype in vitro. Recent advances in cryopreservation technologies allowed enough primary human cells to be stored for screening; these cells are maintained through co-cultivation with non-parenchymal cells. Co-cultures of primary human hepatocytes with murine embryonic J2-3T3 fibroblasts were recently shown to maintain normal hepatocyte phenotype for weeks. These in vitro platforms consisted of hepatocytes surrounded by a co-planar population of fibroblasts. While sufficient for stabilizing hepatocyte functions in vitro, such platforms may limit normal hepatocyte expansion due to contact inhibition. Thus, for this screen, a sparse population of hepatocytes was co-cultivated on top of a confluent feeder layer of J2-3T3 fibroblasts within 384-well plates (FIG. 1A top). This screening platform stabilized hepatocyte phenotypic functions in vitro (FIG. 1A bottom) and was compatible with two separate high-throughput readouts developed for this screen.

The primary readout detected hepatocyte proliferation via automated high-content imaging. This assay quantified hepatocyte nuclei numbers, using nuclear morphologies to separate the hepatocyte and fibroblast subpopulations that co-exist within the screening platform. When visualized with Hoechst stain, hepatocyte nuclei were smaller and more uniform in texture while fibroblast nuclei were larger and punctated (FIG. 1A bottom). Leveraging this distinction, automated image analyses was developed that utilized machine learning algorithms to classify nuclei types and tabulate hepatocyte nuclei numbers. Assay validation data showed that this image-based readout can confidently ($z'>0$) detect doublings in hepatocyte nuclei numbers with low variance (CV<20%) and good reproducibility. Besides quantifying hepatocyte nuclei that have completed mitosis, the number of nuclei in the process of mitosis were also quantified. Two additional analysis pipelines were built to detect nuclear morphologies consistent with cells undergoing metaphase and anaphase.

In order to evaluate the phenotype of treated cells, a secondary readout was included to quantify hepatocyte functions via competitive ELISA. This biochemical assay measured the level of secreted albumin as a marker for protein synthesis functions of the cultured hepatocytes (FIG. 1A bottom).

Example 3: High-Throughput Identification of Small Molecules for Human Hepatocyte Sourcing Using the high-throughput liver platform, 12,480 small molecule compounds were screened. These molecules mainly comprised kinase-biased compounds (KinA) and commercial compounds (ComA), but also include bioactive compounds (BioA), chromatin-biased (CHRM) as well as a small number of natural products (NatP). Of note in the library are ~2,500 diverse synthetic compounds unique to the Broad Institute. These compounds rival the complexity of natural products, which is desirable because many small molecules known to affect biological processes are structurally complex. Structural diversity is also desirable in this screen because every macromolecule in the cellular machinery is a potential target.

Figures 1, 1B:
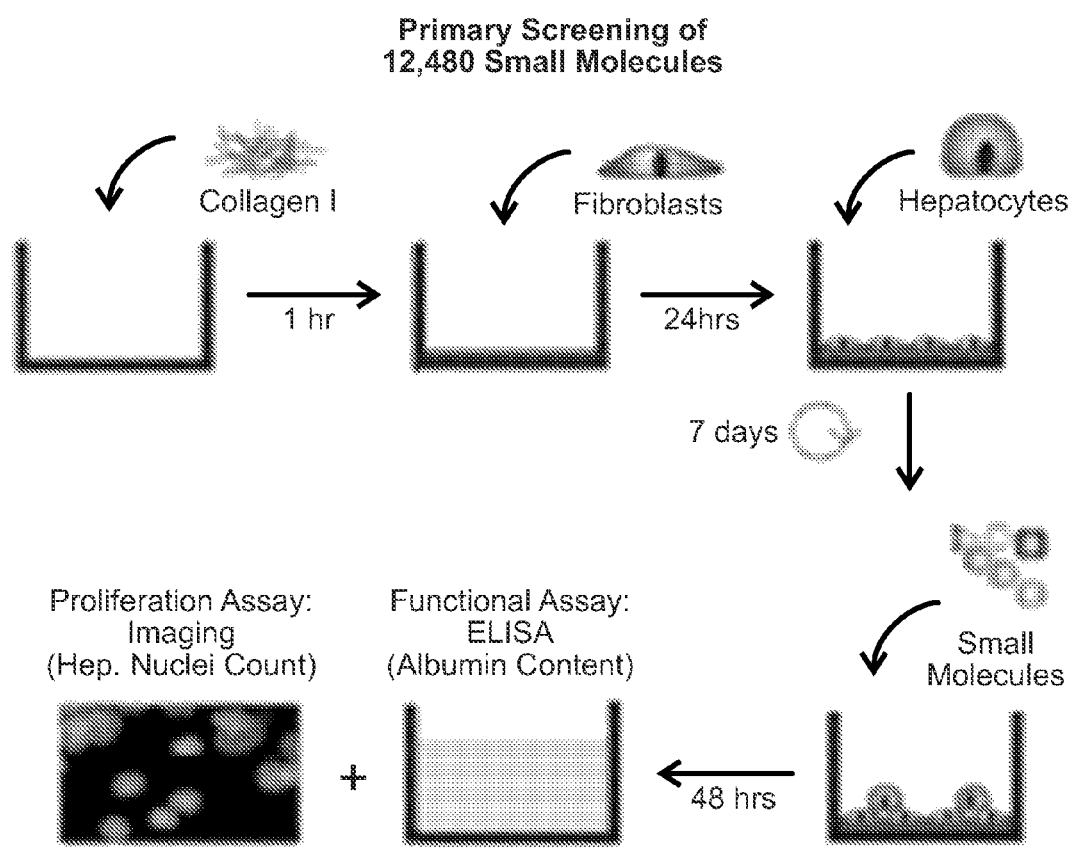
FIG. 1, comprising
Figure 1B:
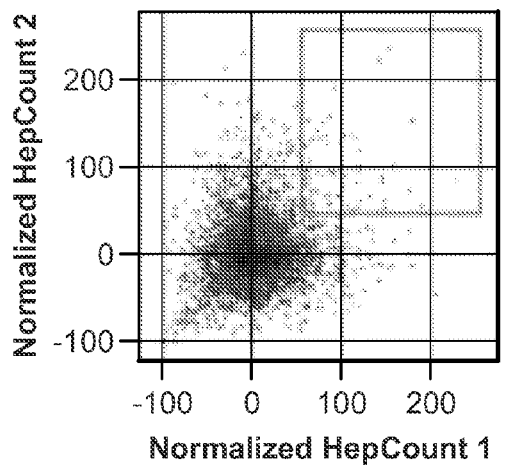
Figure 1:
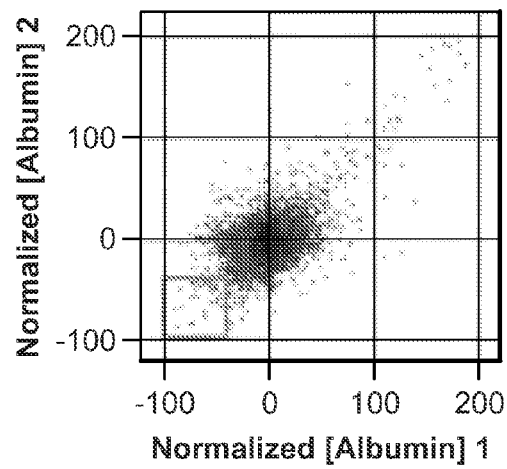

FIG. 1B top summarizes the workflow of the screen. Primary screening was done on human primary hepatocytes, preconditioned for seven days by non-parenchymal cells in the screening platform. Upon stabilization in vitro, cultures were treated with the chemical library for 48 hours. All compounds were tested in duplicates, at a single concentration of 15 µM. This single concentration was selected via a pilot screen of ~2,000 small molecules. All 12,480 small molecules were initially tested on a single donor of cryopreserved hepatocytes (donor a) in order to eliminate noise from donor-to-donor variability. Following compound treatment, media supernatants were collected for functional analyses via ELISA and cultures were fixed in 4% paraformaldehyde for proliferation analyses via imaging.

To identify proliferation hits, three image-based readouts—one each to quantify the number of (1) hepatocyte nuclei in interphase, (2) nuclei in metaphase and (3) nuclei in anaphase—were integrated. z Scores were converted into p values, which were then used to generate ranked lists of compounds based on the efficacy and consistency of effects across the different proliferation readouts. Efficacy was assessed by the product of p values ($p_{prod}=p_{inter} \times p_{meta} \times p_{ana}$); consistency was evaluated by the maximum of p values ($p_{max}=\max(p_{inter}, p_{meta}, p_{ana})$. Compounds were considered proliferation hits if $p_{prod}<1\times10^{-6}$ and $p_{max}<0.25$. Functional hits were selected by an ELISA $p<-0.05$. Compounds with ELISA $z>3.0$ were eliminated as toxic. 93 compounds met all hit selection criteria, qualifying as Functional Proliferation Hits (FPH); FIG. 1B bottom illustrates the types of compounds that constituted this set of hits.

A total of 400 primary hits were retested in eight-point dose-response curves. These included 93 FPHs, as well as additional Proliferation-only Hits (PHs, $z>3.0$ in any of the image-based readouts) and Function-only Hits (FHs, $z<-4.2$ in ELISA). A different donor of cryopreserved hepatocytes (donor B) was used during retest in order to include biological diversity in the screen. Remaining hits were filtered through a cell-free counter screen to eliminate compounds that interfered with the ELISA assay chemically. Ultimately, twelve confirmed hits were obtained.

Among these confirmed hits were two classes of compounds, which enabled two different approaches for generating a renewable source of functional human hepatocytes. One class of hits (FPHs) induces functional proliferation of hepatocytes in vitro, and can thus be used to expand mature human primary hepatocytes. The second class of hits (FHs) enhances the functions of cultured hepatocytes, and thus can be used to differentiate iPS-derived hepatocytes toward a more differentiated phenotype.

Example 4: Expansion of Human Primary Hepatocytes

Figure 2:
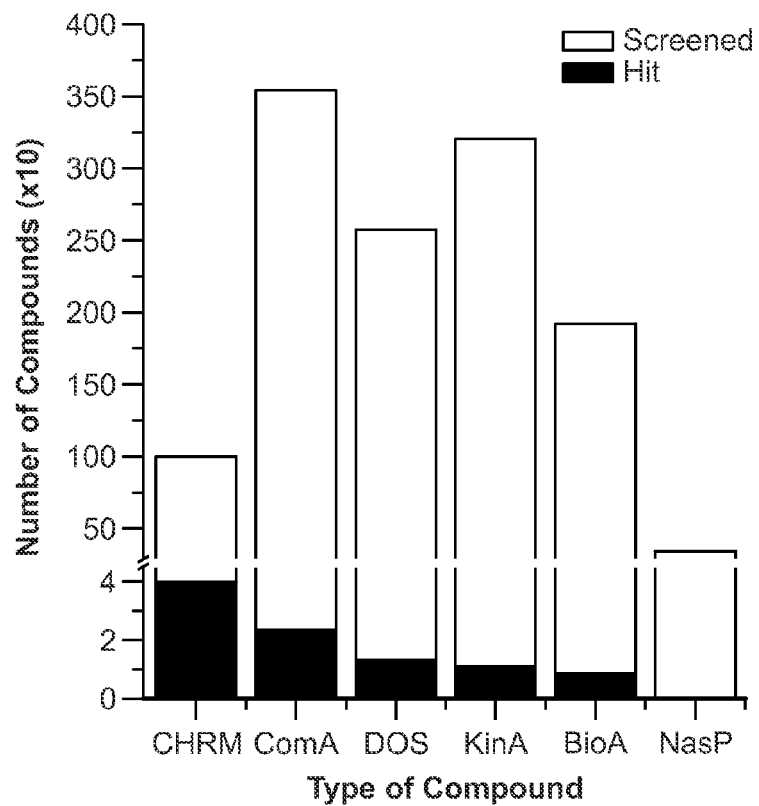
FIG. 2, comprising
Figure 2A:
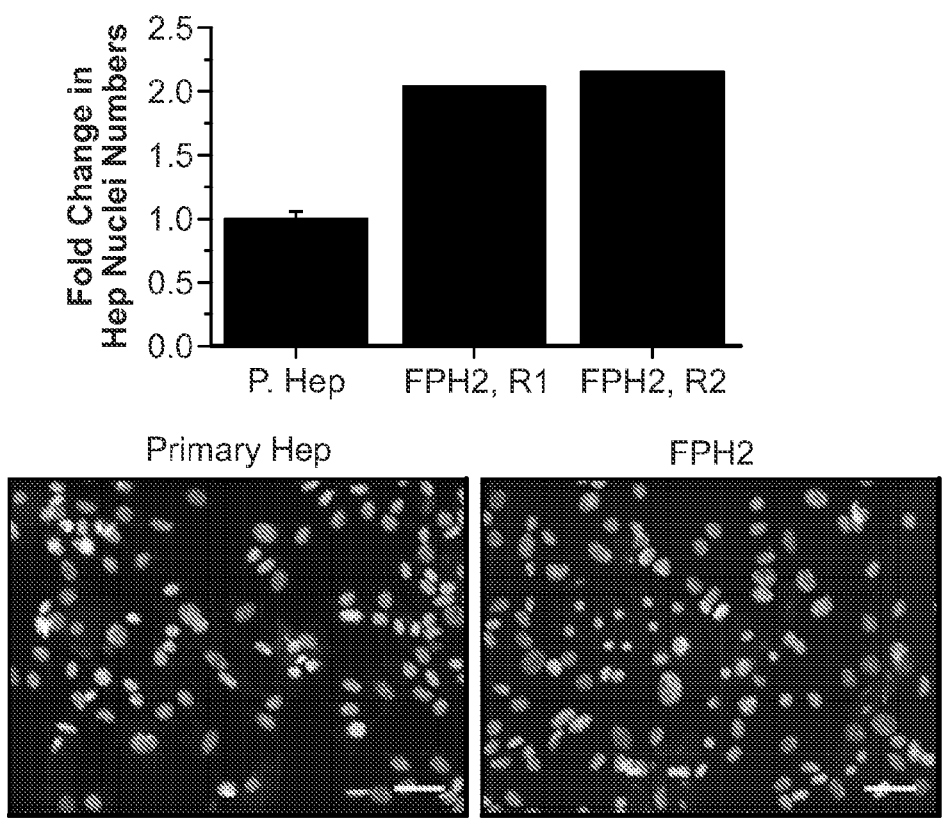
FIGS. 2A-2H, illustrates the results of treatment of hepatocytes with FPHs.
Figure 2B:
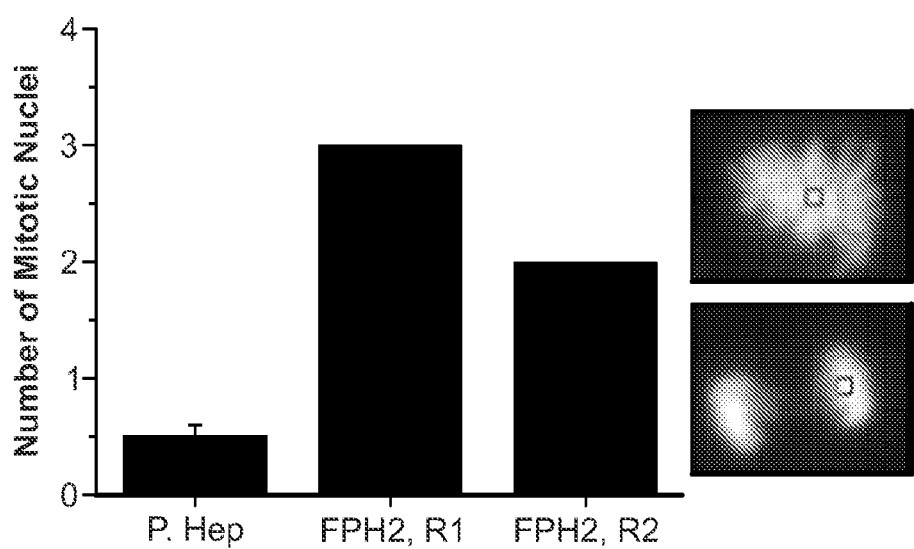
Figure 2C:
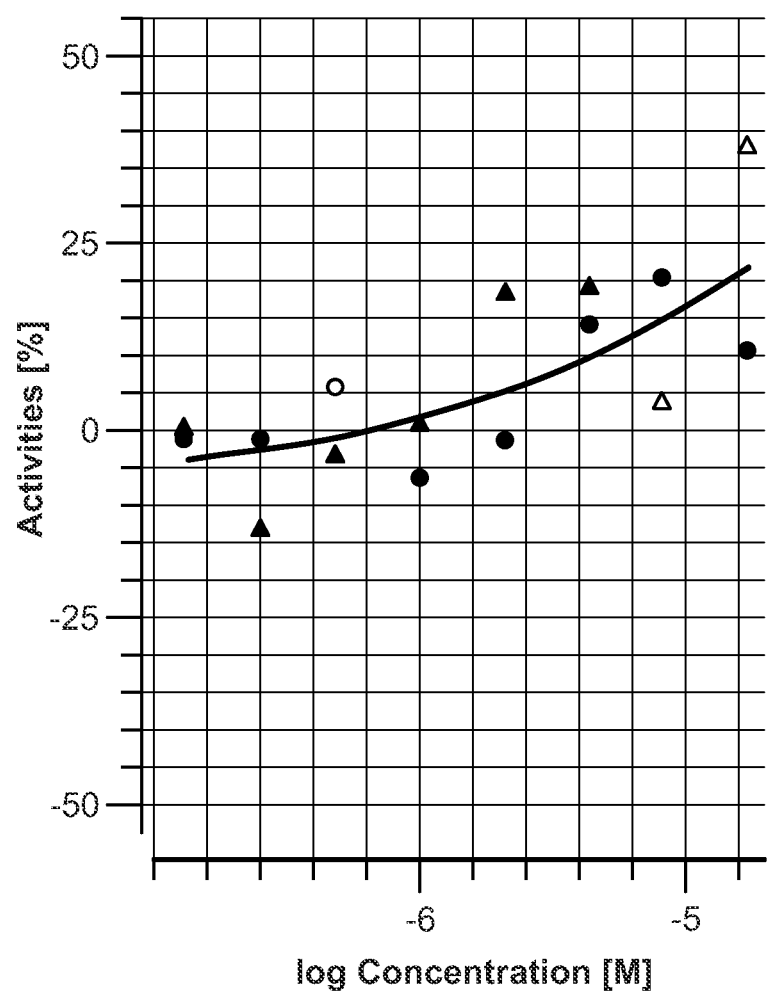

The ability of compounds of the invention (FPHs) to expand human primary hepatocytes in vitro was tested. Prostaglandin E2 (PGE2), which promotes liver regeneration in zebrafish via Wnt signaling, was used as a positive control. PGE2 was tested on human primary hepatocytes in the high-throughput liver platform described herein and found it to be a FPH. Two other compounds of the invention (strong FPHs (FPH1 and FPH2)), identified through unbiased screening, were tested. Both compounds induced a 1.5× increase in hepatocyte nuclei numbers during primary screening (FIG. 2A), elevated the number of nuclei undergoing mitosis (FIG. 2B), and these effects on hepatocytes were dose-responsive (FIG. 2C). Cells treated with these compounds also maintained their liver-specific functions.

Figure 2D:
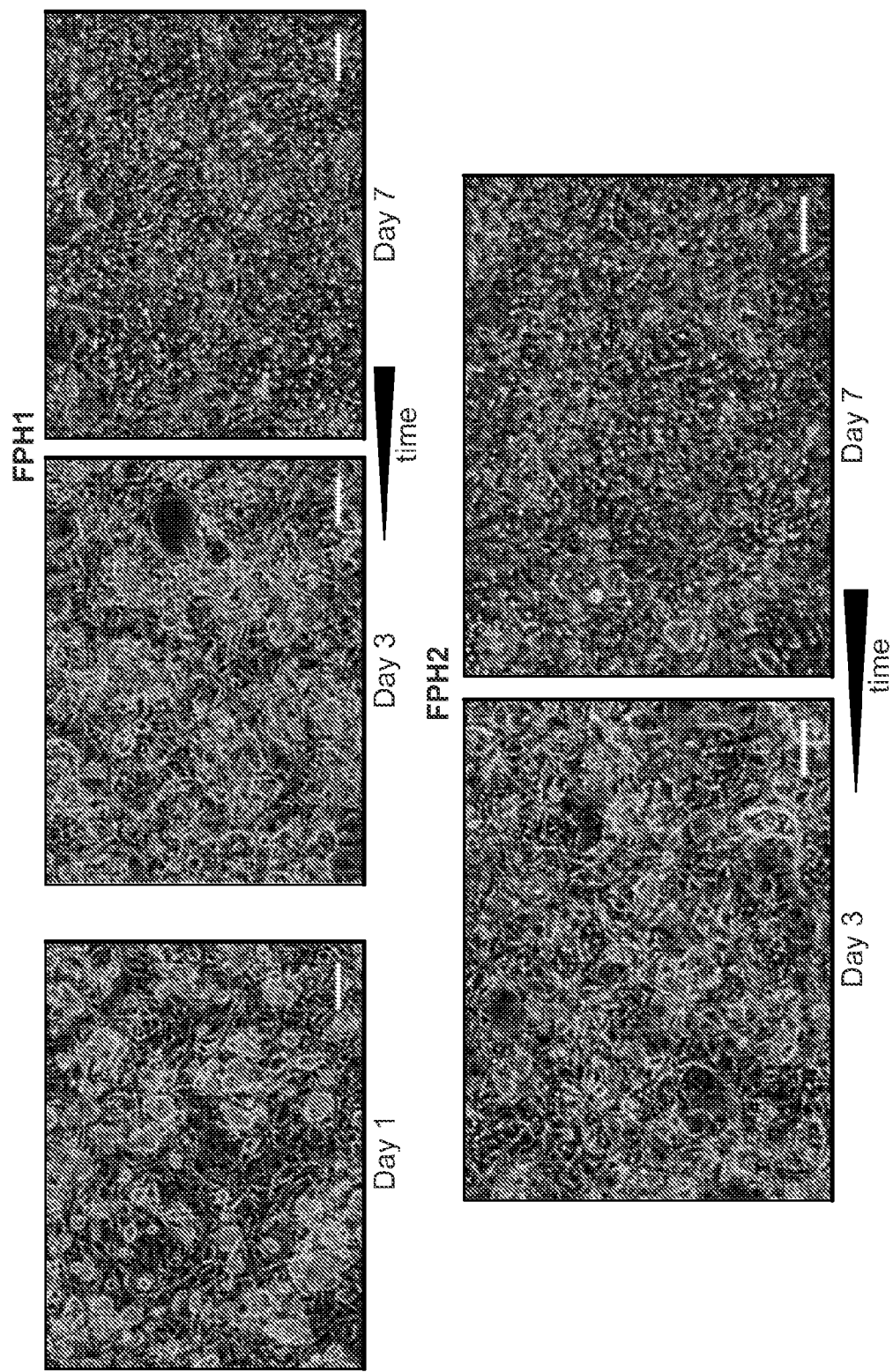
Figure 2E:
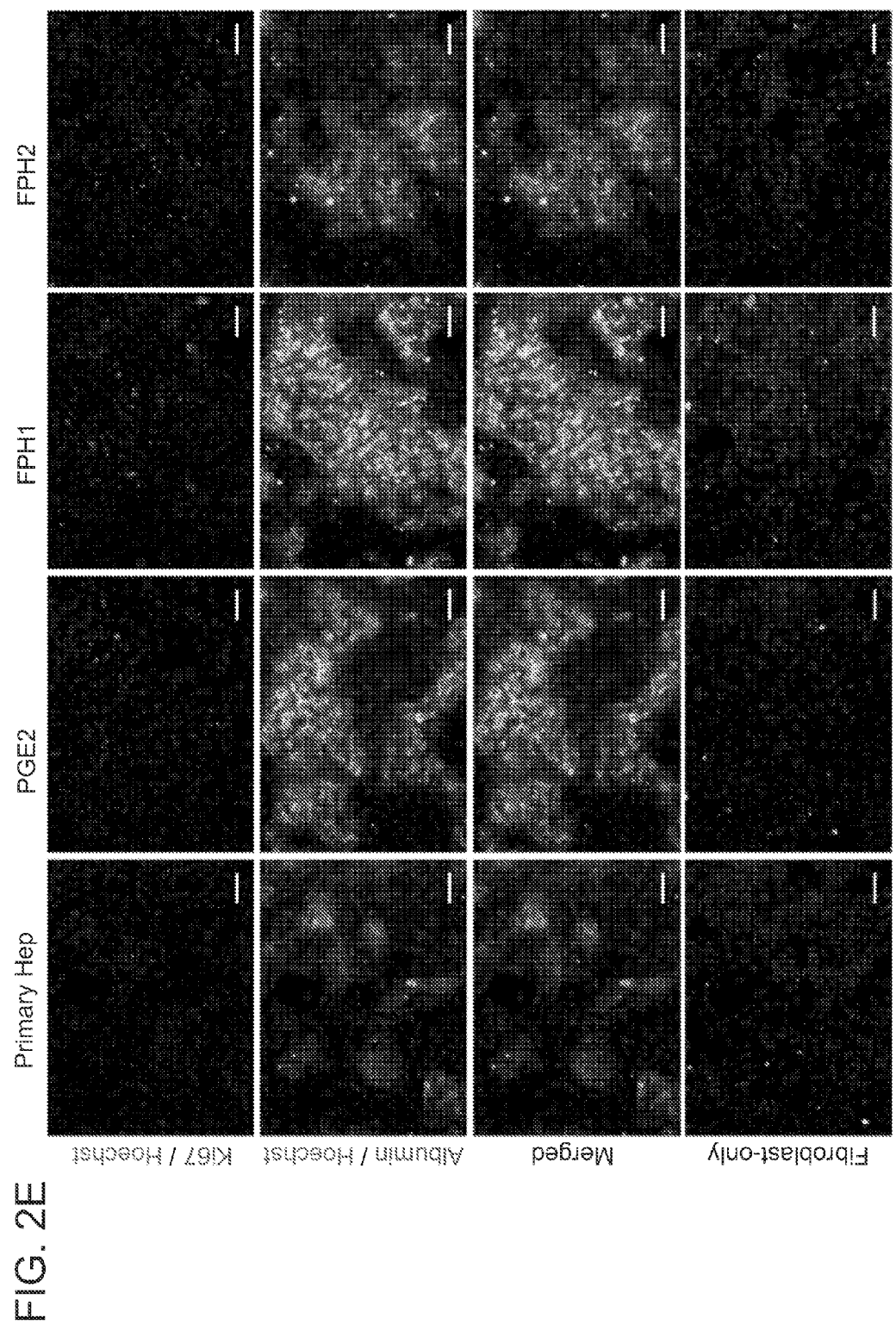
Figure 2F:
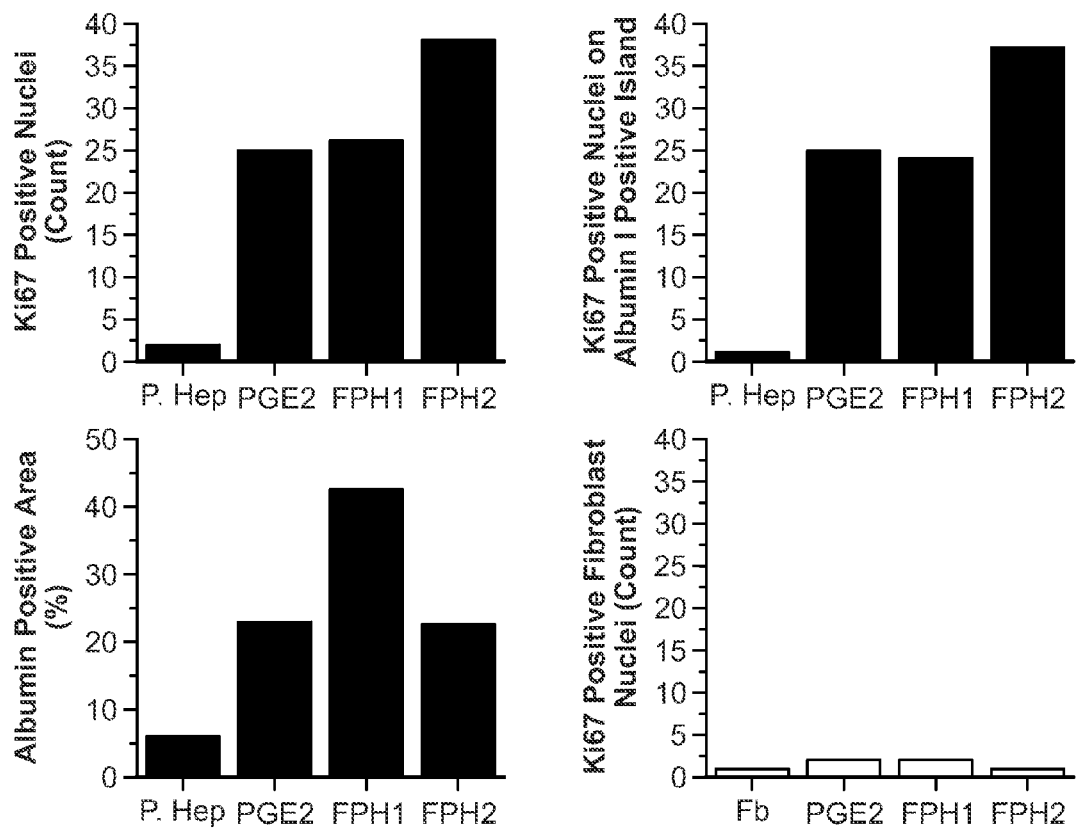

To characterize the effects of FPH1 and FPH2 outside of the screening platform, human primary hepatocytes were seeded at a density of ~20,000 cells/cm$^2$, into standard 12-well tissue culture plates on top of a feeder layer of growth-arrested J2-3T3s. These cells were cultured for 7 days, during which time a single compound/FPH was supplemented into the media on days 1 and 5 at a concentration of 20 μM. Treated hepatocyte colonies increased in size over time, with more hepatocytes populating each colony (FIG. 2D, 2E). Furthermore, compound/FPH treatment increased Ki67 staining, which not only co-localized with Hoechst stains for cell nuclei but also with human albumin stains for hepatocytes (FIG. 2E). Quantitative image analysis showed an up to 6.6- and 3.5 fold increases in the area of albumin-positive colonies upon FPH1 and FPH2 treatment, respectively (FIG. 2F). The vast majority of Ki67-positive nuclei exhibited hepatocyte nuclear morphologies, which was consistent with the lack of proliferating cells in fibroblast-only cultures treated with FPHs. These results strongly indicated that human primary hepatocytes can be induced to proliferate in vitro using FPHs.

Figure 2G:
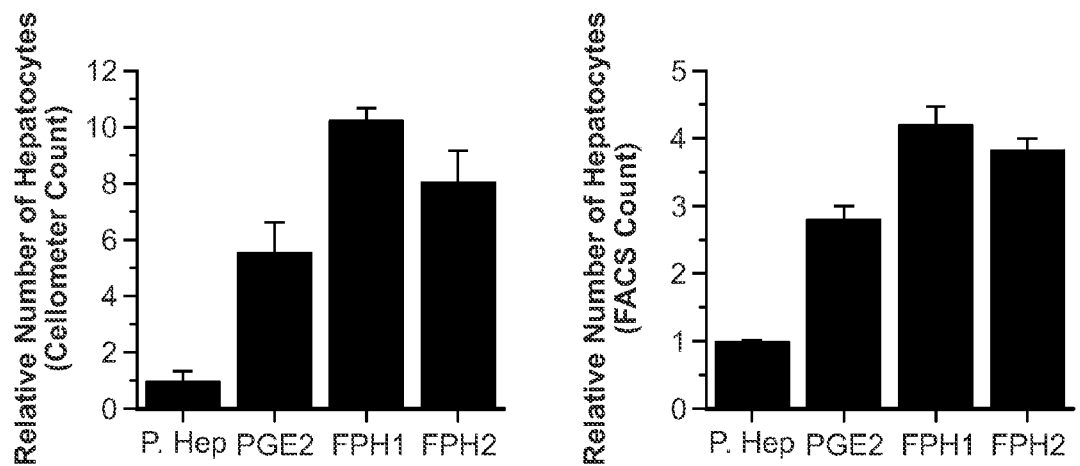

To characterize the degree and kinetics of proliferation, the number of hepatocytes in culture was quantified using both an automated cell counter and FACS analysis. Results showed a dramatic, up to 10-fold increase in the number of hepatocytes when treated with various FPHs (FIG. 2G). This difference in effect, however, may not reflect compound efficacy; the number of Ki67-positive nuclei was more elevated with FPH2 treatment, suggesting that FPH2 effects were simply delayed. The vast majority of Ki67-positive nuclei exhibited hepatocyte nuclear morphologies, which is consistent with the lack of proliferating cells in fibroblast-only cultures treated with FPHs. These results strongly indicated that human primary hepatocytes can be induced to proliferate in vitro using FPHs.

Figure 2H:
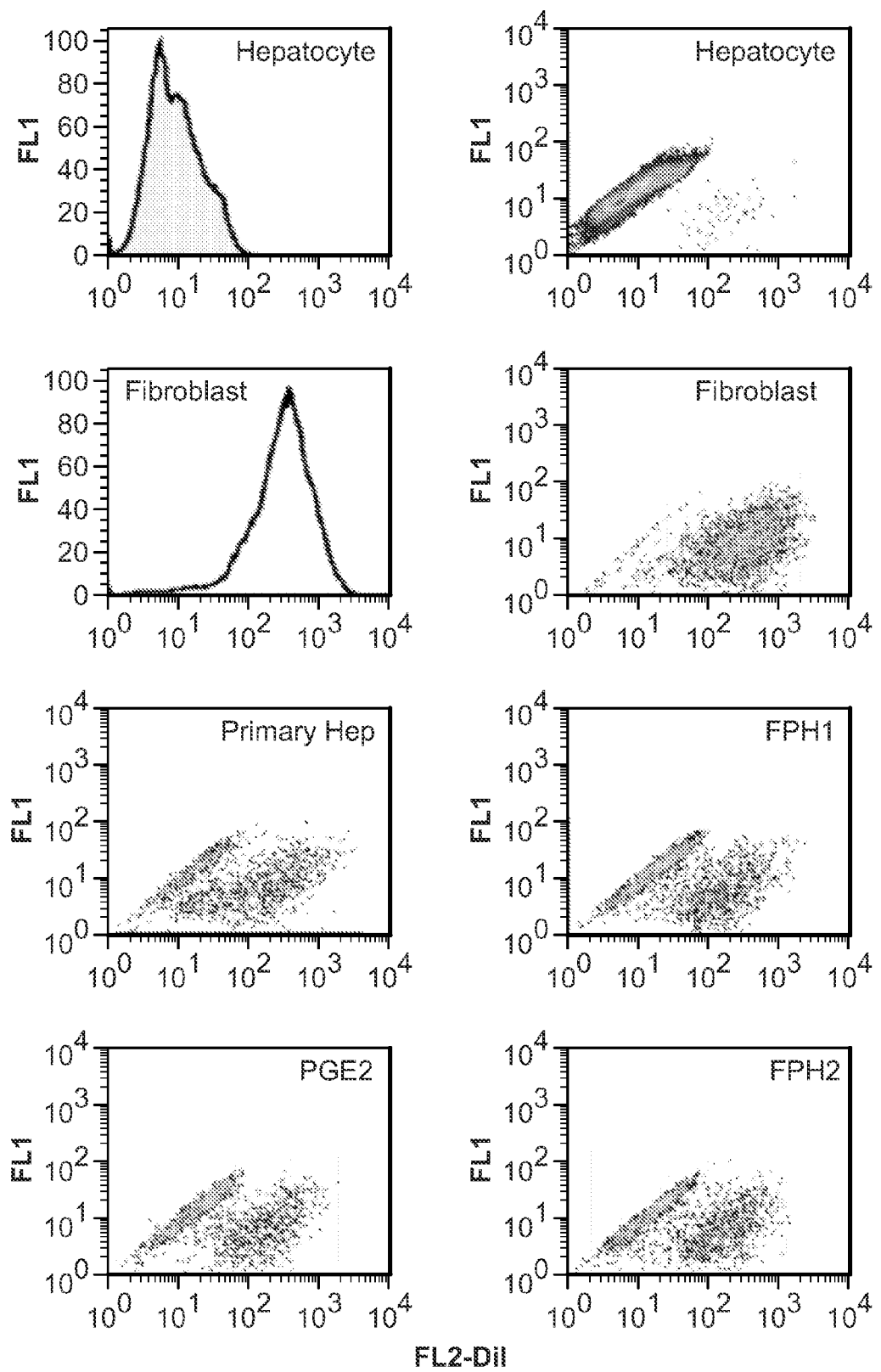

To characterize the degree of proliferation and to obtain a doubling time, cells were counted and fluorescence-activated cell sorting (FACS) was performed (FIG. 2H). For cell counting, FPH-treated cells were trypsinized after seven days in culture. The number of cells was quantified using an automated cell counter. The number of hepatocytes was obtained by subtracting the number of fibroblasts from the total number of cells found in the corresponding co-culture. For FACS analysis, growth arrested J2-3T3s were labeled with CM-DiI prior to initiation of co-culture so that hepatocytes can be identified via negative selection. To enable cell counting during FACS, each sample was supplemented with fluorescent counting beads. The strongest proliferation inducer was FPH1 (FIG. 2G bottom graph). Over 7 days, FPH1 induced hepatocyte doublings at a rate that is consistent with reported liver regeneration kinetics in vivo.

Figure 3A:
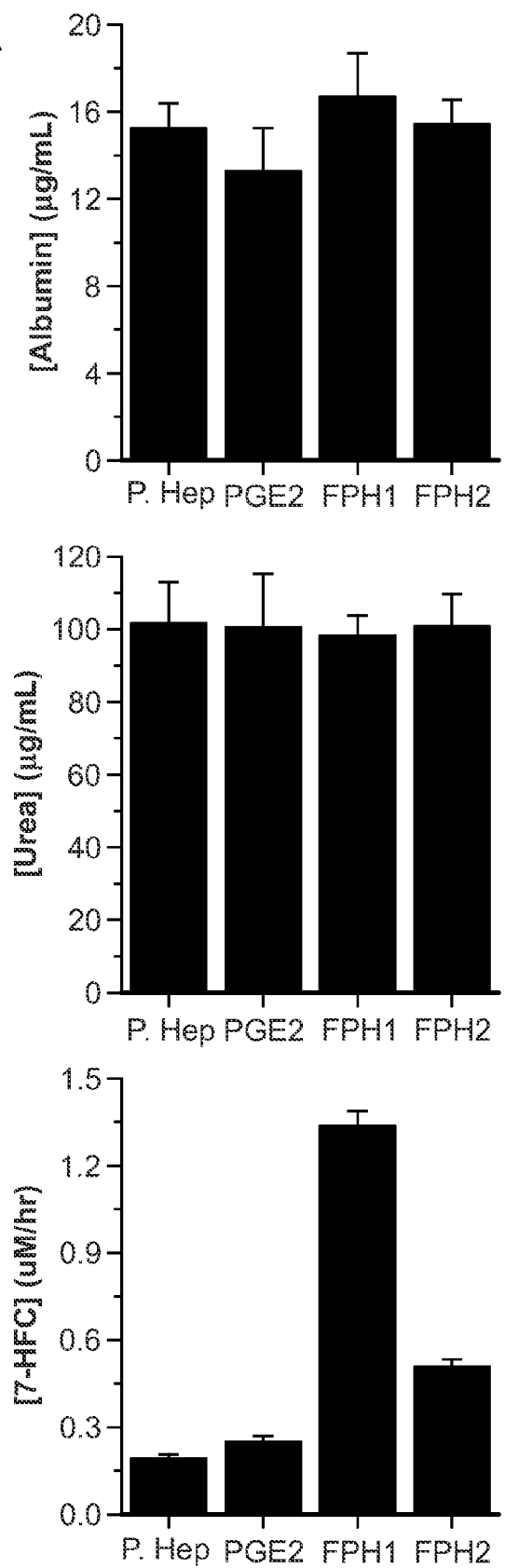
FIGS. 3A-3C, illustrates the characterization of hepatocytes treated with compounds of the invention.
Figure 3B:
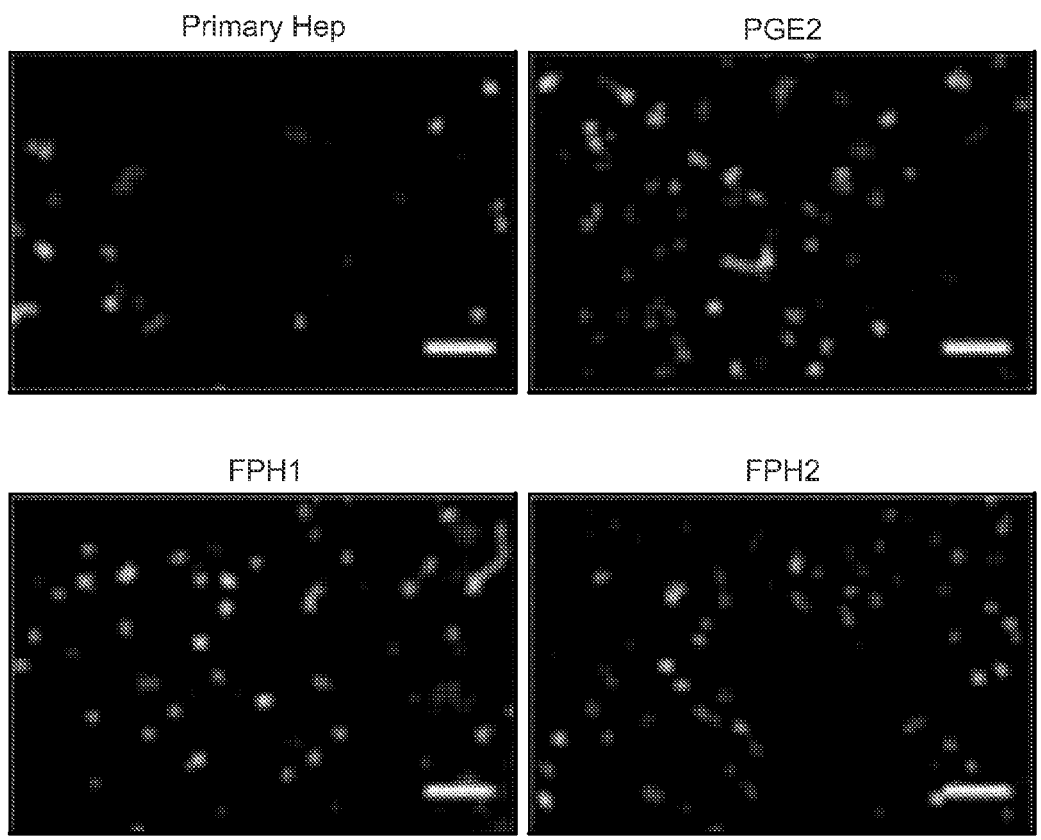
Figures 1, 3C:
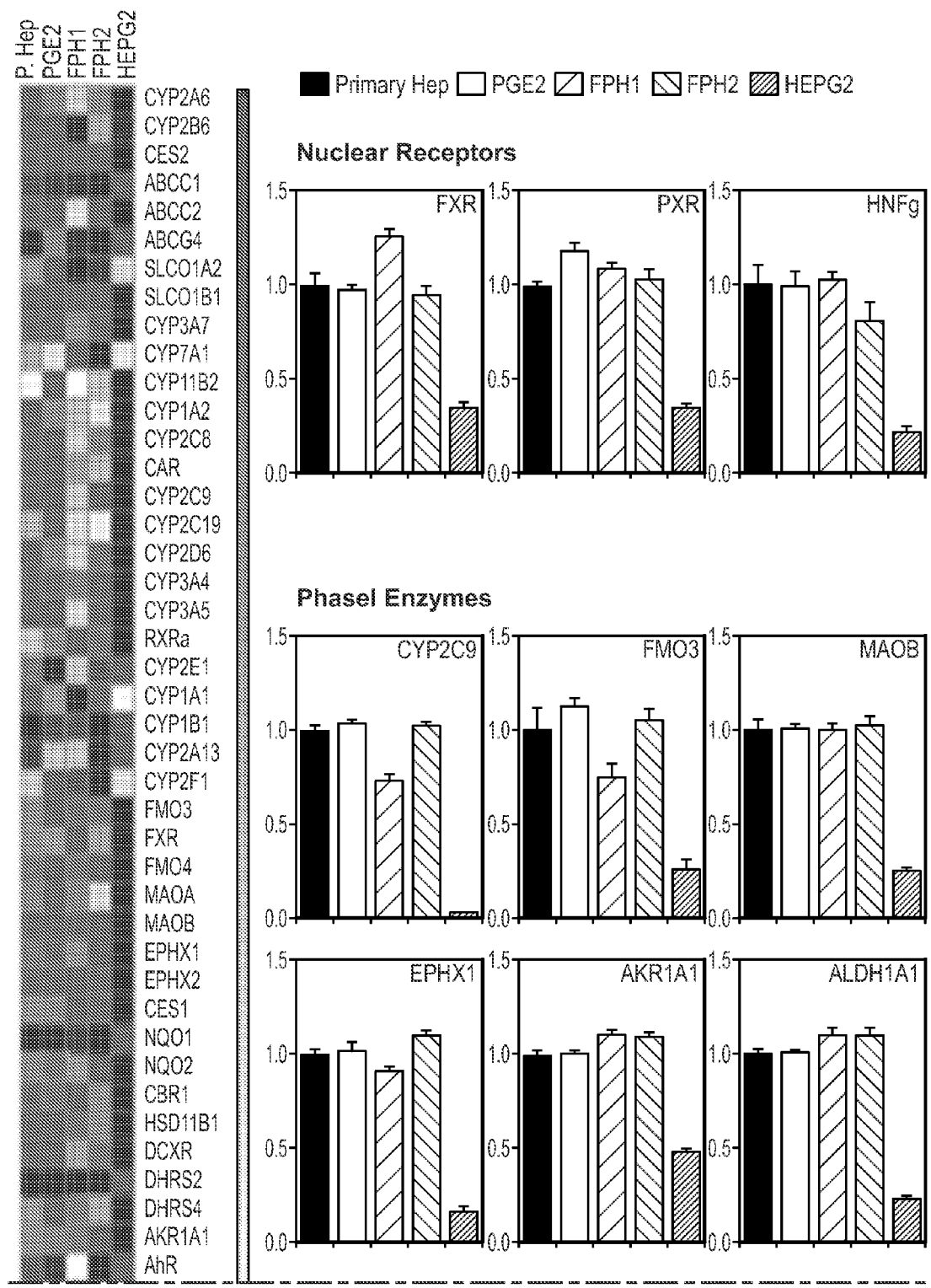
Figures 2, 3C:
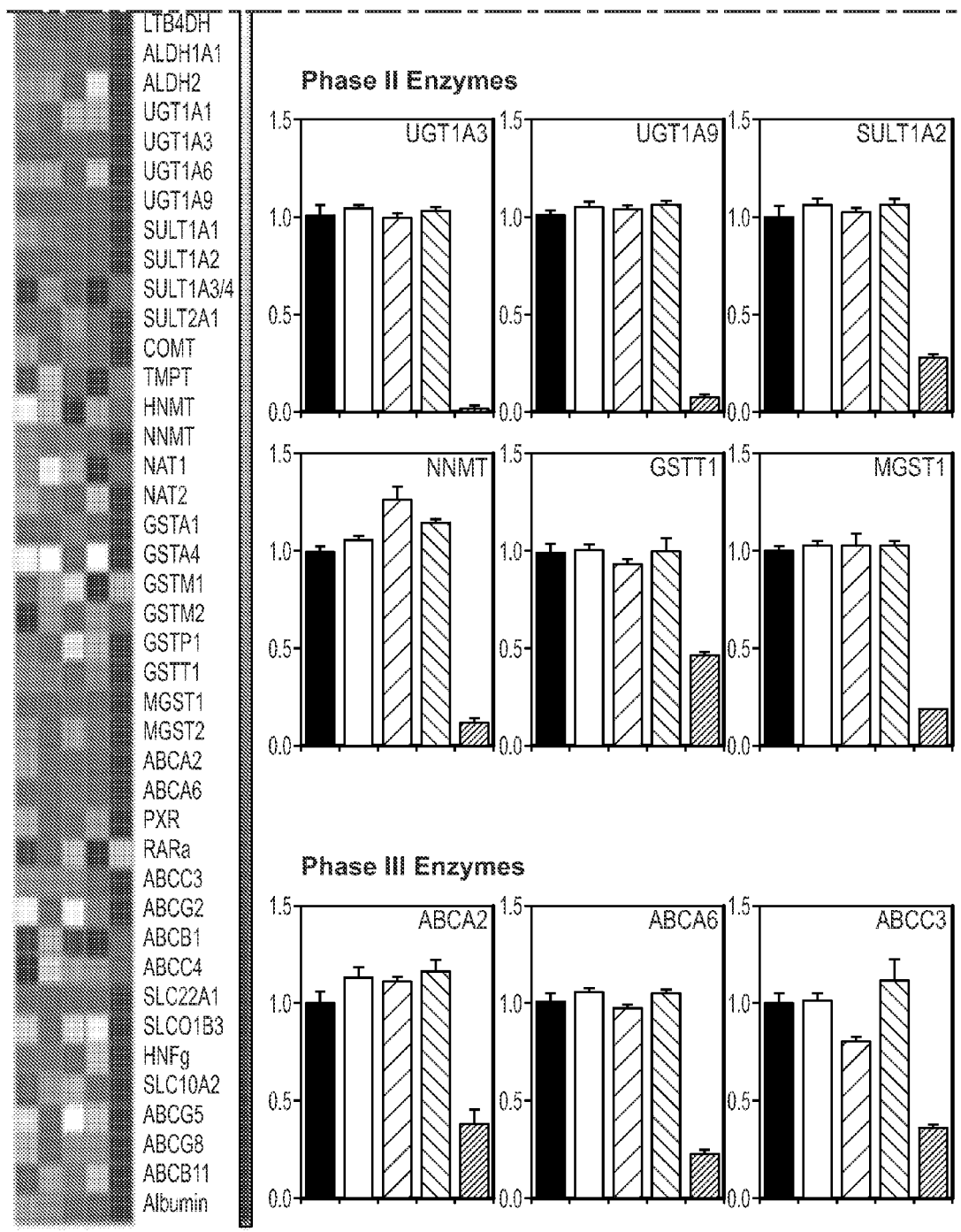

To assess the phenotype of the treated hepatocytes, imaging, biochemical analyses and gene expression profiling were performed. Phase contrast imaging was used to monitor hepatocyte morphology and found that normal morphology was maintained throughout the treatment period (FIG. 2D). Albumin secretion and urea synthesis, a surrogate marker of nitrogen metabolism, were both stable throughout FPH treatment (FIG. 3A top and middle). Metabolic functions were assessed via examinations of cytochrome P450 (CYP450) activity and canalicular transport. Results showed normal CYP450 activities (FIG. 3A bottom) and active transport of a fluorometric substrate into the bile cannaliculi between hepatocytes (FIG. 3B). Gene expression profiling confirmed that there are no significant differences between FPH-treated and untreated hepatocytes (FIG. 3C). These results agree with literature findings of sustained liver functions throughout liver regeneration.

Example 5: Differentiation of Human iPS-Derived Hepatocytes

The ability of compounds of the invention to affect the differentiation and maturation of iHeps was tested. Undifferentiated iPS cells were cultured on Matrigel, supported by primary mouse embryonic fibroblasts. Once confluent, iPS cells were transitioned to differentiation media, with sequential addition of growth factors (Activin A, BMP-4, bFGF, HGF, and OSM) to guide differentiation, first into endoderm, then into hepatic progenitor cells and finally into iHeps. Compound treatment started on day 21 post initiation of differentiation and acted over a period of 9 days. FH1 and FPH2 were used to treat iHeps. FH1 doubled albumin secretion during primary screening (FIG. 4A left) in a dose-responsive manner (FIG. 4A right). FPH2 had similar, but weaker effects on hepatocyte functions.

iHeps treated with FH1 and FPH2 developed more mature hepatocyte phenotypes. Colonies of hepatocyte-like cells increased in size with compound treatment (FIG. 4B), suggesting more differentiation of iPS cells down a hepatic lineage. Treated colonies also exhibited more pronounced hepatocyte morphologies, with more noticeable bile cannaliculi between hepatocytes indicated by yellow arrows in FIG. 4B.

Figures 1, 4C:
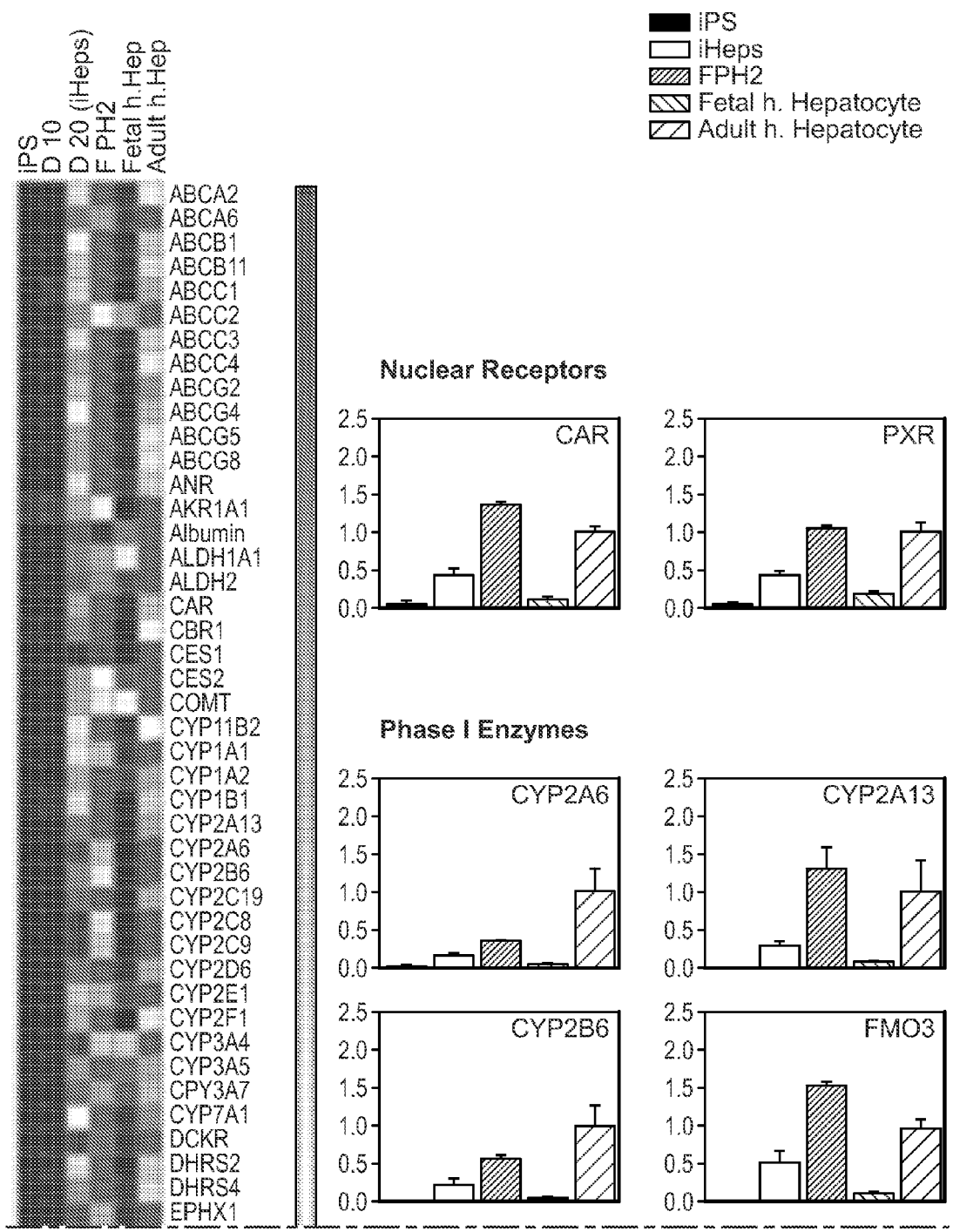
Figures 2, 4C:
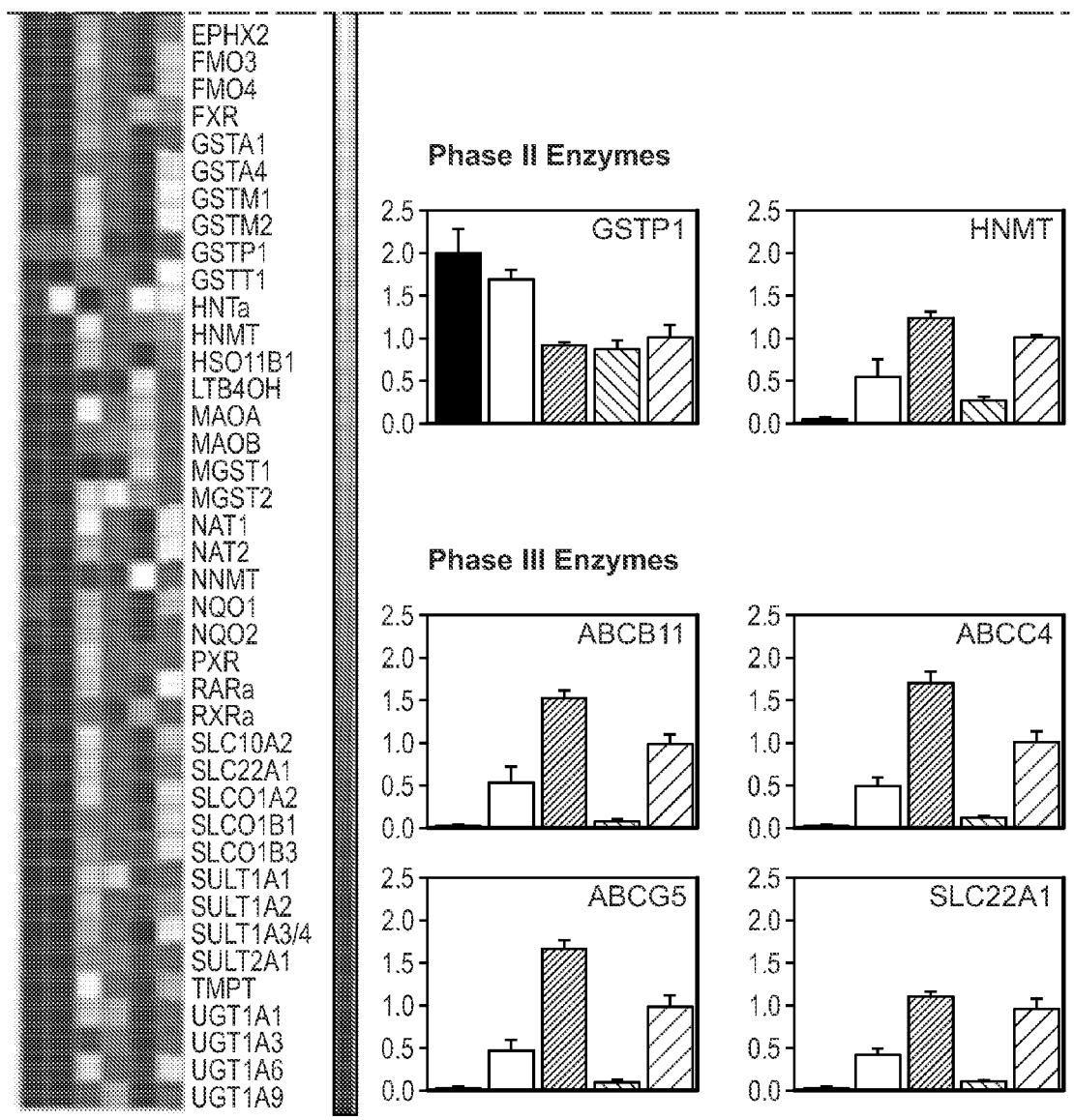
Figures 3, 4C:
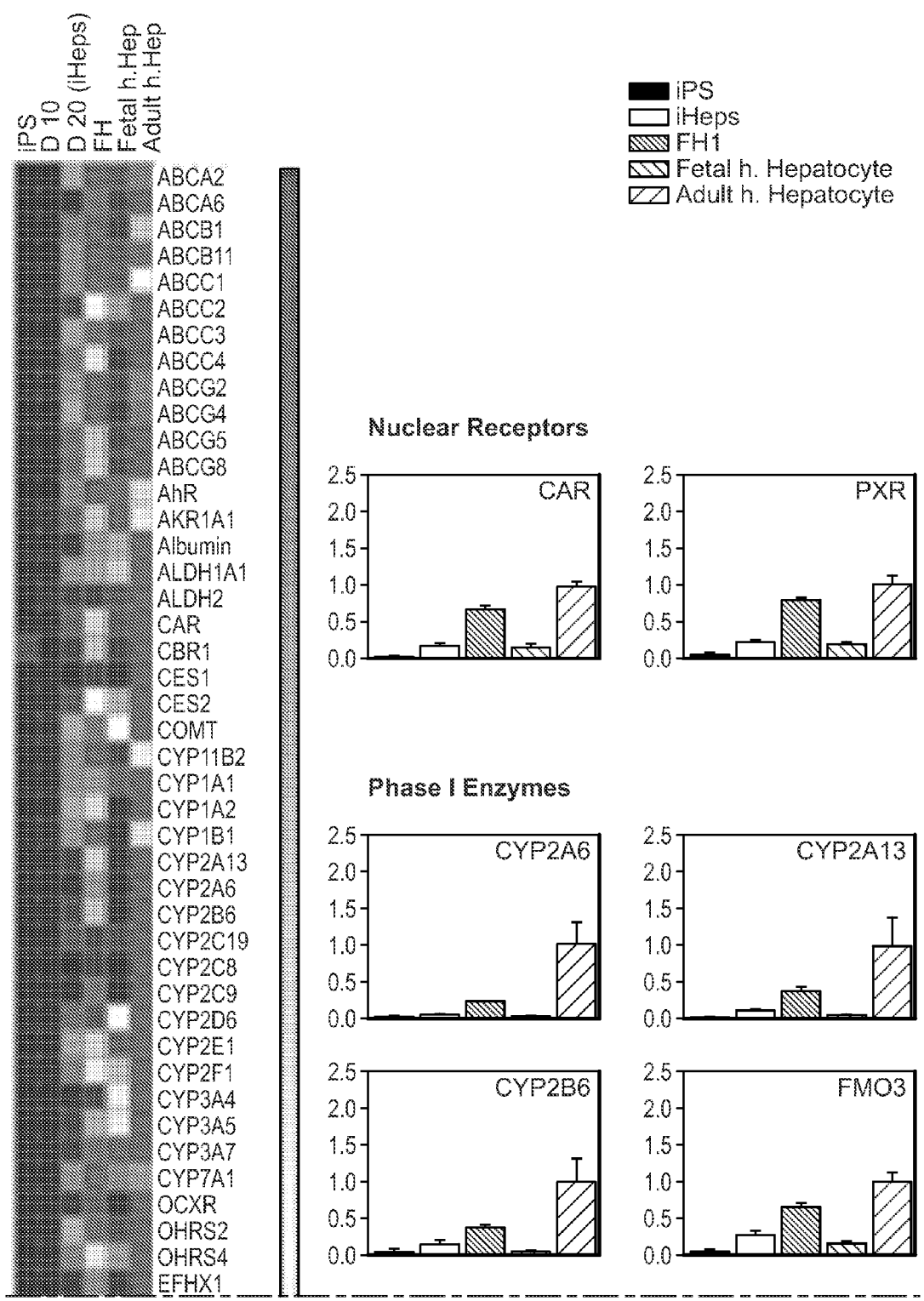
Figures 4, 4C:
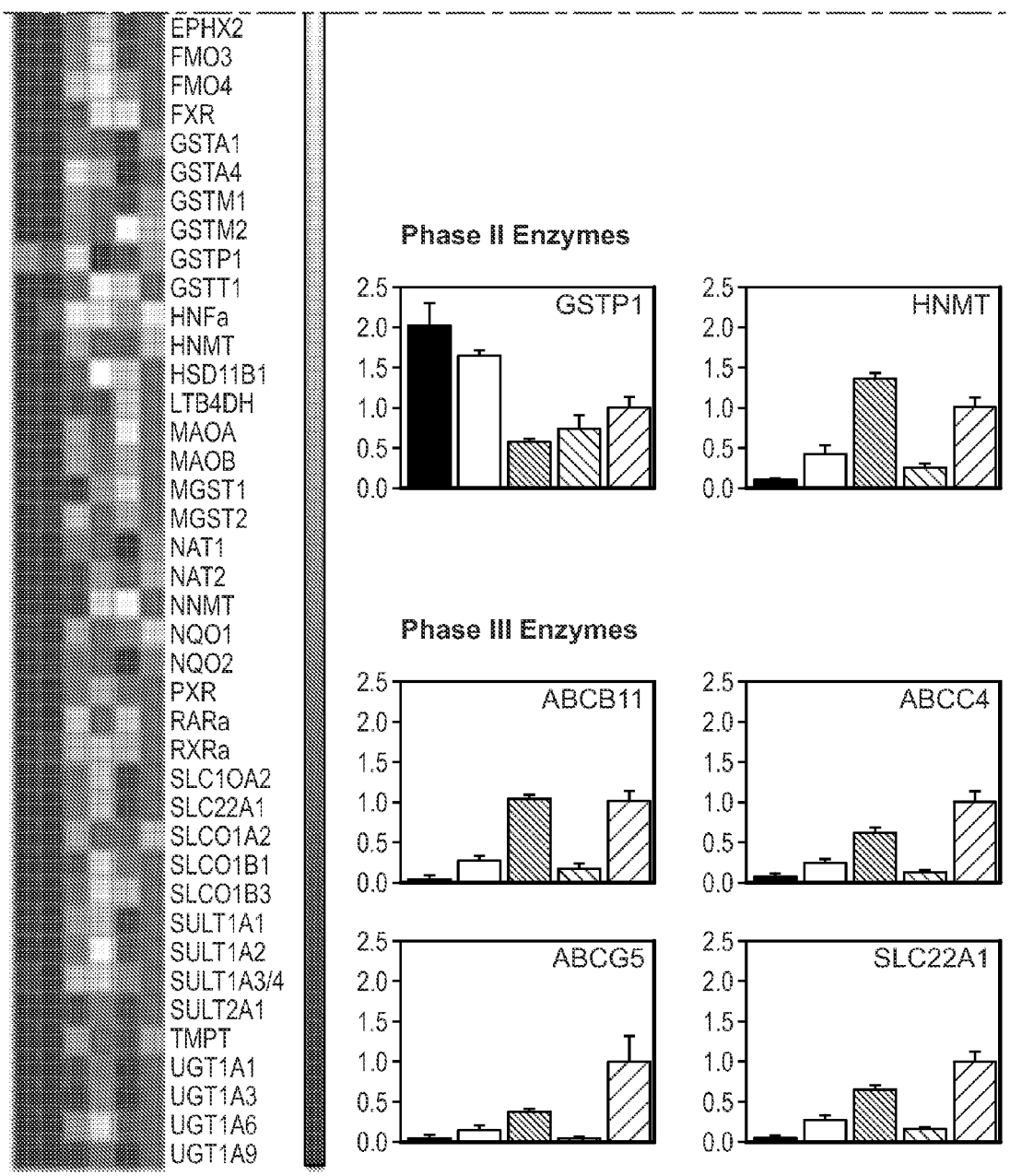

Gene expression profiles showed that treated iHeps more closely resemble mature hepatocytes than untreated cells (FIG. 4C). Euclidian clustering analyses groups untreated cells with fetal hepatocytes and treated cells with mature hepatocytes (FIG. 4C left). Of particular interest are ABC transporters, CYP3A4 and GSTP1 expression levels. ABC transporters are known to mature after birth. ABCB11, also known as bile-salt export pump (BSEP), increased ~3 fold and ~4 fold in expression levels with FPH2 and FH1 treatment, respectively, compared to untreated iHeps. In contrast, GSTP1 expression, whose levels decrease with maturity, remained low upon FPH2 and FH1 treatment compared to untreated iHeps (FIG. 4C right).

To examine the effects of FH1 and FPH2 at the protein level, AFP, albumin and CYP3A4 levels weew visualized via immunofluorescent staining. Images showed dramatic increases in albumin staining upon both FH1 and FPH2 treatment, although the effects of FH1 were more pronounced (FIG. 4D top). This is in agreement with primary screening results as well as earlier morphological findings. Untreated cultures had islands that double stain for albumin and the fetal marker AFP, with very little presence of the mature marker CYP3A4. In contrast, FH1-treated islands double stained strongly for albumin and CYP3A4, with very minimal presence of AFP.

Figures 1, 4D:
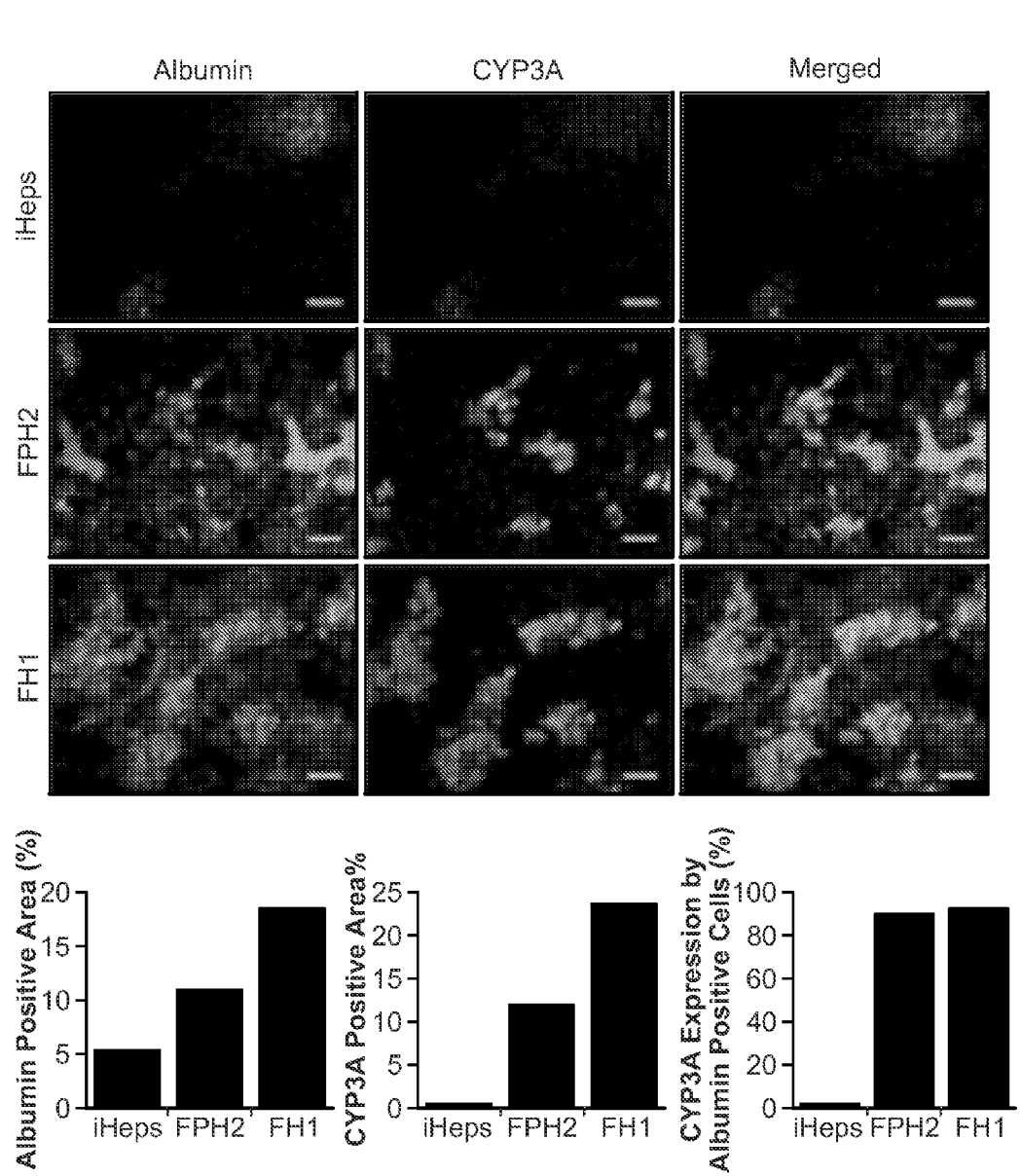
Figures 2, 4D:
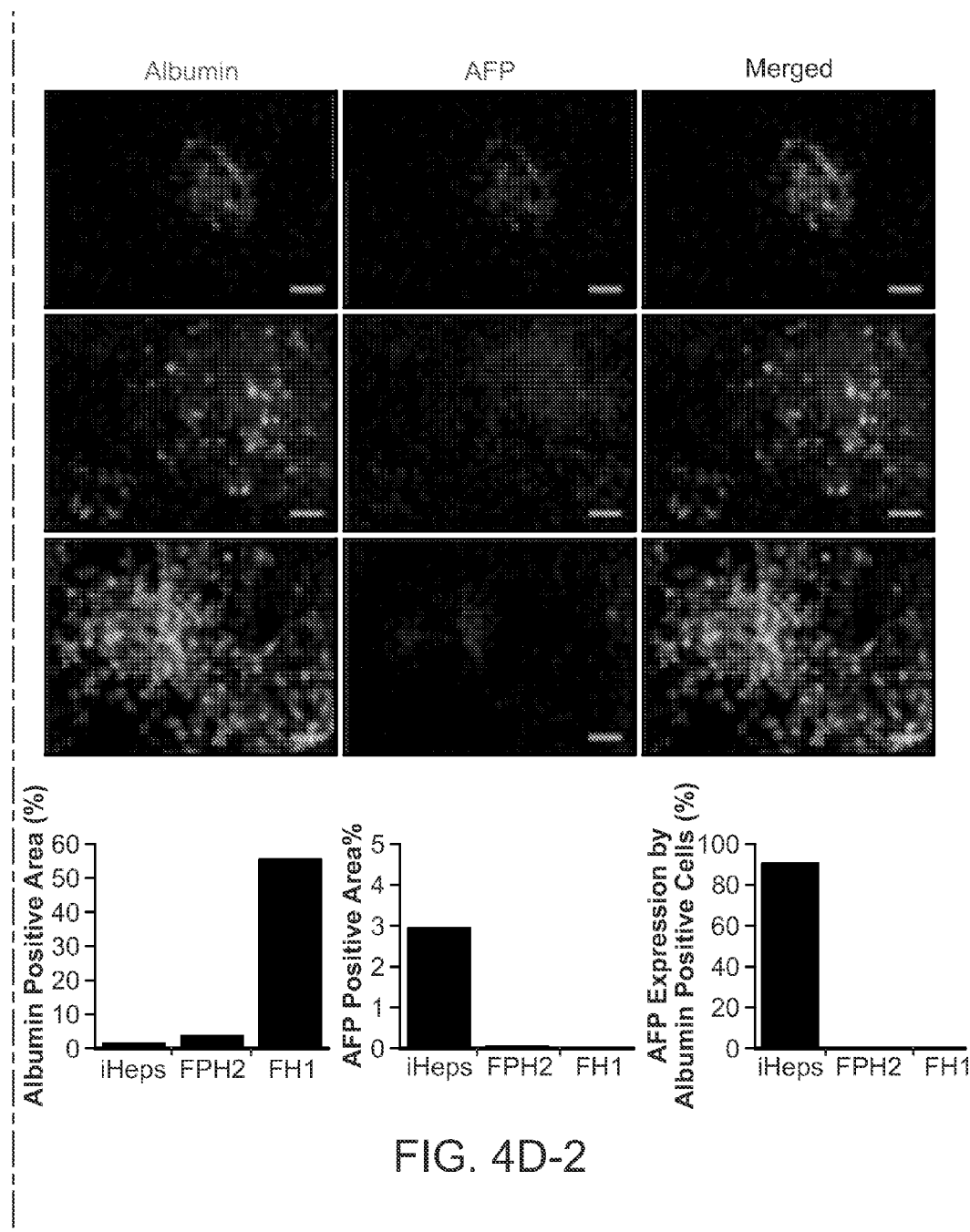
Figure 4E:
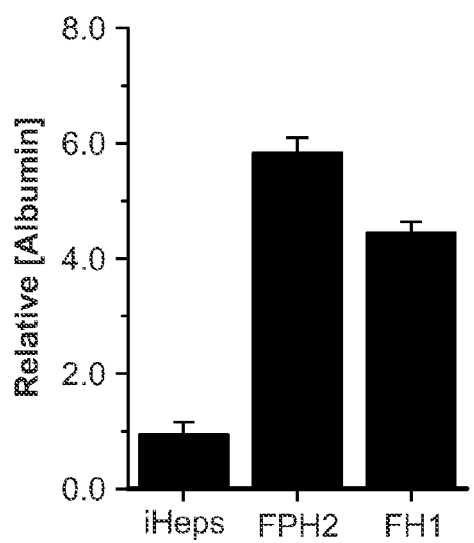
Figure 4E:
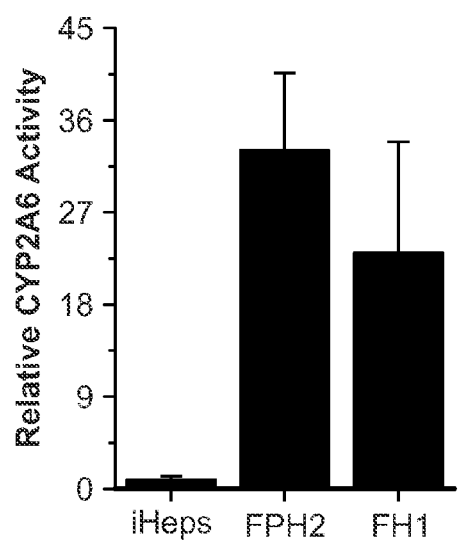
Figure 4E:
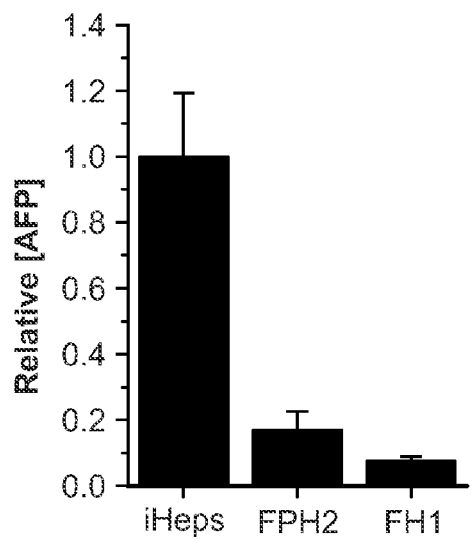
Figure 4E:
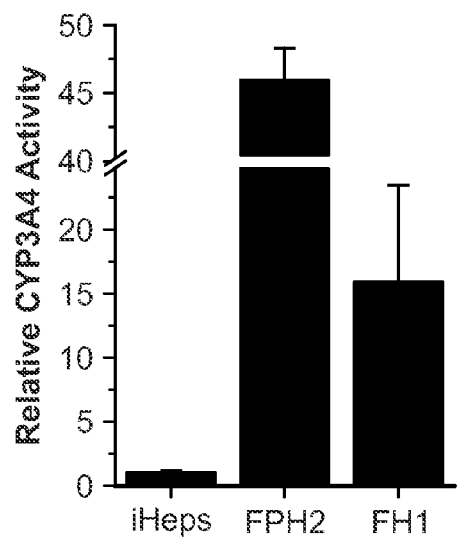
Figure 4F:
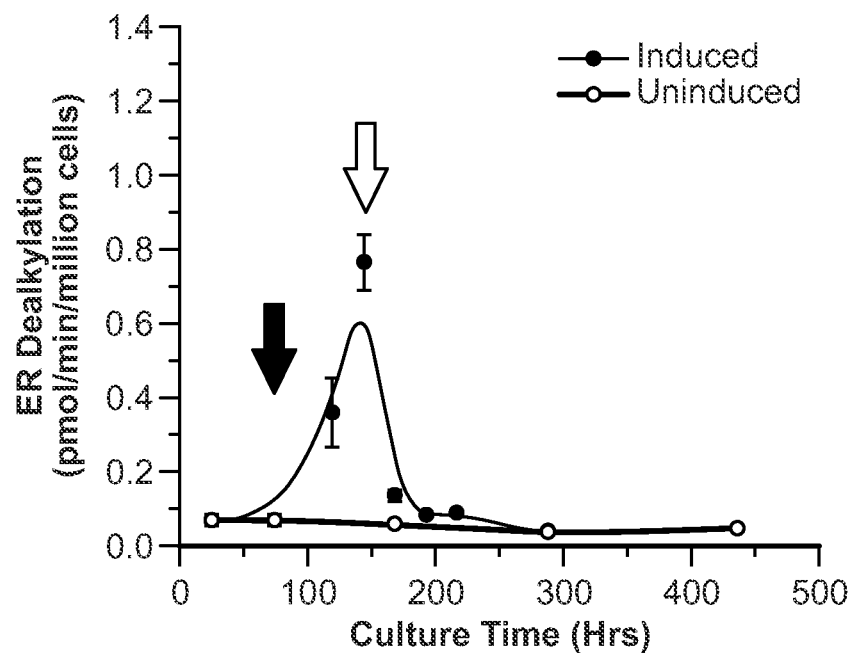
Figure 4F:
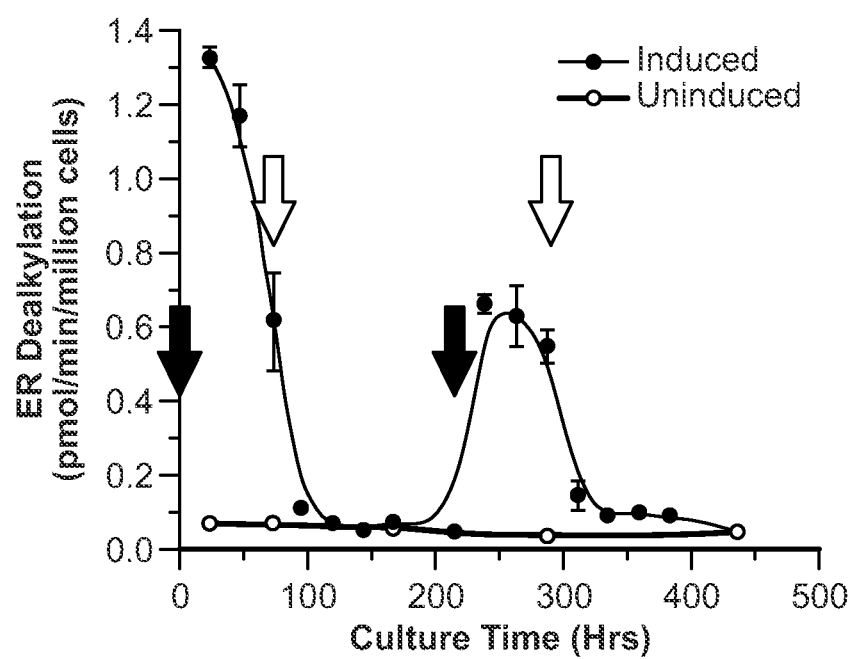

To confirm the staining results, secreted levels of albumin and AFP via ELISA, and CYP450 activities through isoenzyme-specific probes that are either fluorescent or luminescent were measured. ELISA results verified both an increase in albumin secretion and a decrease in AFP secretion by treated iHeps (FIG. 4D bottom). CYP3A4 activity increased by 16 and 45 times upon treatment with FH1 and FPH2, respectively. CYP2A6, another mature CYP450, also increased significantly upon treatment with compound (FIG. 4E). Induction was considered as a possible explanation for these elevations in CYP450 activity. However, this was unlikely based on the following experiments. While human hepatocytes treated with 250 μM β-naphthoflavone (BNF) exhibited elevated CYP450 activity (FIG. 4F left), such elevations were mostly lost 24 hrs after removal of the inducer (FIG. 4F right). Since a period of at least 48 hrs separated compound treatment and the measurement of CYP450 activity, the iHeps were expected to have recovered from any general elevations in CYP450 activity.

Figure 5A:
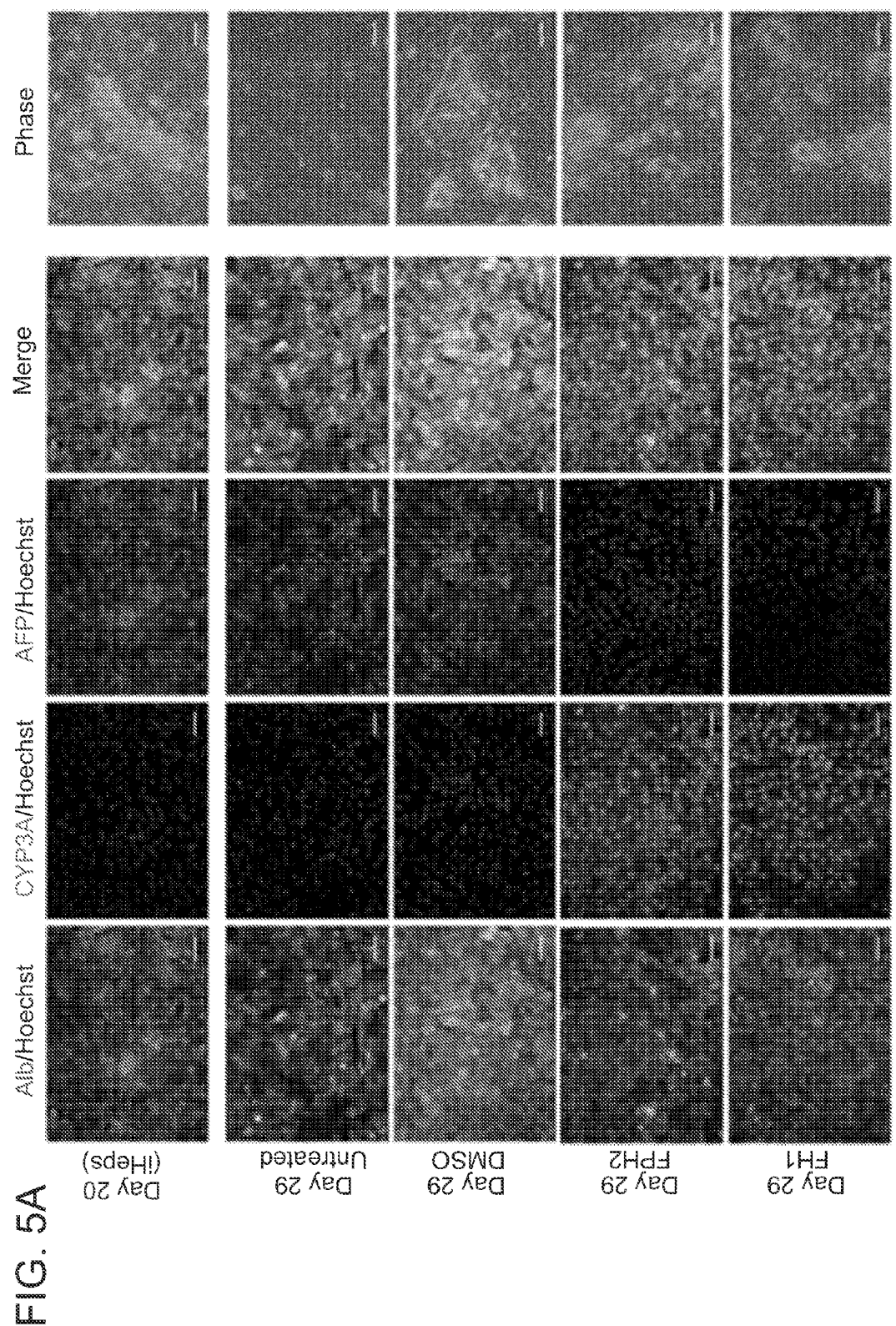
FIGS. 5A-5C, illustrates the effects of treating induced hepatocyte-like cells (iHeps) with compounds of the invention.
Figure 5B:
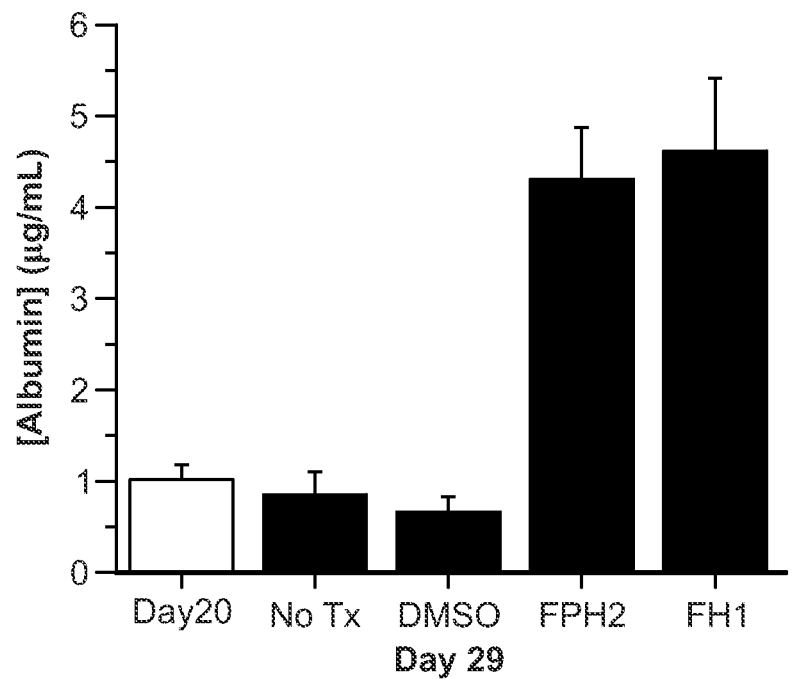
Figure 5B:
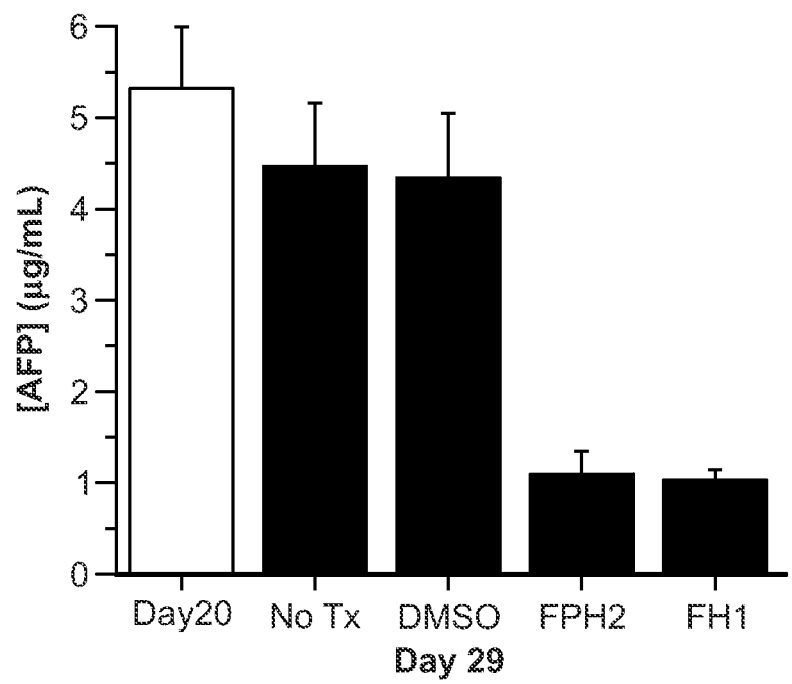
Figure 5C:
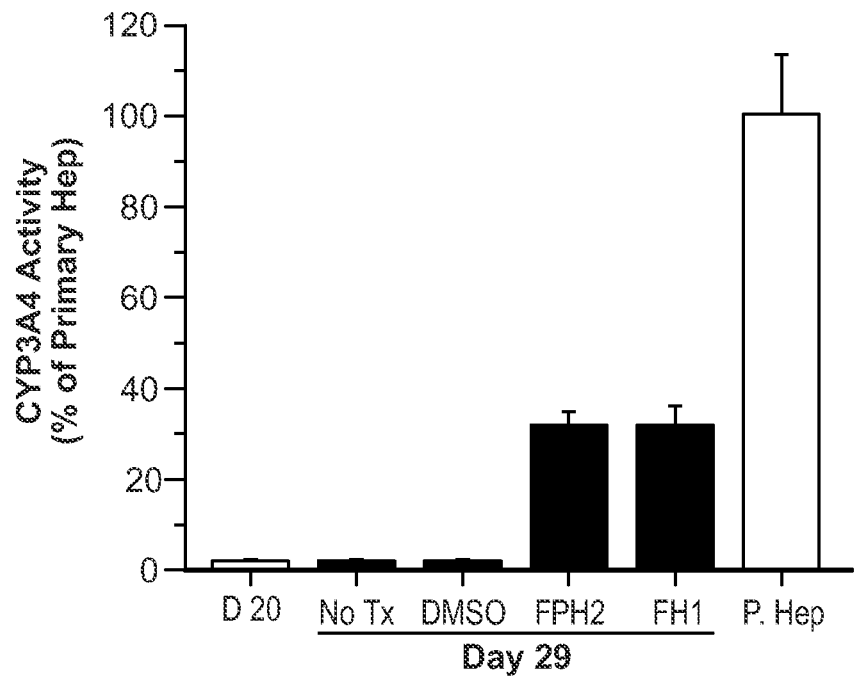
Figure 5C:
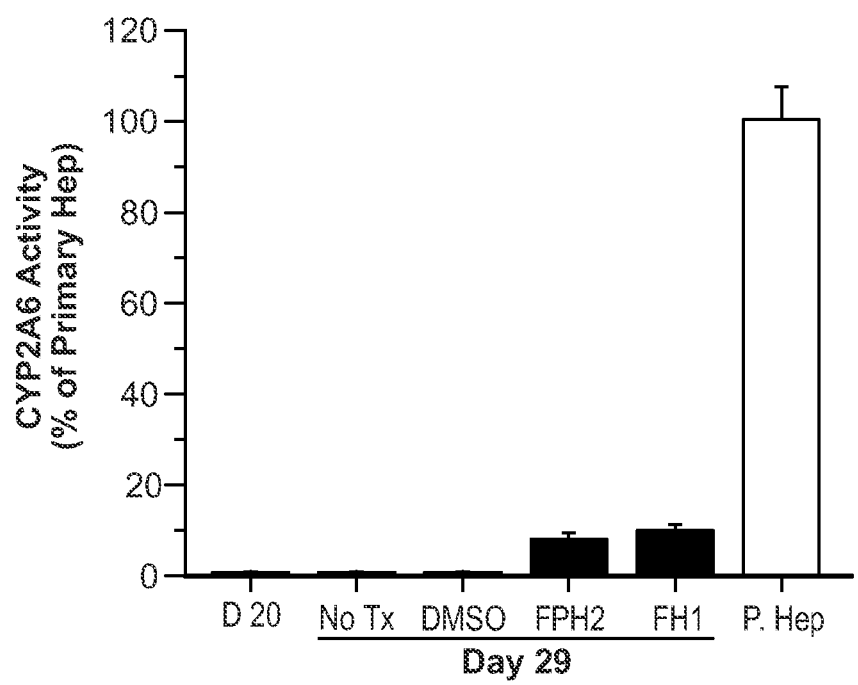

The more mature phenotype exhibited by treat iHep cells was stable for at least 1 week after removal of FH1 and FPH2. iHeps were treated with FH1 and FPH2 once on day 20 and then maintained in normal basal media (without FH1 and FPH2 addition) for 9 days. Phase contrast and immunofluorescent stained images for Albumin, CYP3A and AFP showed that cells maintained a mature phenotype at Day 29 in culture (FIG. 5A). Quantification of secreted albumin, AFP, and CYP3A4 and CYP2A6 activity further demonstrated the stability of mature iHep phenotype (FIGS. 5B-5C).

Together, these results showed that FH1 and FPH2 were able to mature iHeps beyond what is currently achievable using defined factors only, thus alleviating a major obstacle to the use of iPS cells as a source of functional human hepatocytes.

Example 6: Expansion of Multiple Different Donors of Primary Human Hepatocytes

Figure 6A:
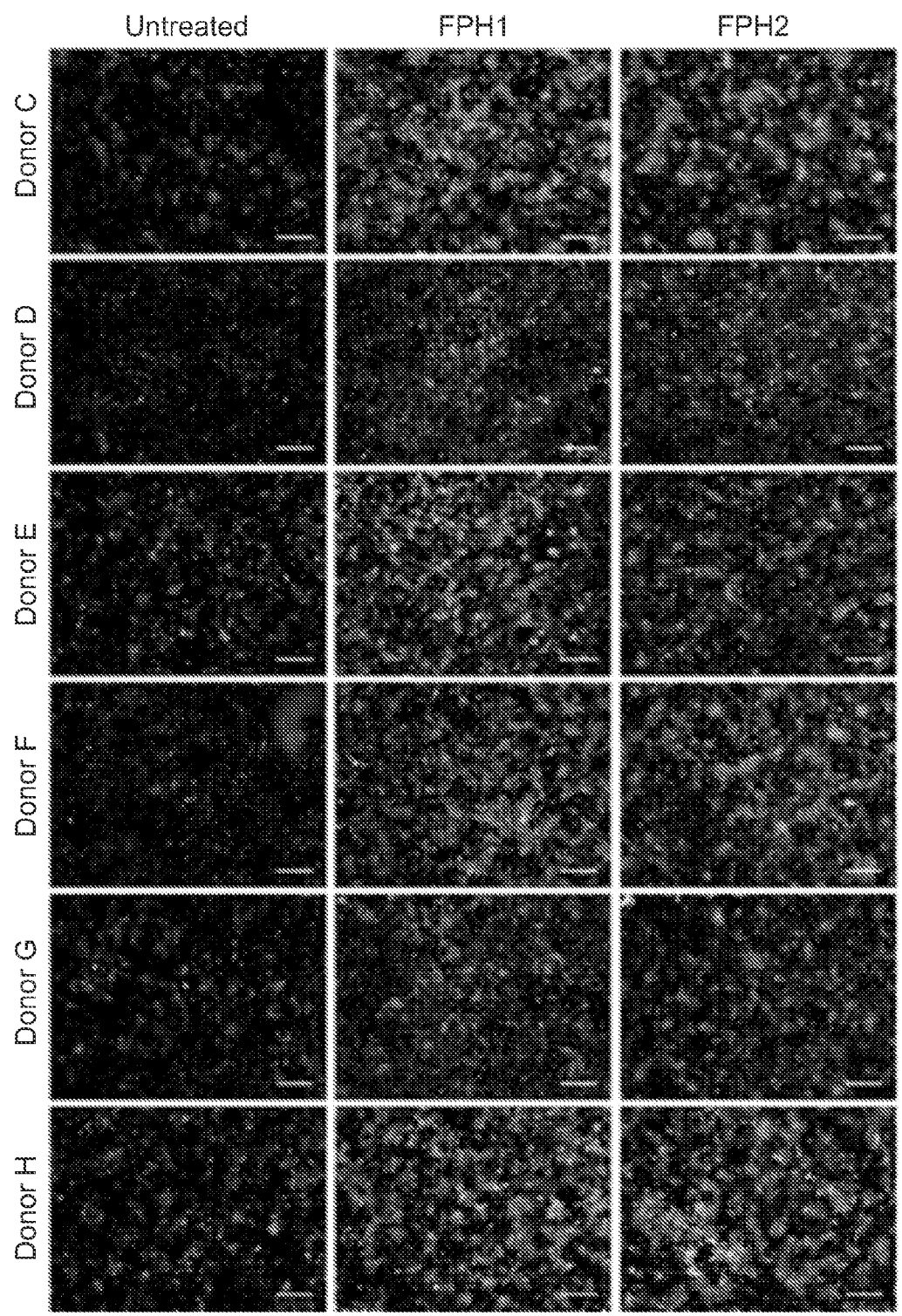
FIGS. 6A-6B, illustrates the effects of compounds of the invention on primary human hepatocytes.
Figure 6B:
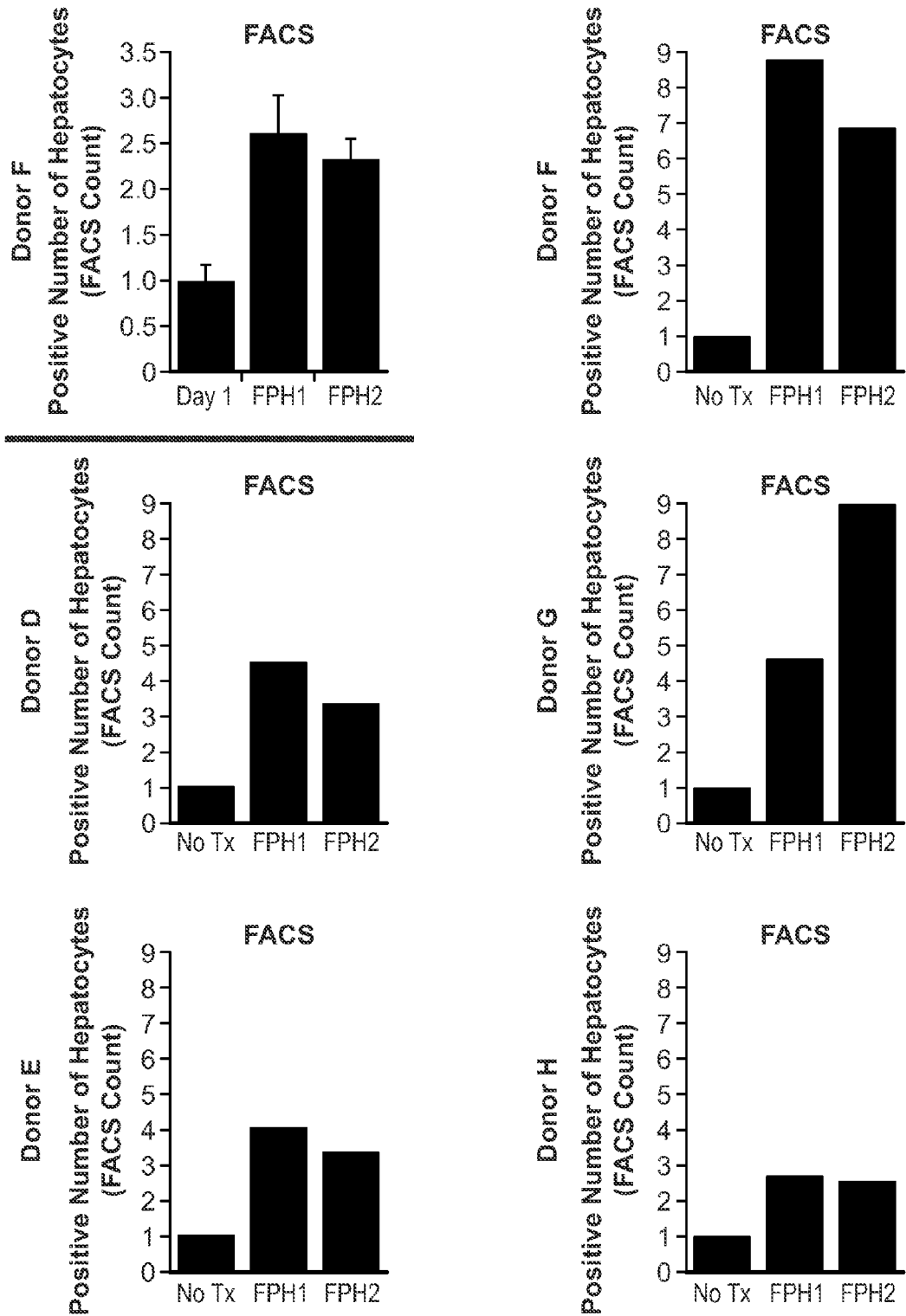

To generalize the findings of compounds of the invention across multiple donors, primary human hepatocytes from six additional cell sources were treated with FPH1 and FPH2 and stained for Ki67 and albumin after six days in culture Immunofluorescent staining showed that treatment with FPH1 and FPH2 resulted in increased Ki67 staining that co-localized with albumin labeled hepatocytes (FIG. 6A). On day seven, the number of hepatocytes was quantified by FACS analysis (FIG. 6B). Day one untreated controls was added to the bar graph for reference. Both compounds induced an increase in the number of hepatocytes in all donor cell treated. These results together suggest that the FPHs are active across a wide range of genetically diverse individuals.

Figure 7A:
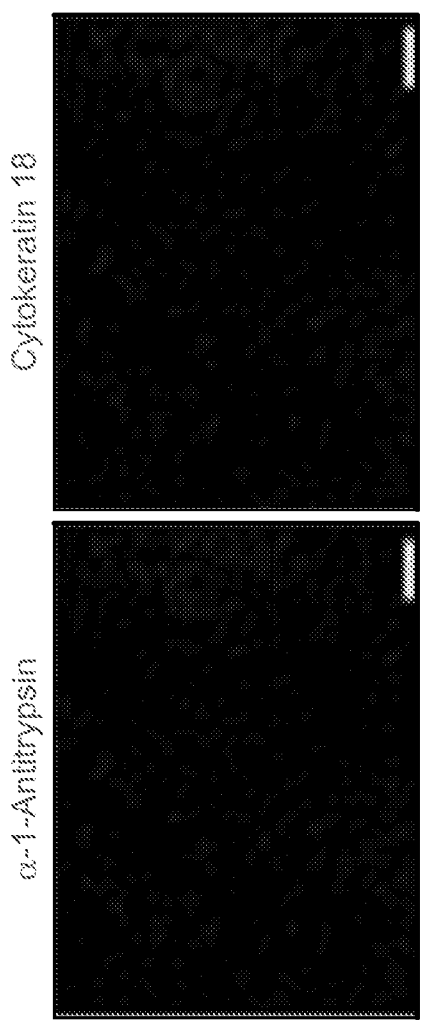
FIGS. 7A-7C, illustrates iPS and iHep cells.
Figure 7B:
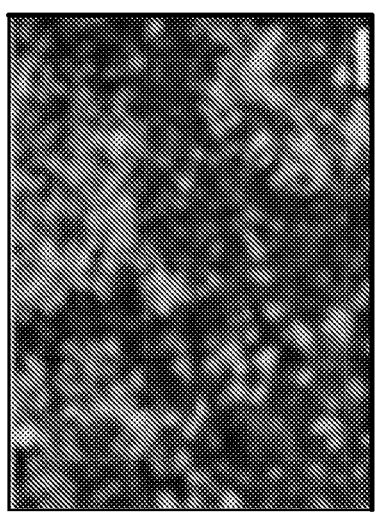
Figure 7C:
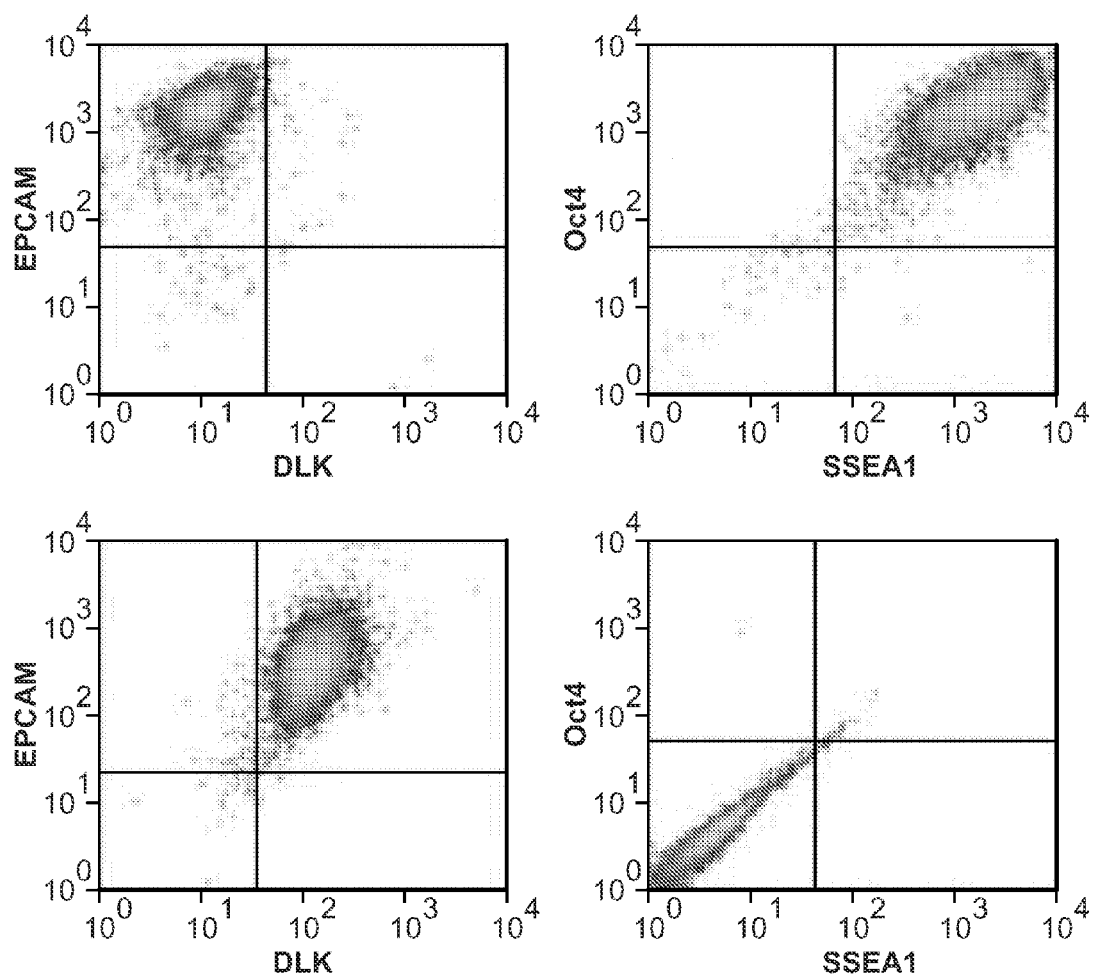

Example 7: Generation of iHeps iHep cells were generated from iPS cells using the methodology described herein (FIG. 7A) Immunostaining of iPS and iHep cells with hepatic lineage marker showed that iHeps express alpha-1-Antitrypsin and Cytokeratin 18, whereas undifferentiated iPS cells do not (FIG. 7B). FACS analysis profiling hepatic progenitor markers (EPCAM and DLK) and immature markers (SSEA1 and Oct 4) illustrated that iHeps exhibit hepatic-like progenitor cell profile in contrast to the undifferentiated profile exhibited of iPS cells (FIG. 7C).

Example 8: Augmentation of Liver Development

Figure 8A:
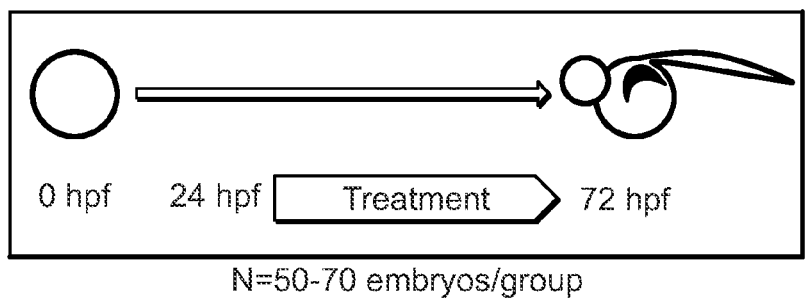
FIGS. 8A-8D, illustrates experiments in which zebrafish were treated with compounds of the invention.
Figure 8B:
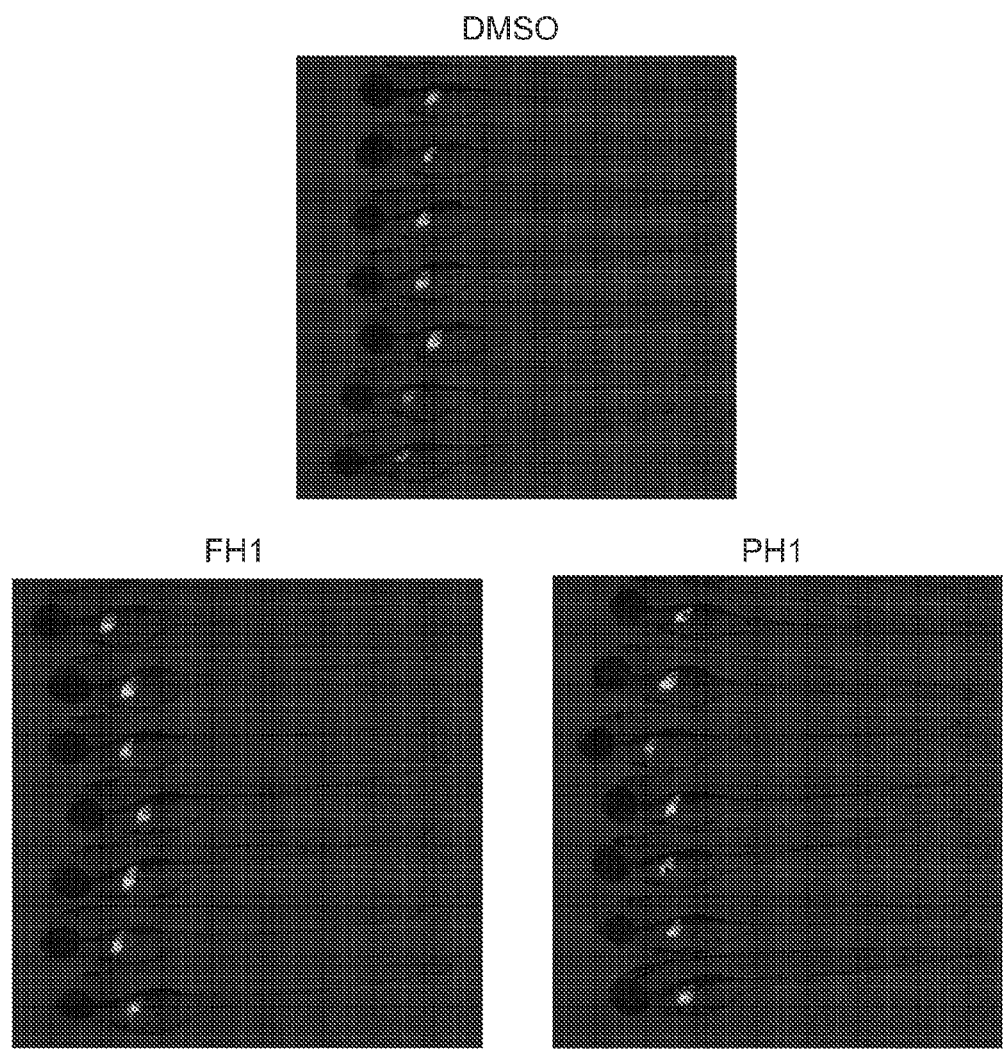
Figure 8C:
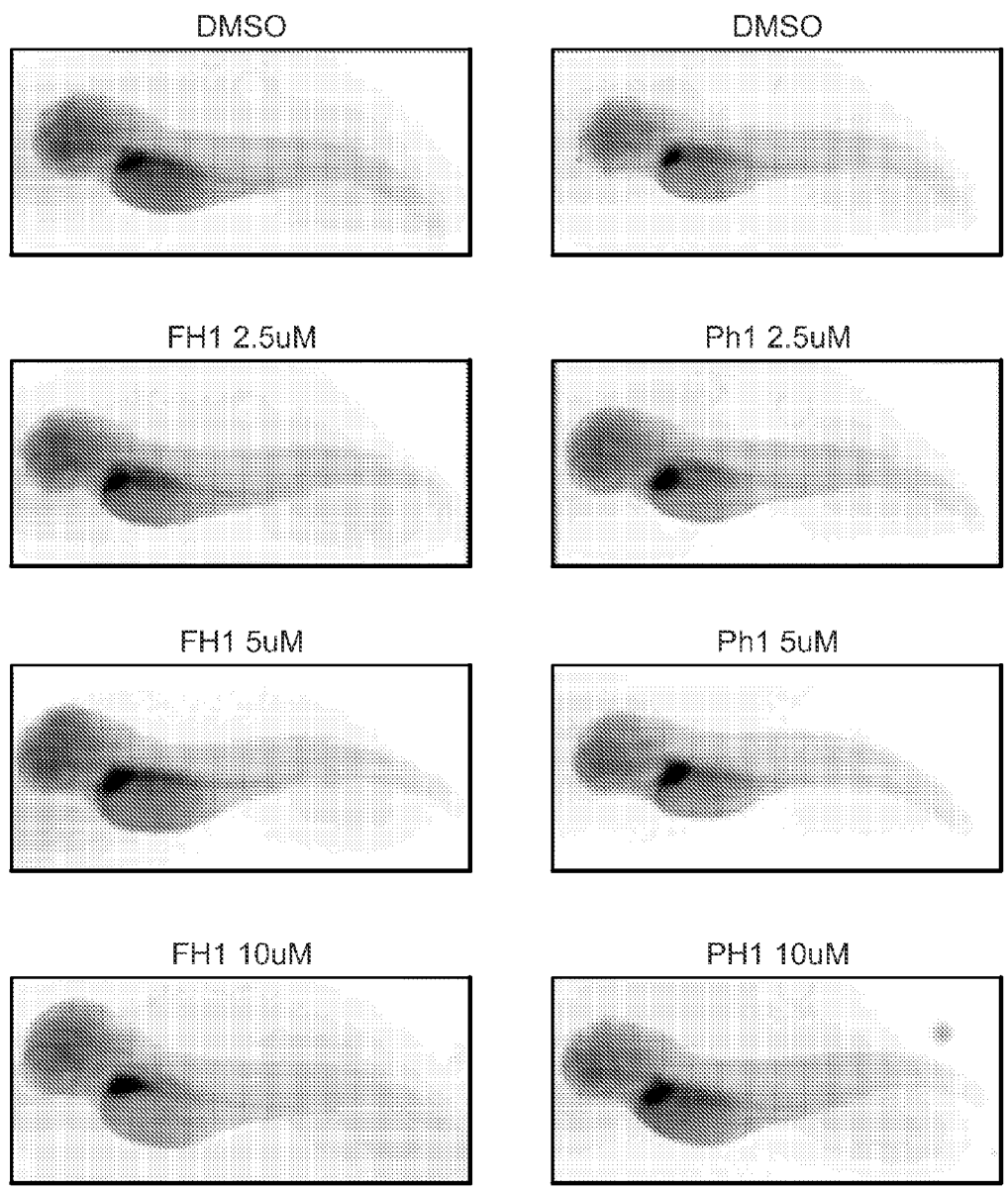
Figure 8D:
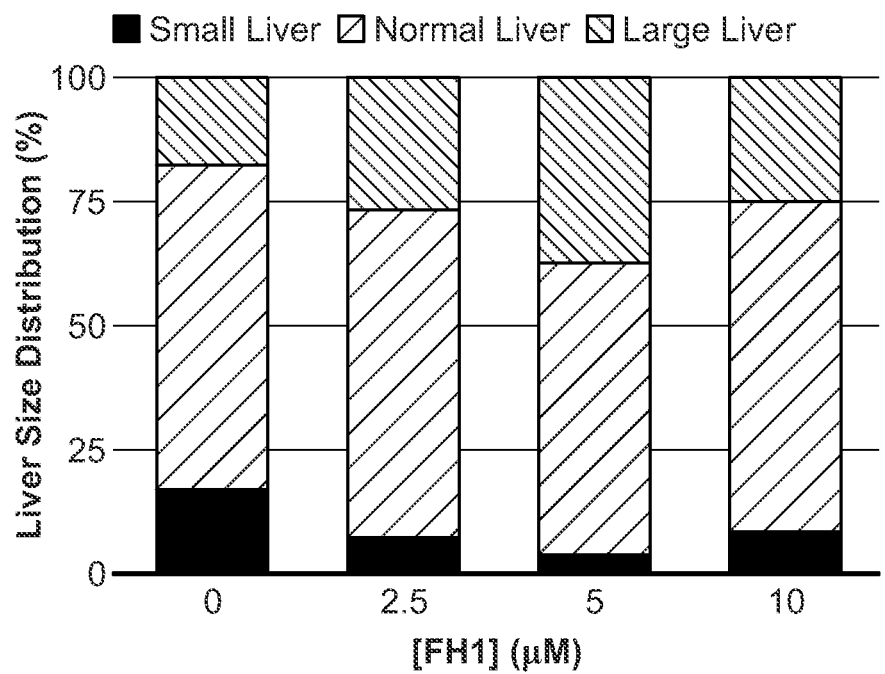
Figure 8D:
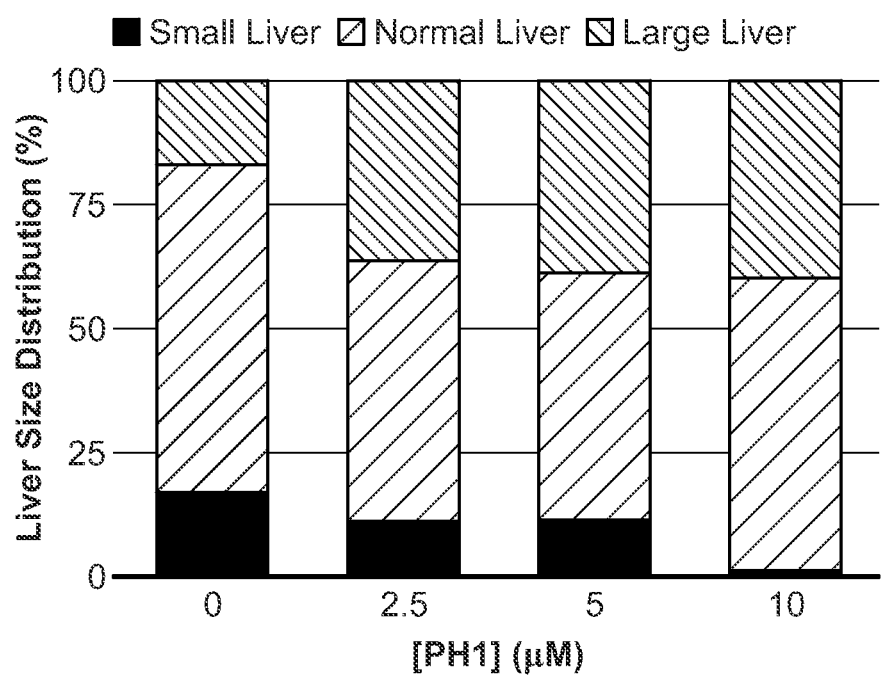

The effects of FH1 and PH1 on liver development were examined in transgenic lfabp:GFP zebrafish, in which GFP expression is restricted to the liver. Zebrafish embryos were allowed to develop normally for 24 hrs post fertilization and then exposed to either FH1 or PH1 until 72 hrs post fertilization (FIG. 8A). Livers were visualized by whole-mount fluorescence imaging (FIG. 8B) and lfabp in situ hybridization (FIG. 8C). Qualitative assessed of liver formation by fluorescent microscopy indicated that treatment with FH1 and PH1 increased liver size compared to DMSO-treated controls (FIG. 8D).

Example 9: Protection Against Acute Liver Injury

Figures 9C, 9D:
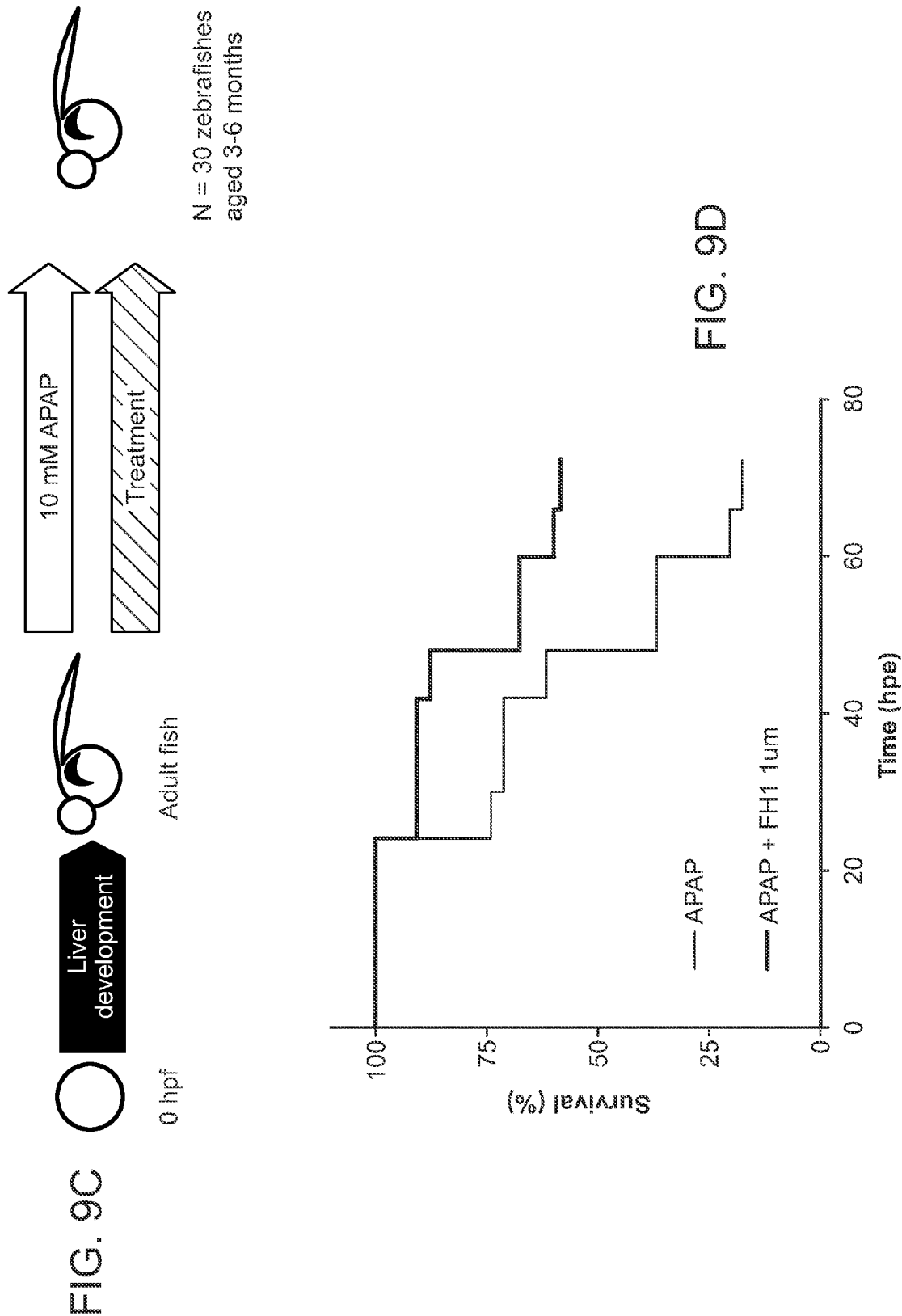

The effect of FH1 on zebrafish survival following APAP-induced toxicity was examined. lfabp:GFP zebrafish embryos were allowed to develop normally for 72 hrs post fertilization and then exposed to a fatal dose of 10 mM APAP concurrently with FH1 (FIG. 9A). FH1 treatment mitigated APAP-induced death resulting in the survival of 71% of FH1-treated embryos compared to 16% of controls (FIG. 9B). Similar protective effects of FH1 were seen in adult lfabp:GFP zebrafish (FIGS. 9C-9D).

Figure 10A:
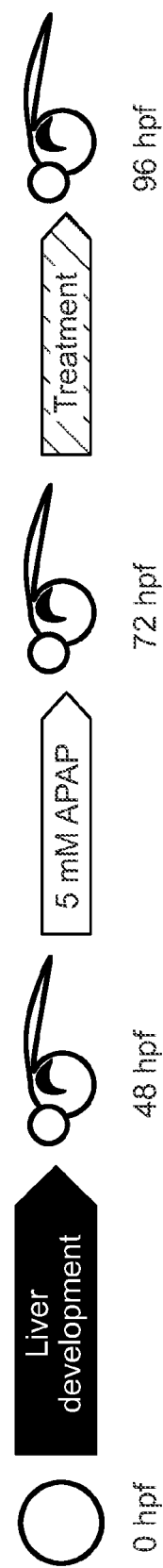
FIGS. 10A-10B, illustrates experiments in which zebrafish were treated with acetyl-para-aminophenol (APAP).
Figure 10B:
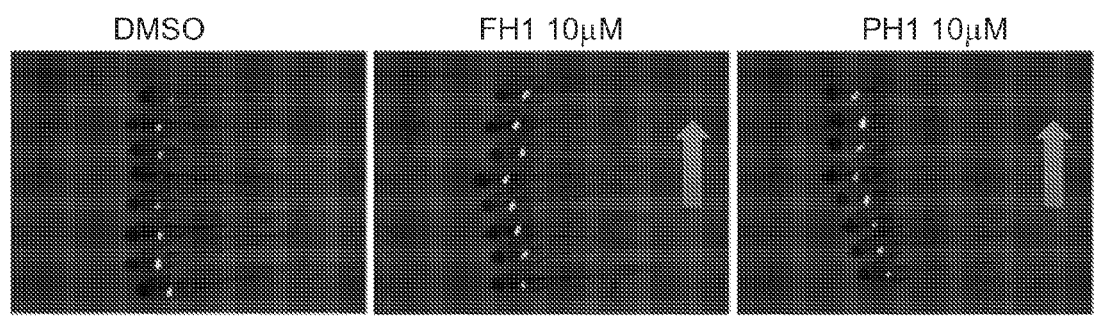

The current clinical treatment for APAP toxicity is the administration of NAC, which has a limited window of efficacy. To examine the therapeutic window of FH1 and PH1 efficacy, lfabp:GFP zebrafish embryos were allowed to develop normally for 48 hrs post fertilization, and then exposed to a non-fatal dose of 5 mM APAP for 24 hrs before initiation of treatment with FH1 or PH1 for an additional 24 hour period (FIG. 10A). At 96 hrs post-implantation, whole-mount fluorescence imaging showed that both FH1 and PH1 mitigated APAP-induced loss of liver mass resulting in enhanced embryonic liver size compared to controls (FIG. 10B). Moreover, efficacy of both FH1 and PH1 exhibited an elongated therapeutic window of least 24 hrs, compared to the typical ~8 hr therapeutic window for NCA.

Example 10: Expansion of Compound-Treated Human Primary Hepatocytes

Figure 11A:
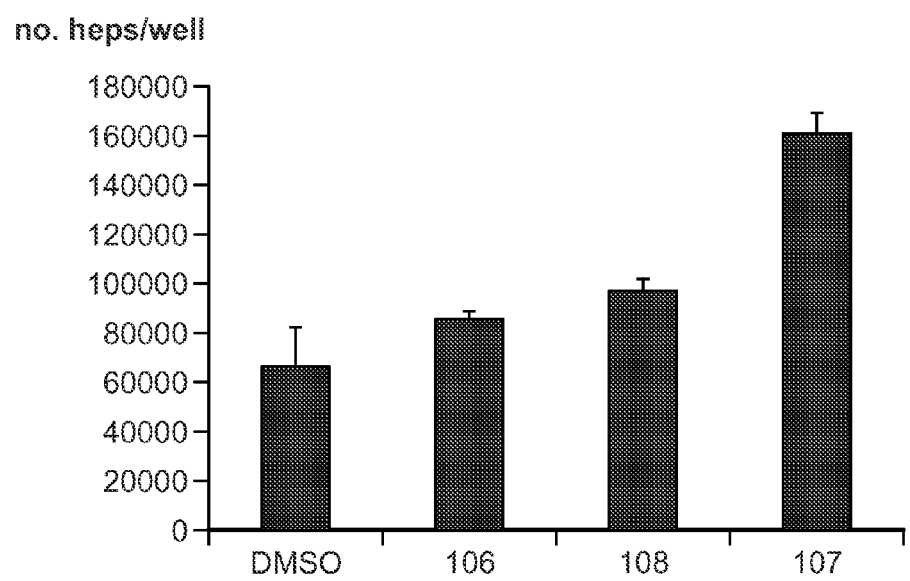
Figure 11B:
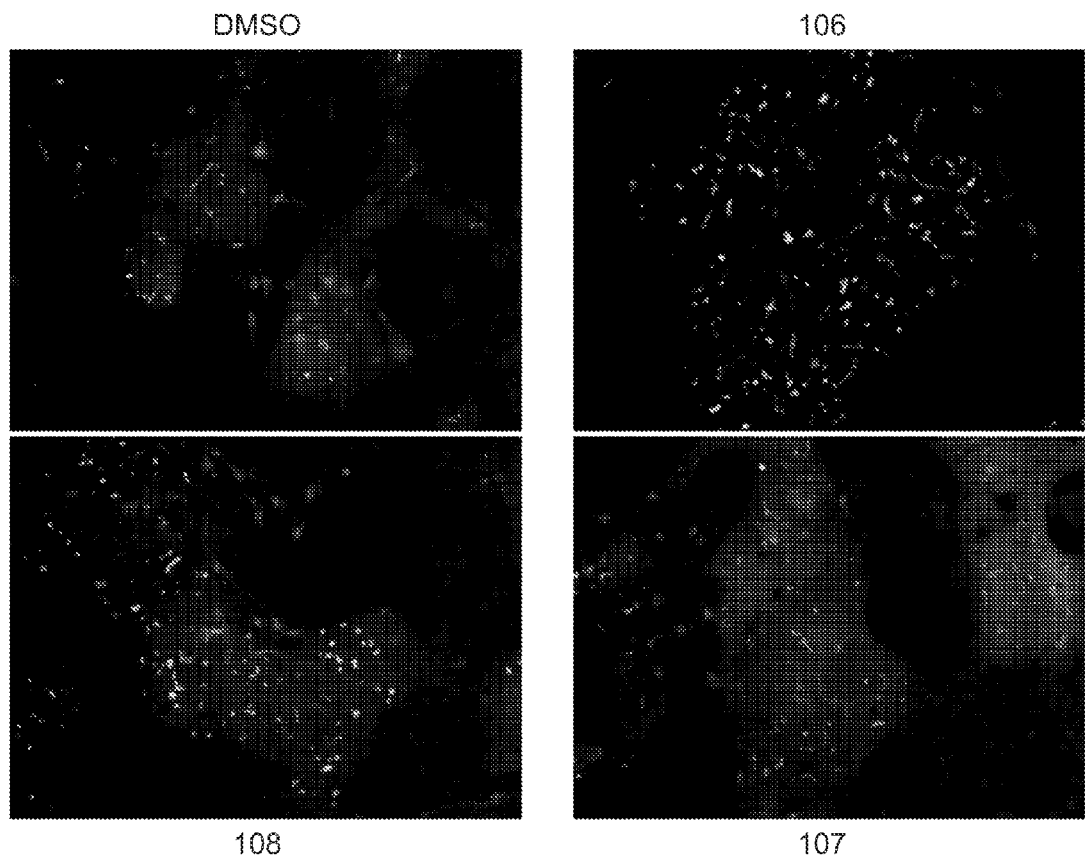
Figure 11C:
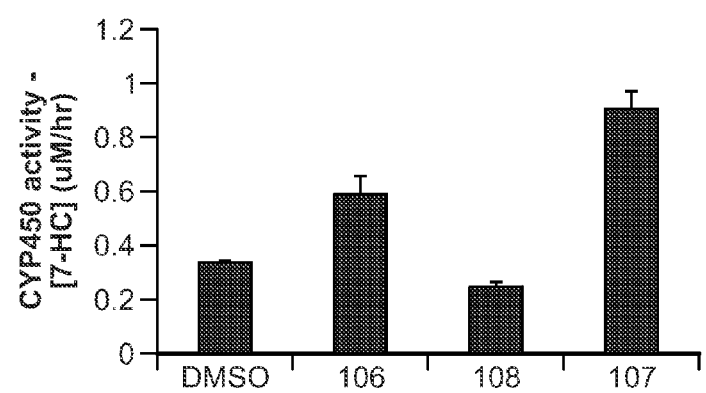
Figure 11D:
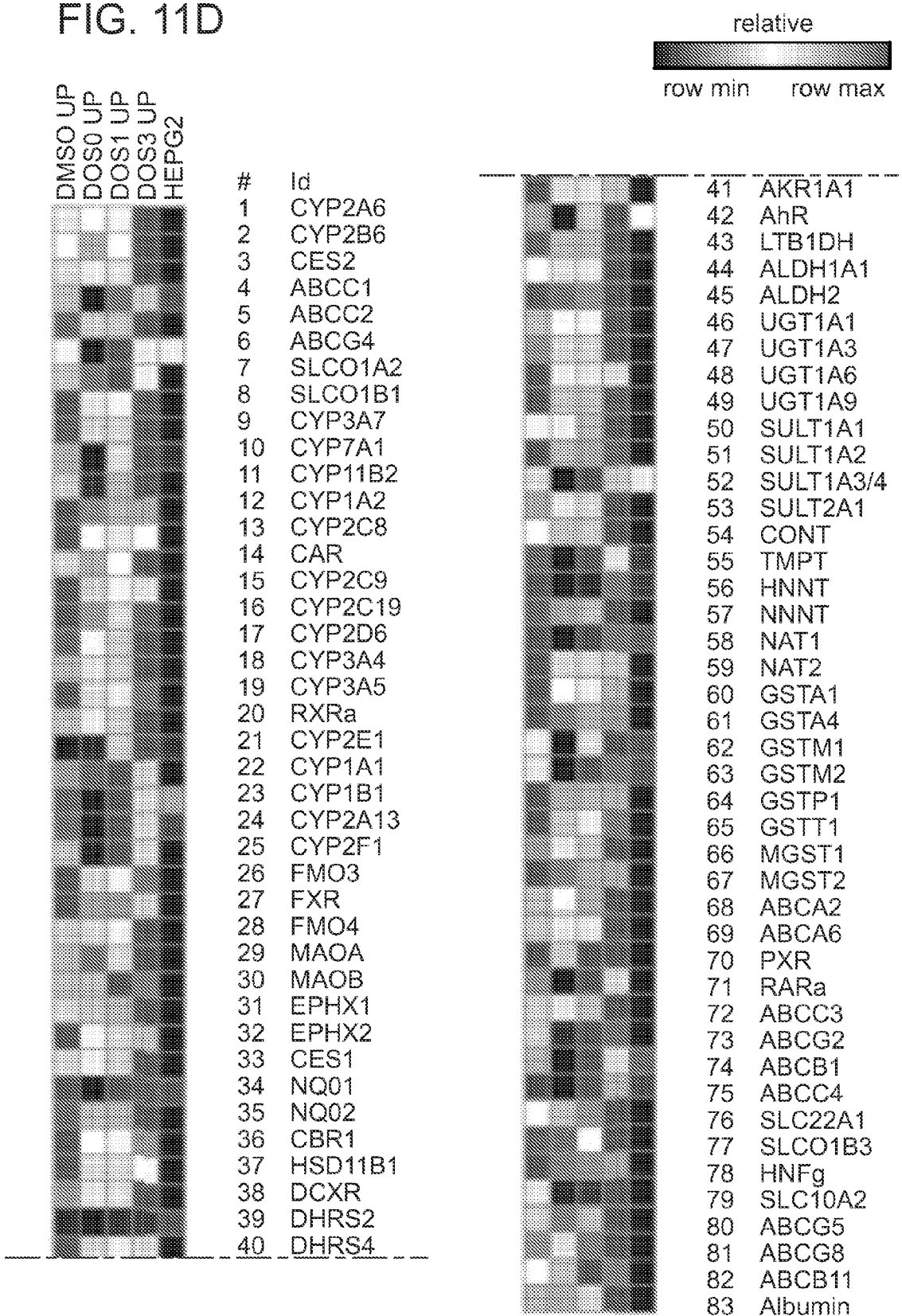
Figure 11E:
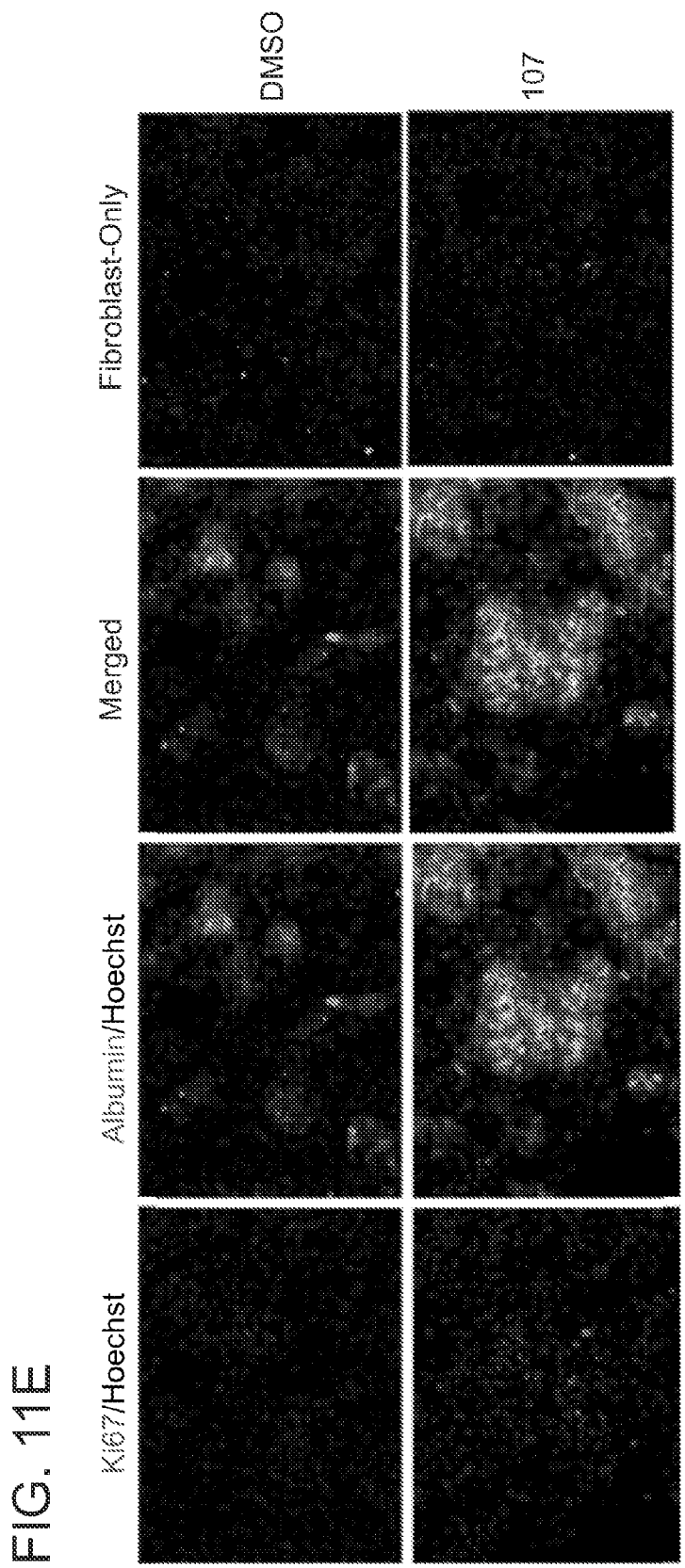

The ability of compounds 106-108 to expand human primary hepatocytes in vitro was tested. Cell counts of treated cultures showed that the number of hepatocytes increased in number relative to controls (FIG. 11A). The metabolic phenotype of the treated hepatocytes was assessed for canalicular transport. Results showed normal active transport of a fluorometric substrate into the bile cannaliculi between hepatocytes (FIG. 11B) and CYP450 activity (FIG. 11C), indicating that cells exhibited normal liver-specific functions. Gene expression profiling confirmed that there was no significant differences between FPH-treated and untreated hepatocytes (FIG. 11D). Furthermore, compound 107 treatment increased Ki67 staining, which not only co-localized with Hoechst stains for cell nuclei but also with human albumin stains for hepatocytes (FIG. 11E), further indicating that compound 107 induced proliferation of human primary hepatocytes.

The ability of compounds 201-212, 215, 217 and 244-258 to expand human primary hepatocytes in vitro was also tested. Cell counts of treated cultures showed that the number of hepatocytes increased in number relative to controls (FIG. 11F).

Example 11: Differentiation of Human iPS-Derived Hepatocytes

The ability of compounds 106 and 108 to affect the differentiation and maturation of iHeps was tested. Undifferentiated iPS cells were cultured on Matrigel, supported by primary mouse embryonic fibroblasts. Once confluent, iPS cells were transitioned to differentiation media, with sequential addition of growth factors (Activin A, BMP-4, bFGF, HGF, and OSM) to guide differentiation, first into endoderm, then into hepatic progenitor cells and finally into iHeps. Compound treatment started on day 21 post initiation of differentiation and acted over a period of 9 days.

Figure 12A:
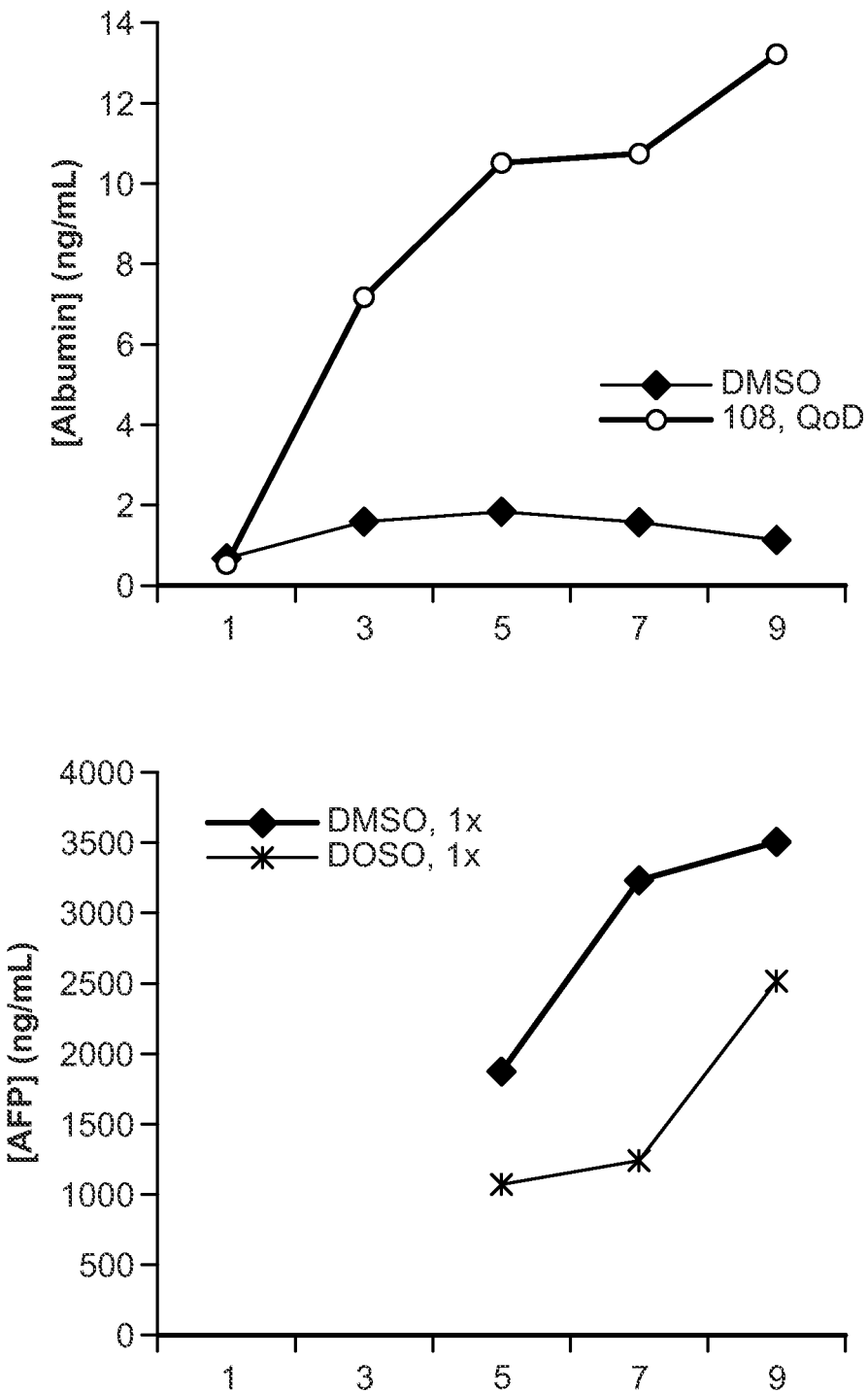
Figure 12B:
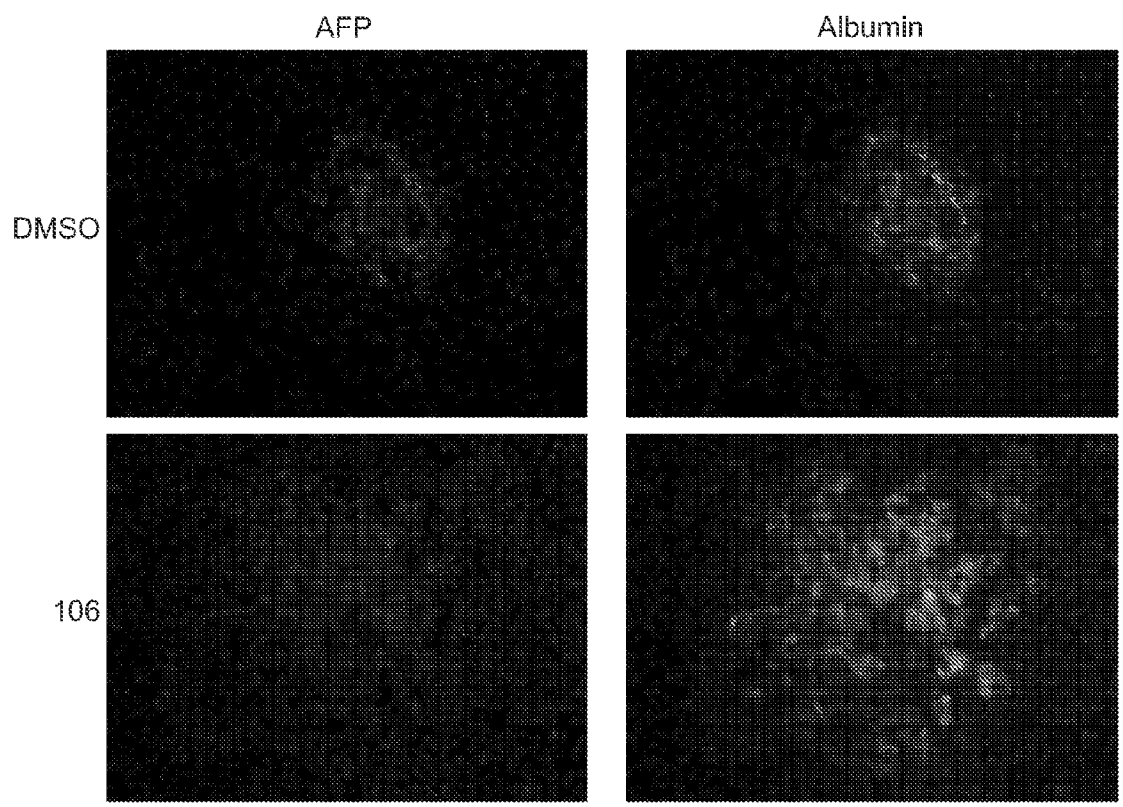

To determine the effects of compounds 106 and 108, secreted levels of albumin and AFP were measured by ELISA. Results showed that treated iHeps exhibited increased levels of albumin secretion and decreased levels of AFP secretion (FIG. 12A). To examine the effects of compound 106 at the protein level, albumin and AFP were visualized via immunofluorescent staining. Images showed dramatic increases in albumin staining upon treatment with compound 106 (FIG. 12B). Consistent with the literature, untreated cultures had islands that double stain for albumin and the fetal marker AFP, with very little presence of the mature marker Albumin. These results demonstrated that iHeps treated with compounds 106 and 108 develop more mature hepatocyte phenotypes.

The ability of compounds 201-212, 217 and 244-258 to affect the differentiation of iHeps was also tested. As evidenced by the increase in CYP3A4 activity in treated iHeps relative to controls (FIG. 12C), these compounds induced differentiation of iHeps.

Example 12: Differentiation of iPS-Derived Endothelial Cells

Figure 13:
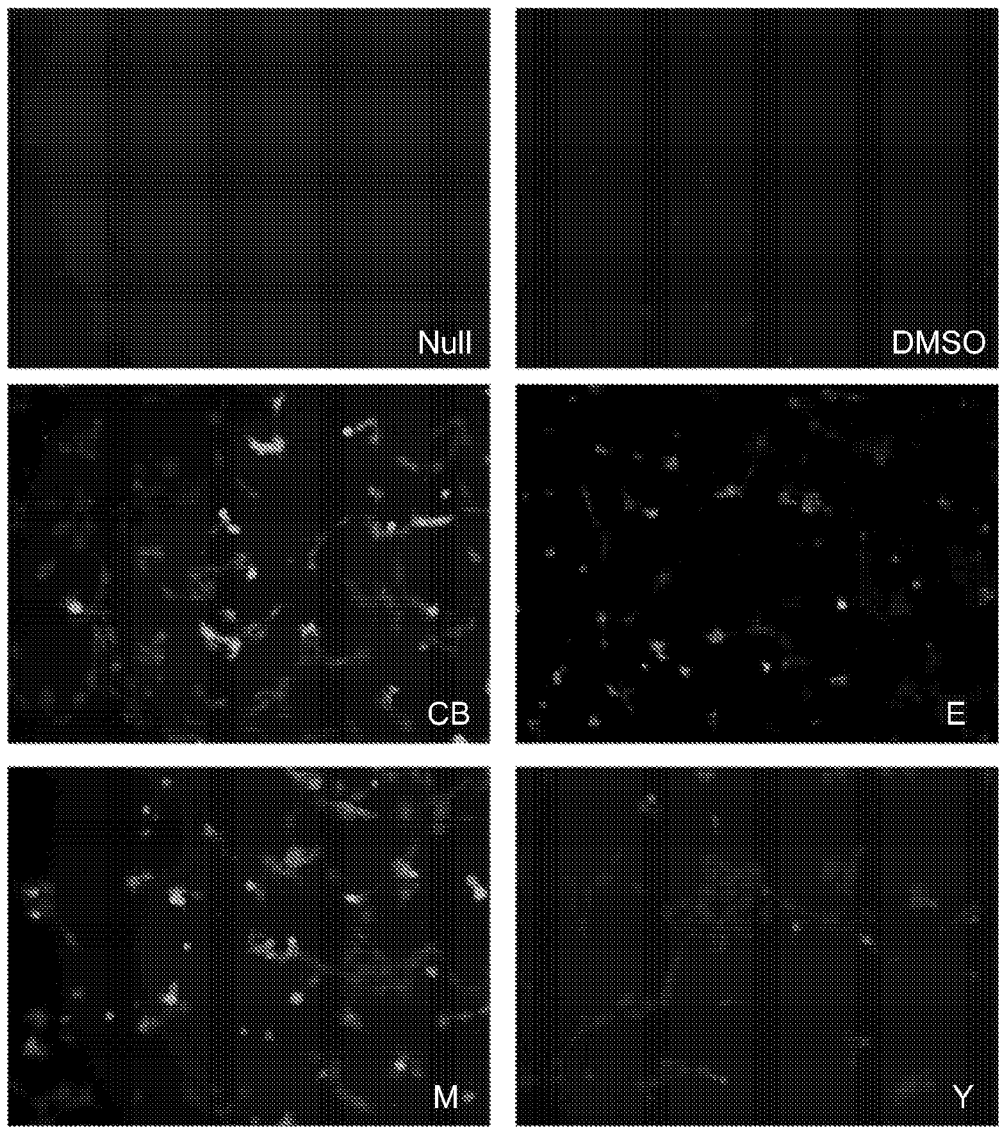
FIG. 13 comprises a set of images illustrating effects of compounds of the invention on differentiation of iPS-derived endothelial cells (Example 12).

In analogy with the iPS-derived hepatocytes of Example 5, iPS-derived endothelial cells were treated with compounds of the invention to assess their ability to induce differentiation. Cells were assayed for nitric oxide (NO), a mature marker for endothelial cells. CB=FPH2, M=FH1, E=PH1, while Null and DMSO are control runs with no additive and vehicle only, respectively. Results are depicted in FIG. 13, showing that FPH2, FH1, and PH1 all induce differentiation of these cells.

Example 13: Functional Analysis of Human Primary Hepatocytes Treated with Compound 102

Compounds of the invention were screened for their ability to increase hepatocyte nuclei count. Compound 102 induced a significant increase in hepatocyte nuclei count (proliferation Z score of 2.24), thus qualifying it as a proliferation-only hit. FPH2 and Compound 102 both share the same 5-chloro-2-methyl substitution on the sulfonamido phenyl ring.

Example 14: Kinome Analysis

Figure 17:
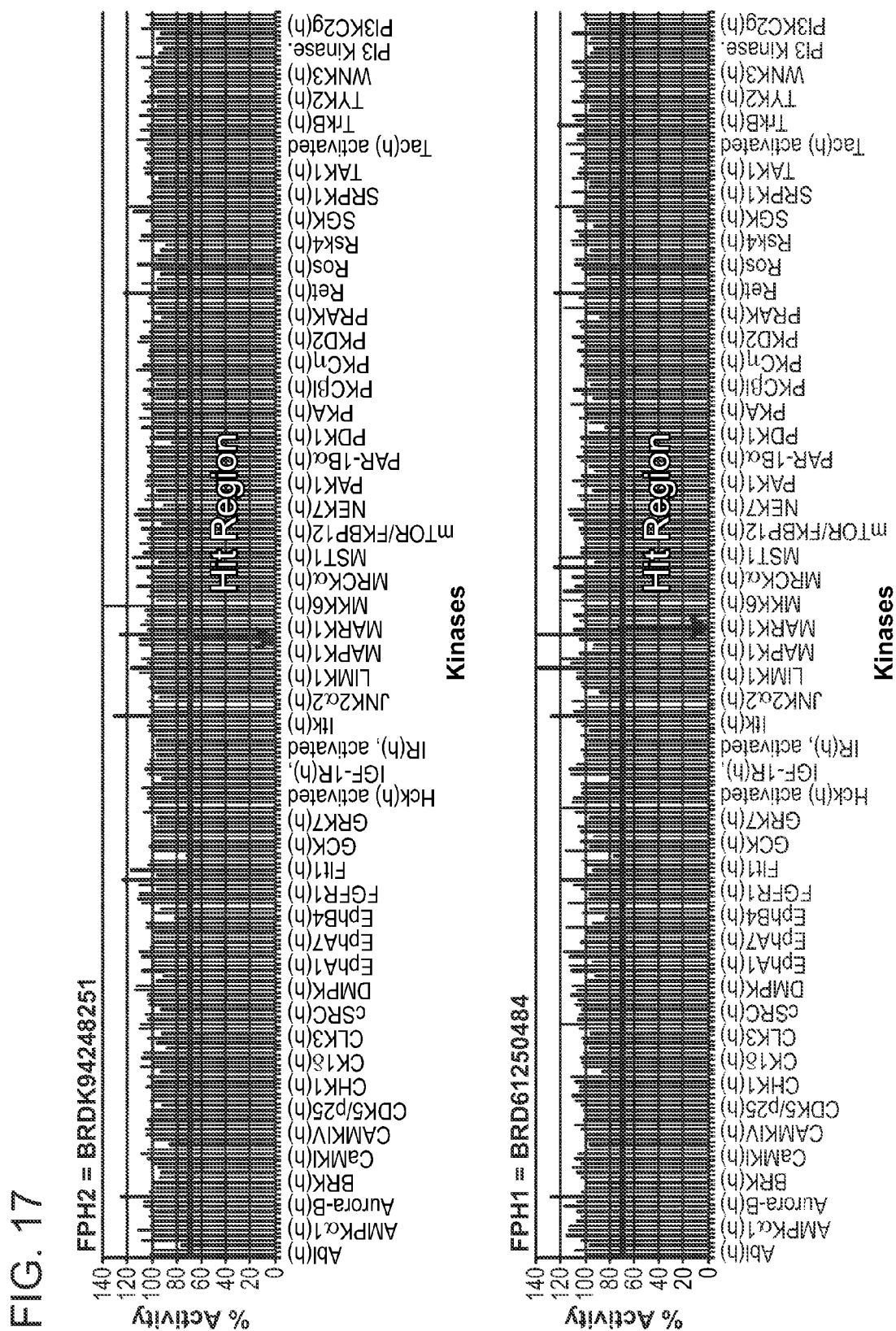
FIG. 17 comprises a set of plots illustrating the kinome analyses for selected compounds of the invention.

Selected compounds of the invention (FPH1 and FPH2; both at 1 µM concentration) were screened against a panel of kinases (FIG. 17).

FPH1 inhibited the activity of the following kinases by 18.4-30.0% (i.e., 70.0-81.6% activity remaining): FMS (23% inhibition; 77% remaining activity) and IGF-1R (21% inhibition; 79% remaining activity). FPH1 inhibited the activity of the following kinases by 6.7-18.4% (i.e., 81.6-93.3% activity remaining): MAPKAP-KII, MAPKAPKV (PRAK), Pim1, CK1 γ2, GRK1, PAK5, MSSK1, SAPK4, eEF-2K, EphB4, KDR and PI3KCγ.

FPH2 inhibited the activity of the following kinases by 18.4-30.0% (i.e., 70.0-81.6% activity remaining): FMS (28% inhibition; 72% remaining activity), ALK (23% inhibition; 77% remaining activity) and EphB4. FPH2 inhibited the activity of the following kinases by 6.7-18.4% (i.e., 81.6-93.3% activity remaining): CaMK1 δ, RSK2, MAPKAPKV (PRAK), RSK3, RSK4, CK1 γ2, PI3KCγ, PI3KC2 α, PDGFRβ, Ron, FAK, eEF-2K, CLK1, CLK4, NEK2, NEK9, CDK5 and DAPK1.

FMS is a member of the CSF1R/PDGF receptor family of tyrosine kinases, and mediates biological effects of CSF1, which affects production, differentiation and cell function of monocyte lineage. Mutations in the FMS kinase are associated with myeloid malignancy.

Example 15: Physico-Chemical Characterization

Selected compounds of the invention were evaluated for physico-chemical properties, including solubility, microsomal stability, protein binding and plasma stability (Table 2).

TABLE 2

Physico-chemical properties.

| | Solubility (µM) - PBS with 1% DMSO | | | |
|---|---|---|---|---|
| Compound | Rep1 | Rep2 | Rep3 | Average |
| BRD-K05085281 | 23 | 28 | 24 | 25 |
| BRD-K17976466 | >100 | >100 | >100 | >100 |
| BRD-K37628956 | 33 | 47 | 41 | 41 |
| Controls | | | | |
| Antipyrine | >100 | >100 | >100 | >100 |
| Clotrimazole | 1.6 | 1.9 | 3.1 | 2.2 |

| | Microsomal stability (% remaining) - Human | | | |
|---|---|---|---|---|
| Compound | Rep1 | Rep2 | Average | No NADPH |
| BRD-K05085281 | 53.9 | 58.1 | 56.0 | 104.2 |
| BRD-K17976466 | 99.4 | 95.3 | 97.4 | 102.3 |
| BRD-K37628956 | 52.4 | 59.3 | 55.8 | 94.4 |
| Controls | | | | |
| Atenolol | 103.1 | 97.8 | 100.4 | 92.1 |
| Verapamil | 6.6 | 7.1 | 6.9 | 92.8 |

| | Protein binding (% bound) - Human | | |
|---|---|---|---|
| Compound | Rep1 | Rep2 | Average |
| BRD-K05085281 | 99.3 | 99.3 | 99.3 |
| BRD-K17976466 | 11.8 | 12.1 | 12.0 |
| BRD-K37628956 | 99.4 | 99.5 | 99.5 |

TABLE 2-continued

Physico-chemical properties.

Controls

| | | | |
|---|---|---|---|
| Verapamil | 92.0 | 92.9 | 92.4 |
| Lidocaine | 58.2 | 60.7 | 59.5 |

| Compound | Plasma stability (% remaining) - Human Average |
|---|---|
| BRD-K05085281 | 98.0 |
| BRD-K17976466 | 104.2 |
| BRD-K37628956 | 87.1 |

Controls

| | |
|---|---|
| Verapamil | 98.5 |
| Eucatropine | 0.5 |

Note:
average percent remaining represents disappearance through both enzymatic and non-enzymatic microsomal mechanisms.

"No NADPH" result represents disappearance through just the non-enzymatic microsomal mechanisms.

Batch of BRD-K05085281 used: BRD-K05085281-001-03-5

Batch of BRD-K17976466 used: BRD-K17976466-001-03-8

Batch of BRD-K37628956 used: BRD-K37628956-001-03-8

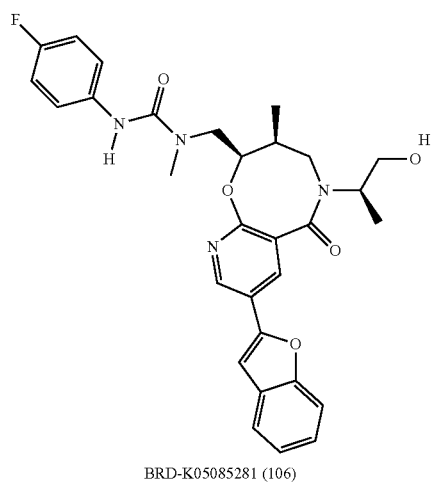

BRD-K05085281 (106)

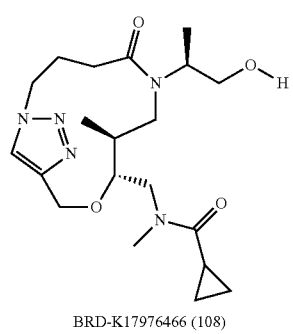 [SMILES: C[C@H]1CN([C@@H](C)CO)C(=O)CCCn2cc(nn2)CO[C@H]1CN(C)C(=O)C1CC1]

BRD-K17976466 (108)

TABLE 2-continued

Physico-chemical properties.

BRD-K37628956 (107)

Example 16: Physico-Chemical Characterization

Selected compounds of the invention were evaluated for physico-chemical properties, including solubility, microsomal stability, protein binding and plasma stability (Table 3).

TABLE 3

Physico-chemical properties.

| | Solubility (µM) - PBS with 1% DMSO | | | |
|---|---|---|---|---|
| Compound | Rep1 | Rep2 | Rep3 | Average |
| BRD-K61250484-001-01-5 | 23 | 22 | 26 | 23 |
| BRD-K94248251 | 23 | 16 | 21 | 20 |
| BRD-K44777625-001-01-9 | 45 | 39 | 36 | 40 |
| BRD-A07207424-001-04-1 | 112 | 114 | 104 | >100 |
| Controls | | | | |
| Antipyrine | 89 | 105 | 86 | 93 |
| Clotrimazole | 3.8 | 2.1 | 2.0 | 2.6 |

| | Microsomal Stability (% remaining) - Human | | | |
|---|---|---|---|---|
| Compound | Rep1 | Rep2 | Average | No NADPH |
| BRD-K61250484-001-01-5 | 4.2 | 4.5 | 4.4 | 110.6 |
| BRD-K94248251 | 41.7 | 39.4 | 40.6 | 123.1 |
| BRD-K44777625-001-01-9 | 71 | 66.7 | 68.9 | 63 |
| BRD-A07207424-001-04-1 | 81.5 | 85.5 | 83.5 | 100.3 |
| Controls | | | | |
| Atenolol | 107.3 | 104.1 | 105.7 | 105.5 |
| Verapamil | 5.0 | 4.9 | 5.0 | 111.3 |

| | Protein Binding (% bound) - Human | | |
|---|---|---|---|
| Compound | Rep1 | Rep2 | Average |
| BRD-K61250484-001-01-5 | 90.9 | 91.6 | 91.2 |
| BRD-K94248251 | 95.7 | 95.9 | 95.8 |
| BRD-K44777625-001-01-9 | 91.0 | 91.0 | 91.0 |
| BRD-A07207424-001-04-1 | 76.2 | 75.0 | 75.6 |

TABLE 3-continued

Physico-chemical properties.

| Controls | | | |
|---|---|---|---|
| Verapamil | 96.3 | 96.2 | 96.3 |
| Lidocaine | 75.7 | 76.0 | 75.8 |

| Compound | Plasma Stability (% remaining) - Human Average |
|---|---|
| BRD-K61250484-001-01-5 | 101.4 |
| BRD-K94248251 | 63.9 |
| BRD-K44777625-001-01-9 | 100.6 |
| BRD-A07207424-001-04-1 | 105.9 |
| Controls | |
| Verapamil | 108.4 |
| Eucatropine | 0.4 |

Note:
The average percent remaining represents disappearance through both enzymatic and non-enzymatic microsomal mechanisms.
The "No NADPH" result represents disappearance through just the non-enzymatic microsomal michanisms.
Batch of BRD-K61250484 used: BRD-K61250484-001-01-5
Batch of BRD-K44777625 used: BRD-K44777625-001-01-9
Batch of BRD-A07207424 used: BRD-A07207424-001-04-1

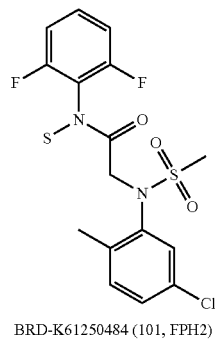 [SMILES: Cc1ccc(Cl)cc1N(CC(=O)N(S)c1c(F)cccc1F)S(C)(=O)=O]

BRD-K61250484 (101, FPH2)

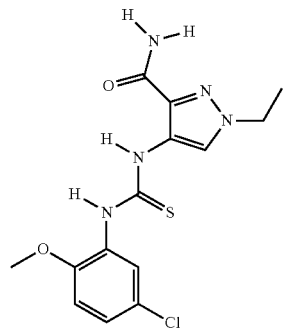

BRD-K94248251 (104, FPH1)

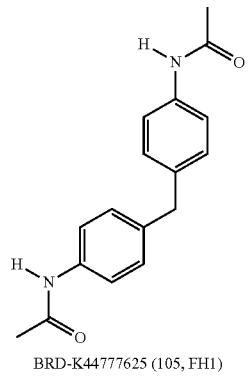 [SMILES: CC(=O)Nc1ccc(Cc2ccc(NC(C)=O)cc2)cc1]

BRD-K44777625 (105, FH1)

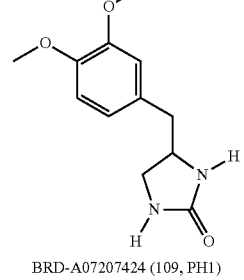

BRD-A07207424 (109, PH1)

Example 17: In Vivo Therapeutic Effects

Figure 18:
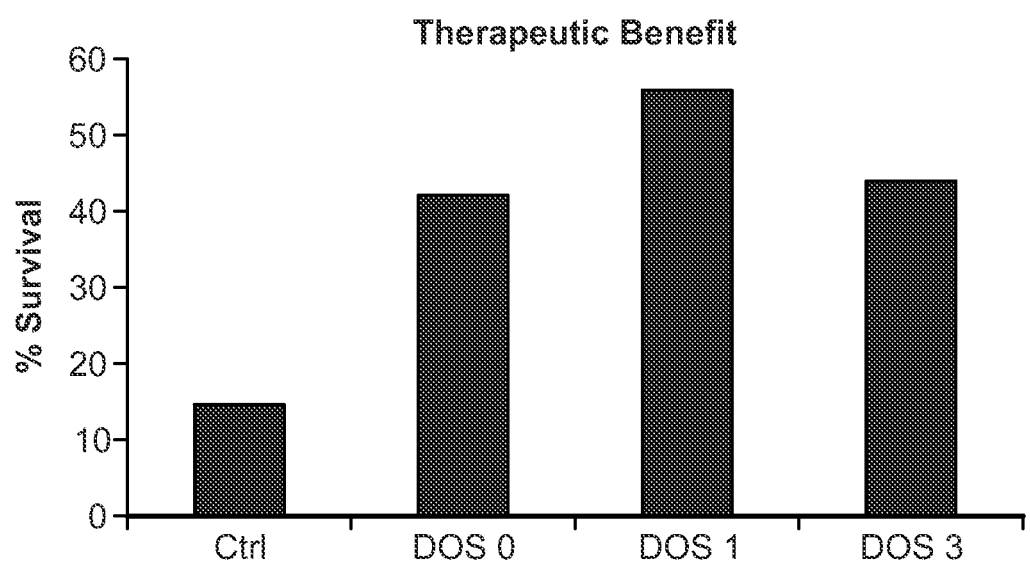
FIG. 18 is a bar graph illustrating the in vivo therapeutic effects of selected compounds of the invention in a zebrafish model of acetaminophen overdose. Compounds tested were DOS 0 (BRD-K05085281; 106), DOS 1 (BRD-K17976466; 108), and DOS 3 (BRD-K37628956; 107).

The In Vivo Therapeutic Effects of Selected Compounds of the Invention were evaluated in a zebrafish model of acetaminophen overdose. Zebrafish embryos were co-administered a lethal dose of acetaminophen and a compound of the invention. The therapeutic benefit of the compound of the invention was assessed through survival of the embryos at 24 hours post exposure to the compounds. Results are illustrated in FIG. 18.

Example 18: In Vitro Maturation Effects

The in vitro maturation effects of selected compounds of the invention on human iPS-derived hepatocyte-like cells (iHeps) were evaluated. Human iPS cells were differentiated into iHeps and treated with selected compounds of the invention for 9 days. Maturity of treated iHeps was evaluated through ELISA quantification of mature (albumin) and immature (AFP) markers. Results are illustrated in FIG. 19.

Figure 19A:
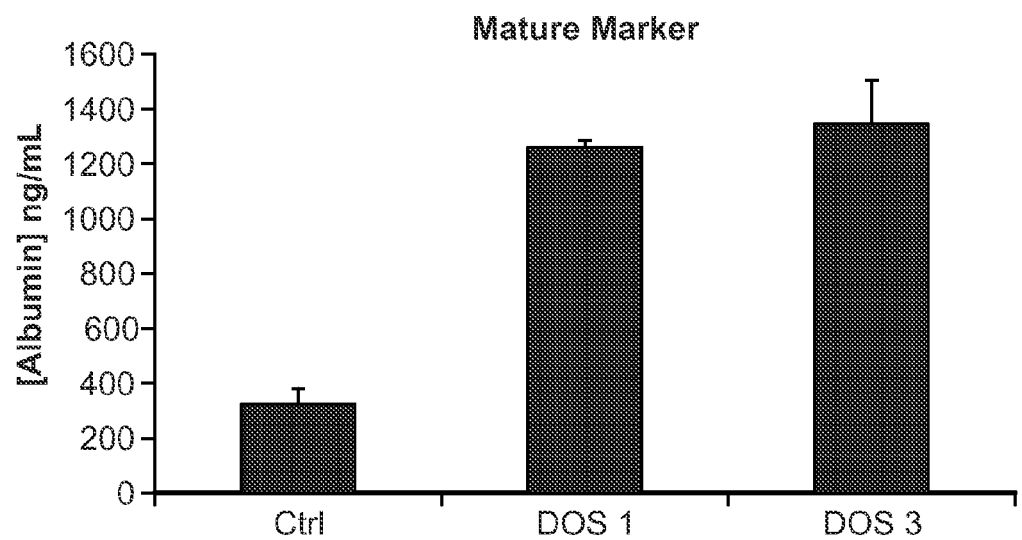
FIGS. 19A-19B, is a set of bar graphs illustrating the in vitro maturation effects of selected compounds of the invention on human iPS-derived hepatocyte-like cells (iHeps).

The results illustrated in FIG. 19A (albumin) were obtained with the DOS 1 concentration of 6.7 μM, and the DOS 3 concentration of 10 μM. The experimental range of effective concentrations was 5-13.3 μM for DOS 1, and 5-20 μM for DOS 3.

Figure 19B:
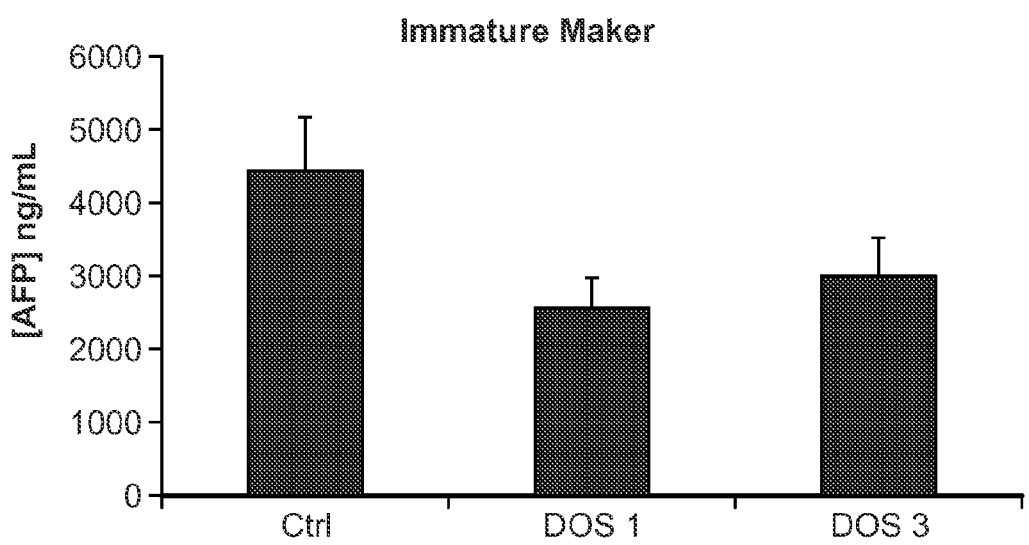

The results illustrated in FIG. 19B (AFP) were obtained with the DOS 1 concentration of 10 μM, and the DOS 3 concentration of 20 μM. The experimental range of effective concentrations was 10-40 μM for DOS 1 and 10-40 μM for DOS 3.

Figure 20A:
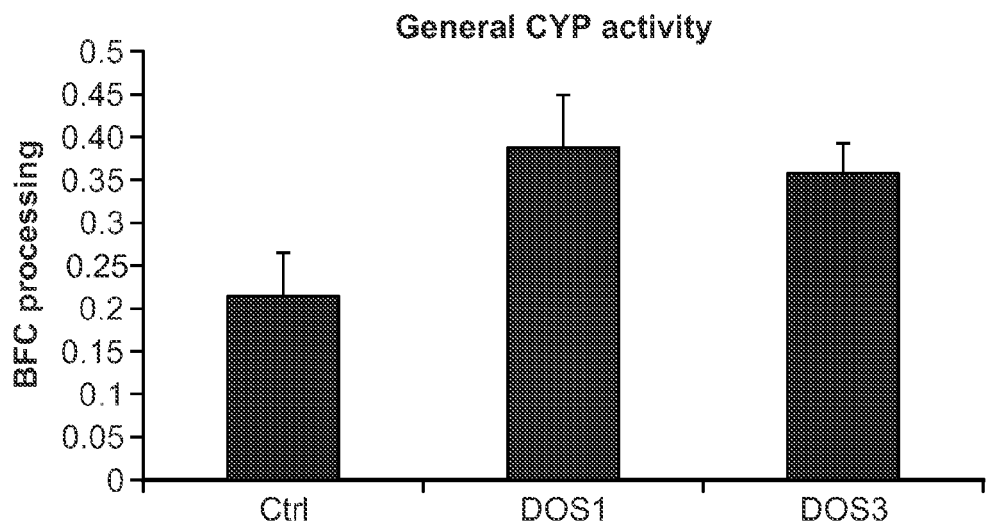
FIGS. 20A-20D, are a set of bar graphs illustrating the cytochrome P450 activity in iHeps treated with compounds of the invention. Compounds tested were DOS 1 (BRD-K17976466; 108), and DOS 3 (BRD-K37628956; 107).

Example 19: Cytochrome P450 Activity iPS Cells were differentiated into iHeps, treated with selected compounds of the invention for 9 days, then assayed for CYP functions. The general CYP activity of the iHeps treated with compounds of the invention were elevated (FIG. 20A). The treated iHeps displayed elevated mature CYP activity, both for CYP3A4 (FIG. 20B) and CYP2A6 (FIG. 20C). On the other hand, the treated iHeps displayed depressed immature CYP activity, as demonstrated for CYP3A7 (FIG. 20D).

The results illustrated in FIG. 20A (general BFC) were obtained with the DOS 1 concentration of 10 μM, and the DOS 3 concentration of 13.3 μM. The experimental range of effective concentrations was 6.7-13.3 μM for DOS 1, and 13.3 μM for DOS 3.

Figure 20B:
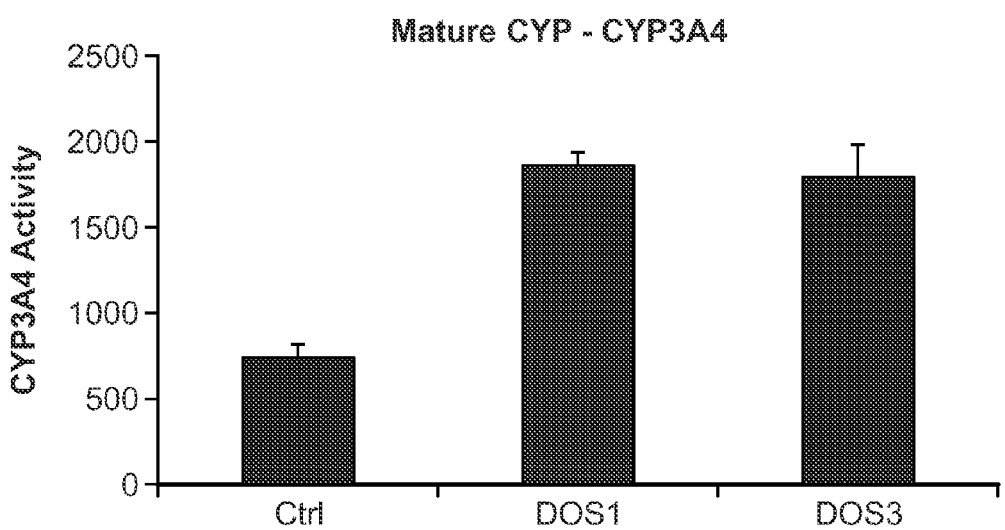
Figure 20C:
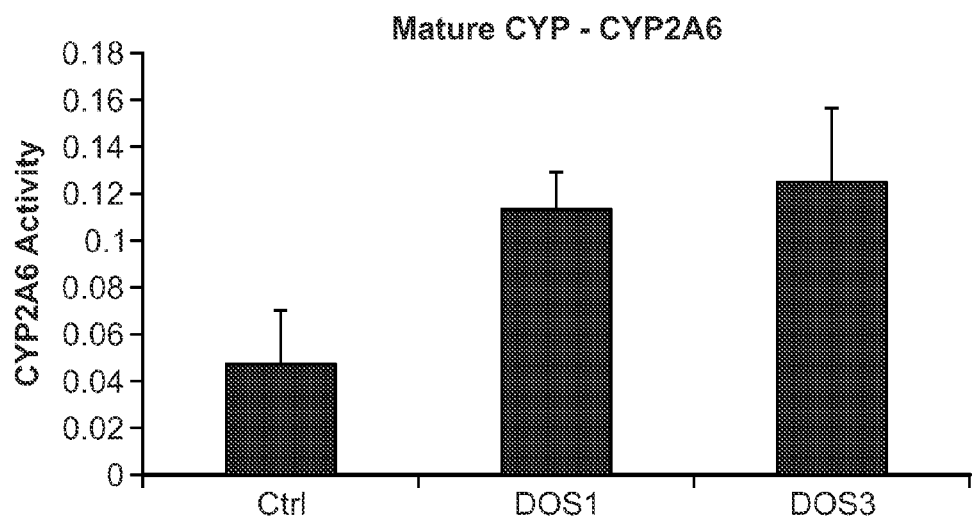
Figure 20D:
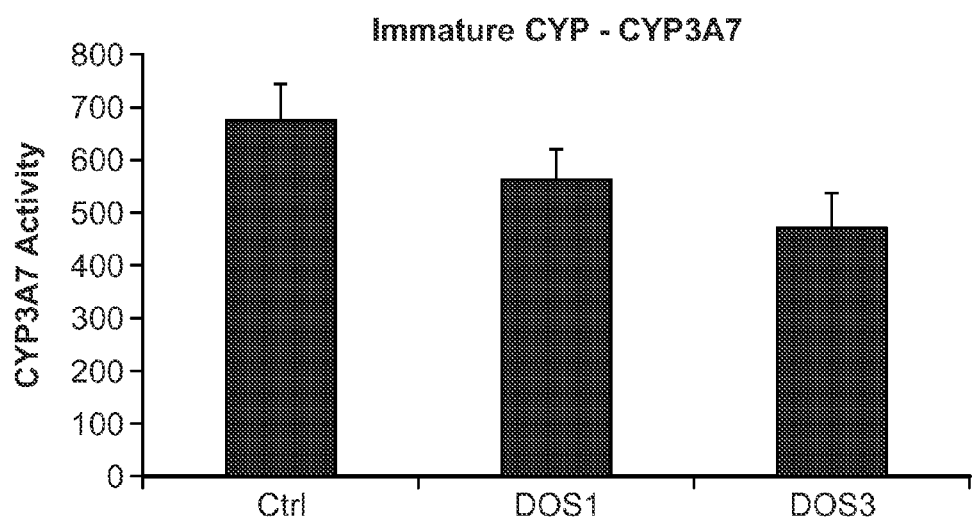

The results illustrated in FIG. 20B (CYP3A4) were obtained with the DOS 1 concentration of 10 µM, and the DOS 3 concentration of 10 µM. The experimental range of effective concentrations was 6.7-13.3 µM for DOS 1, and 6.7-20 µM for DOS 3.

The results illustrated in FIG. 20C (CYP2A6) were obtained with the DOS 1 concentration of 13.3 µM, and the DOS 3 concentration of 26.7 µM. The experimental range of effective concentrations was 10-20 µM for DOS 1, and 10-26.7 µM for DOS 3.

The results illustrated in FIG. 20D (CYP3A7) were obtained with the DOS 1 concentration of 10 µM, and the DOS 3 concentration of 10 µM. The experimental range of effective concentrations was 6.7-10 µM for DOS 1, and 10-13.3 µM for DOS 3.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of inducing differentiation of one or more induced pluripotent stem cell (iPS cell)-derived, immature hepatocyte cells (iHep cells), the method comprising:

contacting the one or more iHep cells with compound 105 (N,N'-(methylenebis(4,1-phenylene))diacetamide); or a pharmaceutically acceptable salt thereof;

wherein said contacting with the compound induces differentiation of the one or more immature iHep cells into mature hepatocytes.

2. The method of claim 1, wherein the mature hepatocytes derived from the one or more iHep cells contacted with compound 105 express elevated levels of albumin in culture.

3. The method of claim 1, wherein the mature hepatocytes derived from the one or more iHep cells contacted with compound 105 express minimal levels of alpha fetoprotein (AFP) in culture.

4. The method of claim 1, wherein the mature hepatocytes derived from the one or more iHep cells contacted with compound 105 express elevated levels of CYP34A and CYP2A6 activity in culture.

5. The method of claim 1, wherein the one or more iHep cells are human iHep cells.

6. The method of claim 1, wherein the one or more iHep cells is contacted with compound 105 ex vivo.

7. A method of inducing differentiation of one or more induced pluripotent stem cell (iPS cell)-derived endothelial cells, the method comprising contacting the one or more iPS cell-derived endothelial cells with compound 105 (N,N'-(methylenebis(4,1-phenylene)) diacetamide), or a pharmaceutically acceptable salt thereof, wherein said contacting with the compound induces differentiation of the one or more iPS cell-derived endothelial cells to produce a population of more mature nitric oxide-producing endothelial cells.

8. The method of claim 7, wherein the one or more iPS cell-derived endothelial cells is contacted with compound 105 ex vivo.

* * * * *